(12) United States Patent
Hu et al.

(10) Patent No.: US 12,122,742 B2
(45) Date of Patent: Oct. 22, 2024

(54) SMALL MOLECULE DIRECT INHIBITORS OF KEAP1-NRF2 PROTEIN-PROTEIN INTERACTION

(71) Applicant: Rutgers, The State University of New Jersey, New Brunswick, NJ (US)

(72) Inventors: Longqin Hu, Belle Mead, NJ (US); Dhulfiqar A. Abed, Babylon (IQ)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 554 days.

(21) Appl. No.: 17/423,688

(22) PCT Filed: Jan. 16, 2020

(86) PCT No.: PCT/US2020/013831
§ 371 (c)(1),
(2) Date: Jul. 16, 2021

(87) PCT Pub. No.: WO2020/150446
PCT Pub. Date: Jul. 23, 2020

(65) Prior Publication Data
US 2022/0112160 A1    Apr. 14, 2022

Related U.S. Application Data

(60) Provisional application No. 62/794,133, filed on Jan. 18, 2019.

(51) Int. Cl.
| | | |
|---|---|---|
| C07C 323/67 | (2006.01) |
| C07C 315/04 | (2006.01) |
| C07D 209/14 | (2006.01) |
| C07D 209/48 | (2006.01) |
| C07D 333/58 | (2006.01) |
| C07D 403/12 | (2006.01) |
| C07D 405/14 | (2006.01) |
| C07D 407/12 | (2006.01) |

(52) U.S. Cl.
CPC .......... *C07C 323/67* (2013.01); *C07C 315/04* (2013.01); *C07D 209/14* (2013.01); *C07D 209/48* (2013.01); *C07D 333/58* (2013.01); *C07D 403/12* (2013.01); *C07D 405/14* (2013.01); *C07D 407/12* (2013.01)

(58) Field of Classification Search
None
See application file for complete search history.

(56) References Cited

PUBLICATIONS

Jain et al: "Probing the Structural Requirements of Non-Electrophilic Naphthalene-Based Nrf2 Activators", Eur J Med Chem. Oct. 20, 2015. vol. 1031, pp. 252-268.
Richardson et al: "Replacement of a Naphthalene Scaffold in Keich-like ECH-Associated Protein 1 (KEAP1)/Nuclear Factor (Erythroid-Derived 2)-like 2 (NRF2) Inhibitors", J Med Chem. Sep. 13, 2018, vol. 61, No. 17, pp. 8029-8047.
Yusada et al: "Synthesis of Keap1-Phosphorylated p62 and Keap1-Nrf2 Protein-Protein Interaction Inhibitors and their Inhibitory Activity", Bioorganic & Medicinal Chemistry Letters, 2016, vol. 26, pp. 5956-5959.
Roy et al: "Bis(sulfonamide) Transmembrane Carriers Allow pH-Gated Inversion of Ion Selectivity", Chem . . . Commun., 2017, vol. 53, pp. 3122-3125.

*Primary Examiner* — Samantha L Shterengarts
(74) *Attorney, Agent, or Firm* — FOX ROTHSCHILD LLP

(57) ABSTRACT

This patent document discloses novel compounds and methods of preventing or treating diseases or conditions related to Keap1-Nrf2 interaction activity by use of the novel compounds. As direct inhibitors of Keap1-Nrf2 interaction, the compounds disclosed herein are more specific and free of various undesirable effects than existing indirect inhibitors, and are potential dmg candidates of chemopreventive and therapeutic agents for treatment of various diseases or conditions involving oxidative stress and/or inflammation, including but not limited to cancers, diabetes, Alzheimer's, Parkinson's, and inflammatory bowel disease including ulcerative colitis.

21 Claims, No Drawings

SMALL MOLECULE DIRECT INHIBITORS OF KEAP1-NRF2 PROTEIN-PROTEIN INTERACTION

CROSS-REFERENCE TO RELATED APPLICATIONS

This application is the U.S. National Phase of International Patent Application Serial No. PCT/US20/13831, filed Jan. 16, 2020, which claims the benefit of priority under 35 U.S.C. § 119(c) to U.S. Provisional Patent Application Ser. No. 62/794,133, filed on Jan. 18, 2019, the entire contents of which are incorporated herein by reference.

TECHNICAL FIELD

The present invention relates to use of Keap1-Nrf2 protein-protein interaction as a target in discovery of drug candidates, and the discovery of small molecule direct inhibitors of Keap1-Nrf2 protein-protein interaction and potent activators of Nrf2 and ARE-mediated genes to modulate inflammatory processes.

BACKGROUND

The Keap1-Nrf2-ARE system represents a crucial antioxidant defense mechanism that protects cells against oxidative stress-related diseases and inflammation. Activation of this system leads to elevated expression of a variety of antioxidant defense proteins and enzymes important for protection against oxidative damage, inflammation and tumorigenesis. The protein-protein interaction (PPI) between Keap1 and Nrf2 has become a hot target for the prevention and treatment of a variety of diseases and conditions including cancer, chronic obstructive pulmonary diseases (COPD), Alzheimer's and Parkinson's diseases, chronic kidney diseases (CKD), diabetes, and inflammatory bowel disease including ulcerative colitis.

Some of the known Nrf2-ARE inducing agents are already in human clinical trials as chemopreventive agents for cancer or as therapeutic agents for conditions involving inflammation. For example, sulforaphane, an isothiocyanate found in cruciferous vegetables and a known ARE inducer, is being tested in clinical trials for the treatment and prevention of prostate cancer and for the treatment of chronic obstructive pulmonary disease (COPD). Bardoxolone methyl, another potent inducer of the Nrf2 pathway, was tested in phase III clinical trials as a first-in-class AIM for the treatment of advanced chronic kidney disease (CKD) in patients with type 2 diabetes mellitus. However, all currently known small molecule Nrf2/ARE inducers are believed to be irreversible modifying agents of cysteine sulfhydryl groups and these include many natural products (e.g., sulforaphane, curcumin, and epigallocatechin gallate from natural sources such as fruits, vegetables, and tea products) and synthetic compounds (e.g., oltipraz, anethole dithiolethione, bardoxolone methyl). All these compounds are either chemically reactive or can be converted to chemically reactive metabolites that readily oxidize or form covalent adduct with the sulfhydryl group of cysteines. It is believed that this modification of cysteine residues in Keap1 is responsible for the disruption of Keap1-Nrf2 complex formation and degradation, leading to subsequent translocation of Nrf2 into the nucleus. Thus, these known modulators are all considered indirect irreversible inhibitors of Keap1-Nrf2 interaction. The reactivity of these compounds raises safety concerns over their long-term use as chemopreventive and therapeutic agents. Development as such is questionable because of concerns about their long-term toxicity. Indeed, bardoxolone methyl was recently withdrawn from Phase III clinical trials citing safety concerns over adverse events and increased rate of death. Direct disruption of Keap1-Nrf2 protein-protein interaction using small molecule inhibitors, though more challenging, represents an attractive novel strategy to promote translocation of Nrf2 to the nucleus and elevate the expression of ARE enzymes. The only direct inhibitors of Keap1-Nrf2 interaction currently known are the peptides based on the Nrf2 Neh domain that are used in the crystallographic studies. Multiple charges are present on these peptides and their poor membrane permeability and susceptibility to proteolysis prevented their use directly in cellular and in vivo assays. Therefore, there is an urgent need to discover potent small molecule direct inhibitors of Keap1-Nrf2 protein-protein interaction as proposed in this application.

SUMMARY

This patent document discloses direct inhibitors of Keap1-Nrf2 PPI, which feature unique scaffolds and function as potent non-electrophilic Nrf2 activators. Furthermore, some of the compounds are efficacious inducers of Nrf2 targeted genes in HepG2 C8 cells, exhibiting activity better than the well-known electrophilic activator, sulforaphane.

An aspect of the invention provides a compound of Formula I or a pharmaceutically acceptable salt, isomer, or prodrug thereof,

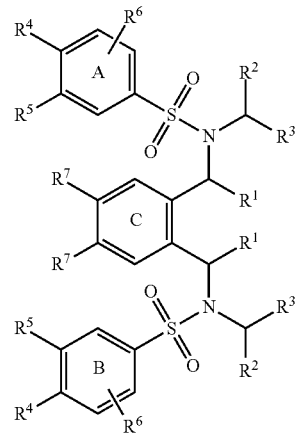

Formula I wherein $R^1$ is
  (a) hydrogen; or
  (b) two $R^1$ groups link up to each other together with the carbons they are attached to and ring C to form a ring (ring D, fused to ring C);
$R^2$ is C1-C4 alkyl;
$R^3$ is carboxylic acid or carboxamide or tetrazole;
$R^4$ is selected from the group consisting of hydrogen, C1-C4 alkoxy, C1-C6 alkyl, halogen, $CF_3$, sulfonamido, amido, carboxamide, amino, nitro, trifluoroacetamido, aryl, heteoaryl, aryloxy heterocyclyloxy and aryl-C1-C2 alkoxy;
$R^5$ is selected from the group consisting of hydrogen, C1-C6 alkyl, C1-C4 alkoxy, halogen, $CF_3$, sulfonamido, amido, trifluoroacetamido, aryl, heteoaryl, and aryl-C1-C2 alkoxy;

alternatively R⁴ and R⁵ link up together with the ring to which they are attached to form a bicylic or tricyclic ring;

R⁶ is hydrogen, C1-C6 alkyl, halogen, or CF3;

R7 is hydrogen, halogen or C1-C3 alkyl or C1-C3 alkoxy;

provided that when the two R¹ groups link up to each other together with the carbons they are attached to and ring C to form the ring (ring D), the compound is one of the following of (a)-(d):

(a) the compound is represented as Formula I-a

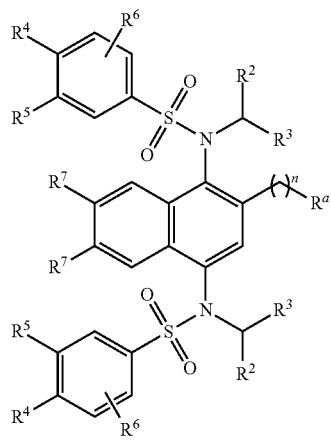

I-a wherein n is an integer of 0 to 5 inclusive (i.e. 0, 1, 2, 3, 4 or 5);

Rᵃ is —CONRᶜRᵈ, aryl, heteroaryl, O-aryl, S-aryl, O-heteroaryl, S-heteroaryl, or phthalimide, wherein the aryl, heteroaryl, O-aryl, S-aryl, O-heteroaryl, S-heteroaryl, or phthalimide is optionally substituted with halogen or C1-C4 alkyl, and wherein Rᶜ and Rᵈ are independently H or alkyl, or Rᶜ and Rᵈ link up to form a ring 3 to 8 membered carbocycle or heterocycle;

(b) the compound is represented as Formula I-b

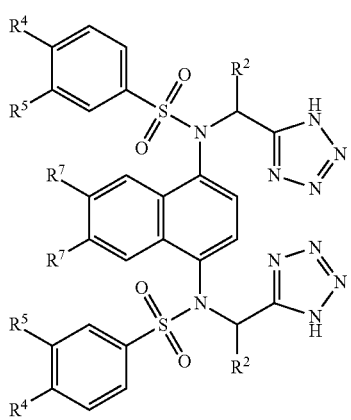

I-b (c) the compound is represented as Formula I-c

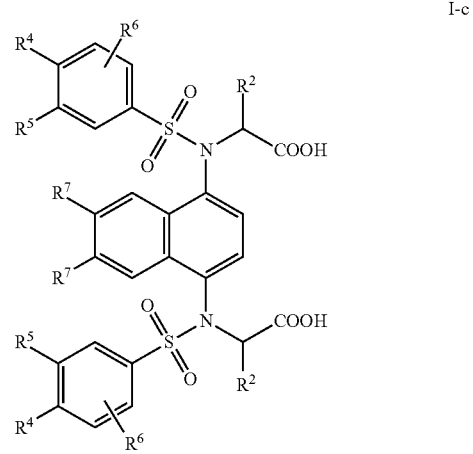

I-c

Wherein R⁴ is sulfonamido, trifluoroacetamido, aryl, heteoaryl, aryloxy, heteoaryloxy, or aryl-C1-C2 alkoxy; and (d) R⁴ and R⁵ link up together with the ring to which they are attached to form a bicylic ring, wherein at least one of the ring atom in the bicyclic ring is a sp3 hybridized carbon, further wherein the bicyclic ring is optionally substituted with halogen or C1-C4 alkyl.

Another aspect of the invention provides a compound or a pharmaceutically acceptable salt, isomer, or prodrug thereof, wherein the compound is represented as Formula II Formula II

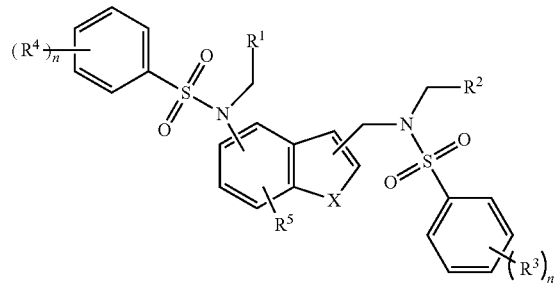

wherein X is S or NRᵃ;

Rᵃ is hydrogen or C1-C4 alkyl;

R¹ and R² are independently carboxylic acid (COOH) or tetrazole;

R³ and R⁴ are independently selected from the group consisting of C1-C4 alkoxy, C1-C6 alkyl, halogen, CF3, sulfonamido, amido, trifluoroacetamido, aryl, heteoaryl, and aryl-C1-C2 alkoxy;

R⁵ is hydrogen, C1-C4 alkyl, or halogen; and n in each instance is independently an integer of 1 to 3, inclusive.

Another aspect of the invention provides a pharmaceutical composition comprising the compound described herein or the pharmaceutically acceptable salt, isomer, or prodrug thereof.

Another aspect of this disclosure provides a method of treating a disease in a subject comprising administering to the subject in need a therapeutically effective amount of a compound of Formula I or Formula II, or a pharmaceutically acceptable salt, isomer, prodrug, or pharmaceutical composition thereof. Specific embodiments of the compound of Formula I and Formula II are as described above. The diseases to be treated with the method of the present invention include cancer, chronic obstructive pulmonary diseases (COPD), Alzheimer's disease, Parkinson's disease, chronic kidney diseases (CKD), diabetes, and inflammatory bowel disease including ulcerative colitis.

DETAILED DESCRIPTION

While the following text may reference or exemplify specific embodiments of a compound or a method of treating a disease or condition, it is not intended to limit the scope of the compound or method to such particular reference or examples. Various modifications may be made by those skilled in the art, in view of practical and economic considerations, such as the substitutions of the compound and the amount or administration of the compound for treating or preventing a disease or condition.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

The term "subject" encompasses any animal, but preferably a mammal, e.g., human, non-human primate, a dog, a cat, a horse, a cow, or a rodent. More preferably, the subject is a human The term "carrier" refers to a chemical compound that facilitates the incorporation of a compound into cells or tissues.

The term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" or "pharmaceutically acceptable" refers to a carrier or diluent that does not abrogate the biological activity and properties of the compound.

The term "therapeutically effective amount" refers to an amount of a compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The term "alkyl" refers to monovalent saturated alkane radical groups particularly having up to about 18 carbon atoms, more particularly as a lower alkyl, from 1 to 8 carbon atoms and still more particularly, from 1 to 6 carbon atoms. The hydrocarbon chain may be either straight-chained or branched. The term "C1-C10 alkyl" refers to alkyl groups having 1, 2, 3, 4, 5, 6, 7, 8, 9 or 10 carbon atoms. Similarly, the term "C1-C4 alkyl" refers to alkyl groups having 1, 2, 3, or 4 carbon atoms. Non-limiting examples of alkyls include groups such as methyl, ethyl, n-propyl, isopropyl, n-butyl, iso-butyl, tert-butyl, n-hexyl, n-octyl, tert-octyl and the like.

The term "C1-C4 alkoxy" includes an alkyoxy group having 1, 2, 3 or 4 carbons. The term "aryl-C1-C2 alkoxy" includes aryl-$CH_2O$— (e.g. benzyloxy) and aryl-$CH_2CH_2O$—.

The term "carbocycle" or "cycloalkyl" refers to 3 to 10 membered cyclic hydrocarbyl groups having only carbon atoms as ring atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

The term "heterocycle" or "heterocycloalkyl" refers to 3 to 10 membered non-armoatic cyclic groups where one or more carbon ring atoms are replaced with hetero atoms or groups containing heteroatoms (e.g. NH, NC1-C4alkyl O, and S). Nonlimiting examples include pyrrolidine, piperidine, and morpholine.

The term "aryl" is intended to mean any stable monocyclic or bicyclic carbon ring of up to 7 members in each ring, wherein at least one ring is aromatic and all ring atoms of the aromatic ring are carbon atoms. Typical aryl groups include, but are not limited to, groups derived from aceanthrylene, acephenanthrylene, anthracene, azulene, benzene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, and the like. Particularly, an aryl group comprises from 6 to 14 carbon atoms.

The term "hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloheteroalkyl.

The term "halogen" refers to F, Cl, Br, or I.

The term "carboxamide" refers to a group of —CONRR, wherein each R is independently a hydrogen, C1-C10 alkyl or an aryl.

The term "amido" refers to a group of —NRCOR', where R is hydrogen or C1-C4 alkyl and R' is C1-C10 alkyl, aryl, heteroaryl, cycloalkyl or heterocyclylakyl.

The term "heteroaryl" refers to groups having 5 to 14 ring atoms, preferably 5, 6, 9, or 10 ring atoms, having 6, 10, or 14 π electrons shared in a cyclic array, wherein at least one ring atom contributing to the shared π electrons in the cyclic array is a heteroatom. Typical heteroaryl groups include, but are not limited to, groups derived from acridine, carbazole, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, phenanthridine, phenanthroline, phenazine, phthalazine, phthalimide, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred.

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In some embodiments, "treating" or "treatment" refers to delaying the onset of the disease or disorder, or even preventing the same. "Prophylactic treatment" is to be construed as any mode of treatment that is used to prevent progression of the disease or is used for precautionary purpose for persons at risk of developing the condition.

This document discloses a novel class of inhibitors of keap1-nrf2 protein interaction. An aspect of the invention provides a compound of Formula I or a pharmaceutically acceptable salt, isomer, or prodrug thereof,

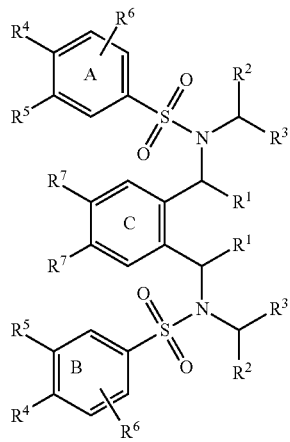

I

Wherein $R^1$ is
(a) hydrogen; or
(b) two $R^1$ groups link up to each other together with the carbons they are attached to and ring C to form a ring;

$R^2$ is C1-C4 alkyl;

$R^3$ is carboxylic acid or carboxamide or tetrazole; $R^4$ is hydrogen, C1-C4 alkoxy, C1-C6 alkyl, halogen, CF3, sulfonamido, amido, carboxamide, amino, nitro, trifluoroacetamido, aryl, heteroaryl, aryloxy heterocyclyloxy or aryl-C1-C2 alkoxy;

$R^5$ is hydrogen, C1-C6 alkyl, C1-C4 alkoxy, halogen, CF3, sulfonamido, amido, trifluoroacetamido, aryl, heteoaryl, or aryl-C1-C2 alkoxy (e.g. benzyloxy);

alternatively $R^4$ and $R^5$ link up together with the ring to which they are attached to form a bicyclic or tricyclic ring;

$R^6$ is hydrogen, C1-C6 alkyl, halogen, or CF3; $R^7$ is hydrogen, halogen or C1-C3 alkyl or C1-C3 alkoxy;

provided that when the two R1 groups link up to each other together with the carbons they are attached to and ring C to form the ring, the compound is one of the following of (a)-(d):

(a) the compound is represented as Formula I-a

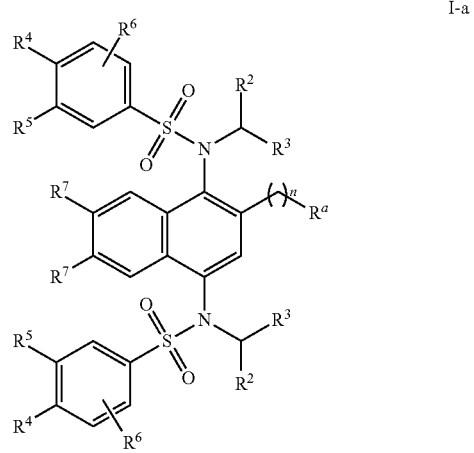

I-a

Wherein
n is an integer of 0 to 5 inclusive (i.e. 0, 1, 2, 3, 4 or 5);

$R^a$ is —$CONR^cR^d$, aryl, heteroaryl, O-aryl, S-aryl, O-heteroaryl, S-heteroaryl, or phthalimide, wherein the aryl, heteroaryl, O-aryl, S-aryl, O-heteroaryl, S-heteroaryl, or phthalimide is optionally substituted with halogen or C1-C4 alkyl, and wherein $R^c$ and $R^d$ are independently H or alkyl, or $R^c$ and $R^d$ link up to form a ring 3 to 8 membered carbocycle or heterocycle;

(b) the compound is represented as Formula I-b

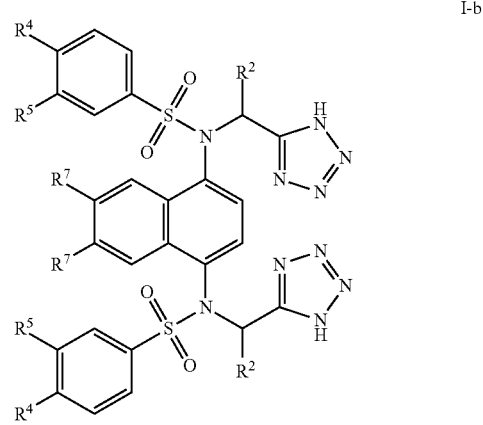

I-b (c) the compound is represented as Formula I-c

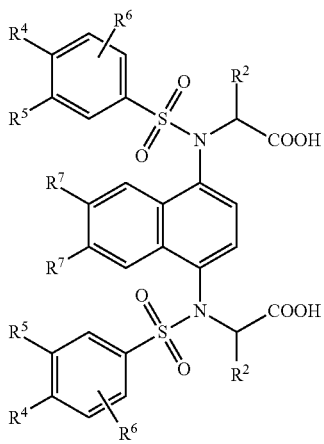

I-c

Wherein R⁴ is sulfonamido, trifluoroacetamido, aryl, heteoaryl, or aryl-C1-C2 alkoxy (e.g. benzyloxy); and
  (d) R⁴ and R⁵ link up together with the ring to which they are attached to form a bicylic ring, wherein at least one of the ring atom in the bicyclic ring is a sp3 hybridized carbon, further wherein the bicyclic ring is optionally substituted with halogen or C1-C4 alkyl.

A compound may have only one R⁴ linking up with its adjacent R⁵ (the other pair of R⁴ and R⁵ not linked up). However, unless otherwise specified, the limitation "R⁴ and R⁵ link up together with the ring to which they are attached to form a bicylic or tricyclic ring" refers to both pairs of R⁴ and R⁵ each linking up to form a bicylic or tricyclic ring, wherein the two resulting bicylic or tricyclic rings have the same structure.

Each substituent (R¹, R², R³, R⁴, R⁵, R⁶, or R⁷) in each occurrence in the same compound can be same or different. In some embodiments, each substituent has the same definition in both occurrences in the same compound (i.e. two R¹ have the same definitions in both occurrences; likewise for two R², two R³, two R⁴, two R⁵, two R⁶, and two R⁷).

In some embodiments, the compounds (except Formula I-a) have a C₂ axis. With regards to Formula I-a, in some embodiments, the compound has a C2 axis for the structure excluding the (CH₂)ₙRᵃ moiety and the hydrogen in the adjacent ring carbon.

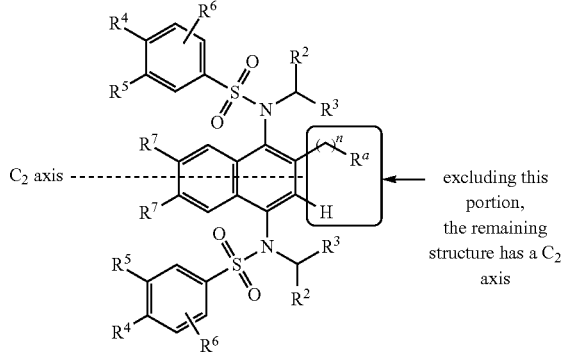

I-a

In some embodiments, one or both of R⁶ and R⁷ are hydrogens.

In some embodiments, the compound is Formula I-a

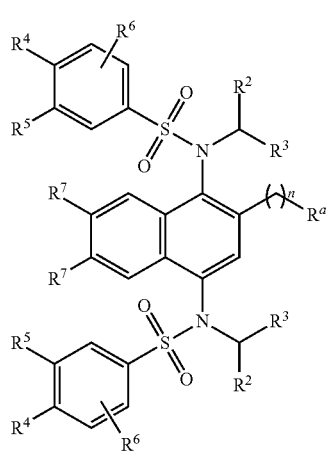

Formula I-a wherein n is an integer of 0 to 5 inclusive. The other substituents are as described as in Formula I.

In some embodiments of Formula I-a, n is an integer of 1, 2, 3, 4 or 5. In some embodiments, Rᵃ is phthalimide optionally substituted with halogen or C1-C4 alkyl, or —CONRᶜRᵈ, wherein Rᶜ and Rᵈ are independently H or alkyl, or Rᶜ and Rᵈ link up to form a ring 3 to 8 membered carbocycle or heterocycle. In some embodiments, R⁴ is C1-C4 alkoxy, C1-C6 alkyl, halogen, CF3, sulfonamido, amido, trifluoroacetamido, aryl, heteoaryl, or aryl-C1-C2 alkoxy; R⁵ is hydrogen, C1-C4 alkyl, or halogen; and Rᵃ is phthalimide optionally substituted with halogen or C1-C4 alkyl, or —CONRᶜRᵈ, wherein Rᶜ and Rᵈ link up to form 3 to 8 membered heterocycle. In some embodiments, Rᵃ is —CONRᶜRᵈ, aryl, heteroaryl, O-aryl, S-aryl, O-heteroaryl, S-heteroaryl, or phthalimide, wherein the aryl, heteroaryl, O-aryl, S-aryl, O-heteroaryl, S-heteroaryl, or phthalimide is optionally substituted with halogen, C1-C3 alkoxy or C1-C4 alkyl.

Non-limiting examples of Rᵃ include the following:

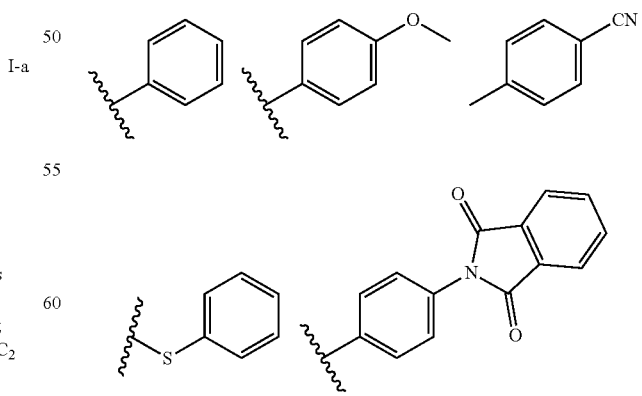

In some embodiments, the compound is Formula I-b. The other substituents are as described as in Formula I.

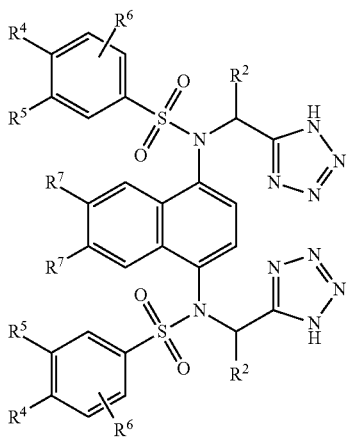

Formula I-b

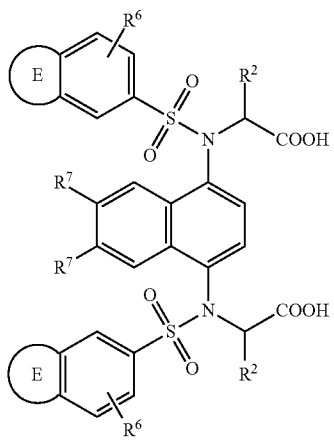

Formula I-d

In some embodiments of Formula I-b, $R^4$ and $R^5$ link up together with the A ring to form a bicylic or tricyclic ring.

In some embodiments, the compound is Formula I-c.

In some embodiments, $R^1$ is hydrogen and the compound is represented as I-e.

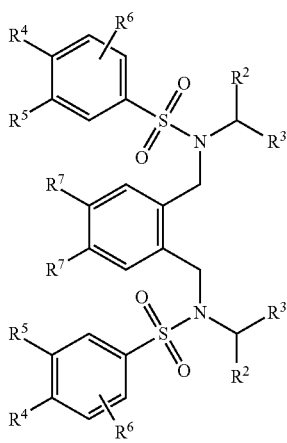

Formula I-e

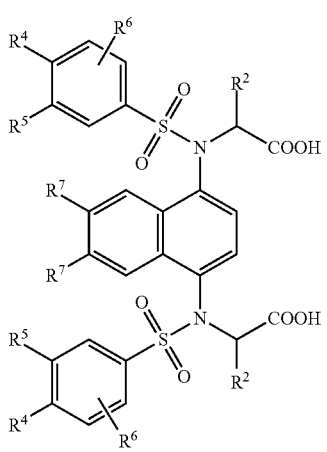

Formula I-c wherein $R^4$ is sulfonamido, trifluoroacetamido, aryl, heteoaryl, or aryl-C1-C2 alkoxy. The other substituents are as described as in Formula I.

In some embodiments of Formula I, $R^4$ and $R^5$ link up together with the ring to which they are attached to form a bicylic ring, wherein at least one of the ring atom in the bicyclic ring is a sp3 hybridized carbon, further wherein the bicyclic ring is optionally substituted with halogen or C1-C4 alkyl. The compound can be represented as Formula I-d. The other substituents are as described as in Formula I. In some embodiments, $R^6$ is a halogen. In some embodiments, $R^6$ is chloro atom.

In some embodiments of Formula I-e, $R^4$ is C1-C4 alkoxy (OMe), C1-C6 alkyl, halogen, CF3, sulfonamido, amido, trifluoroacetamido, aryl, heteoaryl, or aryl-C1-C2 alkoxy; and $R^5$ is hydrogen, C1-C4 alkyl, or halogen. The other substituents are as described as in Formula I.

In some embodiments of Formula I-e, $R^2$ is C1-C4 alkyl; $R^4$ is C1-C4 alkoxy (e.g. OMe, ethoxy, etc.), C1-C6 alkyl, halogen, CF3, sulfonamido, amido, trifluoroacetamido, aryl, heteoaryl, or aryl-C1-C2 alkoxy (e.g. benzyloxy); and $R^5$ is hydrogen, C1-C4 alkyl, or halogen.

In some embodiments of Formula I-e, $R^2$ is hydrogen or C1-C4 alkyl; $R^4$ and $R^5$ link up together with ring A to form a bicyclic or tricyclic ring (e.g. compound I-e-3).

In some embodiments Formula I-e, $R^2$ is C1-C4 alkyl; $R^4$ is C1-C4 alkoxy; and $R^5$ is hydrogen.

In some embodiments Formula I-e, $R^2$ is C1-C4 alkyl; $R^4$ is C1-C4 alkoxy; and $R^5$, $R^6$ and $R^7$ are all hydrogens.

Another aspect of the invention provides a compound or a pharmaceutically acceptable salt, isomer, or prodrug thereof, wherein the compound is represented as Formula II Formula II

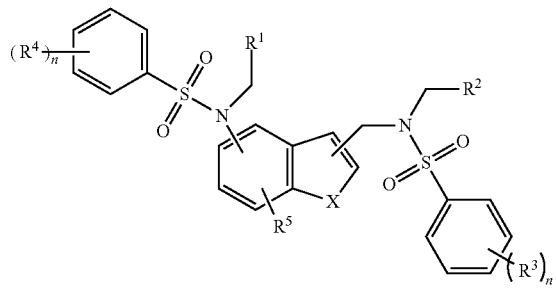

wherein X is S or NR$^a$;

R$^a$ is hydrogen or C1-C4 alkyl;

R$^1$ and R$^2$ are independently carboxylic acid (COOH) or tetrazole;

R$^3$ and R$^4$ are independently selected from the group consisting of C1-C4 alkoxy, C1-C6 alkyl, halogen, CF3, sulfonamido, amido, trifluoroacetamido, aryl, heteroaryl, and aryl-C1-C2 alkoxy;

R$^5$ is hydrogen, C1-C4 alkyl, or halogen; and n in each instance is independently an integer of 1 to 3, inclusive.

In some embodiments, the compound is represented as Formula II-a

Formula II-a

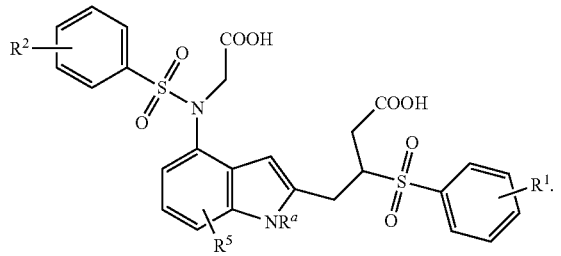

In some embodiments of Formula II-a, R$^a$ is hydrogen. In some embodiments of Formula II-a, R$^a$ is hydrogen, and R$^5$ is a halogen at 7-position of indole ring.

In some embodiments of Formula II, the compound is represented as Formula II-b,

Formula II-b

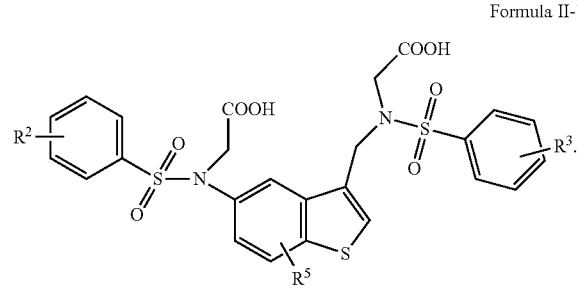

In some embodiments of Formula II-b, R$^5$ is a halogen at 7-position of thiophene ring.

Non-limiting examples of the compounds of the present invention include the following:

Chart 1

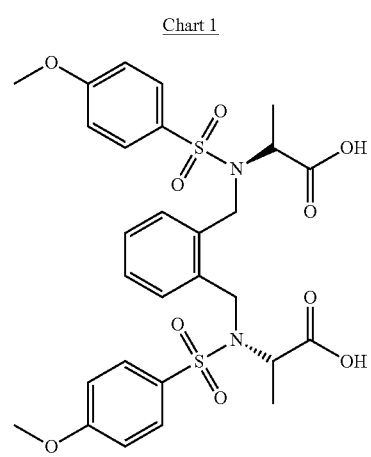

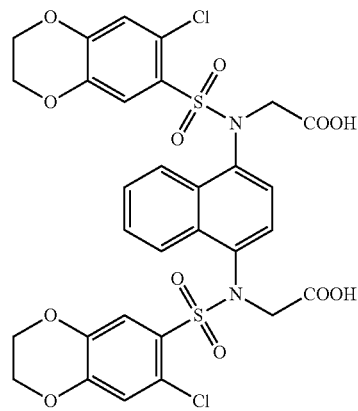

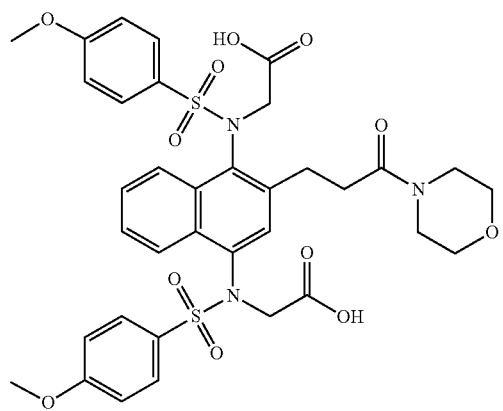

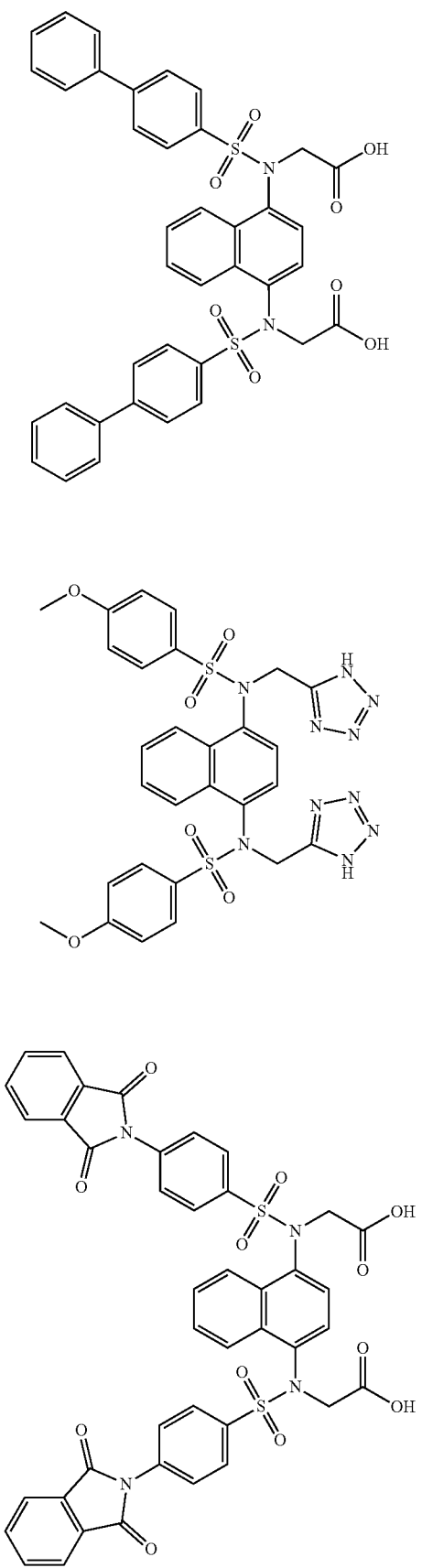
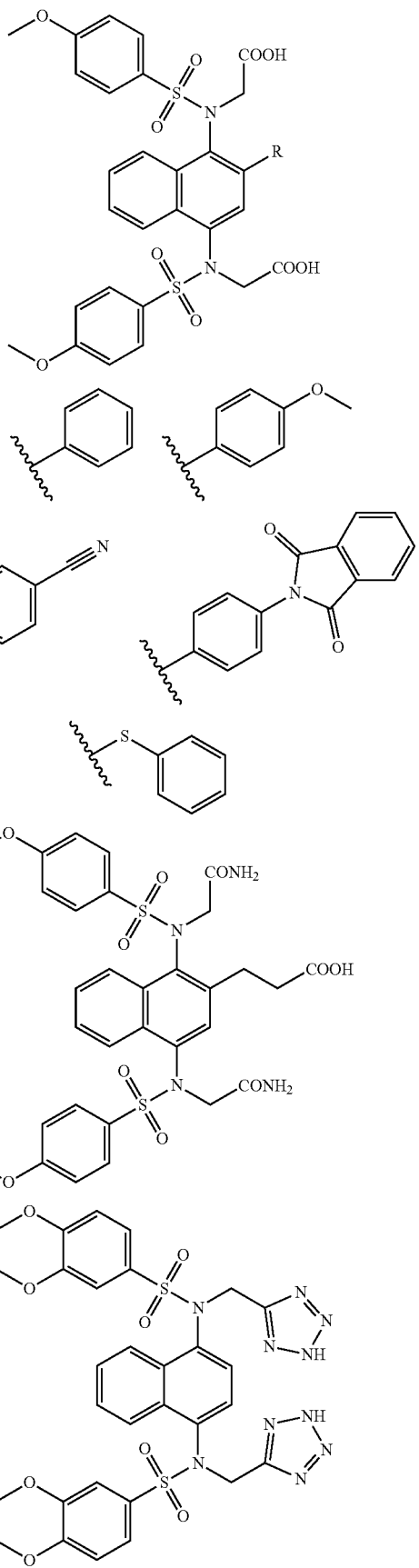

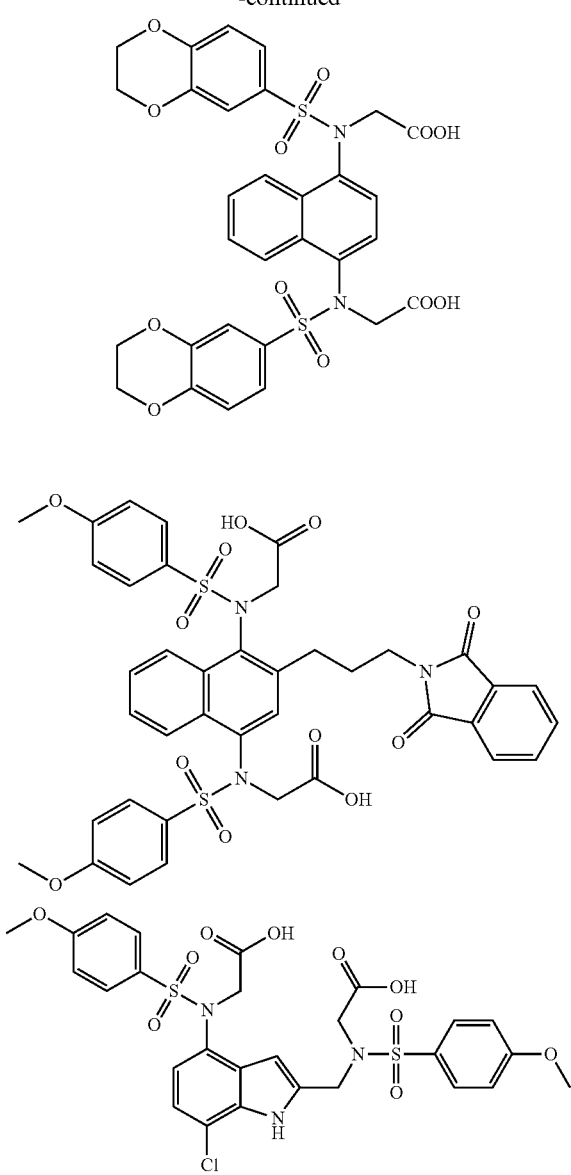
Chart 2
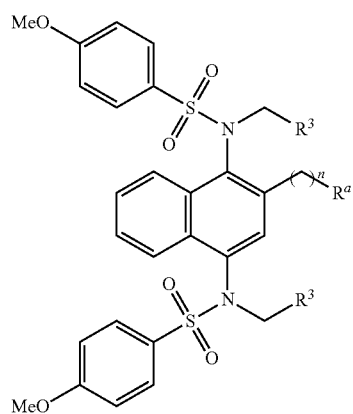
| Cmpd ID | $(CH_2)_nR^a$ | $R^3$ | FP Assay $IC_{50}$ (nM) | TR-FRET Assay $IC_{50}$ (nM) |
|---|---|---|---|---|
| I-a-1 | (propyl-CONH₂) | COOH | 108 ± 7 | 11.7 ± 0.68 |
| I-a-2 | (propyl-CONH-iPr) | COOH | 102 ± 7 | 12.6 ± 0.18 |
| I-a-3 | (propyl-C(O)-morpholine) | COOH | 87 ± 6 | 6.9 ± 0.55 |
| I-a-4 | (propyl-phthalimide) | COOH | 77 ± 5 | 2.5 ± 0.18 |
| I-a-5 | (phenyl) | COOH | 96 ± 6 | 7.7 ± 0.13 |
| I-a-6 | (4-methoxyphenyl) | COOH | 85 ± 6 | 13.1 ± 0.9 |
| I-a-7 | (4-cyanophenyl, gem-dimethyl) | COOH | 117 ± 7 | 9.2 ± 0.32 |
| I-a-8 | (phenylthio) | COOH | 90 ± 6 | 7.1 ± 0.57 |
| I-a-9 | (4-phthalimidophenyl) | COOH | 85 ± 5 | 5.8 ± 0.28 |
| I-a-10 | (propyl-COOH) | CONH₂ | 162 ± 10 | 22.7 ± 1.8 |

Chart 3
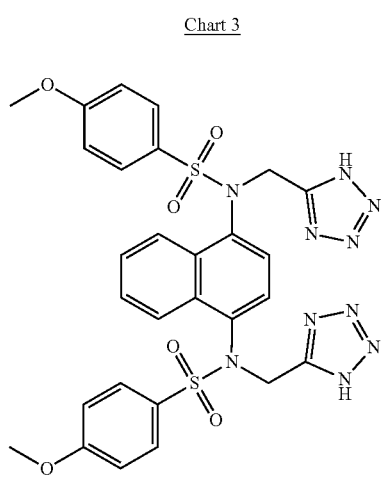
I-b-1
I-b-2
I-b-3
-continued
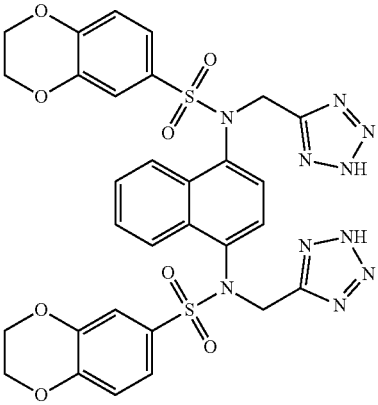
I-b-4
Chart 4
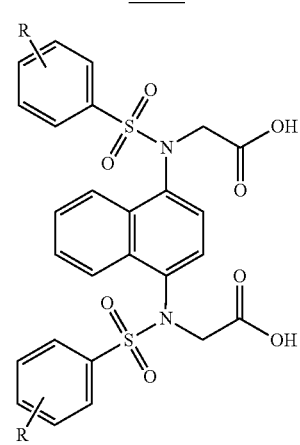
| Cmpd ID | R | % inh. FP assay | | | IC$_{50}$ (nM) |
|---|---|---|---|---|---|
| | | 0.5 (μM) | 5 (μM) | 50 (μM) | |
| I-c-1 | 2-Br, 4-OCH$_3$ | 88.2 | 99.3 | 95.3 | 184 ± 7 |
| I-c-2 | 2-OCH$_3$, 4-Br | 56.1 | 95.2 | 94.6 | ND |
| I-c-3 | 3-CN, 4-OCH$_3$ | 66.5 | 100.7 | 98 | ND |
| I-c-4 | 3-CN, 4-F | 48.9 | 95.2 | 98 | ND |
| I-c-5 | 3-CH$_3$, 4-F | 67.6 | 96.1 | 103 | ND |
| I-c-6 | 2,6-diF | ND | 101 | 101 | 224 ± 50 |
| I-c-7 | 4-NHSO$_2$CH$_3$ | 68.3 | 85.0 | 91.2 | 194 ± 18 |
| I-c-8 | 4-NHC(O)CF$_3$ | 76.1 | 92.1 | 100.6 | 126 ± 13 |
| I-c-9 | 4-Ph | 91.5 | 95.9 | 100.2 | 70 ± 6 |

-continued

| Cmpd ID | R | % inh. FP assay 0.5 (μM) | 5 (μM) | 50 (μM) | IC$_{50}$ (nM) |
|---|---|---|---|---|---|
| I-c-10 | 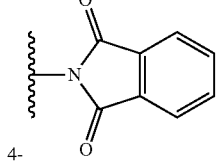 4- | 84.8 | 96.0 | 100.7 | 82 ± 7 |

Chart 5

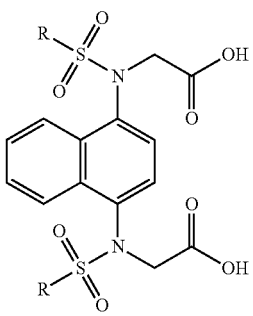

| Cmpd ID | R | % inh. FP assay 0.5 (μM) | 5 (μM) | 50 (μM) | IC$_{50}$ (nM) |
|---|---|---|---|---|---|
| I-d-1 | (2,3-dihydrobenzo[1,4]dioxin-6-yl) | 96 | 100.7 | 101.4 | 120 ± 11 |
| I-d-2 | (7-Cl-2,3-dihydrobenzo[1,4]dioxin-6-yl) | 99.6 | 97.4 | 98.5 | 144 ± 5 |
| I-d-3 | (6-Cl-2,3-dihydrobenzo[1,4]dioxin-7-yl) | 109.6 | 102.1 | 105.2 | 146 ± 09 |
| I-d-4 | (benzo[1,3]dioxol-5-yl) | 85.6 | 96.6 | 98 | 149 ± 13 |
| I-d-5 | (2,3-dihydrobenzofuran-5-yl) | 85.4 | 100.8 | 100.7 | 164 ± 18 |

Chart 6

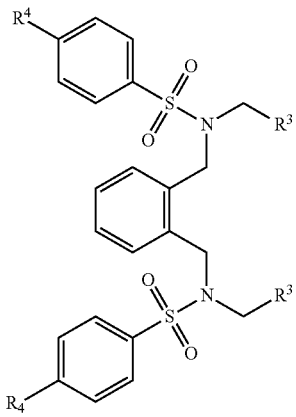

(or, R$^4$, R$^5$, or R$^6$)

| compound | R$^4$, R$^5$, or R$^6$ | R$^3$ | % inh. FP assay 5 (μM) | 50 (μM) | IC$_{50}$ (μM) |
|---|---|---|---|---|---|
| I-e-1 | 2,6-diF | COOH | 86.8 | 98 | 1.78 ± 0.4 |
| I-e-2 | 4-OBn | COOH | 81.9 | 93.5 | 0.57 ± 0.04 |
| I-e-3 | (benzyl 3-,4-) | COOH | 96.2 | 98.1 | 0.42 ± 0.03 |
| I-e-4 | 4-OCH$_3$ | tetrazole | 68.1 | 83.1 | 1.17 ± 0.5 |

Chart 7

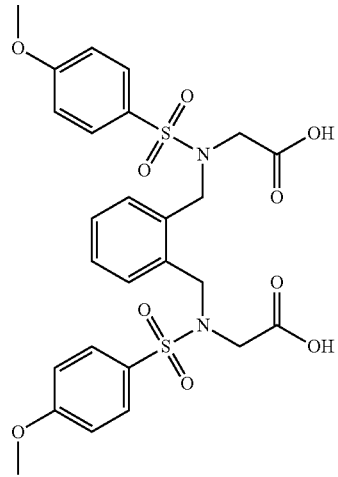

-continued

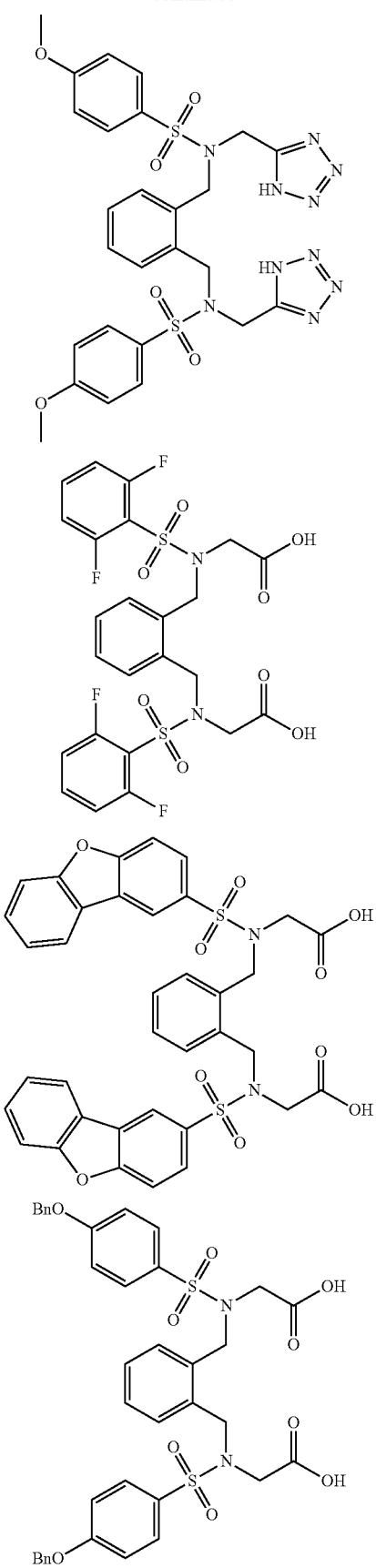

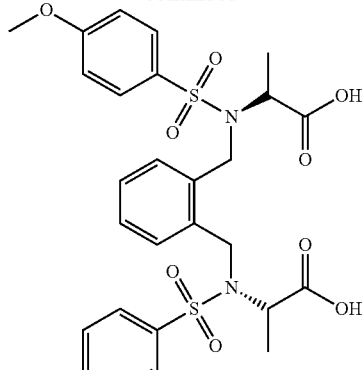

CHART 8

| Cmpd ID | Chemical Structure | % inh. FP assay | | | IC$_{50}$ (nM) |
|---|---|---|---|---|---|
| | | 0.5 (μM) | 5 (μM) | 50 (μM) | |
| II-a-1 | | ND | 77.1 | 100 | ND |
| II-a-2 | | 87.3 | 100 | 100 | 0.26 ± 0.02 |
| II-b-1 | | 45.7 | 84.8 | 107.8 | ND |

Another aspect of the present disclosure provides a pharmaceutical composition containing a therapeutically effective amount of the above described compound and a pharmaceutically acceptable carrier.

The pharmaceutical composition may also contain one or more physiologically acceptable surface active agents, additional carriers, diluents, excipients, smoothing agents, suspension agents, film forming substances, and coating assistants, or a combination thereof; and a composition disclosed herein. Acceptable additional carriers or diluents for therapeutic use are well known in the pharmaceutical art, and are described, for example, in Remington's Pharmaceutical Sciences, 18th Ed., Mack Publishing Co., Easton, PA (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical compounds described herein can be administered to a human patient per se, or in pharmaceutical compositions where they are mixed with other active ingredient(s), as in combination therapy, or suitable carriers or excipient(s). In some embodiments, a dosage form includes those forms in which the compound is administered per se. In addition, a dosage form may include a pharmaceutical composition. In any case, the dosage form may comprise a sufficient amount of the compound to treat a disease as part of a particular administration protocol, as would be understood by those of skill in the art. Techniques for formulation and administration of the compounds of the instant application may be found in "Remington's Pharmaceutical Sciences," Mack Publishing Co., Easton, PA, 18th edition, 1990.

The pharmaceutical compositions may be manufactured in a manner that is itself known, e.g., by means of conventional mixing, dissolving, granulating, dragee-making, levigating, emulsifying, encapsulating, entrapping or tabletting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, diluents, carriers, and excipients may be used as suitable and as understood in the art; e.g., in Remington's Pharmaceutical Sciences, above.

Another aspect of this disclosure provides a method of treating or managing a disease in a subject comprising administering to the subject in need a therapeutically effective amount of a compound of Formula I or Formula II, or a pharmaceutically acceptable salt, isomer, prodrug, or pharmaceutical composition thereo. Specific embodiments of the compound of Formula I and Formula II are as described above.

The compounds of the present invention can function as direct inhibitors of Keap1-Nrf2 protein-protein interaction and administered to a subject in nee thereof for the treatment of a number of oxidative stress-related diseases and conditions, including cancer, chronic obstructive pulmonary diseases (COPD), Alzheimer's and Parkinson's diseases, chronic kidney diseases (CKD), diabetes, and inflammatory bowel disease including ulcerative colitis.

The compositions or pharmaceutical compositions described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intrarticular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; as well as (d) administration topically; as deemed appropriate by those of skill in the art for bringing the active compound into contact with living tissue.

Pharmaceutical compositions suitable for administration include compositions where the active ingredients are contained in an amount effective to achieve its intended purpose. In some embodiments, a therapeutically effective amount of a compound is an amount effective to treat a viral infection, for example, in a mammalian subject (e.g., a human). The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively, dosages may be based and calculated upon the surface area of the patient, as understood by those of skill in the art.

The exact formulation, route of administration and dosage for the pharmaceutical compositions can be chosen by the individual physician in view of the patient's condition. (see e.g., Fingl et al. 1975, in "The Pharmacological Basis of Therapeutics", which is hereby incorporated herein by reference in its entirety, with particular reference to Ch. 1, p. 1). In some embodiments, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, more preferably about 25% to about 250% of the established human dosage may be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free acid. In some embodiments, the composition is administered 1 to 4 times per day. Alternatively the compositions may be administered by continuous intravenous infusion, preferably at a dose of up to about 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety, which are sufficient to maintain the antibiotic effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the infection, the manner of administration and the judgment of the prescribing physician.

Compositions disclosed herein can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound formulated in a compatible pharmaceutical carrier may also be prepared, placed in an appropriate container, and labeled for treatment of an indicated condition.

In some embodiments, in the pharmaceutical industry, it is standard practice to provide substantially pure material when formulating pharmaceutical compositions. Therefore, in some embodiments, "substantially pure" refers to the amount of purity required for formulating pharmaceuticals, which may include, for example, a small amount of other material that will not affect the suitability for pharmaceutical use. In some embodiments, the substantially pure compound contains at least about 96% of the compound by weight, such as at least about 97%, 98%, 99%, or 100% of the compound.

EXAMPLES

General Procedure for Synthesis of Sulfonamides

Method A1

To a mixture of Xylylenediamine dihydrochloride or the free base form (1 mmol) and triethylamine (5 mmol) in DCM (5 mL) at 0° C. under nitrogen atmosphere, a solution of 4-methoxybenzenesulfonyl chloride (2.2 mmol) in DCM (5 mL) was added slowly. Then, the reaction was stirred at room temperature overnight and monitored by TLC and LCMS. Upon completion, reaction mixture was diluted with DCM, washed with 1 N HCl, water, brine, and dried over $Na_2SO_4$, and concentrated under reduced pressure to get the crude products, which were purified by a flash column chromatography using 0-100% EtOAc in hexane.

Method A2

To a solution of 1,4-diaminobenzene (1 mmol) in 5 ml pyridine at 0° C. under $N_2$ (g), 4-methoxybenzenesulfonyl chloride (2.2 mmol) was added and the reaction mixture was stirred at room temperature for 8 h and monitored by TLC and LCMS. Upon completion, the reaction mixture was diluted with DCM and washed with 1 N HCl, water, and brine. Then, the organic layer was dried over $Na_2SO_4$ and concentrated under reduced pressure followed by purification by a flash column chromatography using 0-100% EtOAc in hexanes.

General Procedure for Synthesis of Alkylated Sulfonamides (Method B)

To a solution of sulfonamide (1 mmol) in DMF (3 ml), $K_2CO_3$ (10 mmol) and alkyl bromoacetate (5 mmol) were added. Then, the reaction was stirred at room temperature overnight and monitored by TLC and LCMS. On completion, reaction mixture was diluted with ethyl acetate, washed with 1 N HCl, water, and brine. Then, organic layer was dried over $Na_2SO_4$ and concentrated under reduced pressure to get the crude product, which was purified by flash column chromatography using 0-50% EtOAc/hexane.

General Procedure for Hydrolysis of Ethyl Ester to Get Di-Acidic Compounds

Method C1: Basic Hydrolysis

To a solution of alkylated sulfonamide in EtOH (2 ml), 4 N NaOH in water (2 ml) was added and reaction mixture was stirred at room temperature and monitored by TLC and LCMS. Upon completion, reaction mixture was diluted with ethyl acetate, washed with 1 N HCl, water, and brine. Then, organic layer dried over $Na_2SO_4$ and concentrated under reduced pressure to yield crude product, which was recrystallized using ethyl acetate/hexane, and washed with petroleum ether to afforded pure final product.

Method C2: Removal of Acid Sensitive Protecting Group

To solution of alkylated sulfonamide in DCM (0.5 ml) was cooled to 0° C., a solution of TFA:DCM (1:2) was added dropwise (1.5 ml). Then reaction mixture was stirred at room temperature for 1 hour. Upon completion, reaction mixture was concentrated under reduced pressure to yield crude product, which was recrystallized using ethyl acetate hexane or ethyl ether to afford pure final product.

Method C3: Removal of Benzyl Protecting Group

A solution of starting material in EtOH:THF (1:1) was degassed with Na three times. A catalytic amount of 10% Pd/C was added to the solution and the mixture was purged with H2. The reaction was stirred under H2 (g) for 3 h and then filtered through a celite bed to remove the catalyst. The filtrate was concentrated under vacuum to get the desired product which was recrystallized using ethyl acetate hexane or ethyl ether to afford pure final product.

Intermediate: N,N'-(1,2-Phenylenebis(methylene)) bis(4-methoxybenzenesulfonamide)

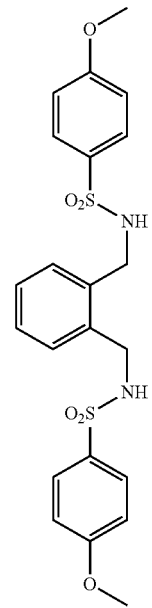 [SMILES: COc1ccc(S(=O)(=O)NCc2ccccc2CNS(=O)(=O)c2ccc(OC)cc2)cc1]

Prepared as described in the general procedure for synthesis of sulfonamides (method A1) to get the title compound as a white solid (391 mg, 82% yield). $^1$H NMR (400 MHz, $CDCl_3$): δ 7.73 (d, 4H, J=8.8 Hz), 7.15 (s, 4H), 6.92 (d, 4H, J=8.8 Hz), 5.17 (t, 2H, J=7.0 Hz), 4.06 (d, 4H, J=7.0 Hz), 3.84 (s, 6H); $^{13}$C NMR (100 MHz), $CDCl_3$): δ 163.1, 134.8, 131.2, 130.3, 129.4, 128.6, 114.5, 55.8, 44.9.

Intermediate: Diethyl 2,2'-((1,2-phenylenebis(methylene))bis(((4-methoxyphenyl) sulfonyl) azanediyl)) diacetate

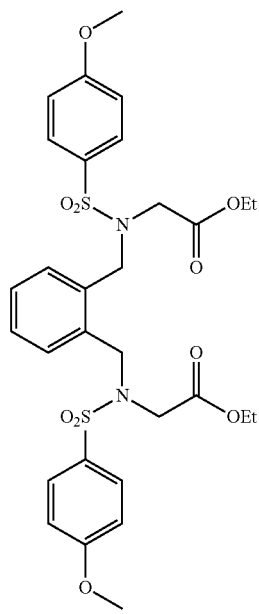 [SMILES: CCOC(=O)CN(Cc1ccccc1CN(CC(=O)OCC)S(=O)(=O)c1ccc(OC)cc1)S(=O)(=O)c1ccc(OC)cc1]

Prepared as described in the general procedure for synthesis of alkylated sulfonamides (Method B) to get the title compound as an oily product (208 mg, 80% yield). $^1$H NMR (400 MHz, CDCl$_3$): δ 7.80 (d, 4H, J=8.8 Hz), 7.36-7.33 (m, 2H), 7.28-7.25 (m, 2H), 6.98 (d, 4H, J=8.8 Hz), 4.57 (s, 4H), 3.94 (q, 4H, J=7.2 Hz), 3.87 (s, 6H), 3.84 (s, 4H), 1.1 (t, 6H, J=7.2 Hz); $^{13}$C NMR (100 MHz, CDCl$_3$): δ 168.59, 163.05, 134.02, 130.81, 129.68, 129.63, 128.39, 114.19, 61.21, 55.61, 49.12, 47.72, 13.92.

Example LH769: 2,2'-((1,2-Phenylenebis(methylene))bis(((4-methoxyphenyl) sulfonyl) azanediyl)) diacetic Acid

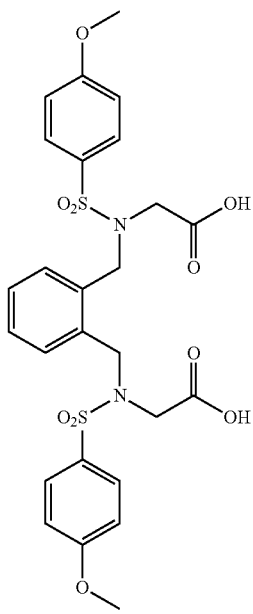

Prepared as described in the general procedure for hydrolysis of ethyl ester to get di-acidic compounds (Method C1) (basic hydrolysis) to get the title compound as a white solid (39 mg, 78% yield). $^1$H NMR (400 MHz, CDCl$_3$): δ 12.64 (s, 2H) 7.77 (d, 4H, J=8.8 Hz), 7.29 (s, 2H), 7.25 (s, 2H), 7.11 (d, 4H, J=8.8 Hz), 4.45 (s, 4H), 3.86 (s, 6H), 3.78 (s, 4H); $^{13}$C NMR (100 MHz, CDCl$_3$): δ 169.84, 162.60, 134.36, 130.56, 129.44, 128.68, 127.58, 114.40, 55.73, 49.09, 48.26. HRMS (ESI) Calcd for C$_{26}$H$_{29}$N$_2$O$_{10}$S$_2$ (M+H)$^+$ 593.1258, found 593.1258.

Intermediate: 1H-Benzo[f]isoindole-1,3(2H)-dione

A mixture of 2,3-Naphthalene dicarboxylic anhydride (218 mg, 1.1 mmole) and urea (140 mg, 2 mmole) was heated at 170° C. for 2 hours. Then, the mixture was triturated with 5 ml water and the resulting solid was collected by filtration. of this reaction. (195 mg, 90% yield), as a white solid. $^1$H NMR (400 MHz, DMSO): δ 11.50 (br, 1H), 8.44 (s, 2H), 8.26-8.25 (m, 2H), 7.77-7.74 (m, 2H). $^{13}$C NMR (100 MHz, DMSO): δ 168.97, 135.03, 130.17, 129.02, 128.67, 124.12.

Intermediate: Naphthalene-2,3-dicarboxamide

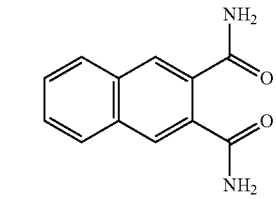 [SMILES: NC(=O)c1cc2ccccc2cc1C(N)=O]

Phthalimide above (190 mg, 0.97 mmole) in anhydrous DMF (2 ml) in sealed tube was cooled to −78° C. using dry ice/acetone bath. Then, NH$_3$ (g) was bubbled into the reaction mixture for 15 min, followed by gradual heating of the reaction mixture to room temperature and then heating at 50° C. for 8 hours (reaction done with protective shield inside the hood because of high pressure). Upon reaction completion, cool down to 0° C. to allow NH$_3$ (g) to be removed and the mixture was purified by a flash column chromatography using 0-20% MeOH/DCM afforded the desired product as a white solid (140 mg, 67%). $^1$H NMR (400 MHz, DMSO): δ 8.04 (s, 2H), 8.00-7.98 (m, 2H), 7.88 (br, 2H), 7.63-7.60 (m, 2H), 7.36 (br, 2H). $^{13}$C NMR (100 MHz, DMSO): δ 170.10, 134.01, 132.24, 128.03, 127.47, 127.16.

Intermediate: tert-Butyl ((4-methoxyphenyl) sulfonyl)-L-alaninate

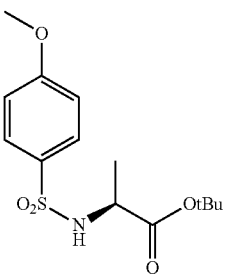 [SMILES: COc1ccc(S(=O)(=O)N[C@@H](C)C(=O)OC(C)(C)C)cc1]

The synthesis of sulfonamide intermediate was done using the general procedure (method A1) using L-alanine tert-butyl ester hydrochloride as the amine starting material to get intermediate (261 mg, 83% yield). $^1$H NMR (400 MHz, (DMSO)): δ 8.02 (d, 1H J=8.0 Hz), 7.69 (d, 2H J=8.0 Hz), 7.07 (d, 2H J=8.4 Hz), 3.80 (s, 3H), 3.66 (t, 1H J=7.2 Hz), 1.24 (s, 9H), 1.12 (d, 3H J=6.8 Hz). $^{13}$C NMR (100 MHz, DMSO): δ 170.74, 161.98, 132.77, 128.50, 114.02, 80.43, 55.44, 51.55, 27.18, 18.33.

Intermediate: Methyl ((4-methoxyphenyl)sulfonyl)-D-alaninate

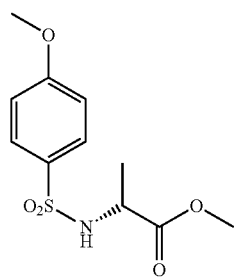

The synthesis of the sulfonamide intermediate was done using the general procedure (method A1) using D-alanine methyl ester hydrochloride as the amine starting material to get intermediate (246 mg, 91% yield). $^1$H NMR (400 MHz, (DMSO)): δ 7.75 (d, 2H J=8.8 Hz), 6.93 (d, 2H J=8.8 Hz), 5.38 (d, 1H J=8.8 Hz), 3.98-3.91 (m, 1H), 3.52 (s, 3H), 1.34 (d, 3H J=8.8 Hz). $^{13}$C NMR (100 MHz, DMSO): δ 172.66, 163.00, 131.39, 129.34, 114.18, 55.62, 52.55, 51.41, 19.67.

Intermediate: tert-Butyl ((4-methoxyphenyl)sulfonyl)-L-asparaginate

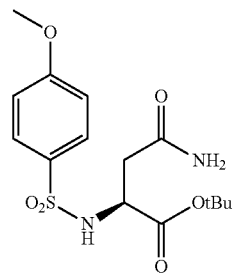 [SMILES: COc1ccc(S(=O)(=O)N[C@@H](CC(N)=O)C(=O)OC(C)(C)C)cc1]

The synthesis of the sulfonamide intermediate was done using the general procedure (method A1) using L-Alanine tert-butyl ester hydrochloride as the amine starting material to get intermediate (261 mg, 83% yield). $^1$H NMR (400 MHz, (DMSO)): δ 7.94 (d, 1H J=8.8 Hz), 7.71 (d, 2H J=8.8 Hz), 7.33 (br, 1H), 7.07 (d, 2H J=8.8 Hz), 6.88 (br, 1H), 4.04-3.98 (m, 1H), 3.81 (s, 3 H), 2.50-2.41 (m, 2H), 2.29-2.23 (m, 2H), 1.22 (s, 9H). $^{13}$C NMR (100 MHz, DMSO): δ 170.15, 169.36, 161.93, 132.76, 128.53, 113.92, 80.45, 55.42, 52.88, 27.09.

Intermediate: Di-tert-butyl 2,2'-((1,2-phenylenebis(methylene))bis(((4-methoxyphenyl)sulfonyl)azanediyl))(2S,2'S)-dipropionate

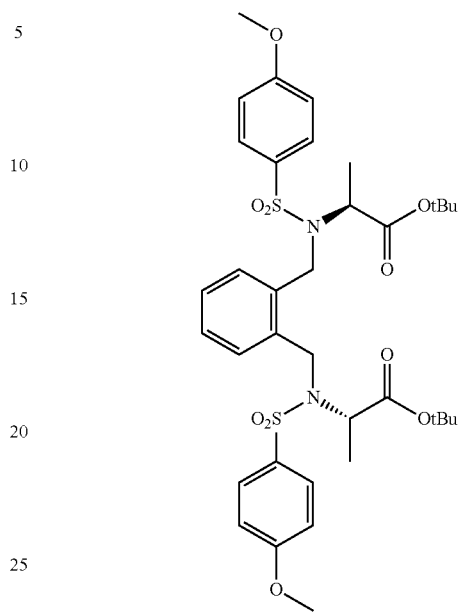

The synthesis of the alkylated sulfonamide intermediate was d using the general procedure (method B) to get intermediate (131 mg, 71% yield). $^1$H NMR (400 MHz, (CD$_3$)$_2$ CO): δ 7.79 (d, 4H J=9.0 Hz), 7.52-7.50 (m, 2H), 7.23-7.21 (m, 2H), 7.07 (d, 4H J=9.0 Hz), 4.70-4.58 (m, 4H), 4.44 (q, 2H J=7.2 Hz), 3.89 (s, 6H), 1.33 (s, 18H), 1.25 (d, 6H J=7.2 Hz). $^{13}$C NMR (100 MHz, (CD$_3$)$_2$ CO): δ 206.29, 170.98, 163.98, 136.56, 133.08, 130.57, 129.14, 127.74, 115.11, 82.06, 57.05, 56.17, 46.99, 16.90.

Intermediate: Dimethyl 2,2'-(1,2-phenylenebis(methylene))bis(((4-methoxyphenyl)sulfonyl)azanediyl))(2R,2'R)-dipropionate

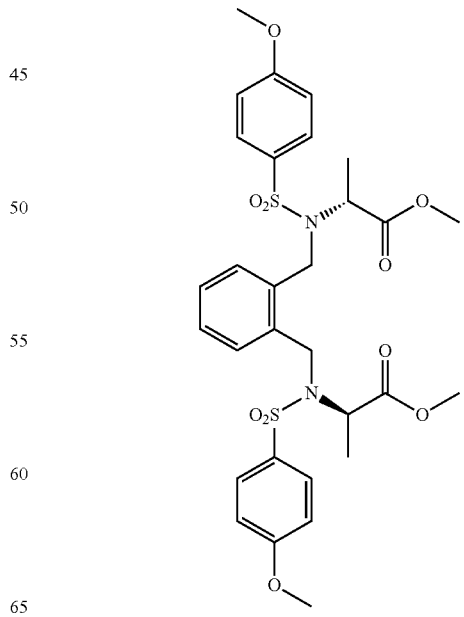

The synthesis of the alkylated sulfonamide intermediate was done using the general procedure (method B) to get intermediate (211 mg, 74% yield). $^1$H NMR (400 MHz, CDCl$_3$): δ 7.77 (d, 4H J=8.8 Hz), 7.42-7.39 (m, 2H), 7.21-7.19 (m, 2H), 6.96 (d, 4H J=8.8 Hz), 4.65-4.54 (m, 4H), 4.50 (q, 2H J=7.2 Hz), 3.85 (s, 6H), 3.39 (s, 6H), 1.17 (d, 6H J=7.2 Hz). $^{13}$C NMR (100 MHz, CDCl$_3$): δ 171.48, 163.06, 134.98, 131.44, 129.71, 129.05, 127.73, 114.26, 55.69, 55.05, 52.22, 46.95, 15.40.

Intermediate: tert-Butyl N2-(2-(((N—((R)-4-amino-1-(tert-butoxy)-1,4-dioxobutan-2-yl)-4-di-tert-butyl 2,2'-(1,2-phenylenebis(methylene))bis(((4-methoxyphenyl)sulfonyl)azanediyl)) (2S,2'S)-bis(4-amino-4-oxobutanoate)

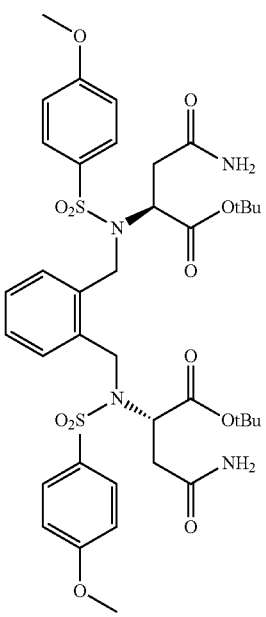 [SMILES: COc1ccc(S(=O)(=O)N(Cc2ccccc2CN([C@@H](CC(N)=O)C(=O)OC(C)(C)C)S(=O)(=O)c2ccc(OC)cc2)[C@@H](CC(N)=O)C(=O)OC(C)(C)C)cc1]

The synthesis of the alkylated sulfonamide intermediate was do using the general procedure (method B) to get intermediate as oily product (131 mg, 71% yield). $^1$H NMR (400 MHz, (CD$_3$CN): δ 7.79 (d, 4H J=8.8 Hz), 7.37-7.35 (m, 2H), 7.23-7.21 (m, 2H), 7.03 (d, 4H J=8.8 Hz), 6.08 (br, 2H), 5.63 (br, 2H), 4.60-4.57 (m, 4H), 4.45 (s, 4H), 3.85 (s, 6H), 2.78-2.72 (m, 2H), 2.31-2.27 (m, 2H), 1.28 (s, 18H). $^{13}$C NMR (100 MHz, (CD$_3$CN): δ 172.28, 169.64, 163.96, 135.62, 132.25, 130.55, 129.52, 128.20, 118.04, 115.10, 82.63, 58.18, 56.32, 48.09, 36.66, 27.83.

Example LH945: (2S,2'S)-2,2'-(1,2-Phenylenebis(methylene))bis(((4-methoxyphenyl)sulfonyl)azanediyl)) dipropionic Acid

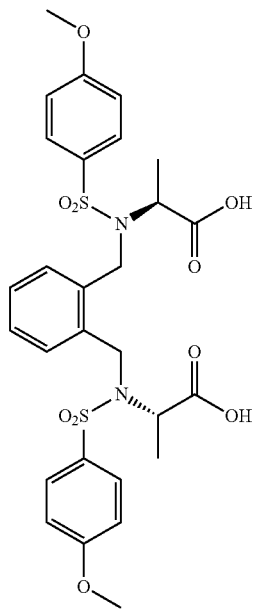 [SMILES: COc1ccc(S(=O)(=O)N(Cc2ccccc2CN([C@@H](C)C(=O)O)S(=O)(=O)c2ccc(OC)cc2)[C@@H](C)C(=O)O)cc1]

The synthesis of diacid final compound was done using the general procedure (method C2) to get compound as a white solid (23 mg, 74% yield). $^1$H NMR (400 MHz, (CD$_3$)$_2$CO): δ 7.82 (d, 4H J=9.0 Hz), 7.53-7.51 (m, 2H), 7.23-7.21 (m, 2H), 7.05 (d, 4H J=9.0 Hz), 4.61 (s, 4H), 4.52 (q, 4H J=7.2 Hz), 3.89 (s, 6H), 1.31 (d, 6H J=7.2 Hz). $^{13}$C NMR (100 MHz, (CD$_3$)$_2$ CO): δ 206.25, 172.47, 163.73, 136.12, 132.65, 130.42, 129.20, 127.65, 114.77, 55.91, 55.87, 47.10, 16.26. HRMS (ESI) Calcd for C$_{28}$H$_{32}$N$_2$O$_{10}$S$_2$ (M+H)$^+$ 621.1571, found 621.1567.

Example LH967: (2R,2'R)-2,2'-(1,2-Phenylenebis(methylene))bis(((4-methoxyphenyl)sulfonyl)azanediyl)) dipropionic Acid

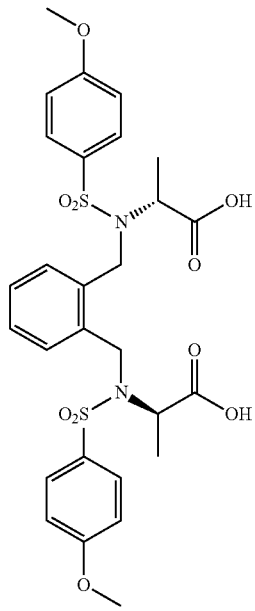 [SMILES: COc1ccc(S(=O)(=O)N(Cc2ccccc2CN([C@H](C)C(=O)O)S(=O)(=O)c2ccc(OC)cc2)[C@H](C)C(=O)O)cc1]

The synthesis of diacid final compound was done using the general procedure (method C1) to get compound as a white solid (31 mg, 79% yield). ¹H NMR (400 MHz, CD₃CN): δ 7.76-7.73 (m, 4H), 7.41-7.38 (m, 2H), 7.22-7.19 (m, 2H), 7.02-6.99 (m, 4H), 4.59-4.39 (m, 6H), 3.85 (s, 6H), 1.22 (d, 6H J=7.2 Hz). ¹³C NMR (100 MHz, CD₃CN): δ. 172.59, 163.86, 135.91, 132.08, 130.40, 129.25, 127.94, 114.91, 56.24, 55.92, 47.44, 15.88. HRMS (ESI) Calcd for C₂₈H₃₂N₂O₁₀S₂ (M+H)⁺ 621.1571, found 621.1577.

Example LH968: (2S,2'S)-2,2'-((1,2-Phenylenebis (methylene))bis(((4-methoxyphenyl)sulfonyl) azanediyl)) bis(4-amino-4-oxobutanoic Acid)

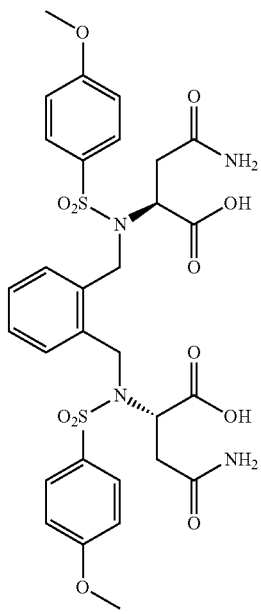 [SMILES: COc1ccc(S(=O)(=O)N(Cc2ccccc2CN([C@@H](CC(N)=O)C(=O)O)S(=O)(=O)c2ccc(OC)cc2)[C@@H](CC(N)=O)C(=O)O)cc1]

The synthesis of diacid final compound was done using the general procedure (method C2) to get compound as a white solid (33 mg, 77% yield). ¹H NMR (400 MHz, DMSO): δ 7.77 (d, 4H J=8.4 Hz), 7.30-7.28 (m, 4H), 7.17-7.14 (m, 2H), 7.06 (d, 4H J=8.8 Hz), 6.85 (br, 2H), 4.54-4.51 (m, 2H), 4.48-4.24 (m, 4 H), 3.84 (s, 4H), 2.80-2.73 (m, 2H), 2.21-2.16 (m, 2H). ¹³C NMR (100 MHz, DMSO): δ 171.09, 170.53, 162.53, 134.37, 130.86, 129.61, 128.49, 127.14, 114.21, 56.05, 55.62, 46.95, 35.07. HRMS (ESI) Calcd for C₃₀H₃₄N₄O₁₂S₂ (M+H)⁺ 707.1687, found 707.1663.

Intermediate: tert-Butyl ((4-methoxyphenyl)sulfonyl)-L-isoleucinate

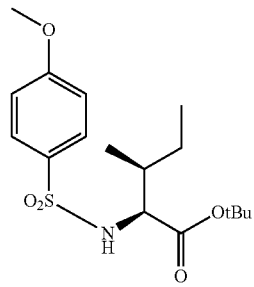 [SMILES: CC[C@H](C)[C@H](NS(=O)(=O)c1ccc(OC)cc1)C(=O)OC(C)(C)C]

Prepared as described in the general procedure for synthesis of sulfonamides (method A1) to get the title compound; using L-isoleucine tert-butyl ester hydrochloride as the amine starting material to get intermediate white solid (329 mg, 92% yield). ¹H NMR (400 MHz, (CD₃)₂CO): δ 7.76 (d, 2H, J=8.8 Hz), 7.07 (d, 2H, J=8.8 Hz), 6.43 (d, 1H, J=9.8 Hz), 3.87 (s, 3H), 3.65-3.61 (dd, 1H, J=9.8 Hz, 5.8 Hz), 1.77-1.72 (m, 1H), 1.51-1.46 (m, 1H), 1.25 (s, 9H), 1.21-1.13 (m, 1H), 0.91 (d, 3H, J=6.8 Hz), 0.86 (t, 3H, J=7.4 Hz). ¹³C NMR (100 MHz, (CD₃)₂CO): δ 170.63, 163.56, 133.68, 129.91, 114.76, 81.82, 61.45, 55.90, 39.01, 27.74, 25.39, 15.66, 11.37.

Intermediate: Di-tert-butyl 2,2'-((1,2-phenylenebis (methylene))bis(((4-methoxyphenyl)sulfonyl) azanediyl)) (2S,2'S,3S,3'S)-bis(3-methylpentanoate)

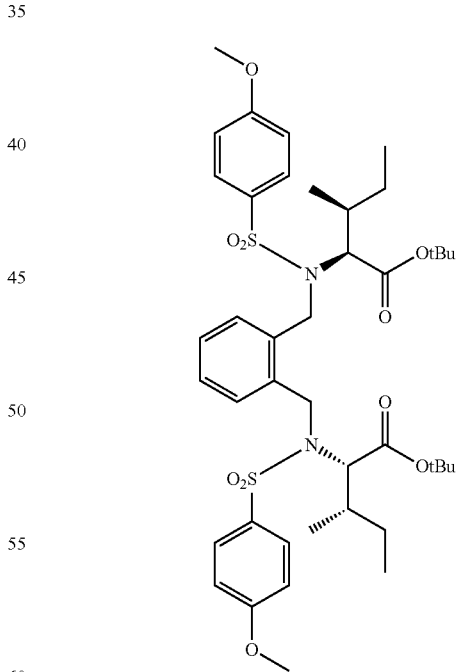

Prepared as described in the general procedure for synthesis of alkylated sulfonamides (method B) to get the title compound as a white solid product; (129 mg, 79% yield). ¹H NMR (400 MHz, CDCl₃): δ 7.68 (d, 4H J=8.8 Hz), 7.44-7.42 (m, 2H), 7.02-6.99 (m, 2H), 6.85 (d, 4H J=8.8 Hz), 4.91-4.80 (m, 4H), 4.20 (d, 2H J=10.0 Hz), 3.83 (s, 6H), 1.71-1.67 (m, 2H), 1.59-1.52 (m, 2H), 1.29 (s, 18H), 1.05-0.97 (m, 2H), 0.81 (d, 6H, J=6.8), 0.61 (t, 6H, J=7.6).

Example LH946: (2S,2'S,3S,3'S)-2,2'-(1,2-Phenylenebis(methylene))bis(((4-methoxyphenyl)sulfonyl)azanediyl))bis(3-methylpentanoic Acid)

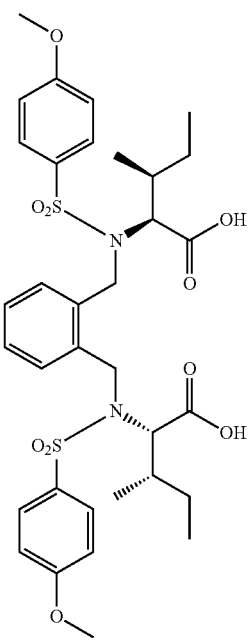 [SMILES: CC[C@H](C)[C@@H](C(=O)O)N(Cc1ccccc1CN([C@H](C(=O)O)[C@@H](C)CC)S(=O)(=O)c1ccc(OC)cc1)S(=O)(=O)c1ccc(OC)cc1]

Prepared as described in the general procedure for hydrolysis of ethyl ester to get di-acidic compounds (Method C1) (basic hydrolysis) to get the title compound as a white solid; (32 mg, 72% yield). $^1$H NMR (400 MHz, (CD$_3$)$_2$ CO): δ 7.74 (d, 4H J=8.8 Hz), 7.56-7.53 (m, 2H), 7.14-7.12 (m, 2H), 6.98 (d, 4H J=8.8 Hz), 4.90 (d, 2H J=16.8 Hz), 4.74 (d, 2H J=16.8 Hz), 4.22 (d, 2H J=10.0 Hz), 3.87 (s, 6H), 1.65-1.58 (m, 4H), 0.96-0.88 (m, 2H), 0.82 (d, 6H, J=6.8), 0.57 (t, 6H, J=7.6). $^{13}$C NMR (100 MHz, (CD$_3$)$_2$ CO): δ 171.92, 163.86, 136.41, 132.87, 130.57, 129.51, 127.32, 114.82, 65.47, 56.07, 45.78, 35.42, 26.88, 15.99, 11.03. HRMS (ESI) Calcd for C$_{34}$H$_{44}$N$_2$O$_{10}$S$_2$ (M+H)$^+$ 705.2510, found 705.2510.

Intermediate: tert-Butyl ((4-methoxyphenyl)sulfonyl)-L-leucinate

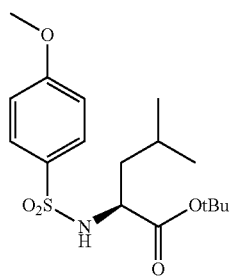 [SMILES: COc1ccc(S(=O)(=O)N[C@@H](CC(C)C)C(=O)OC(C)(C)C)cc1]

Prepared as described in the general procedure for synthesis of sulfonamides (method A1) to get the title compound as a white solid; using L-Leucine tert-butyl ester hydrochloride as the amine starting material to get intermediate (268 mg, 75% yield). $^1$H NMR (400 MHz, (CDCl$_3$)): δ 7.76 (d, 2H, J=8.8 Hz), 6.93 (d, 2H, J=8.8 Hz), 5.07 (d, 1H, J=10.0 Hz), 3.83 (s, 3H), 3.78-3.71 (m, 1H), 1.86-1.80 (m, 1H), 1.42 (t, 2H, J=7.2 Hz), 1.22 (s, 9H), 0.90 (d, 6H, J=6.6 Hz). $^{13}$C NMR (100 MHz, CDCl$_3$): δ171.57, 162.98, 131.53, 129.51, 114.16, 82.08, 55.61, 54.66, 42.66, 27.62, 24.34, 22.84, 21.46.

Intermediate: Di-tert-butyl 2,2'-((1,2-phenylenebis(methylene))bis(((4-methoxyphenyl)sulfonyl)azanediyl))(2S,2'S)-bis(4-methylpentanoate)

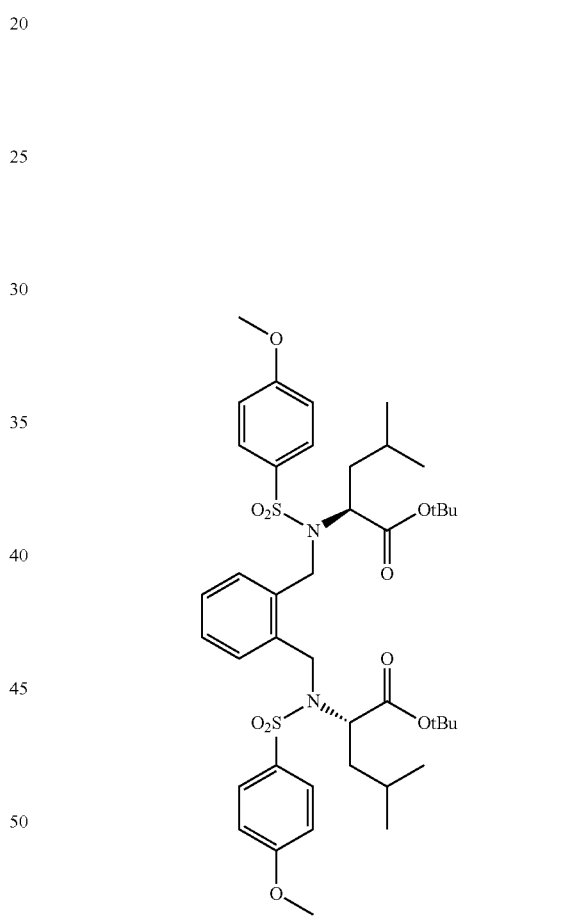

Prepared as described in the general procedure for synthesis of alkylated sulfonamides (method B) to get the title compound as oily product; (119 mg, 73% yield). $^1$H NMR (400 MHz, (CDCl$_3$)): δ 7.73 (d, 4H, J=8.8 Hz), 7.49-7.47 (m, 2H), 7.16-7.13 (m, 2H), 6.90 (d, 2H, J=8.8 Hz), 4.73-4.63 (m, 4H), 4.42 (t, 2H, J=6.4 Hz), 3.84 (s, 6H), 1.60-1.32 (m, 6H), 1.30 (s, 18H), 0.86 (d, 6H, J=6.4 Hz), 0.68 (d, 6H, J=6.8 Hz). $^{13}$C NMR (100 MHz, CDCl$_3$): δ 170.31, 162.67, 134.94, 132.07, 129.61, 129.45, 128.25, 126.87, 113.95, 81.54, 58.88, 55.48, 45.58, 45.58, 39.62, 27.74, 27.62, 24.99, 22.05.

Example LH947: (2S,2'S)-2,2'-(1,2-Phenylenebis(methylene))bis(((4-methoxyphenyl)sulfonyl)azanediyl))bis(4-methylpentanoic Acid)

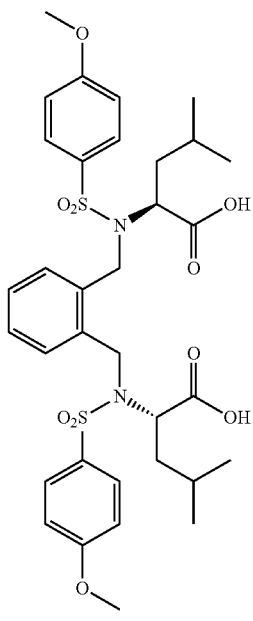 [SMILES: COc1ccc(S(=O)(=O)N(Cc2ccccc2CN([C@@H](CC(C)C)C(=O)O)S(=O)(=O)c2ccc(OC)cc2)[C@@H](CC(C)C)C(=O)O)cc1]

Prepared as described in the general procedure for hydrolysis of ethyl ester to get di-acidic compounds (Method C1) (basic hydrolysis) to get the title compound as a white solid; (15 mg, 72% yield). $^1$H NMR (400 MHz, (CD$_3$)$_2$CO): δ 7.86 (d, 4H, J=8.8 Hz), 7.67-7.64 (m, 2H), 7.32-7.29 (m, 2H), 7.11 (d, 2H, J=8.8 Hz), 4.79-4.61 (m, 4H), 4.62-4.59 (m, 2H), 3.96 (s, 6H), 1.76-1.60 (m, 4H), 1.52-1.45 (m, 2H), 0.95 (d, 6H, J=6.4 Hz), 0.75 (d, 6H, J=6.4 Hz). $^{13}$C NMR (100 MHz, (CD$_3$)$_2$CO): δ 172.58, 163.94, 136.56, 132.71, 130.61, 129.39, 127.64, 114.95, 58.92, 56.13, 46.70, 40.22, 25.65, 22.62, 22.24. HRMS (ESI) Calcd for C$_{34}$H$_{44}$N$_2$O$_{10}$S$_2$ (M+H)$^+$ 705.2510, found 705.2505.

Intermediate: Methyl ((4-methoxyphenyl)sulfonyl)-D-phenylalaninate

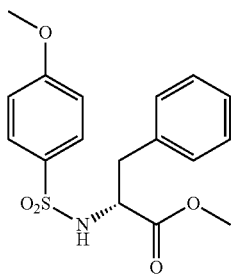

Prepared as described in the general procedure for synthesis of sulfonamides (method A1) to get the title compound as a white solid; using D-Phenylalanine methyl ester hydrochloride as the amine starting material to get intermediate (298 mg, 85% yield). $^1$H NMR (400 MHz, (DMSO)): δ 8.33 (d, 1H J=8.8), 7.53 (d, 2H J=8.8 Hz), 7.24-7.16 (m, 3H), 7.11-7.09 (m, 2H), 6.98 (d, 2H J=8.8 Hz), 3.94-3.88 (m, 1H), 3.81 (s, 3H), 3.34 (s, 3H), 2.92-2.87 (m, 1H), 2.78-2.74 (m, 1H). $^{13}$C NMR (100 MHz, DMSO): δ 171.21, 162.04, 136.27, 132.33, 126.66, 114.03, 57.31, 57.31, 55.60, 51.72, 37.70.

Intermediate: Dimethyl 2,2'-((1,2-phenylenebis(methylene))bis(((4-methoxyphenyl)sulfonyl)azanediyl))(2R,2'R)-bis(3-phenylpropanoate)

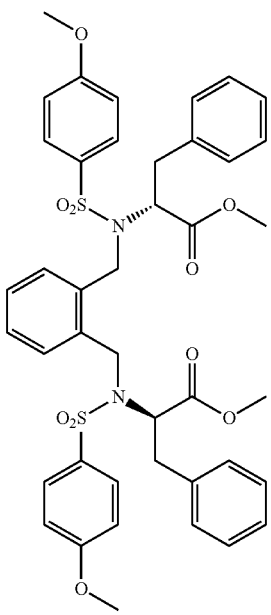 [SMILES: COC(=O)[C@@H](Cc1ccccc1)N(Cc1ccccc1CN([C@H](Cc1ccccc1)C(=O)OC)S(=O)(=O)c1ccc(OC)cc1)S(=O)(=O)c1ccc(OC)cc1]

Prepared as described in the general procedure for synthesis of alkylated sulfonamides (method B) to get the title compound as oily product; (109 mg, 68% yield). $^1$H NMR (400 MHz, CDCl$_3$): δ 7.89 (d, 4H J=8.8 Hz), 7.38-7.23 (m, 10H), 7.13-7.09 (m, 4H), 7.03 (d, 4H J=8.8 Hz), 4.78-4.60 (m, 6H), 3.89 (s, 6H), 3.78 (s, 6H), 3.16-3.09 (m, 2H), 2.82-2.77 (m, 2H). $^{13}$C NMR (100 MHz, CDCl$_3$): δ 170.27, 163.14, 137.06, 134.75, 131.50, 129.96, 129.57, 129.44, 129.40, 128.48, 127.79, 126.81, 114.25, 60.91, 55.71, 52.06, 47.27, 36.50.

Example LH887: (2R,2'R)-2,2'-((1,2-Phenylenebis(methylene))bis(((4-methoxyphenyl)sulfonyl)azanediyl))bis(3-phenylpropanoic Acid)

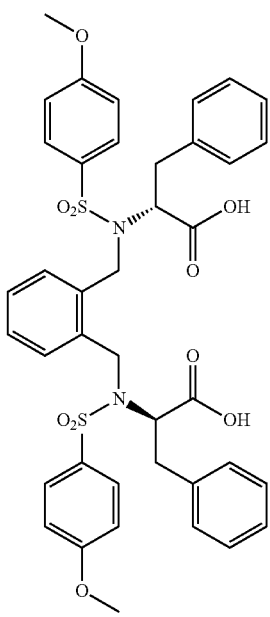 [SMILES: COc1ccc(S(=O)(=O)N(Cc2ccccc2CN([C@H](Cc2ccccc2)C(=O)O)S(=O)(=O)c2ccc(OC)cc2)[C@H](Cc2ccccc2)C(=O)O)cc1]

Prepared as described in the general procedure for hydrolysis of ethyl ester to get di-acidic compounds (Method C1) (basic hydrolysis) to get the title compound as a white solid; (19 mg, 78% yield). $^1$H NMR (400 MHz, DMSO): δ 7.84 (m, 4H), 7.25-7.21 (m, 9H), 7.13-7.06 (m, 9H), 4.62-4.44 (m, 6H), 3.83-3.79 (m, 6H), 3.09-3.01 (m, 2H), 2.69-2.59 (m, 2H). $^{13}$C NMR (100 MHz, DMSO): δ 170.75, 162.67, 137.13, 134.70, 130.96, 129.65, 129.59, 129.16, 129.02, 128.95, 128.46, 128.23, 128.12, 127.96, 126.67, 126.48, 114.35, 114.31, 113.95, 60.75, 55.65, 55.62, 55.54, 45.89, 45.75, 36.01, 35.67. HRMS (ESI) Calcd for $C_{40}H_{40}N_2O_{10}S_2$ (M+H)$^+$ 773.2197, found 773.2190.

Intermediate: N,N'-(1,2-Phenylenebis(methylene))dibenzenesulfonamide

Prepared as described in the general procedure for synthesis of sulfonamides (method A1) to get the title compound as a white solid; (305 mg, 73% yield). $^1$H NMR (400 MHz, (MeOH-d4)): δ 7.85-7.82 (m, 4H), 7.85-7.82 (m, 4H), 7.61-7.52 (m, 6H), 7.20-7.16 (m, 4H), 4.08 (s, 4H), $^{13}$C NMR (100 MHz, MeOH-d4): δ 141.75, 136.45, 133.61, 130.42, 130.22, 128.92, 128.02, 45.16.

Intermediate: Diethyl 2,2'-(1,2-phenylenebis(methylene))bis((phenylsulfonyl)azanediyl))diacetate

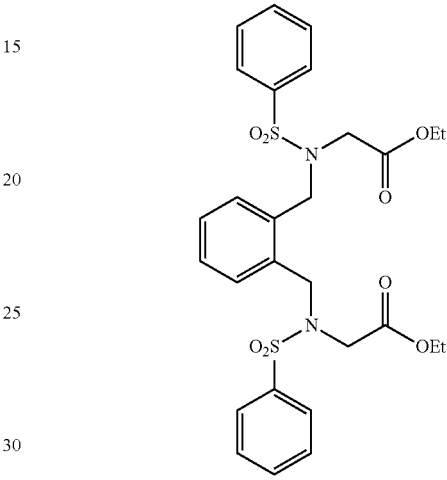

Prepared as described in the general procedure for synthesis of alkylated sulfonamides (method B) to get the title compound as oily product; (98 mg, 83% yield). $^1$H NMR (400 MHz, (CDCl$_3$)): δ 7.79 (d, 4H J=7.2 Hz), 7.53-7.49 (m, 2H), 7.47-7.43 (m, 4H), 7.27-7.25 (m, 2H), 7.21-7.18 (m, 2H), 4.54 (s, 4H), 3.85 (t, 4H J=7.2 Hz), 3.79 (s, 4H), 0.99 (t, 6H J=7.2 Hz). $^{13}$C NMR (100 MHz, CDCl$_3$): δ 168.38, 139.21, 133.87, 132.80, 129.69, 129.03, 128.49, 127.47, 61.24, 49.13, 47.67, 29.68, 22.67, 13.87.

Example LH786: 2,2'-((1,2-Phenylenebis(methylene))bis((phenylsulfonyl)azanediyl))diacetic Acid

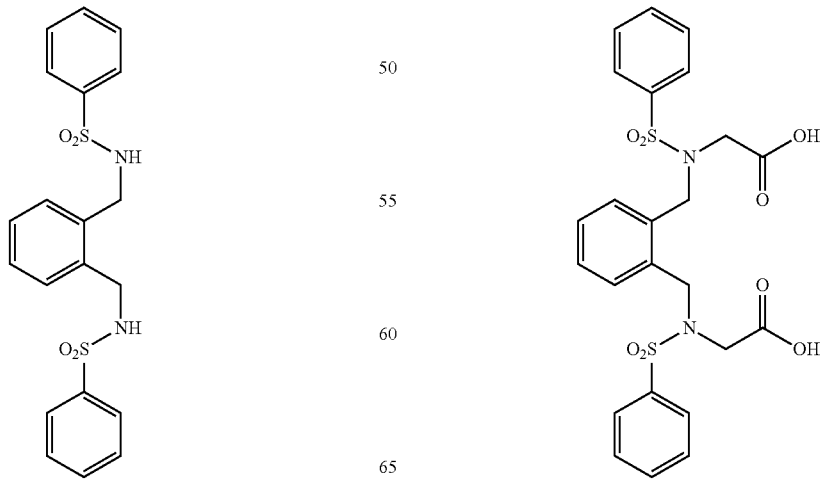

Prepared as described in the general procedure for hydrolysis of ethyl ester to get di-acidic compounds (Method C1) (basic hydrolysis) to get the title compound as a white solid; (19 mg, 72% yield). $^1$H NMR (400 MHz, (MeOH-d$_4$)): δ 7.86-7.84 (m, 4H), 7.63-7.53 (m, 6H), 7.30-7.22 (m, 4H), 4.58 (s, 4H), 3.84 (s, 4H). $^{13}$C NMR (100 MHz, MeOH-d$_4$): δ 171.89, 140.63, 135.61, 134.04, 130.94, 130.25, 129.29, 128.62, 50.63, 48.83. HRMS (ESI) Calcd for C$_{24}$H$_{24}$N$_2$O$_8$S$_2$ (M+H)$^+$ 533.1047, found 533.1031.

Example LH813: 2,2'-((1,2-Phenylenebis(methylene))bis(((4-hydroxyphenyl) sulfonyl) azanediyl)) diacetic Acid

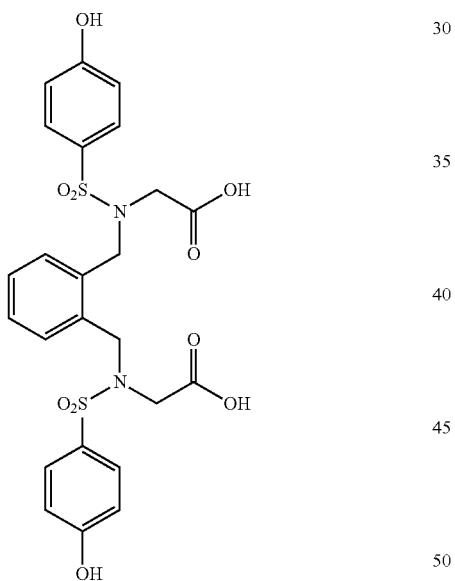

To a suspension of compound LH769 (65 mg, 0.1 mmole) dry DCM (1 ml), 1 ml solution of BBr3 (1M, in DCM) was added and reaction stirred at room temperature overnight. Then, reaction quenched with water and diluted with DCM and washed with water, brine, and dried over sodium sulfate. The crude product purified on an ISCO silica gel (0-20% MeOH/DCM). The total amount of pure product was (6.8 mg, 12% yield). $^1$H NMR (400 MHz, (DMSO)): δ 7.69 (d, 4H J=8.8 Hz), 7.23 (s, 4H), 7.86 (d, 4H J=8.8 Hz), 4.47 (s, 4H), 3.52 (s, 4H). $^{13}$C NMR (100 MHz, DMSO): δ 169.97, 161.69, 134.56, 129.59, 128.80, 128.65, 127.57, 115.75, 49.14, 48.35. HRMS (ESI) Calcd for C$_{24}$H$_{24}$N$_2$O$_{10}$S$_2$ (M+H)$^+$ 565.0945, found 565.0936.

Intermediate: N,N'-(1,2-Phenylenebis(methylene)) bis(4-nitrobenzenesulfonamide)

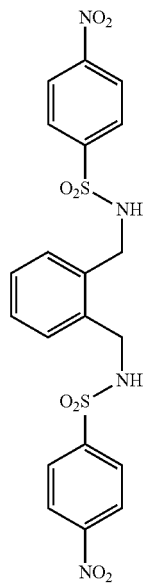 [SMILES: O=[N+]([O-])c1ccc(S(=O)(=O)NCc2ccccc2CNS(=O)(=O)c2ccc([N+](=O)[O-])cc2)cc1]

Prepared as described in the general procedure for synthesis of sulfonamides (method A1) to get the title compound as a yellow solid; (324 mg, 64% yield). $^1$H NMR (400 MHz, (DMSO)): δ 8.41 (t, 2H J=6.0 Hz), 8.37 (d, 2H J=8.4 Hz), 8.00 (d, 2H J=8.4 Hz), 7.17 (s, 4H), 4.06 (d, 4H J=6.0 Hz), $^{13}$C NMR (100 MHz, DMSO): δ 149.42, 146.11, 134.74, 128.68, 128.00, 127.45, 124.44, 43.23.

Intermediate: Diethyl 2,2'-((1,2-phenylenebis(methylene))bis(((4-nitrophenyl) sulfonyl) azanediyl)) diacetate

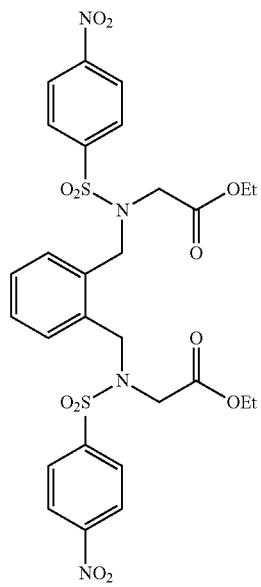 [SMILES: CCOC(=O)CN(Cc1ccccc1CN(CC(=O)OCC)S(=O)(=O)c1ccc([N+](=O)[O-])cc1)S(=O)(=O)c1ccc([N+](=O)[O-])cc1]

Prepared as described in the general procedure for synthesis of alkylated sulfonamides (method B) to get the title compound as oily product; (103 mg, 76% yield). $^1$H NMR (400 MHz, (CDCl$_3$)): δ 8.36 (d, 4H J=8.8 Hz), 8.05 (d, 4H J=8.8 Hz), 7.34-7.29 (m, 4H), 4.67 (s, 4H), 3.98 (q, 4H J=7.2 Hz), 3.95 (s, 4H), 1.12 (t, 6H J=7.2 Hz). $^{13}$C NMR (100 MHz, CDCl$_3$): δ 168.19, 150.34, 145.02, 133.36, 130.03, 129.15, 128.95, 124.37, 61.74, 49.16, 47.54, 29.85, 14.12.

Example LH790: 2,2'-((1,2-Phenylenebis(methylene)) bis (((4-nitrophenyl)sulfonyl) azanediyl)) diacetic Acid

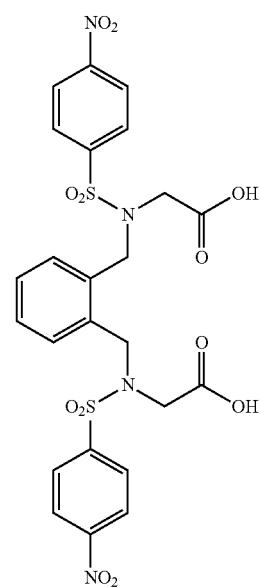 [SMILES: O=C(O)CN(Cc1ccccc1CN(CC(=O)O)S(=O)(=O)c1ccc([N+](=O)[O-])cc1)S(=O)(=O)c1ccc([N+](=O)[O-])cc1]

Prepared as described in the general procedure for hydrolysis of ethyl ester to get di-acidic compounds (Method C1) (basic hydrolysis) to get the title compound as a yellow solid; (23 mg, 79% yield). $^1$H NMR (400 MHz, (DMSO)): δ 8.35 (d, 4H J=8.8 Hz), 8.08 (d, 4H J=8.8 Hz), 7.26 (s, 4H), 4.52 (s, 4H), 3.79 (s, 4H). $^{13}$C NMR (100 MHz, DMSO): δ 169.56, 149.76, 144.53, 133.80, 128.27, 128.58, 127.88, 124.39, 49.05, 48.33. HRMS (ESI) Calcd for C$_{24}$H$_{22}$N$_4$O$_{12}$S$_2$ (M+H)$^+$ 623.0748, found 623.0743

Example LH792: 2,2'-(1,2-Phenylenebis(methylene))bis(((4-aminophenyl)sulfonyl)azanediyl))diacetic Acid

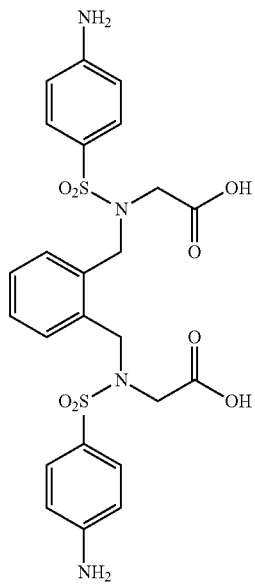

A solution of compound LH790 (13 mg, 0.02 mmole) in EtOH 5 ml was degassed with N$_2$ three times. A catalytic amount of 10% Pd/C (5 mg) was added to the solution and the reaction was purged with H$_2$. The reaction was stirred under H$_2$ for 3 h and then filtered through a celite bed to remove the catalyst. The filtrate was concentrated under vacuum to give an off-white solid (11 mg, 94% yield). $^1$H NMR (400 MHz, (MeOH-d$_4$)): δ 7.52 (d, 4H J=8.8 Hz), 7.25-7.19 (m, 4H), 6.56 (d, 4H J=8.8 Hz), 5.86 (s, 4H), 4.47 (s, 4H), 3.38 (s, 4H). $^{13}$C NMR (100 MHz, MeOH-d$_4$): δ 172.44, 154.38, 135.95, 130.85, 130.68, 128.96, 126.01, 114.51, 50.74. HRMS (ESI) Calcd for C$_{24}$H$_{26}$N$_4$O$_8$S$_2$ (M+H)$^+$ 563.1265, found 563.1254.

Intermediate: N,N'-(1,2-Phenylenebis(methylene)) bis(4-fluorobenzenesulfonamide)

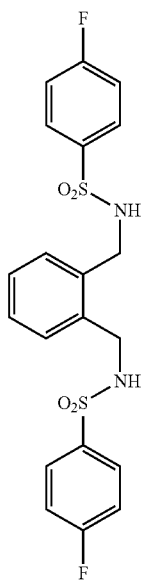 [SMILES: O=S(=O)(NCc1ccccc1CNS(=O)(=O)c1ccc(F)cc1)c1ccc(F)cc1]

Prepared as described in the general procedure for synthesis of sulfonamides (method A1) to get the title compound as a white solid; (321 mg, 71% yield). $^1$H NMR (400 MHz, (MeOH-d$_4$)): δ 7.89-7.85 (m, 4H), 7.28-7.24 (m, 4H), 7.21-7.16 (m, 4H), 4.09 (s, 4H). $^{13}$C NMR (100 MHz, MeOH-d$_4$): δ 167.60, 165.09, 138.02, 136.35, 131.02, 130.93, 130.43, 128.97, 117.30, 117.07, 45.19. $^{19}$F NMR (377 MHz, MeOH-d$_4$): δ−108.51 (s, 2F).

Intermediate: Diethyl 2,2'-(1,2-phenylenebis(methylene))bis(((4-fluorophenyl)sulfonyl)azanediyl))diacetate

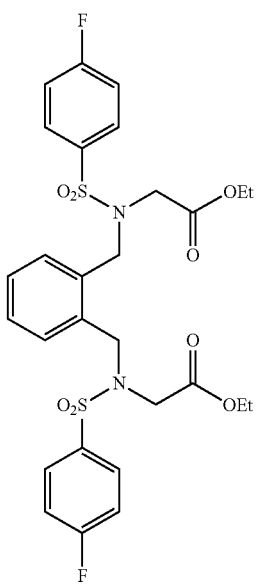 [SMILES: CCOC(=O)CN(Cc1ccccc1CN(CC(=O)OCC)S(=O)(=O)c1ccc(F)cc1)S(=O)(=O)c1ccc(F)cc1]

Prepared as described in the general procedure for synthesis of alkylated sulfonamides (method B) to get the title compound as oily product; (43 mg, 69% yield). $^1$H NMR (400 MHz, (CDCl$_3$)): δ 7.90-7.87 (m, 4H), 7.32-7.26 (m, 4H), 7.22-7.18 (m, 4H), 4.60 (s, 4H), 3.96 (q, J=7.2 Hz, 4H), 3.88 (s, 4H), 1.12 (t, J=7.2 Hz, 6H). $^{13}$C NMR (100 MHz, CDCl$_3$): δ 168.45, 166.60, 164.07, 135.34, 133.77, 130.41, 130.32, 129.81, 128.75, 116.46, 116.23, 61.45, 49.13, 47.60, 14.04.

Example LH811: 2,2'-(1,2-Phenylenebis(methylene))bis(((4-fluorophenyl)sulfonyl)azanediyl))diacetic Acid (46e)

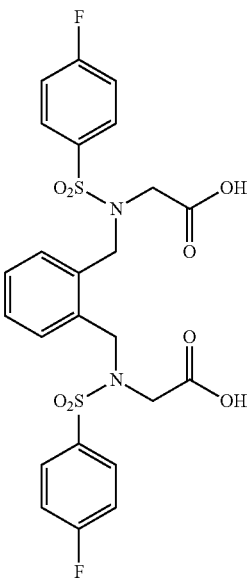 [SMILES: O=C(O)CN(Cc1ccccc1CN(CC(=O)O)S(=O)(=O)c1ccc(F)cc1)S(=O)(=O)c1ccc(F)cc1]

Prepared as described in the general procedure for hydrolysis of ethyl ester to get di-acidic compounds (Method C1) (basic hydrolysis) to get the title compound as a white solid; (11 mg, 76% yield). $^1$H NMR (400 MHz, (MeOH-d$_4$)): δ 7.93-7.89 (m, 4H), 7.33-7.25 (m, 8H), 4.59 (s, 4H), 3.87 (s, 4H). $^{13}$C NMR (100 MHz, MeOH-d$_4$): δ 171.80, 167.93, 165.48, 136.95, 135.54, 131.69, 131.60, 130.89, 129.37, 117.31, 117.08, 50.47, 48.38. $^{19}$F NMR (377 MHz, MeOH-d$_4$): δ 107.92 (s, 2F). HRMS (ESI) Calcd for C$_{24}$H$_{22}$F$_2$N$_2$O$_8$S$_2$ (M+H)$^+$ 569.0858, found 569.0851.

Intermediate: N,N'-(1,2-Phenylenebis(methylene))bis(3-fluorobenzenesulfonamide)

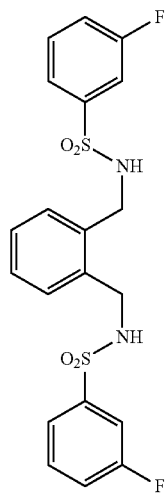 [SMILES: O=S(=O)(NCc1ccccc1CNS(=O)(=O)c1cccc(F)c1)c1cccc(F)c1]

Prepared as described in the general procedure for synthesis of sulfonamides (method A1) to get the title compound as a white solid; (335 mg, 74% yield). n¹H NMR (400 MHz, (MeOH-d₄)): δ 7.66-7.64 (m, 2H), 7.59-7.51 (m, 4H), 7.38-7.33 (m, 2H), 7.21-7.16 (m, 4H), 4.11 (s, 4H). $^{13}$C NMR (100 MHz, MeOH-d₄): δ 165.08, 162.60, 144.08, 144.01, 136.30, 132.37, 132.29, 130.46, 129.01, 124.01, 123.98, 120.65, 120.44, 115.18, 114.93, 45.13. $^{19}$F NMR (377 MHz, MeOH-d₄): δ 112.30 (s, 2F).

Intermediate: Diethyl 2,2'-(1,2-phenylenebis(methylene))bis(((2,6-difluorophenyl) sulfonyl) azanediyl)) diacetate

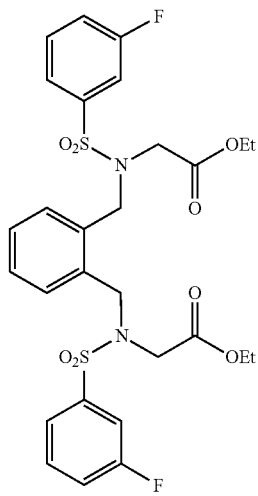 [SMILES: CCOC(=O)CN(Cc1ccccc1CN(CC(=O)OCC)S(=O)(=O)c1cccc(F)c1)S(=O)(=O)c1cccc(F)c1]

Prepared as described in the general procedure for synthesis of alkylated sulfonamides (method B) to get the title compound as oily product; (101 mg, 76% yield). $^1$H NMR (400 MHz, (CDCl₃)): δ 7.67-7.65 (m, 2H), 7.56-7.49 (m, 4H), 7.33-7.27 (m, 6H), 4.62 (s, 4H), 3.95 (q, 4H J=7.2 Hz), 3.89 (s, 4H), 1.09 (t, 6H J=7.2 Hz). $^{13}$C NMR (100 MHz, CDCl₃): δ 168.29, 163.70, 161.21, 141.26, 141.19, 133.66, 130.99, 130.91, 129.85, 128.79, 123.37, 123.34, 120.22, 120.01, 115.04, 114.79, 61.48, 49.11, 47.62, 13.98.

Example LH810: 2,2'-((1,2-Phenylenebis(methylene))bis(((3-fluorophenyl)sulfonyl)azanediyl))diacetic Acid

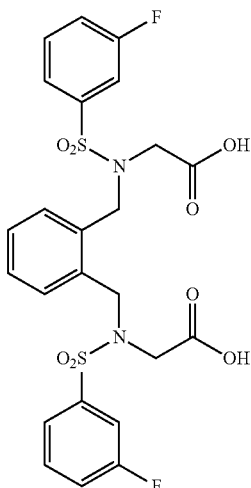 [SMILES: O=C(O)CN(Cc1ccccc1CN(CC(=O)O)S(=O)(=O)c1cccc(F)c1)S(=O)(=O)c1cccc(F)c1]

Prepared as described in the general procedure for hydrolysis of ethyl ester to get di-acidic compounds (Method C1) (basic hydrolysis) to get the title compound as a white solid; (13 mg, 70% yield). $^1$H NMR (400 MHz, (DMSO)): δ 12.68 (br, 2H), 7.68-7.60 (m, 6H), 7.56-7.53 (m, 2H), 7.23-7.22 (m, 4H), 4.51 (s, 4H), 3.98-3.86 (m, 4H). $^{13}$C NMR (100 MHz, DMSO): δ 169.71, 168.76, 163.01, 160.55, 141.07, 141.00, 134.04, 133.93, 131.66, 131.54, 131.46, 128.78, 128.56, 127.77, 127.67, 123.40, 120.36, 120.19, 119.98, 114.36, 114.12, 51.76, 49.17, 49.17, 49.09, 48.52, 48.36. HRMS (ESI) Calcd for $C_{24}H_{22}F_2N_2O_8S_2$ (M+H)$^+$ 569.0858, found 569.0852.

Intermediate: N,N'-(1,2-Phenylenebis(methylene)) bis(2,4-difluorobenzenesulfonamide)

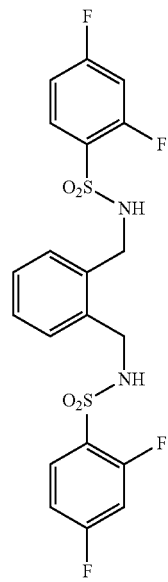 [SMILES: O=S(=O)(NCc1ccccc1CNS(=O)(=O)c1ccc(F)cc1F)c1ccc(F)cc1F]

Prepared as described in the general procedure for synthesis of sulfonamides (method A1) to get the title compound as a white solid; (371 mg, 76% yield). $^1$H NMR (400 MHz, (MeOH-d$_4$)): δ 7.82-7.79 (m, 2H), 7.19-7.01 (m, 8H), 4.18 (s, 4H). $^{13}$C NMR (100 MHz, MeOH-d$_4$): δ 168.38, 168.27, m 135.85, 165.73, 162.23, 162.10, 159.68, 159.55, 136.09, 133.19, 133.18, 133.18, 133.08, 130.51, 128.93, 126.69, 126.65, 126.55, 126.51, 112.87, 112.84, 112.65, 112.61, 106.69, 106.43, 106.17, 44.74. $^{19}$F NMR (377 MHz, MeOH-d$_4$): δ 103.97 (d, J=12 Hz, 1F), −106.31 (d, J=12 Hz, 1F).

Intermediate: Diethyl 2,2'-(1,2-phenylenebis(methylene))bis(((2,4-difluorophenyl) sulfonyl) azanediyl)) diacetate

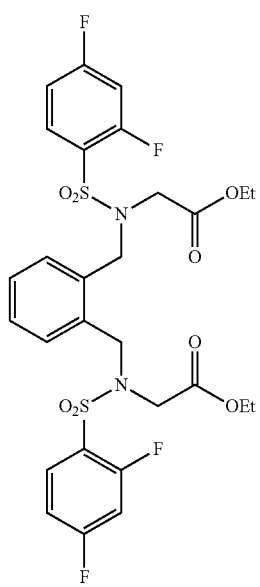 [SMILES: CCOC(=O)CN(Cc1ccccc1CN(CC(=O)OCC)S(=O)(=O)c1ccc(F)cc1F)S(=O)(=O)c1ccc(F)cc1F]

Prepared as described in the general procedure for synthesis of alkylated sulfonamides (method B) to get the title compound as oily product; (109 mg, 83% yield). $^1$H NMR (400 MHz, (CDCl$_3$)): δ 7.88-7.82 (m, 2H), 7.34-7.28 (m, 4H), 6.98-6.92 (m, 4H), 4.68 (s, 4H), 4.01 (q, J=7.2 Hz, 4H), 3.97 (s, 4H), 1.14 (t, J=7.2 Hz, 6H). $^{13}$C NMR (100 MHz, CDCl$_3$): δ 168.41, 167.25, 167.13, 164.69, 164.58, 161.47, 161.34, 158.91, 158.78, 133.77, 132.46, 132.36, 129.78, 128.78, 124.67, 124.53, 124.49, 111.81, 111.78, 111.59, 111.56, 106.01, 105.76, 105.50, 61.55, 48.82, 48.79, 47.59, 14.06. $^{19}$F NMR (377 MHz, CDCl$_3$): δ−100.67 (d, J=12 Hz, 1F), 102.01 (d, J=12 Hz, 1F).

Example LH807: 2,2'-((1,2-Phenylenebis(methylene))bis(((2,4-difluorophenyl) sulfonyl) azanediyl)) diacetic Acid

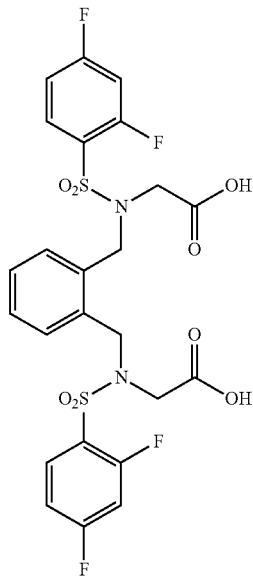 [SMILES: O=C(O)CN(Cc1ccccc1CN(CC(=O)O)S(=O)(=O)c1ccc(F)cc1F)S(=O)(=O)c1ccc(F)cc1F]

Prepared as described in the general procedure for hydrolysis of ethyl ester to get di-acidic compounds (Method C1) (basic hydrolysis) to get the title compound as a white solid; (16 mg, 72% yield). $^1$H NMR (400 MHz, (DMSO)): δ 7.85-7.79 (m, 2H), 7.29-7.24 (m, 4H), 7.19-7.14 (m, 2H), 7.06-7.02 (m, 2H), 4.65 (s, 4H), 3.95 (s, 4H). $^{13}$C NMR (100 MHz, DMSO): δ 171.79, 168.61, 168.49, 166.07, 165.95, 162.76, 162.61, 160.19, 160.05, 135.43, 133.57, 133.46, 130.87, 129.44, 129.35, 126.15, 126.11, 126.00, 125.97, 112.79, 112.76, 112.57, 112.53, 106.90, 106.63, 106.37, 65.77, 48.80. $^{19}$F NMR (377 MHz, CDCl$_3$): δ−103.55 (d, J=12 Hz, 1F), 103.74 (d, J=12 Hz, 1F). HRMS (ESI) Calcd for C$_{24}$H$_{20}$F$_4$N$_2$O$_8$S$_2$(M+PH)$^+$ 605.0670, found 605.0661.

Intermediate: N,N'-(1,2-Phenylenebis(methylene)) bis(3,4-difluorobenzenesulfonamide)

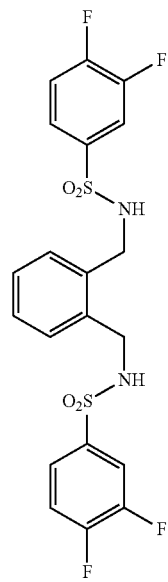 [SMILES: O=S(=O)(NCc1ccccc1CNS(=O)(=O)c1ccc(F)c(F)c1)c1ccc(F)c(F)c1]

Prepared as described in the general procedure for synthesis of sulfonamides (method A1) to get the title compound as a white solid; (386 mg, 79% yield). $^1$H NMR (400 MHz, (MeOH-d$_4$)): δ 7.72-7.65 (m, 4H), 7.47-7.41 (m, 2H), 7.22-7.18 (m, 4H), 4.12 (s, 4H). $^{13}$C NMR (100 MHz, MeOH-d$_4$): δ 155.42, 155.29, 152.89, 152.77, 152.62, 152.49, 150.12, 149.99, 139.12, 139.07, 139.03, 136.25, 130.51, 129.05, 125.65, 125.62, 125.58, 125.54, 119.40, 119.21, 117.91, 117.71, 45.16. $^{19}$F NMR (377 MHz, MeOH-d4): δ−133.69 (d, 2F J=2 Hz), 137.16 (d, 2F J=2 Hz).

Intermediate: Diethyl 2,2'-(1,2-phenylenebis(methylene))bis(((3,4-difluorophenyl) sulfonyl) azanediyl)) diacetate

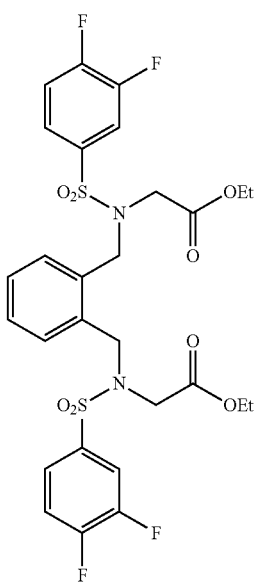 [SMILES: CCOC(=O)CN(Cc1ccccc1CN(CC(=O)OCC)S(=O)(=O)c1ccc(F)c(F)c1)S(=O)(=O)c1ccc(F)c(F)c1]

Prepared as described in the general procedure for synthesis of alkylated sulfonamides (method B) to get the title compound as oily product; (48 mg, 73% yield). $^1$H NMR (400 MHz, (CDCl$_3$)): δ 7.72-7.65 (m, 4H), 7.35-31 (m, 6H), 4.59 (s, 4H), 4.00 (q, J=6.8 Hz, 4H), 3.89 (s, 4H), 1.14 (t, J=6.8 Hz, 6H). $^{13}$C NMR (100 MHz, CDCl$_3$): δ 168.36, 136.13, 133.56, 129.96, 129.88, 128.96, 124.80, 118.33, 118.15, 117.71, 117.52, 117.38, 61.62, 61.49, 49.08, 48.95, 47.56, 14.08.

Example LH809: 2,2'-((1,2-Phenylenebis(methylene))bis(((3,4-difluorophenyl) sulfonyl) azanediyl)) diacetic Acid

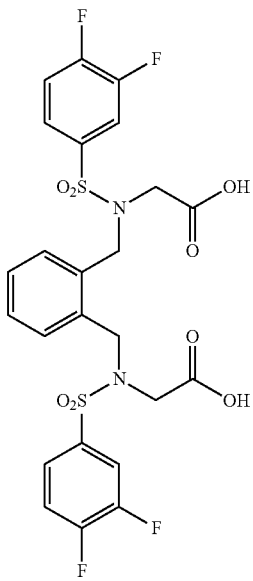 [SMILES: O=C(O)CN(Cc1ccccc1CN(CC(=O)O)S(=O)(=O)c1ccc(F)c(F)c1)S(=O)(=O)c1ccc(F)c(F)c1]

Prepared as described in the general procedure for hydrolysis of ethyl ester to get di-acidic compounds (Method C1) (basic hydrolysis) to get the title compound as a white solid; (9 mg, 65% yield). $^1$H NMR (400 MHz, (DMSO)): δ 7.67-59 (m, 6H), 7.55-7.51 (m, 2H), 7.23 (s, 4H), 4.49 (s, 4H), 3.98 (s, 1H), 3.84 (s, 3H). $^{13}$C NMR (100 MHz, DMSO): δ 169.60, 168.65, 162.98, 162.89, 160.51, 160.42, 141.07, 141.00, 140.64, 140.58, 140.48, 133.95, 133.89, 133.86, 133.79, 131.55, 131.47, 131.40, 131.32, 128.67, 128.46, 127.71, 127.65, 127.54, 123.29, 120.26, 120.03, 119.82, 114.26, 114.01, 51.65, 49.20, 49.06, 48.98, 48.85, 48.42, 48.32, 48.24. HRMS (ESI) Calcd for C$_{24}$H$_{20}$F$_4$N$_2$O$_8$S$_2$ (M+H)$^+$ 605.0670, found 605.0700.

Intermediate: N,N'-(1,2-Phenylenebis(methylene)) bis(2,6-difluorobenzenesulfonamide)

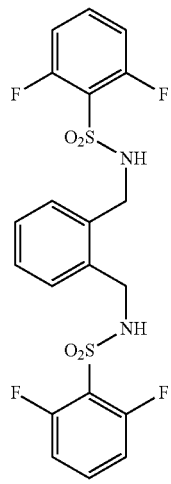 [SMILES: O=S(=O)(NCc1ccccc1CNS(=O)(=O)c1c(F)cccc1F)c1c(F)cccc1F]

Prepared as described in the general procedure for synthesis of sulfonamides (method A1) to get the title compound as a yellow solid; (317 mg, 66% yield). $^1$H NMR (400 MHz, (MeOH-d$_4$)): δ 7.55-7.51 (m, 2H), 7.21-7.19 (m, 2H), 7.09-6.99 (m, 6H), 4.31 (s, 4H). $^{13}$C NMR (100 MHz, MeOH-d4): δ 161.88 (d, J=16 Hz), 159.33 (d, J=20 Hz), 135.81 (dd, J=64 Hz, J=16 Hz), 130.70, 129.02, 119.85 (d, 64), 114.18, 113.94 (d, J=16 Hz). $^{19}$F NMR (377 MHz, MeOH-d4): δ-109.55 (s, 2F).

Intermediate: Diethyl 2,2'-(1,2-phenylenebis(methylene))bis(((2,6-difluorophenyl) sulfonyl) azanediyl)) diacetate

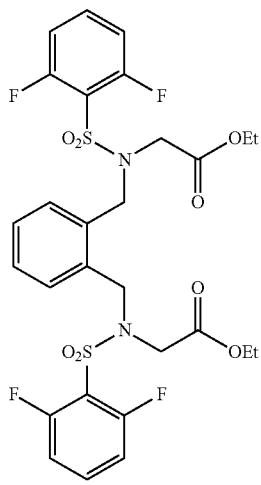 [SMILES: CCOC(=O)CN(Cc1ccccc1CN(CC(=O)OCC)S(=O)(=O)c1c(F)cccc1F)S(=O)(=O)c1c(F)cccc1F]

Prepared as described in the general procedure for synthesis of alkylated sulfonamides (method B) to get the title compound as oily product; (101 mg, 76% yield). $^1$H NMR (400 MHz, (CDCl$_3$)): δ 7.54-7.47 (m, 2H), 7.37-7.34 (m, 2H), 7.31-7.26 (m, 2H), 7.03-6.98 (m, 4H), 4.72 (s, 4H), 4.05 (s, 4H), 4.01 (q, J=6.8 Hz, 4H), 1.12 (t, J=6.8 Hz, 6H). $^{13}$C NMR (100 MHz, CDCl$_3$): δ 168.37, 161.21 (d, J=16 Hz), 158.63 (d, J=16 Hz), 134.60 (t, J=44 Hz), 133.63, 129.93, 128.84, 118.04, 113.15 (dd, J=96 Hz, J=20 Hz), 61.60, 48.66, 47.86, 14.03. $^{19}$F NMR (377 MHz, CDCl$_3$): δ)-105.15 (s, 2F).

Example LH806: 2,2'((1,2-Phenylenebis(methylene))bis(((2,6-difluorophenyl) sulfonyl) azanediyl)) diacetic Acid

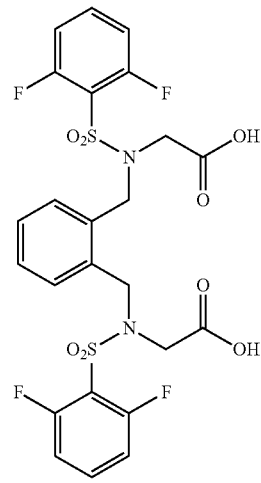 [SMILES: O=C(O)CN(Cc1ccccc1CN(CC(=O)O)S(=O)(=O)c1c(F)cccc1F)S(=O)(=O)c1c(F)cccc1F]

Prepared as described in the general procedure for hydrolysis of ethyl ester to get di-acidic compounds (Method C1) (basic hydrolysis) to get the title compound as an off-white solid; (16 mg, 72% yield). $^1$H NMR (400 MHz, (DMSO)): δ 7.75-7.67 (m, 2H), 7.27-7.23 (m, 8H), 4.63 (s, 4H), 3.97 (s, 4H). $^{13}$C NMR (100 MHz, (DMSO)): δ 169.96, 161.91, 159.34, 137.54, 137.45, 136.78, 136.67, 136.55, 133.62, 128.96, 128.76, 128.21, 128.04, 124.86, 124.78, 114.25, 114.02, 55.37. HRMS (ESI) Calcd for C$_{24}$H$_{20}$ F$_4$N$_2$O$_8$S$_2$ (M+H)$^+$ 605.0670, found 605.0669.

Intermediate: N,N'-(1,2-Phenylenebis(methylene)) bis(2,4-dimethoxybenzenesulfonamide)

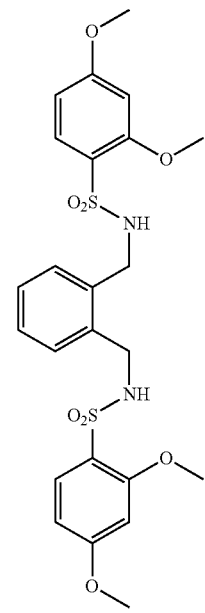 [SMILES: COc1ccc(S(=O)(=O)NCc2ccccc2CNS(=O)(=O)c2ccc(OC)cc2OC)c(OC)c1]

Prepared as described in the general procedure for synthesis of sulfonamides (method A1) to get the title compound as a white solid; (369 mg, 69% yield). $^1$H NMR (400 MHz, (CDCl$_3$)): δ 7.80 (d, 2H J=8.8 Hz), 7.15 (d, 4H J=2.4 Hz), 6.55 (dd, 2H J=8.8, J=2.4 Hz), 6.49 (d, 2H, J=2.4), 5.25 (t, 2H J=6.4 Hz), 4.02 (d, 4H J=6.4 Hz), 3.89 (s, 3H), 3.87 (s, 3H). $^{13}$C NMR (100 MHz, CDCl$_3$): δ 164.93, 157.66, 135.08, 132.11, 129.98, 128.28, 119.15, 104.62, 99.47, 56.42, 55.77, 44.90.

Intermediate: Diethyl 2,2'-((1,2-phenylenebis(methylene)) bis(((2,4-dimethoxyphenyl) sulfonyl) azanediyl)) diacetate

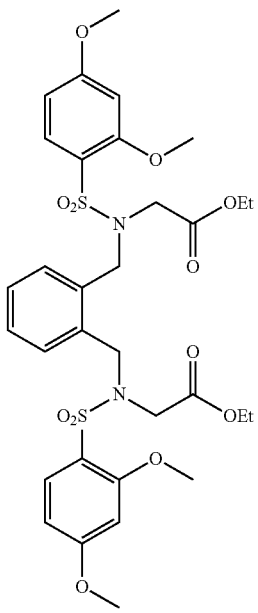 [SMILES: CCOC(=O)CN(Cc1ccccc1CN(CC(=O)OCC)S(=O)(=O)c1ccc(OC)cc1OC)S(=O)(=O)c1ccc(OC)cc1OC]

Prepared as described in the general procedure for synthesis of alkylated sulfonamides (method B) to get the title compound as oily product; (115 mg, 81% yield). $^1$H NMR (400 MHz, (CDCl$_3$)): δ 7.81 (d, 2H J=8.8 Hz), 7.35-7.33 (m, 2H), 7.26-7.23 (m, 2H), 6.50-6.46 (m, 4H), 4.69 (s, 4H), 3.96-3.93 (m, 8H), 3.91 (s, 6H), 3.86 (s, 6H), 1.09 (t, 6H J=7.2 Hz). $^{13}$C NMR (100 MHz, CDCl$_3$): δ 169.15, 164.94, 158.77, 134.84, 132.91, 129.85, 128.25, 120.58, 104.16, 99.48, 61.09, 56.22, 55.82, 49.36, 48.00, 13.97.

Example LH805: 2,2'(((1,2-Phenylenebis(methylene))bis(((2,4-dimethoxyphenyl) sulfonyl) azanediyl)) diacetic Acid

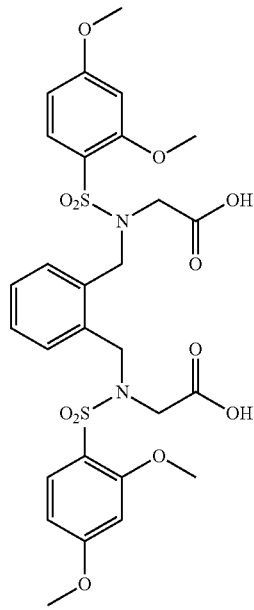 [SMILES: COc1ccc(S(=O)(=O)N(CC(=O)O)Cc2ccccc2CN(CC(=O)O)S(=O)(=O)c2ccc(OC)cc2OC)c(OC)c1]

Prepared as described in the general procedure for hydrolysis of ethyl ester to get di-acidic compounds (Method C1) (basic hydrolysis) to get the title compound as a white solid; (13 mg, 81% yield). $^1$H NMR (400 MHz, (DMSO)): δ 12.53 (s, 2H), 7.60 (d, 2H J=8.8 Hz), 7.17 (s, 4H), 6.67 (d, 4H J=2.0 Hz), 6.55 (dd, 2H, J=8.8 Hz, J=2.0 Hz), 4.46 (s, 4H), 3.86 (s, 4H), 3.83 (s, 6H), 3.81 (s, 6H). $^{13}$C NMR (100 MHz, DMSO): δ 170.06, 164.32, 158.19, 134.48, 131.69, 128.47, 127.31, 119.87, 104.61, 99.30, 56.03, 55.72, 48.34, 47.94. HRMS (ESI) Calcd for $C_{28}H_{32}N_2O_{12}S_2$ (M+H)$^+$ 653.1469 found 653.1460.

Intermediate: N,N'-(1,2-Phenylenebis(methylene)) bis(4-(benzyloxy)benzenesulfonamide)

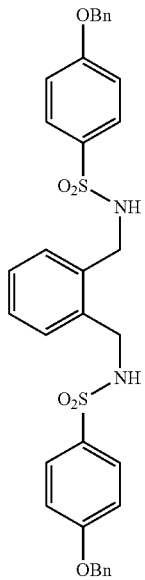 [SMILES: O=S(=O)(NCc1ccccc1CNS(=O)(=O)c1ccc(OCc2ccccc2)cc1)c1ccc(OCc2ccccc2)cc1]

To sodium 4-(benzyloxy) benzenesulfonate (500 mg, 1.7 mmole) in DCM (10 ml), PCl5 (545 mg, 2.6 mmole) was added at room temperature and reaction stirred at 40 C for 24 hours. Upon completion, DCM was removed, and toluene was added and filter the mixture through celite, rotovap to get off-white solid 4-(benzyloxy) benzenesulfonyl chloride which used directly for next step (345 mg, 71%). The synthesis of sulfonamide intermediate was done using Prepared as described in the general procedure for synthesis of sulfonamides (method A1) to get the title compound as a beige solid; 87 mg, 69% yield). $^1$H NMR (400 MHz, (Acetone-d$_6$)): δ 7.83-7.80 (m, 4H), 7.52-7.50 (m, 4H), 7.44-7.36 (m, 7H), 7.27-7.24 (m, 2H), 7.19-7.17 (m, 5H), 6.65 (t, 2H J=6.4 Hz), 5.23 (s, 4H), 4.15 (d, 4H J=6.4 Hz). $^{13}$C NMR (100 MHz, Acetone-d$_6$): δ 162.78, 137.60, 136.36, 133.68, 130.13, 130.00, 129.98, 129.41, 128.92, 128.61, 128.49, 115.92, 70.90, 44.99, 44.90.

Intermediate: Diethyl 2,2'-((1,2-phenylenebis(methylene))bis(((4-(benzyloxy)phenyl) sulfonyl) azanediyl)) diacetate

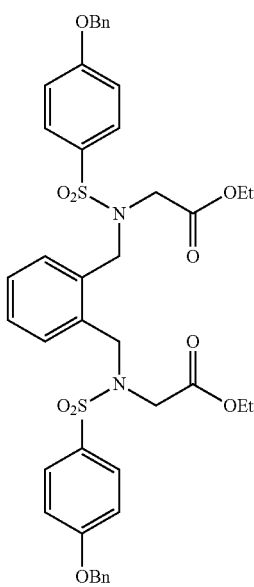 [SMILES: CCOC(=O)CN(Cc1ccccc1CN(CC(=O)OCC)S(=O)(=O)c1ccc(OCc2ccccc2)cc1)S(=O)(=O)c1ccc(OCc2ccccc2)cc1]

Prepared as described in the general procedure for synthesis of alkylated sulfonamides (method B) to get the title compound as oily product; (113 mg, 71% yield). $^1$H NMR (400 MHz, (CDCl$_3$)): δ 7.73 (d, 4H J=8.8 Hz), 7.37-7.26 (m, 12H), 7.19-7.17 (m, 2H), 6.99 (d, 4H J=8.8 Hz), 5.05 (s, 4H), 4.50 (s, 4H), 3.85 (t, 4H, J=7.2 Hz), 3.77 (s, 4H), 1.01 (t, 6H J=7.2 Hz). $^{13}$C NMR (100 MHz, CDCl$_3$): δ 168.73, 162.30, 136.03, 134.13, 131.19, 129.83, 129.78, 128.87, 128.55, 128.47, 127.67, 115.17, 61.36, 49.27, 47.85, 14.07.

Example LH886: 2,2'((1,2-Phenylenebis(methylene))bis(((4-(benzyloxy) phenyl) sulfonyl) azanediyl)) diacetic Acid

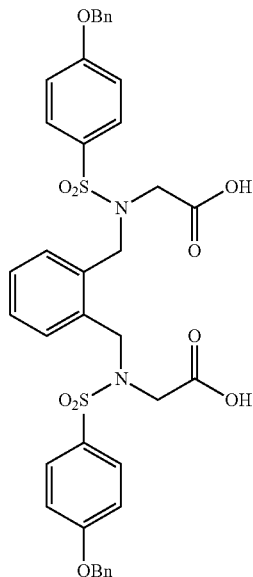 [SMILES: O=C(O)CN(Cc1ccccc1CN(CC(=O)O)S(=O)(=O)c1ccc(OCc2ccccc2)cc1)S(=O)(=O)c1ccc(OCc2ccccc2)cc1]

Prepared as described in the general procedure for hydrolysis of ethyl ester to get di-acidic compounds (Method C1) (basic hydrolysis) to get the title compound as an off-white solid; (17 mg, 76% yield). $^1$H NMR (400 MHz, (DMSO)): δ 7.76 (d, 4H J=9.2 Hz), 7.48-7.46 (m, 4H), 7.42-7.35 (m, 6H), 7.28-7.25 (m, 2H), 7.21-7.16 (m, 6H), 5.19 (s, 4H), 4.44 (s, 4H), 3.75 (s, 4H). $^{13}$C NMR (100 MHz, DMSO): δ 169.86, 161.62, 136.29, 134.29, 130.82, 129.38, 128.60, 128.51, 128.09, 127.89, 127.48, 115.06, 69.71, 48.96, 48.31. HRMS (ESI) Calcd for C$_{38}$H$_{36}$N$_2$O$_{10}$S$_2$ (M+H)$^+$ 745.1884, found 745.1872.

Intermediate: N,N'-(1,2-Phenylenebis(methylene)) bis(dibenzo[b,d]furan-2-sulfonamide)

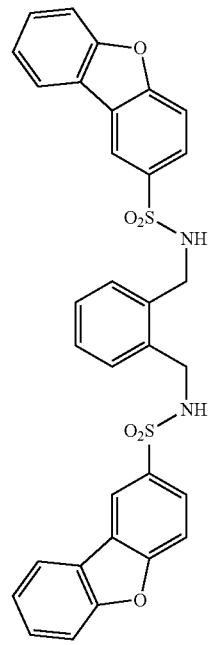 [SMILES: O=S(=O)(NCc1ccccc1CNS(=O)(=O)c1ccc2oc3ccccc3c2c1)c1ccc2oc3ccccc3c2c1]

Prepared as described in the general procedure for synthesis of sulfonamides (method A1) to get the title compound as a beige solid; (373 mg, 62% yield). $^1$H NMR (400 MHz, (DMSO)): δ 8.58 (d, 2H J=1.2 Hz), 8.27 (d, 2H J=3.8 Hz), 8.02 (t, 2H J=6.4 Hz), 7.93-7.91 (m, 2H), 7.83 (d, 2H J=8.8 Hz), 7.77 (d, 2H J=8.4 Hz), 7.60 (t, 2H J=7.6 Hz), 7.45 (t, 2H J=7.6 Hz), 7.22-7.19 (m, 2H), 7.31-7.09 (m, 2H), 4.07 (d, 4H J=6.4 Hz). $^{13}$C NMR (100 MHz, DMSO): δ 156.97, 156.21, 135.59, 135.19, 128.63, 128.58, 127.17, 125.98, 123.91, 123.71, 122.71, 121.82, 120.44, 112.30, 111.91, 43.38.

Intermediate: Diethyl 2,2'-((1,2-phenylenebis(methylene))bis((dibenzo[b,d]furan-2-ylsulfonyl)azanediyl)) diacetate

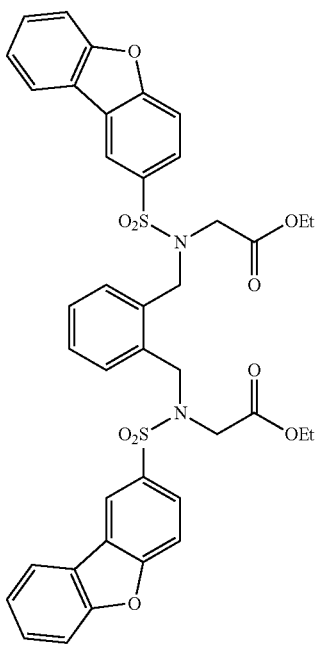 [SMILES: CCOC(=O)CN(Cc1ccccc1CN(CC(=O)OCC)S(=O)(=O)c1ccc2oc3ccccc3c2c1)S(=O)(=O)c1ccc2oc3ccccc3c2c1]

Prepared as described in the general procedure for synthesis of alkylated sulfonamides (method B) to get the title compound as oily product; (125 mg, 81% yield). $^1$H NMR (400 MHz, (CDCl$_3$)): δ 8.49 (d, 2H J=1.4 Hz), 8.03-7.97 (m, 4H), 7.67-7.60 (m, 4H), 7.55-7.51 (m, 2H), 7.41-7.35 (m, 4H), 7.34-7.25 (m, 2H), 4.71 (s, 4H), 3.94 (s, 4H), 3.87 (q, 4H J=6.8 Hz), 1.03-0.99 (m, 6H). $^{13}$C NMR (100 MHz, CDCl$_3$): δ 169.82, 168.62, 134.08, 133.93, 129.87, 128.62, 128.54, 126.73, 124.97, 123.71, 123.33, 121.44, 121.19, 112.31, 112.10, 61.35, 49.42, 49.71, 13.97.

Example LH883: 2,2'-((1,2-Phenylenebis(methylene))bis((dibenzo[b,d]furan-2-ylsulfonyl)azanediyl)) diacetic Acid

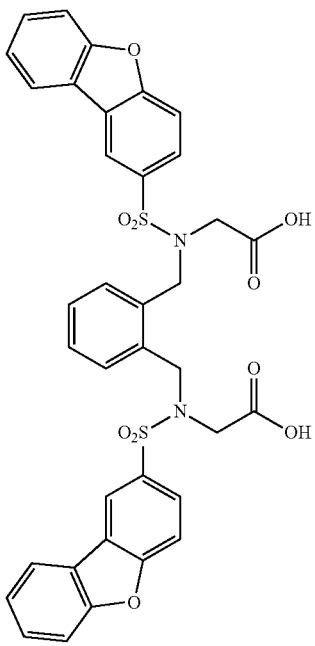 [SMILES: O=C(O)CN(Cc1ccccc1CN(CC(=O)O)S(=O)(=O)c1ccc2oc3ccccc3c2c1)S(=O)(=O)c1ccc2oc3ccccc3c2c1]

Prepared as described in the general procedure for hydrolysis of ethyl ester to get di-acidic compounds (Method C1) (basic hydrolysis) to get the title compound as a beige solid; (14 mg, 78% yield). $^1$H NMR (400 MHz, (Acetone-d$_6$)): δ 8.65 (d, 2H J=1.2 Hz), 8.25 (d, 2H J=8.0 Hz), 8.05 (dd, 2H J=2.0 Hz, J=8.8 Hz), 7.77 (d, 2H J=8.8 Hz), 7.70 (d, 2H J=8.8 Hz), 7.62-7.58 (m, 2H), 7.46-7.42 (m, 2H), 7.40-7.38 (m, 2H), 7.24-7.23 (m, 2H), 4.74 (s, 4H), 4.02 (s, 4H). $^{13}$C NMR (100 MHz, Acetone-d$_6$): δ 170.17, 158.86, 157.76, 135.54, 135.49, 130.28, 129.43, 128.76, 127.84, 125.52, 124.54, 124.19, 122.67, 122.15, 112.92, 112.65, 50.29, 48.73. HRMS (ESI) Calcd for $C_{36}H_{28}N_2O_{10}S_2$ (M+H)$^+$ 713.1258, found 713.1252.

Intermediate: N,N'-(1,2-Phenylenebis(methylene))bis(N-(cyanomethyl)-4-methoxybenzene-sulfonamide)

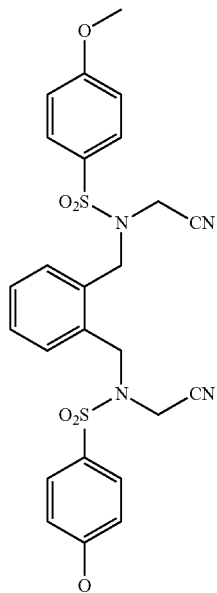 [SMILES: COc1ccc(S(=O)(=O)N(CC#N)Cc2ccccc2CN(CC#N)S(=O)(=O)c2ccc(O)cc2)cc1]

Prepared as described in the general procedure for synthesis of alkylated sulfonamides (method B) to get the title compound as oily product; (119 mg, 71% yield). $^1$H NMR (400 MHz, (CDCl$_3$)): δ 7.86 (d, 4H J=8.8 Hz), 7.45-7.38 (m, 4H), 7.08 (d, 2H J=8.8 Hz), 4.51 (s, 4H), 4.03 (s, 4H), 3.89 (s, 4H). $^{13}$C NMR (100 MHz, CDCl$_3$): δ 164.01, 132.78, 130.29, 130.10, 129.44, 127.77, 55.70, 48.57, 34.90. HRMS (ESI) Calcd for C$_{26}$H$_{26}$N$_4$O$_6$S$_2$ (M+H)$^+$ 555.1367, found 555.1362.

Example LH785: N-((1H-Tetrazol-5-yl)methyl)-N-(2-(((N-((1H-tetrazol-5-yl)methyl)-4-methoxyphenyl) sulfonamido)methyl)benzyl)-4-methoxybenzenesulfonamide (48), General procedure for synthesis of tetrazole (Method D)

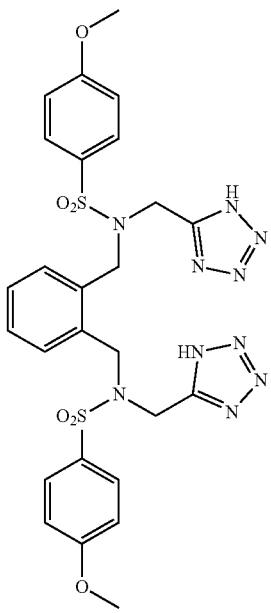 [SMILES: COc1ccc(S(=O)(=O)N(Cc2nnn[nH]2)Cc2ccccc2CN(Cc2nnn[nH]2)S(=O)(=O)c2ccc(OC)cc2)cc1]

N,N'-(1,2-Phenylenebis(methylene))bis(N-(cyanomethyl)-4-methoxy-benzenesulfonamide) (50 mg, 0.09 mmole) dissolved in DMF (1.5 ml) and triethyl ammonium chloride (37 mg, 0.27 mmole) and sodium azide (35 mg, 0.45 mmole) were added at room temperature and the reaction mixture stirred at 120° C. for 4 hr and then checked by TLC and LCMS. Then, acidify reaction mixture with 1 N HCl, and extract with ethyl acetate, washed with water, brine, and dried over sodium sulfate. Purification was done with a flash column chromatography using 0-20% MeOH/DCM to get compound (52 mg, 90% yield). $^1$H NMR (400 MHz, (DMSO)): δ 7.73 (d, 4H J=8.8 Hz), 7.30-7.28 (m, 2H), 7.17-7.16 (m, 2H), 7.06 (d, 4H J=8.8 Hz), 4.50 (s, 4H), 3.84 (s, 4H). $^{13}$C NMR (100 MHz, DMSO): δ 163.86, 153.23, 132.88, 129.81, 129.43, 128.84, 55.84, 41.38, 29.75. HRMS (ESI) Calcd for C$_{26}$H$_{28}$N$_{10}$O$_6$S$_2$ (M+H)$^+$ 640.1707, found 641.1687.

Intermediate: 3,4-Bis(bromomethyl)benzonitrile

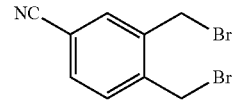

To a solution of 3,4-dimethyl benzonitrile (300 mg, 2.3 mmole) dissolved in CH$_3$Cl (10 ml), NBS (897 mg, 5 mmole) and AIBN (75 mg, 0.45 mmole) were added at room temperature and the reaction mixture stirred at 75° C. for overnight and then checked by TLC. Then, dilute the reaction mixture with DCM and filter through celite followed by purification by ISCO using 0-50% EtOAc in hexane to get compound as a white solid (560 mg, 84% yield). $^1$H NMR (400 MHz, (CDCl$_3$)): δ 7.67 (d, 1H, J=1.6 Hz), 7.59 (dd, 2H, J=1.6 Hz, J=8.0 Hz), 7.49 (d, 1H, J=8.0 Hz), 4.62 (s, 2H), 4.61 (s, 2H), $^{13}$C NMR (100 MHz, DMSO): δ 141.68, 138.10, 134.47, 132.80, 131.92, 117.78, 113.37, 28.11, 27.95.

General Procedure for Reduction of Nitro Group (Method E1):

A solution of 4-nitronaphthalen-1-amine (1 mmol) in THF:EtOH (1:1) was degassed with N$_2$ three times. Then, a catalytic amount of 10% Pd/C (5 mg) was added to the solution and the reaction was purged with H$_2$. The reaction was stirred under H$_2$ for 8 h and then filtered through a celite bed to remove the catalyst. The filtrate was concentrated under reduced pressure to give the desired product. The crude product was used without further purification.

(Method E2):

To a solution of the nitro containing starting material (1 equiv.) in DMF (1 ml), SnCl$_2$·H$_2$O (5 equiv.) was slowly added while reaction mixture stirring at room temperature. Then, stir the reaction mixture at room temperature for overnight. Upon completion, dilute the mixture with ethyl acetate and extract with saturated solution of sodium bicarbonate, dried over sodium sulfate and concentrated under reduced pressure. The crude product used without further purification.

Intermediate: Naphthalene-1,4-diamine

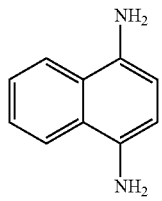

Prepared as described in the general procedure for reduction of nitro group (method E1) to get the title compound as a dark pink solid, the yield (1.52 g (96% yield). ¹H NMR (400 MHz) (CDCl₃) δ 7.86-7.84 (m, 2H), 7.48-7.46 (m, 2H), 6.65 (s, 2H), 3.77 (br, 4H). ¹³C NMR (100 MHz) (CDCl₃) δ 134.63, 124.86, 121.62, 110.79.

Intermediate: N,N'-(Naphthalene-1,4-diyl)bis(4-(trifluoromethyl)benzenesulfonamide)

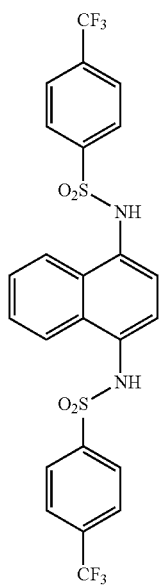 [SMILES: O=S(=O)(Nc1ccc(NS(=O)(=O)c2ccc(C(F)(F)F)cc2)c2ccccc12)c1ccc(C(F)(F)F)cc1]

Prepared as described in the general procedure for synthesis of sulfonamides (method A2) to get the title compound as a pink solid, the yield (419 mg, 72% yield). ¹H NMR (400 MHz) (DMSO) δ 10.47 (s, 2H), 7.86-7.80 (m, 10 H), 7.34-7.32 (m, 2H), 7.07 (s, 2H). ¹³C NMR (100 MHz) (CDCl₃) δ 143.71, 132.87, 132.54, 132.22, 131.89, 130.86, 130.15, 127.62, 127.41, 126.25, 126.17, 124.70, 123.46, 123.11, 121.99. ¹⁹F NMR (377 MHz, DMSO): δ–61.76 (s, 3F), –61.78 (s, 3F).

Intermediate: Diethyl 2,2'-(naphthalene-1,4-diylbis(((4-(trifluoromethyl) phenyl)sulfonyl) azanediyl)) diacetate

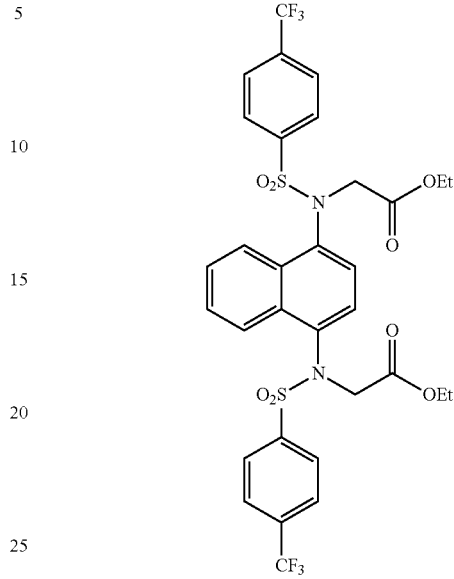

Prepared as described in the general procedure for synthesis of alkylated sulfonamides (method B) to get the title compound as a light pink solid, the yield (103 mg, 69% yield). ¹H NMR (400 MHz) (CDCl₃) δ 8.02-7.86 (m, 6 H), 7.75-7.71 (m, 4H), 7.60-7.50 (m, 2H), 7.25-7.24 (m, 2H), 4.88-4.75 (m, 2H), 4.25-4.07 (m, 6H), 1.23-1.15 (m, 6H). ¹³C NMR (100 MHz) (CDCl₃) δ 168.64, 142.98, 137.11, 136.97, 133.02, 132.90, 128.80, 128.72, 128.38, 128.19, 128.11, 128.02, 126.11, 124.07, 123.98, 61.87, 53.22, 14.14. ¹⁹F NMR (377 MHz, DMSO): δ–63.13 (s, 3F), –63.16 (s, 3F).

Example LH818: 2,2'-(Naphthalene-1,4-diylbis(((4-methoxyphenyl)sulfonyl)azanediyl))diacetic Acid

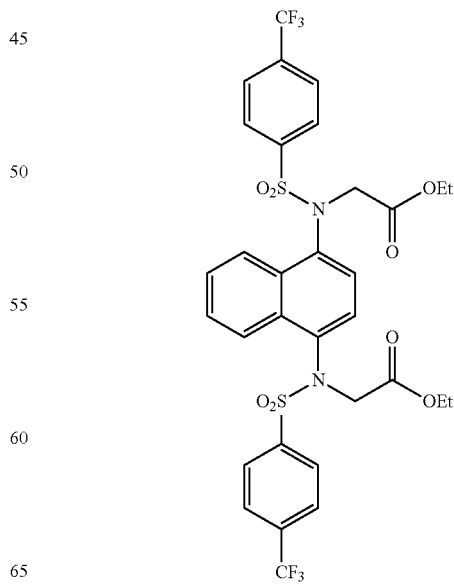

Prepared as described in the general procedure for hydrolysis of ethyl ester to get di-acidic compounds (Method C1) (basic hydrolysis) to get the title compound as a beige solid; the yield (42 mg, 69% yield). $^1$H NMR (400 MHz) (MeOH-d4) δ 8.03-8.00 (m, 1H), 7.98-7.96 (m, 1H), 7.92-7.79 (m, 8H), 7.49-7.45 (m, 2H), 7.39 (s, 1H), 7.27 (s, 1H), 4.81-4.71 (m, 2H), 4.37-4.30 (m, 2H). $^{13}$C NMR (100 MHz) (MeOH-d4) δ 171.81, 144.15, 143.93, 138.39, 138.34, 134.17, 130.04, 129.88, 129.42, 129.30, 128.34, 127.20, 125.28, 125.24, 123.52, 54.17. $^{19}$F NMR (377 MHz, MeOH-d4): δ−64.59 (s, 3F), −64.60 (s, 3F). HRMS (ESI) Calcd for $C_{28}H_{20}F_6N_2O_8S_2$ (M+H)$^+$ 691.0638, found 691.0639.

Intermediate: 4-Bromo-N-(4-((4-hydroxyphenyl) sulfonamido) naphthalen-1-yl) benzenesulfonamide

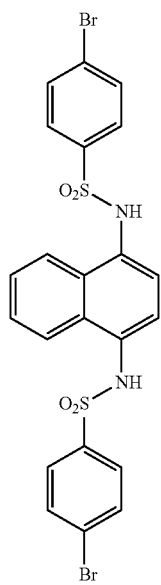

Prepared as described in the general procedure for synthesis of sulfonamides (method A2) to get the title compound as a pink solid, the yield (416 mg, 78% yield). $^1$H NMR (400 MHz) (DMSO) δ 10.46 (s, 2H), 8.15-8.12 (m, 2H), 7.82-7.80 (m, 2H), 7.49-7.42 (m, 6H), 7.07 (s, 2H). $^{13}$C NMR (100 MHz) (DMSO) δ 138.85, 135.42, 134.29, 131.24, 130.67, 130.25, 128.09, 126.35, 123.36, 122.77, 119.35.

Intermediate: Diethyl 2,2'-(naphthalene-1,4-diylbis (((4-bromophenyl) sulfonyl) azanediyl)) diacetate

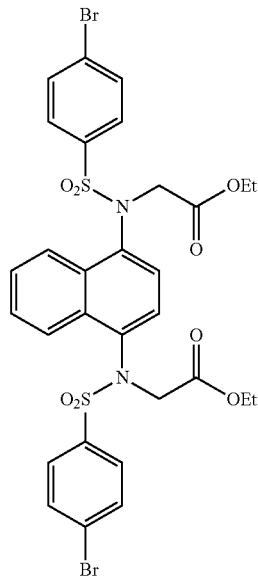 [SMILES: CCOC(=O)CN(c1ccc(N(CC(=O)OCC)S(=O)(=O)c2ccc(Br)cc2)c2ccccc12)S(=O)(=O)c1ccc(Br)cc1]

Prepared as described in the general procedure for synthesis of alkylated sulfonamides (method B) to get the title compound as a light pink solid, the yield (109 mg, 71% yield). $^1$H NMR (400 MHz) (CDCl$_3$) δ 8.07-8.01 (m, 2H), 7.64-7.57 (m, 10H), 7.22 (s, 1H), 7.19 (s, 1H), 4.81-4.68 (m, 2H), 4.24-4.08 (m, 6H), 1.22-1.16 (m, 6H). $^{13}$C NMR (100 MHz) (CDCl$_3$) δ 168.69, 138.40, 138.03, 137.17, 137.06, 133.08, 133.00, 132.25, 129.80, 129.71, 128.40, 128.34, 128.13, 128.03, 127.93, 124.17, 61.77, 53.26, 53.19, 14.32, 14.14.

Example LH832: 2,2'-(Naphthalene-1,4-diylbis(((4-bromophenyl)sulfonyl)azanediyl))diacetic Acid

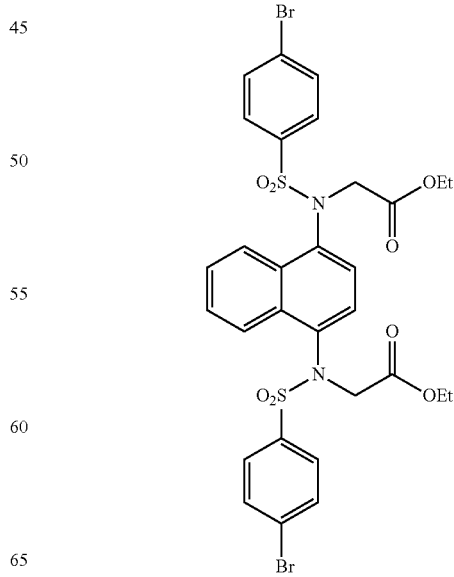

Prepared as described in the general procedure for hydrolysis of ethyl ester to get di-acidic compounds (Method C1) (basic hydrolysis) to get the title compound as a yellow solid; the yield (9 mg, 67% yield). $^1$H NMR (400 MHz) (DMSO) δ 8.22 (s, 1H), 8.15 (s, 1H), 7.81-7.72 (m, 3H), 7.60-7.52 (m, 5H), 7.23 (s, 1H), 6.89 (s, 1H), 4.46-4.09 (m, 4H). $^{13}$C NMR (100 MHz) (DMSO) δ 170.54, 138.02, 137.38, 136.88, 136.66, 132.83, 132.06, 131.95, 130.58, 129.91, 129.62, 127.74, 126.97, 126.57, 126.40, 124.62, 54.44. HRMS (ESI) Calcd for $C_{26}H_{20}Br_2N_2O_8S_2$ (M+H)$^+$ 710.9101, found 710.9105.

Intermediate: N,N'-(Naphthalene-1,4-diyl)bis(2-chlorobenzenesulfonamide)

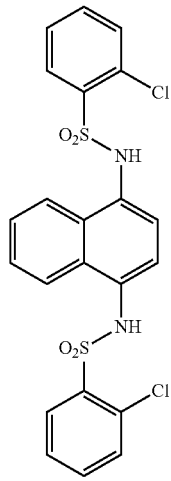 [SMILES: O=S(=O)(Nc1ccc(NS(=O)(=O)c2ccccc2Cl)c2ccccc12)c1ccccc1Cl]

Prepared as described in the general procedure for synthesis of sulfonamides (method A2) to get the title compound as a pink solid; the yield (401 mg, 79% yield). $^1$H NMR (400 MHz) (DMSO) δ 10.49 (s, 2H), 8.10-8.09 (m, 2H), 7.76-7.73 (m, 2H), 7.62-7.60 (m, 2H), 7.62-7.36 (m, 8H), 7.05 (s, 2H), $^{13}$C NMR (100 MHz) (DMSO) δ 136.77, 133.95, 131.41, 130.52, 130.39, 130.25, 129.85, 127.17, 125.97, 122.82, 122.47.

Intermediate: Diethyl 2,2'-(naphthalene-1,4-diylbis(((2-chlorophenyl)sulfonyl)azanediyl))diacetate

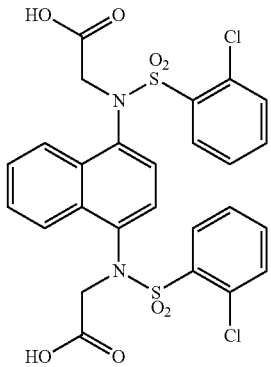 [SMILES: O=C(O)CN(c1ccc(N(CC(=O)O)S(=O)(=O)c2ccccc2Cl)c2ccccc12)S(=O)(=O)c1ccccc1Cl]

Prepared as described in the general procedure for synthesis of alkylated sulfonamides (method B) to get the title compound as oily product; the yield (98 mg, 72% yield). $^1$H NMR (400 MHz) (CDCl$_3$) δ 8.01-7.95 (m, 2H), 7.78-7.72 (m, 2H), 7.60-7.37 (m, 8H), 7.22-7.18 (m, 2H), 5.07-4.98 (m, 2 H), 4.37-4.30 (m, 2H), 4.19-4.09 (m, 4H), 1.28-1.19 (m, 6H). $^{13}$C NMR (100 MHz) (CDCl$_3$) δ 168.97, 168.87, 137.54, 137.15, 136.44, 136.22, 134.02, 132.54, 132.45, 132.35, 132.18, 129.58, 129.42, 127.57, 127.41, 127.11, 123.63, 123.51, 61.69, 54.06, 53.89, 14.18.

Example LH829: 2,2'-(Naphthalene-1,4-diylbis(((2-chlorophenyl)sulfonyl)azanediyl))diacetic Acid

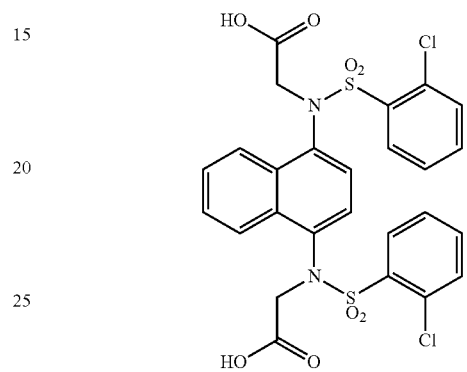

Prepared as described in the general procedure for hydrolysis of ethyl ester to get di-acidic compounds (Method C1) (basic hydrolysis) to get the title compound as an off-white solid; the yield (21 mg, 72% yield). $^1$H NMR (400 MHz) (DMSO) δ 12.98 (s, 2H), 7.98-7.96 (m, 2H), 7.73-7.54 (m, 8H), 7.42-7.36 (m, 4H), 4.86-4.76 (m, 2H), 4.46-4.37 (m, 2H). $^{13}$C NMR (100 MHz) (DMSO) δ 170.03, 169.90, 162.29, 136.41, 136.04, 135.96, 135.82, 134.74, 132.11, 131.89, 131.07, 128.83, 127.72, 127.60, 126.87, 126.73, 123.42, 53.67. HRMS (ESI) Calcd for $C_{26}H_{20}Cl_2N_2O_8S_2$ (M+H)$^+$ 623.0111, found 623.0108.

Intermediate: N,N'-(Naphthalene-1,4-diyl)bis(2-(trifluoromethyl)benzenesulfonamide)

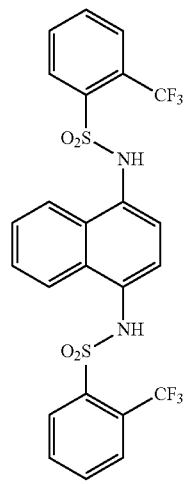 [SMILES: O=S(=O)(Nc1ccc(NS(=O)(=O)c2ccccc2C(F)(F)F)c2ccccc12)c1ccccc1C(F)(F)F]

Prepared as described in the general procedure for synthesis of sulfonamides (method A2) to get the title compound as a beige solid; the yield (766 mg, 81% yield). $^1$H NMR (400 MHz) (MeOH-d4) δ 7.91-7.85 (m, 4H), 7.80 (d, 2H, J=8.0 Hz), 7.68 (t, 2H, J=7.6 Hz), 7.53 (t, 2H, J=7.6 Hz), 7.34-7.31 (m, 2H), 7.19 (s, 2H). $^{13}$C NMR (100 MHz) (MeOH-d4) δ 140.13, 134.14, 133.49, 132.95, 132.47, 132.18, 129.35, 129.28, 127.58, 125.19, 124.02. $^{19}$F NMR (377 MHz, MeOH-d4): δ 58.62 (s, 6F).

Intermediate: Diethyl 2,2'-(naphthalene-1,4-diylbis (((2-(trifluoromethyl) phenyl) sulfonyl) azanediyl)) diacetate

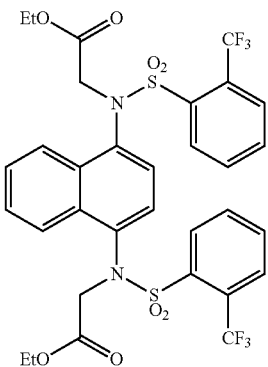 [SMILES: CCOC(=O)CN(c1ccc(N(CC(=O)OCC)S(=O)(=O)c2ccccc2C(F)(F)F)c2ccccc12)S(=O)(=O)c1ccccc1C(F)(F)F]

Prepared as described in the general procedure for synthesis of alkylated sulfonamides (method B) to get the title compound as oily product; the yield (110 mg, 73% yield). $^1$H NMR (400 MHz) (CDCl$_3$) δ 7.87-7.76 (m, 5H), 7.69 (s, 1H), 7.63-7.60 (m, 4H), 7.47-7.39 (m, 3H), 7.29-7.28 (m, 1H), 5.05-4.96 (m, 2H), 4.20-4.09 (m, 6H), 1.25-1.20 (m, 6H). $^{13}$C NMR (100 MHz) (CDCl$_3$) δ 168.98, 138.89, 138.38, 136.67, 136.26, 133.05, 132.88, 132.57, 132.35, 132.20, 130.06, 129.43, 128.17, 127.76, 127.49, 123.43, 123.10, 121.29, 61.78, 53.42, 53.32, 14.20. $^{19}$F NMR (377 MHz, MeOH-d4): δ−57.17 (s, 3F), −57.28 (s, 3F).

Example LH820: N-(4-((N-(Carboxymethyl)-2-(trifluoromethyl)phenyl)sulfonamido)naphthalen-1-yl)-N-((2-(trifluoromethyl)phenyl)sulfonyl)glycine

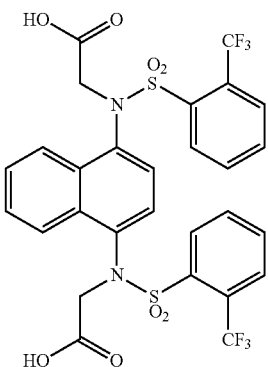 [SMILES: O=C(O)CN(c1ccc(N(CC(=O)O)S(=O)(=O)c2ccccc2C(F)(F)F)c2ccccc12)S(=O)(=O)c1ccccc1C(F)(F)F]

Prepared as described in the general procedure for hydrolysis of ethyl ester to get di-acidic compounds (Method CO (basic hydrolysis) to get the title compound as a light yellow solid; the yield (19 mg, 76% yield). $^1$H NMR (400 MHz) (DMSO) δ 8.02-7.31 (m, 14H), 4.76-4.69 (m, 2H), 4.37-4.23 (m, 2 H). $^{13}$C NMR (100 MHz) (DMSO) δ 169.91, 137.32, 135.74, 133.83, 132.98, 132.37, 131.71, 129.14, 128.05, 126.77, 122.93, 53.16. $^{19}$F NMR (377 MHz, DMSO): δ 55.97 (s, 6F). HRMS (ESI) Calcd for C$_{28}$H$_{20}$F$_6$N$_2$O$_8$S$_2$ (M+H)$^+$ 691.0638, found 691.0628.

Intermediate: N,N'-(Naphthalene-1,4-diyl)bis(2-bromo-4-fluorobenzenesulfonamide)

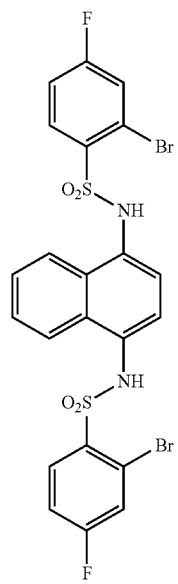 [SMILES: O=S(=O)(Nc1ccc(NS(=O)(=O)c2ccc(F)cc2Br)c2ccccc12)c1ccc(F)cc1Br]

Prepared as described in the general procedure for synthesis of sulfonamides (method A2) to get the title compound as a beige solid; the yield (411 mg, 65% yield). $^1$H NMR (400 MHz) (DMSO) δ 10.52 (s, 2H), 8.12-8.10 (m, 2H), 7.85-7.78 (m, 4H), 7.49-7.47 (m, 2H), 7.31-7.27 (m, 2H). $^{13}$C NMR (100 MHz) (DMSO) δ 164.61, 162.06, 135.34, 135.31, 133.46, 133.37, 130.48, 130.19, 126.29, 123.21, 122.91, 122.68, 122.43, 120.77, 120.66, 115.12, 114.91. $^{19}$F NMR (377 MHz, DMSO): δ−104.85 (s, 2F).

Intermediate: Diethyl 2,2'-(naphthalene-1,4-diylbis (((2-bromo-4-fluorophenyl)sulfonyl)azanediyl)) diacetate

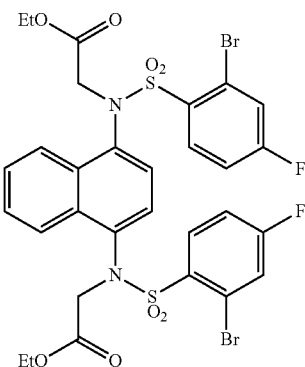 [SMILES: CCOC(=O)CN(c1ccc(N(CC(=O)OCC)S(=O)(=O)c2ccc(F)cc2Br)c2ccccc12)S(=O)(=O)c1ccc(F)cc1Br]

Prepared as described in the general procedure for synthesis of alkylated sulfonamides (method B) to get the title compound as oily product; the yield (109 mg, 68% yield). $^1$H NMR (400 MHz) (CDCl$_3$) δ 8.00-7.93 (m, 2H), 7.84-7.78 (m, 2H), 7.69 (s, 1H), 7.63 (s, 1H), 7.48-7.41 (m, 4H), 6.96-6.93 (m, 2H), 5.11-5.04 (m, 2H), 4.33 (s, 3H), 4.29 (s, 3H), 4.20-4.13 (m, 4H), 1.24-1.21 (m, 6H). $^{13}$C NMR (100 MHz) (CDCl$_3$) δ 168.91, 168.84, 165.57, 162.98, 136.40, 136.21, 135.56, 135.37, 134.80, 134.77, 134.71, 134.67, 132.46, 132.33, 129.84, 129.56, 127.72, 127.59, 123.60, 123.46, 123.20, 122.95, 121.91, 121.81, 121.77, 115.00, 114.87, 114.78, 114.66, 61.79, 54.22, 54.14, 14.20. $^{19}$F NMR (377 MHz, CDCl$_3$): δ 103.46 (s, 1F), 103.60 (s, 1F).

Example LH825: 2,2'-(Naphthalene-1,4-diylbis(((2-bromo-4-methoxyphenyl) sulfonyl) azanediyl)) diacetic Acid

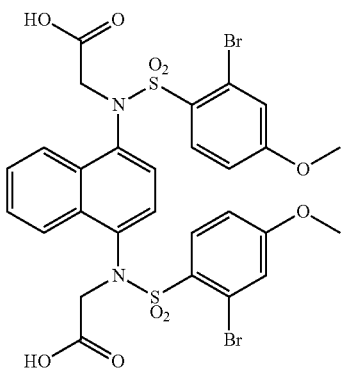 [SMILES: COc1ccc(S(=O)(=O)N(CC(=O)O)c2ccc(N(CC(=O)O)S(=O)(=O)c3ccc(OC)cc3Br)c3ccccc23)c(Br)c1]

Prepared as described in the general procedure for hydrolysis of ethyl ester to get di-acidic compounds (Method C1) (basic hydrolysis) to get the title compound as a beige solid; the yield (17 mg, 75% yield). $^1$H NMR (400 MHz) (DMSO) δ 8.00-7.94 (m, 2H), 7.69-7.61 (m, 4H), 7.40-733 (m, 4H), 6.89 (d, 2H, J=8.4 Hz), 4.75-4.63 (m, 2H), 4.22-4.11 (m, 2H), 3.80 (s, 6H). $^{13}$C NMR (100 MHz) (DMSO) δ 162.35, 135.81, 133.56, 131.88, 130.48, 129.23, 126.16, 123.62, 120.89, 120.55, 112.97, 56.10, 55.02. HRMS (ESI) Calcd for C$_{24}$H$_{24}$Br$_2$N$_2$O$_{10}$S$_2$ (M+H)$^+$ 770.9312, found 770.9335.

Intermediate: N,N'-(Naphthalene-1,4-diyl)bis(4-bromo-2-methoxybenzenesulfonamide)

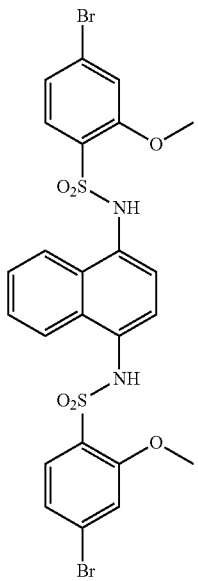 [SMILES: COc1cc(Br)ccc1S(=O)(=O)Nc1ccc(NS(=O)(=O)c2ccc(Br)cc2OC)c2ccccc12]

Prepared as described in the general procedure for synthesis or sulfonamides (method A2) to get the title compound as a white solid; the yield (518 mg, 79% yield). $^1$H NMR (400 MHz) (DMSO) δ 10.19 (s, 2H), 8.09-8.07 (m, 2H), 7.72-7.69 (m, 2H), 7.61 (d, 2H, J=2.4 Hz), 7.48-7.46 (m, 2H), 7.18 (s, 2H), 7.18-7.09 (m, 2H), 3.67 (s, 6H). $^{13}$C NMR (100 MHz) (DMSO) δ 156.07, 137.74, 131.67, 131.31, 130.54, 129.48, 126.71, 123.56, 123.51, 115.59, 111.15, 56.42.

Intermediate: Diethyl 2,2'-(naphthalene-1,4-diylbis(((4-bromo-2-methoxyphenyl) sulfonyl) azanediyl)) diacetate

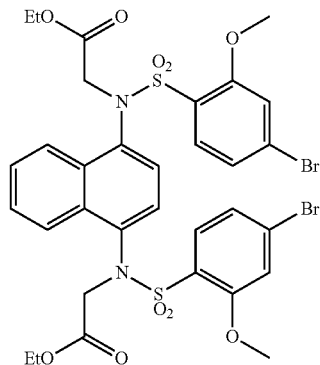 [SMILES: CCOC(=O)CN(c1ccc(N(CC(=O)OCC)S(=O)(=O)c2ccc(Br)cc2OC)c2ccccc12)S(=O)(=O)c1ccc(Br)cc1OC]

Prepared as described in the general procedure for synthesis of alkylated sulfonamides (method B) to get the title compound as oily product; the yield (108 mg, 65% yield). $^1$H NMR (400 MHz) (MeOH-d4) δ 7.82-7.79 (m, 1H), 7.71-7.68 (m, 1H), 7.56 (d, 1H, J=2.4 Hz), 7.46 (d, 2H, J=2.4 Hz), 7.41-7.37 (m, 3H), 7.30 (s, 1H), 7.26-7.20 (m, 2H), 6.79 (d, 1H, J=8.8 Hz), 6.72 (d, 1H, J=8.8 Hz), 4.67-4.62 (m, 2H), 4.23-4.12 (m, 2H), 3.92-3.87 (m, 5H), 3.67 (s, 3H), 3.42 (s, 3H) 1.00-0.95 (m, 6H).

Example LH821: 2,2'-(Naphthalene-1,4-diylbis(((4-bromo-2-methoxyphenyl) sulfonyl)azanediyl)) diacetic Acid

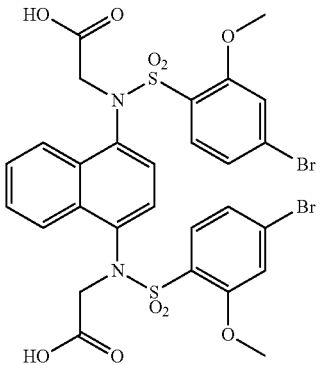 [SMILES: COc1cc(Br)ccc1S(=O)(=O)N(CC(=O)O)c1ccc(N(CC(=O)O)S(=O)(=O)c2ccc(Br)cc2OC)c2ccccc12]

Prepared as described in the general procedure for hydrolysis of ethyl ester to get di-acidic compounds (Method C1) (basic hydrolysis) to get the title compound as a white solid; (19 mg, 64% yield). $^1$H NMR (400 MHz) (DMSO) δ 12.77 (br, 2H), 8.02-7.98 (m, 2H), 7.78 (d, 2H, J=8.8 Hz), 7.56 (d, 2H, J=8.8 Hz), 7.51 (s, 4H), 7.24-7.20 (m, 2H), 4.74-4.67 (m, 2H), 4.45-4.35 (m, 2H), 3.80 (s, 3H), 3.71 (s, 3H). $^{13}$C NMR (100 MHz) (DMSO) δ 170.16, 155.85, 137.65, 136.27, 132.06, 131.98, 131.94, 128.76, 128.39, 126.75, 123.76, 123.67, 115.51, 115.46, 110.94, 56.28, 56.10, 53.50. HRMS (ESI) Calcd for $C_{28}H_{24}Br_2N_2O_{10}S_2$ $(M+H)^+$ 770.9312, found 770.9304.

Intermediate: N,N'-(Naphthalene-1,4-diyl)bis(4-bromo-2-(trifluoromethoxy)benzenesulfonamide)

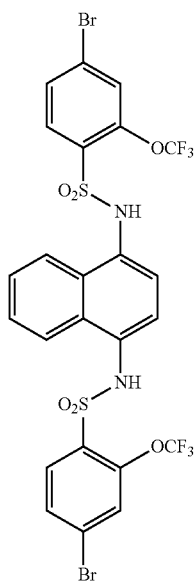 [SMILES: O=S(=O)(Nc1ccc(NS(=O)(=O)c2ccc(Br)cc2OC(F)(F)F)c2ccccc12)c1ccc(Br)cc1OC(F)(F)F]

Prepared as described in the general procedure for synthesis of sulfonamides (method A2) to get the title compound as a light yellow solid; the yield (589 mg, 77% yield). $^1$H NMR (400 MHz) (CDCl$_3$) δ 8.01-7.99 (m, 2H), 7.69 (d, 2H, J=8.8 Hz), 7.58-7.56 (m, 2H), 7.52 (t, 2H, J=1.5 Hz), 7.44 (dd, 2H, J=8.8, 1.5 Hz), 7.12 (s, 2H), 7.01 (br, 2H). $^{13}$C NMR (100 MHz) (CDCl$_3$) δ 146.27, 132.47, 130.51, 130.18, 130.03, 129.87, 129.87, 128.98, 127.78, 123.59, 123.57, 122.24, 121.55, 118.97. $^{19}$F NMR (377 MHz, CDCl$_3$): δ−56.24 (s, 6F).

Intermediate: Diethyl 2,2'-(naphthalene-1,4-diylbis (((4-bromo-2-(trifluoromethoxy) phenyl) sulfonyl) azanediyl)) diacetate

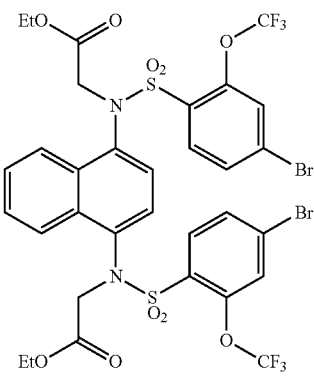 [SMILES: CCOC(=O)CN(c1ccc(N(CC(=O)OCC)S(=O)(=O)c2ccc(Br)cc2OC(F)(F)F)c2ccccc12)S(=O)(=O)c1ccc(Br)cc1OC(F)(F)F]

Prepared as described in the general procedure for synthesis of alkylated sulfonamides (method B) to get the title compound as oily product; the yield (109 mg, 66% yield). $^1$H NMR (400 MHz) (CDCl$_3$) δ 8.02-7.93 (m, 2H), 7.66-7.42 (m, 10H), 5.02-4.91 (m, 2H), 4.27-4.07 (m, 6H), 1.22 (t, 6H, J=7.2 Hz). $^{13}$C NMR (100 MHz) (CDCl$_3$) δ 168.68, 146.46, 136.50, 132.92, 132.68, 132.59, 131.41, 129.85, 128.95, 128.71, 128.02, 127.85, 123.58, 123.48, 61.70, 53.42, 53.18. $^{19}$F NMR (377 MHz, CDCl$_3$): δ−56.26 (s, 3F), −56.47 (s, 3F).

Example LH822: 2,2'-(Naphthalene-1,4-diylbis(((4-bromo-2-(trifluoromethoxy) phenyl) sulfonyl) azanediyl)) diacetic Acid

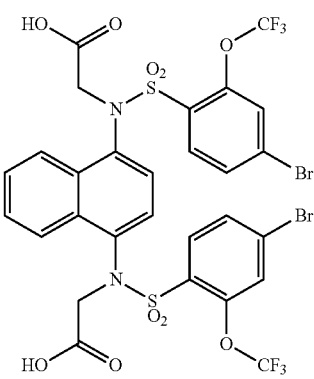 [SMILES: O=C(O)CN(c1ccc(N(CC(=O)O)S(=O)(=O)c2ccc(Br)cc2OC(F)(F)F)c2ccccc12)S(=O)(=O)c1ccc(Br)cc1OC(F)(F)F]

Prepared as described in the general procedure for hydrolysis of ethyl ester to get di-acidic compounds (Method C1) (basic hydrolysis) to get the title compound as a beige solid; the yield (17 mg, 63% yield). $^1$H NMR (400 MHz) (CDCl$_3$) δ) 8.06-8.00 (m, 2H), 7.85 (s, 1H), 7.77-7.69 (m, 4H), 7.61-7.58 (m, 3H), 7.48 (s, 1H), 7.39 (s, 1H), 4.74-4.63 (m, 2H), 4.41-4.02 (m, 2H). $^{13}$C NMR (100 MHz) (CDCl$_3$) δ 169.62, 169.52, 145.33, 136.09, 132.83, 132.73, 132.16, 132.01, 130.82, 130.61, 130.49, 128.18, 128.10, 128.01, 127.18, 124.32, 123.85, 123.67, 123.56, 52.99. HRMS (ESI) Calcd for $C_{28}H_{18}Br_2F_6N_2O_{10}S_2$ (M+H)$^+$ 878.8747, found 878.8773.

Intermediate: N,N'-(Naphthalene-1,4-diyl)bis(3-cyano-4-fluorobenzenesulfonamide)

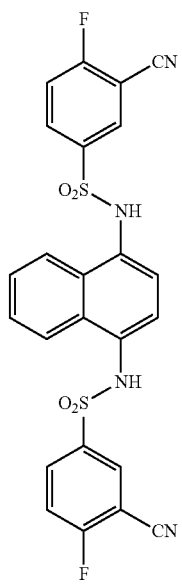 [SMILES: N#Cc1cc(S(=O)(=O)Nc2ccc(NS(=O)(=O)c3ccc(F)c(C#N)c3)c3ccccc23)ccc1F]

Prepared as described in the general procedure for synthesis or sulfonamides (method A2) to get the title compound as a beige solid; the yield (415 mg, 79% yield). $^1$H NMR (400 MHz) (CDCl$_3$) δ 10.44 (s, 2H), 8.18-8.16 (m, 2H), 8.00-7.95 (m, 4H), 7.65 (t, 2H, J=8.8 Hz), 7.50-7.47 (m, 2H), 7.00 (s, 2H). $^{13}$C NMR (100 MHz) (CDCl$_3$) δ 165.57, 162.96, 137.02, 134.44, 134.34, 132.57, 130.61, 130.22, 126.44, 123.41, 123.16, 117.83, 117.62, 112.47, 101.49, 101.32. $^{19}$F NMR (377 MHz, CDCl$_3$): δ −101.54 (s, 2F).

Intermediate: Diethyl 2,2'-(naphthalene-1,4-diylbis (((3-cyano-4-fluorophenyl)sulfonyl)azanediyl)) diacetate

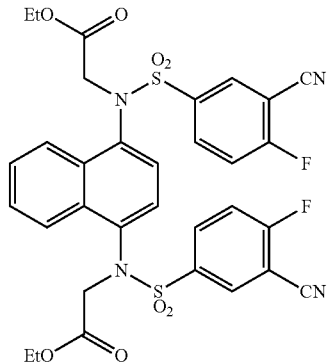

Prepared as described in the general procedure for synthesis of alkylated sulfonamides (method B) to get the title compound as oily product; the yield (102 mg, 71% yield). $^1$H NMR (400 MHz) (DMSO) δ) 8.44-8.42 (m, 1H), 8.26-8.16 (m, 3H), 8.03-7.91 (m, 2H), 7.71-7.56 (m, 4H), 7.19 (s, 1 H), 7.12 (s, 1H), 4.74-4.52 (m, 4H), 4.11-3.98 (m, 4H), 1.14-1.05 (m, 6H). $^{13}$C NMR (100 MHz) (DMSO) δ 168.25, 168.17, 166.23, 166.13, 163.61, 163.51, 136.61, 136.56, 135.60, 135.50, 135.31, 135.27, 135.23, 135.09, 135.06, 133.95, 133.80, 132.64, 132.53, 127.15, 126.78, 124.17, 124.07, 117.52, 117.31, 112.49, 112.29, 101.92, 101.81, 101.76, 101.64, 60.99, 60.92, 53.19, 13.42, 13.35. $^{19}$F NMR (377 MHz, CDCl$_3$): δ−101.11 (s, 1F), −101.24 (s, 1F).

Example LH824: 2,2'-(Naphthalene-1,4-diylbis(((3-cyano-4-methoxyphenyl) sulfonyl) azanediyl)) diacetic Acid

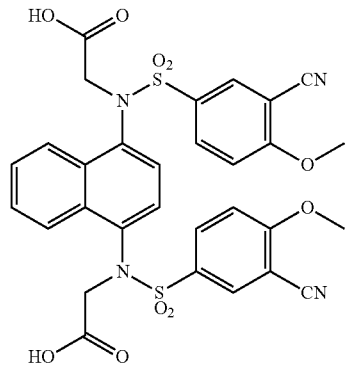 [SMILES: COc1ccc(S(=O)(=O)N(CC(=O)O)c2ccc(N(CC(=O)O)S(=O)(=O)c3ccc(OC)c(C#N)c3)c3ccccc23)cc1C#N]

Prepared as described in the general procedure for hydrolysis of ethyl ester to get di-acidic compounds (Method C1) (basic hydrolysis) to get the title compound as a light yellow solid; yield (21 mg, 69% yield). $^1$H NMR (400 MHz) (DMSO) δ) 8.25-8.16 (m, 4H), 7.95-7.89 (m, 1H), 7.77 (d, 1H, J=8.8 Hz), 7.61-7.59 (m, 2H), 7.41 (d, 1H, J=9.2 Hz), 7.31 (d, 1H, J=8.8 Hz), 7.19 (s, 1H), 7.11 (s, 1H), 4.57-4.32 (m, 4H), 4.03 (s, 3H), 3.99 (s, 3H). $^{13}$C NMR (100 MHz) (DMSO) δ 169.98, 164.04, 137.02, 134.99, 134.76, 133.94, 133.71, 132.95, 130.90, 130.64, 126.93, 124.56, 112.79, 101.25, 57.34, 53.65. HRMS (ESI) Calcd for C$_{30}$H$_{24}$N$_4$O$_{10}$S$_2$ (M+H)$^+$665.1007, found 665.0997.

Intermediate: Dibenzyl 2,2'-(naphthalene-1,4-diylbis (((3-cyano-4-fluorophenyl) sulfonyl) azanediyl)) diacetate

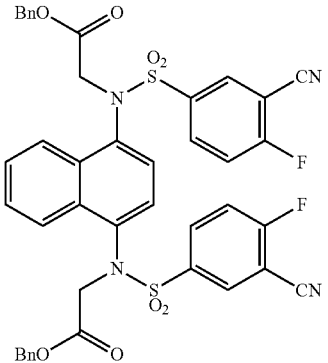 [SMILES: N#Cc1cc(S(=O)(=O)N(CC(=O)OCc2ccccc2)c2ccc(N(CC(=O)OCc3ccccc3)S(=O)(=O)c3ccc(F)c(C#N)c3)c3ccccc23)ccc1F]

Prepared as described in the general procedure for synthesis of alkylated sulfonamides (method B) to get the title compound as oily product; the yield (122 mg, 74% yield). $^1$H NMR (400 MHz) (CDCl$_3$) δ 8.09-7.95 (m, 5H), 7.65-7.61 (m, 2H), 7.42-7.22 (m, 15H), 5.23-4.93 (m, 6H), 4.31-4.17 (m, 2H). $^{13}$C NMR (100 MHz) (CDCl$_3$) δ 168.63, 168.59, 137.06, 137.03, 136.81, 135.23, 135.11, 135.01, 134.81, 134.73, 134.22, 132.92, 128.92, 128.87, 128.83, 128.65, 128.62, 128.54, 128.08, 128.01, 123.88, 117.56, 117.44, 117.35, 117.23, 112.44, 112.27, 102.67, 102.50, 67.89, 67.76, 53.33, 53.26.

Example LH828: 2,2'-(Naphthalene-1,4-diylbis(((3-cyano-4-fluorophenyl)sulfonyl)azanediyl))diacetic Acid

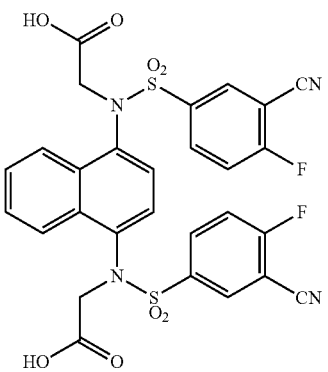 [SMILES: N#Cc1cc(S(=O)(=O)N(CC(=O)O)c2ccc(N(CC(=O)O)S(=O)(=O)c3ccc(F)c(C#N)c3)c3ccccc23)ccc1F]

Prepared as described in the general procedure for hydrolysis of ethyl ester to get di-acidic compounds (Method C3) to get the title compound as a yellow solid; the yield (21 mg, 69% yield). $^1$H NMR (400 MHz) (DMSO) δ) 8.51-8.49 (m, 1H), 8.43-8.41 (m, 1H), 8.25-8.23 (m, 1H), 8.18-8.16 (m, 1H), 8.02-7.98 (m, 1H), 7.89-7.86 (m, 1H), 7.75 (t, 1H, J=8.8 Hz), 7.65-7.61 (m, 1H), 7.22 (s, 1H), 7.11 (s, 1H), 4.66-4.45 (m, 4H). $^{13}$C NMR (100 MHz) (DMSO) δ 169.98, 136.83, 136.00, 135.76, 135.38, 134.28, 134.13, 132.83, 132.66, 127.41, 127.08, 126.98, 124.46, 117.63, 117.44, 112.97, 112.80, 101.86, 101.69, 53.72. $^{19}$F NMR (377 MHz, CDCl$_3$): δ –101.31 (s, 1 F), –101.42 (s, 1 F). HRMS (ESI) Calcd for C$_{28}$H$_{18}$F$_2$N$_4$O$_8$S$_2$ (M+H)$^+$ 641.0607, found 641.0599.

Intermediate: N,N'-(Naphthalene-1,4-diyl)bis(4-fluoro-3-methylbenzenesulfonamide)

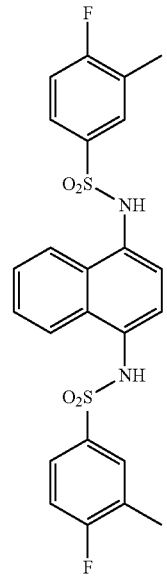 [SMILES: Cc1cc(S(=O)(=O)Nc2ccc(NS(=O)(=O)c3ccc(F)c(C)c3)c3ccccc23)ccc1F]

Prepared as described in the general procedure for synthesis of sulfonamides (method A2) to get the title compound as a white solid; the yield (397 mg, 79% yield). $^1$H NMR (400 MHz) (DMSO) δ 10.17 (s, 2H), 7.98-7.95 (m, 2H), 7.60-7.57 (m, 2H), 7.52-7.50 (m, 2H), 7.44-7.42 (m, 2H), 7.25 (t, 2H, J=8.8 Hz), 7.03 (s, 2H). $^{13}$C NMR (100 MHz) (DMSO) δ 164.01, 161.52, 135.84, 135.80, 130.98, 130.38, 130.31, 130.18, 126.99, 126.90, 126.19, 125.78, 125.59, 123.31, 123.03, 115.87, 115.63, 48.56, 13.93, 13.90. $^1$H NMR (377 MHz, DMSO): δ 110.52 (s, 2F).

Intermediate: Diethyl 2,2'-(naphthalene-1,4-diylbis (((4-fluoro-3-methylphenyl)sulfonyl)azanediyl)) diacetate

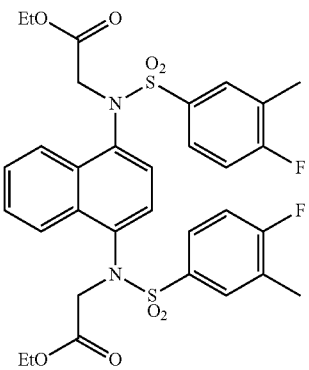 [SMILES: CCOC(=O)CN(c1ccc(N(CC(=O)OCC)S(=O)(=O)c2ccc(F)c(C)c2)c2ccccc12)S(=O)(=O)c1ccc(F)c(C)c1]

Prepared as described in the general procedure for synthesis of alkylated sulfonamides (method B) to get the title compound as oily product; the yield (97 mg, 72% yield). $^1$H NMR (400 MHz) (DMSO) δ 8.20-8.16 (m, 2H), 7.73-7.72 (m, 2H), 7.59-7.57 (m, 3H), 7.52-7.48 (m, 2H), 7.37-7.27 (m, 2H), 7.10 (s, 1H), 7.07 (s, 1H), 4.62-4.53 (m, 4H), 4.07-4.00 (m, 4H), 2.30 (s, 1H), 2.23 (s, 1H), 1.10-1.03 (m, 6H). $^{13}$C NMR (100 MHz) (DMSO) δ 168.38, 168.35, 164.55, 162.09, 162.05, 136.82, 133.49, 132.71, 131.44, 128.16, 128.07, 127.94, 127.84, 126.88, 126.78, 126.71, 126.17, 126.06, 125.99, 125.87, 124.35, 115.97, 115.86, 115.73, 115.62, 60.89, 53.25, 13.98, 13.95, 13.86, 13.75. $^{19}$F NMR (377 MHz, DMSO): δ−109.48 (s, 1F) 109.53 (s, 1F).

Example LH834: 2,2'-(Naphthalene-1,4-diylbis(((4-fluoro-3-methylphenyl)sulfonyl)azanediyl))diacetic Acid

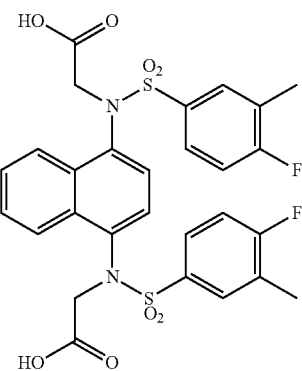 [SMILES: Cc1cc(S(=O)(=O)N(CC(=O)O)c2ccc(N(CC(=O)O)S(=O)(=O)c3ccc(F)c(C)c3)c3ccccc23)ccc1F]

Prepared as described in the general procedure for hydrolysis of ethyl ester to get di-acidic compounds (Method C1) (basic hydrolysis) to get the title compound as a white solid; the yield (26 mg, 79% yield). $^1$H NMR (400 MHz) (DMSO) δ) 8.20-8.16 (m, 2H), 7.74-7.72 (m, 1H), 7.59-7.56 (m, 3H), 7.53-7.49 (m, 2H), 7.37-7.28 (m, 2H), 7.15 (s, 1H), 7.13 (s, 1H), 4.55-4.39 (m, 4H), 2.30 (s, 3H), 2.24 (s, 3H). $^{13}$C NMR (100 MHz) (DMSO) δ 169.88, 164.52, 162.06, 136.92, 136.87, 133.74, 132.73, 131.51, 131.47, 128.16, 128.06, 127.94, 127.85, 127.05, 126.96, 126.72, 126.08, 126.01, 125.89, 125.82, 124.41, 115.95, 115.82, 115.72, 115.58, 53.19, 14.03, 13.94, 13.92. $^{19}$F NMR (377 MHz, DMSO): δ−109.67 (s, 1 F), −109.69 (s, 1 F). HRMS (ESI) Calcd for $C_{28}H_{24}F_2N_2O_8S_2$ (M+H)$^+$ 619.1015, found 619.1009.

Intermediate: N,N'-(Naphthalene-1,4-diyl)bis(2,6-difluorobenzenesulfonamide)

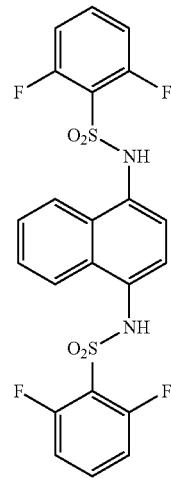 [SMILES: O=S(=O)(Nc1ccc(NS(=O)(=O)c2c(F)cccc2F)c2ccccc12)c1c(F)cccc1F]

Prepared as described in the general procedure for synthesis of sulfonamides (method A2) to get the title compound as a yellow product; the yield (399 mg, 78% yield). $^1$H NMR (400 MHz) (DMSO) δ 10.17 (s, 2H), 7.98-7.95 (m, 2H), 7.60-7.57 (m, 2H), 7.52-7.50 (m, 2H), 7.44-7.42 (m, 2H), 7.25 (t, 2H, J=8.8 Hz), 7.03 (s, 2H). $^{19}$F NMR (377 MHz, DMSO): δ−104.90 (s, 2F), −105.35 (s, 2F).

Intermediate: Diethyl 2,2'-(naphthalene-1,4-diylbis(((2,6-difluorophenyl) sulfonyl) azanediyl)) diacetate

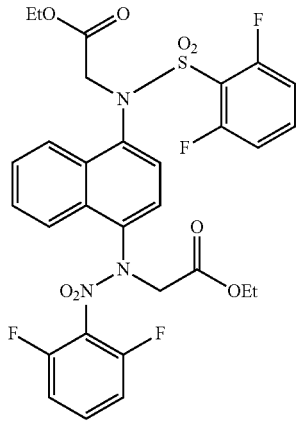

Prepared as described in the general procedure for synthesis of alkylated sulfonamides (method B) to get the title compound as oily product; yield (86 mg, 63% yield). $^1$H NMR (400 MHz) (CDCl$_3$) δ 8.08-8.03 (m, 2H), 7.59-7.49 (m, 6H), 7.01-6.92 (m, 4H), 5.10-4.94 (m, 2H), 4.39-4.04 (m, 6H), 1.25-1.18 (m, 6H). $^{13}$C NMR (100 MHz) (CDCl$_3$) δ 169.78, 164.20, 160.65, 136.93, 136.83, 135.52, 135.11, 132.73, 128.15, 128.07, 127.87, 124.07, 113.95, 113.82, 53.68. $^{19}$F NMR (377 MHz, CDCl$_3$): δ−104.25 (s, 2F)−104.29 (s, 2F).

Example LH812: 2,2'-(Naphthalene-1,4-diylbis(((2,6-difluorophenyl)sulfonyl)azanediyl))diacetic Acid

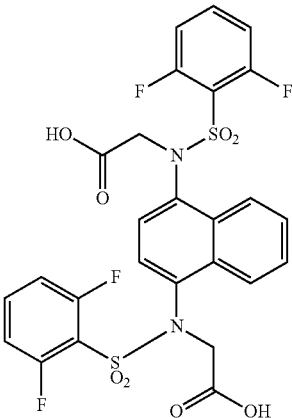 [SMILES: O=C(O)CN(c1ccc(N(CC(=O)O)S(=O)(=O)c2c(F)cccc2F)c2ccccc12)S(=O)(=O)c1c(F)cccc1F]

Prepared as described in the general procedure for hydrolysis of ethyl ester to get di-acidic compounds (Method C1) (basic hydrolysis) to get the title compound as an off-white solid, the yield (9 mg, 61% yield). $^1$H NMR (400 MHz) (DMSO) δ) 8.19-8.17 (m, 1H), 8.10-8.08 (m, 1H), 7.75-7.59 (m, 3H), 7.50 (s, 1H), 7.35 (s, 1H), 7.29-7.12 (m, 4H), 4.73-4.58 (m, 2H), 4.38-4.32 (m, 2H). $^{13}$C NMR (100 MHz) (DMSO) δ 168.78, 168.60, 158.65, 136.49, 136.13, 135.13, 135.02, 132.78, 128.33, 128.05, 127.77, 123.69, 113.34, 113.11, 61.74, 53.57, 53.23. $^{19}$F NMR (377 MHz, DMSO): δ−104.90 (s, 2F), −105.35 (s, 2F). HRMS (ESI) Calcd for $C_{26}H_{18}F_4N_2O_8S_2$ (M+H)$^+$ 627.0513, found 627.0512.

Intermediate: 4-(1,3-Dioxoisoindolin-2-yl)benzenesulfonic Acid

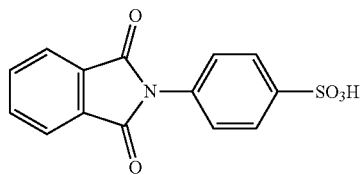 [SMILES: O=C1c2ccccc2C(=O)N1c1ccc(S(=O)(=O)O)cc1]

To a mixture of sulfanilic acid (540 mg, 3.13 mmol) and Phthalic anhydride (463 mg, 3.13 mmol), DMF (15 ml) and pyridine (0.25 ml) were added. Then, the mixture was heated to 100° C. with stirring for 20 min (majority of the solid material dissolved). Then, the reaction mixture was poured into 100 ml acetone and kept at 0° C. for 20 min. Then, the suspension filtered and washed with diethyl ether to get a white solid which was taken in glacial acetic acid (20 ml) and refluxed for 2 hours. Upon completion, the mixture was cooled to room temperature and the solution was filtered to (remove insoluble solid). Then, add diethyl ether (50 ml) was added and filter the suspension followed by washing of the solid with diethyl ether to get beige color solid (503 mg, 53% yield). $^1$H NMR (400 MHz) (DMSO) δ 7.88-7.84 (m, 4H), 7.69 (d, 2H, J=8.0 Hz), 7.47 (s, 1H), 7.36 (d, 2H, J=8.0 Hz). $^{13}$C NMR (100 MHz) (DMSO) δ 166.96, 147.62, 146.00, 142.50, 134.79, 132.01, 131.53, 126.77, 126.10, 123.47.

Intermediate: 4-(1,3-Dioxoisoindolin-2-yl)benzenesulfonyl Chloride

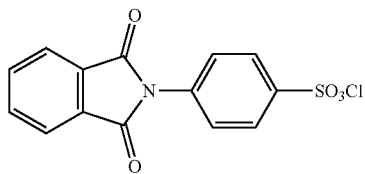

To a solution of the corresponding sulfonic acid (455 mg, 1.5 mmol) in DMF (3 ml), thionyl chloride (0.15 ml) was added. Then, the mixture was stirred at room temperature for 2 hours and then checked by TLC. After completion, the reaction mixture was extracted with ice water:DCM. Wash the organic layer with brine and dried over sodium sulfate and remove the organic solvent by rotovap to get a yellow solid (371 mg, 77% yield). $^1$H NMR (400 MHz) (DMSO) δ 7.94-7.86 (m, 2H), 7.72 (d, 1H, J=8.4 Hz), 7.69 (d, 1H, J=8.4 Hz), 7.64-7.53 (m, 2H), 7.39 (d, 1H, J=8.4 Hz), 7.30 (d, 1H, J=8.4 Hz). $^{13}$C NMR (100 MHz) (DMSO) δ 167.00, 147.58, 135.82, 130.84, 128.39, 126.83, 126.13, 123.52.

Intermediate: N,N'-(Naphthalene-1,4-diyl)bis(4-(1,3-dioxoisoindolin-2-yl)benzenesulfonamide)

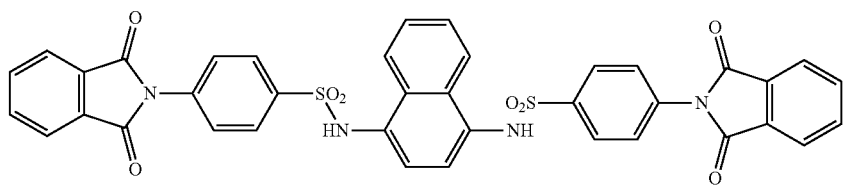

Prepared as described in the general procedure for synthesis of sulfonamides (method A1) to get the title compound as a yellow solid; the yield (215 mg, 59% yield). ¹H NMR (400 MHz) (DMSO) δ 10.40 (s, 2H), 8.04-8.01 (m, 2H), 7.89-7.83 (m, 12H), 7.64 (d, 4H, J=8.8 Hz), 7.46-7.44 (m, 2H), 7.13 (s, 2 H). ¹³C NMR (100 MHz) (DMSO) δ 166.42, 138.69, 135.65, 134.83, 131.32, 131.03, 130.17, 127.47, 127.33, 126.41, 123.51, 123.38, 122.86.

Intermediate: tert-Butyl N-(4-((4-(1,3-dioxoisoindolin-2-yl)-N-(2-ethoxy-2-oxoethyl)phenyl) sulfonamido) naphthalen-1-yl)-N-((4-(1,3-dioxoisoindolin-2-yl)phenyl)sulfonyl) glycinate

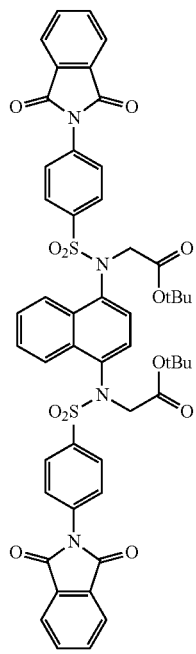 [SMILES: CC(C)(C)OC(=O)CN(c1ccc(N(CC(=O)OC(C)(C)C)S(=O)(=O)c2ccc(N3C(=O)c4ccccc4C3=O)cc2)c2ccccc12)S(=O)(=O)c1ccc(N2C(=O)c3ccccc3C2=O)cc1]

Prepared as described in the general procedure for synthesis of alkylated sulfonamides (method B) to get the title compound as oily product; the yield (71 mg, 76% yield). ¹H NMR (400 MHz) (CDCl₃) δ 8.09-8.04 (m, 2H), 7.98-7.96 (m, 2H), 7.87-7.77 (m, 10H), 7.72-7.64 (m, 4H), 7.57-7.52 (m, 2H), 7.33 (s, 1H), 4.65-4.55 (m, 2H), 4.23-4.10 (m, 2H), 1.38 (s, 9H), 1.34 (s, 9H). ¹³C NMR (100 MHz) ((CDCl₃) δ 167.44, 167.35, 166.48, 137.75, 137.42, 137.19, 137.04, 136.14, 134.85, 134.70, 133.08, 132.98, 131.50, 131.42, 128.89, 128.80, 127.71, 127.62, 127.53, 126.10, 126.01, 124.25, 124.18, 124.04, 123.95, 82.65, 82.51, 54.05, 53.93, 27.95.

Intermediate: tert-Butyl N-(4-((4-amino-N-(2-ethoxy-2-oxoethyl)phenyl)sulfonamido)naphthalen-1-yl)-N-((4-aminophenyl)sulfonyl)glycinate

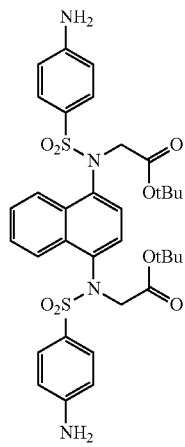 [SMILES: CC(C)(C)OC(=O)CN(c1ccc(N(CC(=O)OC(C)(C)C)S(=O)(=O)c2ccc(N)cc2)c2ccccc12)S(=O)(=O)c1ccc(N)cc1]

To a stirred solution of the above intermediate (60 mg, 0.06 mmol) in mixture of DCM:MeOH (1:1), hydrazine monohydrate was added (40 uL) and the reaction stirred at room temperature for 1 hour. Upon completion, the organic solvent removed under reduced pressure and then purify the crude product using a silica gel ISCO column ethyl acetate/hexane to get the desired product as a beige solid, the yield (36 mg, 89% yield). ¹H NMR (400 MHz) (CDCl₃) δ 8.36-8.34 (m, 1 H), 8.24-8.22 (m, 1H), 7.59-7.56 (m, 2H), 7.25-7.22 (m, 4H), 7.03 (s, 1H), 6.82 (s, 1H), 6.65 (d, 2H, J=8.4 Hz), 6.55 (d, 2H, J=8.4 Hz), 6.13-6.11 (br, 4H), 4.38-4.02 (m, 4H), 1.25 (s, 9H), 1.20 (s, 9H). ¹³C NMR (100 MHz) ((CDCl₃) δ 167.31, 153.32, 137.23, 137.14, 133.06, 132.96, 129.81, 129.61, 126.28, 125.75, 125.48, 124.84, 124.67, 121.94, 121.48, 112.50, 81.26, 81.18, 54.15, 53.90, 27.39.

Intermediate: tert-Butyl N-(4-((N-(2-ethoxy-2-oxoethyl)-4-(methylsulfonamido) phenyl) sulfonamido) naphthalen-1-yl)-N-((4-(methylsulfonamido)phenyl) sulfonyl)glycinate

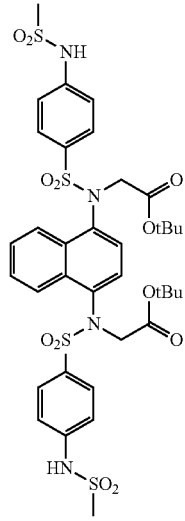 [SMILES: CC(C)(C)OC(=O)CN(c1ccc(N(CC(=O)OC(C)(C)C)S(=O)(=O)c2ccc(NS(C)(=O)=O)cc2)c2ccccc12)S(=O)(=O)c1ccc(NS(C)(=O)=O)cc1]

Prepared as described in the general procedure for synthesis of alkylated sulfonamides (method B) to get the title compound as oily product; the yield (18 mg, 82% yield). $^1$H NMR (400 MHz) (CDCl$_3$) δ 8.26-8.24 (m, 1 H), 8.18-8.16 (m, 1H), 7.87 (br, 2H), 7.69-7.49 (m, 8H), 7.28 (s, 1H), 7.26-7.22 (m, 1H), 7.14 (s, 1H), 6.86 (s, 1H), 4.63-4.49 (m, 2H), 4.22-4.09 (m, 2H), 3.07 (s, 6H), 1.33 (s, 18H). $^{13}$C NMR (100 MHz) ((CDCl$_3$) δ 167.61, 141.82, 136.99, 133.30, 132.94, 130.33, 130.06, 127.70, 127.55, 127.26, 124.45, 124.34, 118.12, 117.80, 82.56, 54.26, 40.10, 27.91.

Example LH921: 2,2'-(Naphthalene-1,4-diylbis(((4-(methylsulfonamido) phenyl) sulfonyl) azanediyl)) diacetic Acid

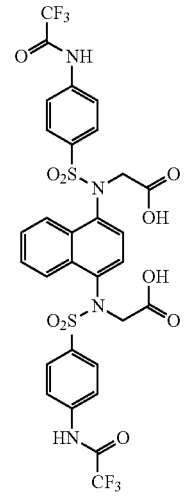

Prepared as described in the general procedure for removal of am sensitive protecting group (Method C2) to get the title compound as a white solid; the yield (9 mg, 58% yield). $^1$H NMR (400 MHz) (MeOH-d4) δ 8.05-8.01 (m, 2H), 7.64 (d, 2H, J=8.8 Hz), 7.61 (d, 2H, J=8.8 Hz), 7.47-7.45 (m, 2H), 7.33 (dd, 4H, J=2.8 Hz, 8.8 Hz), 7.26 (d, 2H, J=8.8 Hz), 4.69-4.60 (m, 2H), 4.36-4.30 (m, 2H), 3.06 (s, 3H), 3.04 (s, 3H). $^{13}$C NMR (100 MHz) (MeOH-d4) δ 172.07, 144.54, 138.64, 134.60, 134.39, 134.30, 130.91, 130.80, 129.20, 128.03, 125.49, 119.25, 54.13, 54.05, 40.07, 39.97. HRMS (ESI) Calcd for C$_{28}$H$_{28}$N$_4$O$_{12}$S$_4$ (M+H)$^+$ 741.0659, found 741.0671.

Intermediate: Di-tert-butyl 2,2'-(naphthalene-1,4-diylbis(((4-(2,2,2-trifluoroacetamido) phenyl) sulfonyl) azanediyl))diacetate

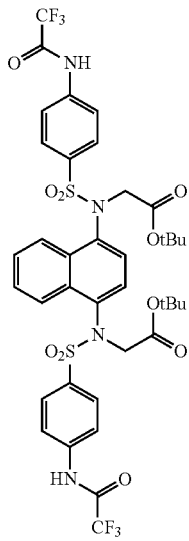 [SMILES: CC(C)(C)OC(=O)CN(c1ccc(N(CC(=O)OC(C)(C)C)S(=O)(=O)c2ccc(NC(=O)C(F)(F)F)cc2)c2ccccc12)S(=O)(=O)c1ccc(NC(=O)C(F)(F)F)cc1]

To a stirred solution of corresponding amine intermediate (16 mg, 0.026 mmol) in 1 ml pyridine at 0° C., TFAA (7.8 uL, 0.06 mmol) was added and the reaction stirred at 0° C. for 1 hour. Upon completion, reaction quenched with ice water and extracted with ethyl acetate, washed the organic layer with water, brine, and dried over sodium sulfate. The organic solvent removed under reduced pressure and then purify the crude product using a silica gel ISCO column ethyl acetate/hexane to get the desired product, the yield (21 mg, 82% yield). $^1$H NMR (400 MHz) (CDCl$_3$) δ 8.83 (br, 2H), 8.30-8.29 (m, 2H), 7.75 (d, 2H, J=8.8 Hz), 7.73-7.59 (m, 6H), 6.79 (s, 2H), 4.64-4.50 (m, 2H), 4.20-4.13 (m, 2H), 1.33 (s, 18H). $^{13}$C NMR (100 MHz) (CDCl$_3$) δ 167.65, 139.60, 137.12, 135.11, 133.62, 129.92, 129.71, 127.91, 127.49, 127.03, 124.57, 120.46, 120.20, 82.77, 54.48, 28.01.

Example LH926: 2,2'-(Naphthalene-1,4-diylbis(((4-(2,2,2-trifluoroacetamido) phenyl) sulfonyl) azanediyl)) diacetic Acid Prepared as described in the general procedure for removal of acid sensitive protecting group (Method C2) to get the title compound as a white solid; the yield (8 mg, 62% yield). $^1$H NMR (400 MHz) (DMSO) δ 12.84 (br, 2H), 11.59 (br, 2H), 8.27-8.16 (m, 2H), 7.92-7.85 (m, 4H), 7.72-7.69 (m, 4H), 7.58-7.55 (m, 2H), 7.16 (s, 1H), 7.01 (s, 1H), 4.54-4.38 (m, 4H). $^{13}$C NMR (100 MHz) (DMSO) δ 169.77, 169.74, 155.12, 154.75, 140.75, 140.69, 136.97, 136.90, 134.38, 133.92, 132.83, 132.74, 129.07, 128.90, 126.96, 126.75, 126.59, 124.50, 124.39, 120.80, 120.73, 116.95, 114.08, 59.72. HRMS (ESI) Calcd for $C_{30}H_{22}F_6N_4O_{10}S_2$ (M+H)$^+$ 777.0754, found 777.0759.

Intermediate: N,N'-(Naphthalene-1,4-diyl)bis(([1,1'-biphenyl]-4-sulfonamide))

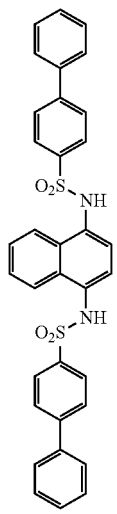

Prepared as described in the general procedure for synthesis of sulfonamides (method A1) to get the title compound as a light yellow solid; the yield (485 mg, 82% yield). $^1$H NMR (400 MHz) (DMSO) δ 10.27 (s, 2H), 7.96-7.94 (m, 2H), 7.76-7.62 (m, 12H), 7.46-7.34 (m, 8H), 7.12 (s, 2H). $^{13}$C NMR (100 MHz) (DMSO) δ. 144.06, 138.58, 138.19, 131.02, 130.09, 129.07, 128.90, 128.51, 127.50, 127.34, 127.13, 126.92, 126.69, 126.14, 125.97, 123.30, 123.01.

Intermediate: Di-tert-butyl 2,2'-(naphthalene-1,4-diylbis(([1,1'-biphenyl]-4-ylsulfonyl) azanediyl)) diacetate

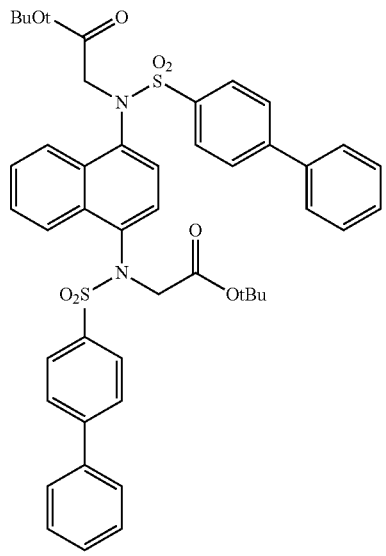

Prepared as described in the general procedure for synthesis of alkylated sulfonamides (method B) to get the title compound as oily product; the yield (116 mg, 71% yield). $^1$H NMR (400 MHz) (CDCl$_3$) δ 8.16-8.14 (m, 1H), 8.04-8.02 (m, 1H), 7.78 (d, 4H, J=8.4 Hz), 7.65-7.63 (m, 4H), 7.60-7.54 (m, 5H), 7.50-7.42 (m, 7H), 7.29-7.25 (m, 2H), 4.65-4.56 (m, 2H), 4.25-4.15 (m, 2H), 1.37 (s, 18H). $^{13}$C NMR (100 MHz) (CDCl$_3$) δ 167.60, 167.54, 145.92, 145.87, 139.23, 139.17, 137.49, 137.27, 137.13, 133.22, 132.99, 129.12, 129.08, 128.64, 128.61, 128.57, 127.81, 127.60, 127.45, 127.33, 124.40, 124.22, 82.50, 54.01, 53.91, 27.93.

Example LH922: 2,2'-(Naphthalene-1,4-diylbis(([1,1'-biphenyl]-4-ylsulfonyl)azanediyl))diacetic Acid

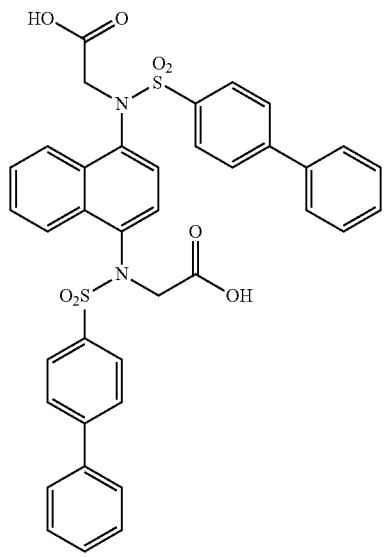 [SMILES: O=C(O)CN(c1ccc(N(CC(=O)O)S(=O)(=O)c2ccc(-c3ccccc3)cc2)c2ccccc12)S(=O)(=O)c1ccc(-c2ccccc2)cc1]

Prepared as described in the general procedure for removal of acid sensitive protecting group (Method C2) to get the title compound as a light yellow solid; the yield (24 mg, 84% yield). $^1$H NMR (400 MHz) (DMSO) δ) 7.99-7.97 (m, 2H), 7.73-7.70 (m, 4H), 7.63-7.50 (m, 8H), 7.45-7.35 (m, 8H), 7.32 (s, 1H), 7.26 (s, 1H), 4.70-4.61 (m, 2H), 4.28-4.18 (m, 2H). $^{13}$C NMR (100 MHz) (DMSO) δ 170.82, 170.78, 146.22, 139.33, 139.21, 137.56, 137.36, 137.27, 137.19, 133.15, 133.10, 129.28, 129.21, 128.75, 128.63, 128.35, 128.27, 127.64, 127.56, 127.45, 127.40, 124.33, 124.27, 53.20. HRMS (ESI) Calcd for C34130N$_2$O$_8$S$_2$ (M+H)$^+$ 707.1516, found 707.1529.

Example LH923: 2,2'-(Naphthalene-1,4-diylbis(((4-(1,3-dioxoisoindolin-2-yl)phenyl) sulfonyl) azanediyl)) diacetic Acid

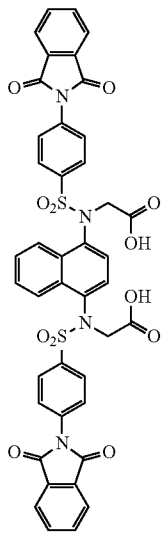 [SMILES: O=C(O)CN(c1ccc(N(CC(=O)O)S(=O)(=O)c2ccc(N3C(=O)c4ccccc4C3=O)cc2)c2ccccc12)S(=O)(=O)c1ccc(N2C(=O)c3ccccc3C2=O)cc1]

Prepared as described in the general procedure for removal sensitive protecting group (Method C2) to get the title compound as a light yellow solid; the yield (9 mg, 59% yield). $^1$H NMR (400 MHz) (DMSO) δ 12.94 (br, 2 H), 8.37-8.35 (m, 1H), 8.10-8.08 (m, 1H), 7.99-7.54 (m, 18H), 7.33 (s, 1H), 6.93 (s, 1H), 4.68-4.41 (m, 4H). $^{13}$C NMR (100 MHz) ((DMSO) δ 169.93, 166.45, 137.27, 136.97, 136.30, 136.24, 136.11, 134.97, 134.92, 133.09, 132.67, 131.50, 131.39, 128.74, 128.37, 127.38, 127.08, 126.98, 126.89, 126.50, 124.75, 124.34, 123.67, 123.53, 53.50. HRMS (ESI) Calcd for C$_{42}$H$_{28}$N$_4$O$_{12}$S$_2$ (M+H)$^+$ 845.1218, found 845.1230.

Intermediate: N,N'-(Naphthalene-1,4-diyl)bis(5,5,8,8-tetramethyl-5,6,7,8-tetrahydronaphthalene-2-sulfonamide)

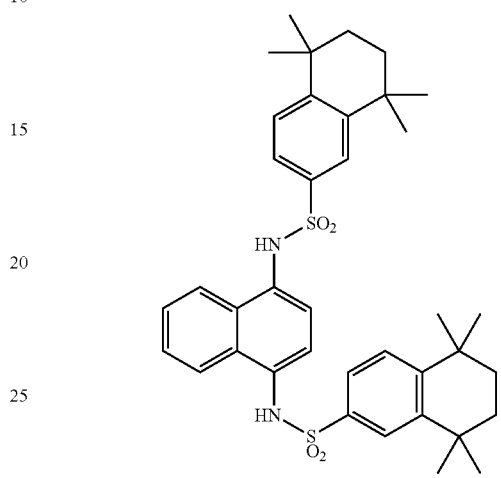

Prepared as described in the general procedure for synthesis of sulfonamides (method A1) to get the title compound as an off-white solid; the yield (515 mg, 78% yield). $^1$H NMR (400 MHz) (CDCl$_3$) δ 7.63-7.61 (m, 2 H), 7.42-7.37 (m, 4H), 7.29-7.19 (m, 5H), 1.57-1.52 (m, 8H), 7.161.17 (s, 12H), 0.94 (s, 12H). $^{13}$C NMR (100 MHz) (CDCl$_3$) δ 150.52, 145.99, 136.15, 131.05, 130.33, 127.39, 126.18, 125.62, 123.64, 123.54, 122.56, 34.53, 34.49, 31.47, 31.21.

Intermediate: Diethyl 2,2'-(naphthalene-1,4-diylbis((((5,5,8,8-tetramethyl-5,6,7,8-tetrahydro-naphthalen-2-yl) sulfonyl) azanediyl))diacetate

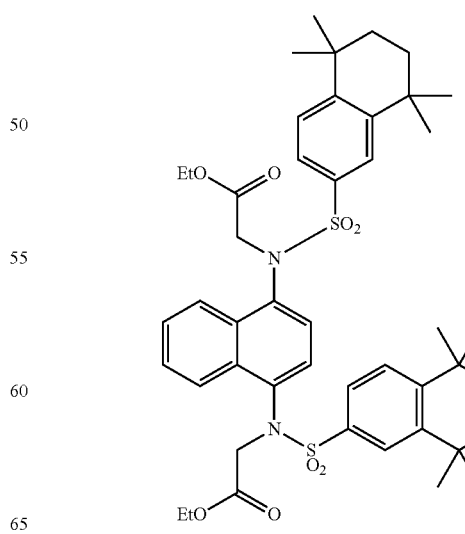

Prepared as described in the general procedure for synthesis of alkylated sulfonamides (method B) to get the title compound as oily product; the yield (68 mg, 82% yield). $^1$H NMR (400 MHz) (CDCl$_3$) δ) 7.80-7.77 (m, 2H), 7.56-7.52 (m, 2H), 7.49 (s, 1H), 7.44-7.33 (m, 7H), 4.68-4.56 (m, 2H), 4.23-4.08 (m, 6H), 1.67-1.60 (m, 8H), 1.30-1.13 (m, 24H), 1.00-1.88 (m, 2 H). $^{13}$C NMR (100 MHz) (CDCl$_3$) δ 168.75, 150.91, 150.86, 146.38, 146.07, 137.17, 135.90, 135.76, 132.98, 128.60, 128.55, 127.54, 127.18, 126.98, 126.73, 124.54, 124.44, 124.12, 61.52, 53.30, 53.16, 34.83, 34.80, 34.72, 34.55, 31.87, 31.82, 31.72, 31.69, 31.26, 14.20, 14.14.

Example LH827: 2,2'-(Naphthalene-1,4-diylbis(((5,5,8,8-tetramethyl-5,6,7,8-tetrahydronaphthalen-2-yl)sulfonyl)azanediyl))diacetic Acid

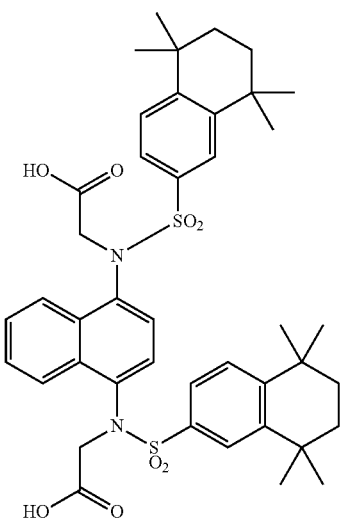 [SMILES: CC1(C)CCC(C)(C)c2cc(S(=O)(=O)N(CC(=O)O)c3ccc(N(CC(=O)O)S(=O)(=O)c4ccc5c(c4)C(C)(C)CCC5(C)C)c4ccccc34)ccc21]

Prepared as described in the general procedure for hydrolysis of ethyl ester to get di-acidic compounds (Method C1) (basic hydrolysis) to get the title compound as a white solid; the yield (28 mg, 85% yield). $^1$H NMR (400 MHz) (DMSO) δ) 12.50 (br, 2H), 7.74-7.72 (m, 2H), 7.56-7.52 (m, 4 H), 7.38-7.26 (m, 5H), 7.17 (s, 1H), 4.57-4.51 (m, 2H), 4.26-4.21 (m, 2H), 1.63-1.53 (m, 8H), 1.28-1.22 (m, 15H), 1.18 (s, 3H), 1.17 (s, 3H), 1.04 (s, 3H). $^{13}$C NMR (100 MHz) (DMSO) δ 169.96, 169.87, 150.22, 145.54, 145.31, 136.63, 136.50, 135.39, 135.04, 132.29, 132.22, 127.87, 127.63, 126.32, 125.74, 124.03, 123.91, 123.85, 52.86, 34.32, 34.26, 33.97, 33.93, 33.86, 31.38, 31.33, 31.25, 31.13, 30.97, 30.74, 30.64. HRMS (ESI) Calcd for C$_{42}$H$_{50}$N$_2$O$_8$S$_2$ (M+H)$^+$ 775.3081, found 775.3059.

Intermediate: N,N'-(Naphthalene-1,4-diyl)bis(quinoline-8-sulfonamide)

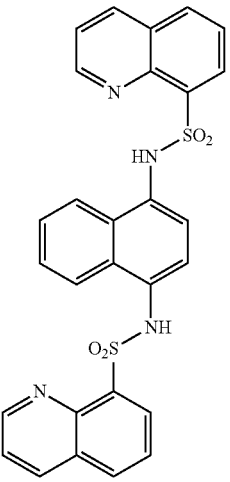 [SMILES: O=S(=O)(Nc1ccc(NS(=O)(=O)c2cccc3cccnc23)c2ccccc12)c1cccc2cccnc12]

Prepared as described in the general procedure for synthesis of sulfonamides (method A1) to get the title compound as a light yellow solid; the yield (379 mg, 70% yield). $^1$H NMR (400 MHz) (MeOH-d4) δ 9.27 (s, 2H), 9.26 (d, 1H, J=4.0 Hz), 9.05 (dd, 2H, J=2.0 Hz, 4.0 Hz), 8.50 (dd, 1H, J=1.6 Hz, 4.4 Hz), 8.37 (dd, 1H, J=1.2 Hz, 7.2 Hz), 8.30 (d, 1H, J=7.6 Hz), 8.21 (dd, 1H, J=1.2 Hz, 8.0 Hz), 8.07 (dd, 1H, J=1.2 Hz, 7.2 Hz), 7.95 (dd, 1H, J=1.6 Hz, 6.4 Hz), 7.88-7.84 (m, 2H), 7.86 (t, 1H, J=7.6 Hz), 7.71-7.68 (m, 2H), 7.58 (t, 2H, J=7.6 Hz), 7.18-7.15 (m, 1H), 6.75 (s, 2H). $^{13}$C NMR (100 MHz) (DMSO) δ 151.03, 142.48, 136.71, 135.66, 133.68, 130.90, 130.84, 130.41, 129.79, 128.52, 128.14, 125.32, 125.26, 123.14, 122.27, 121.75, 121.66

Intermediate: Diethyl 2,2'-(naphthalene-1,4-diylbis((quinolin-8-ylsulfonyl)azanediyl))diacetate

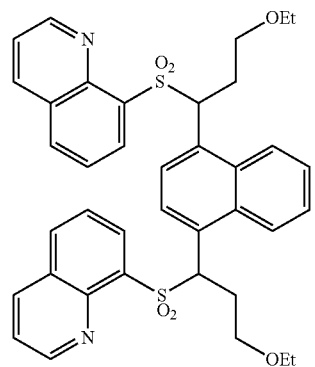 [SMILES: CCOCCC(c1ccc(C(CCOCC)S(=O)(=O)c2cccc3cccnc23)c2ccccc12)S(=O)(=O)c1cccc2cccnc12]

Prepared as described in the general procedure for synthesis of alkylated sulfonamides (method B) to get the title compound as oily product; the yield (113 mg, 79% yield). $^1$H NMR (400 MHz) (CDCl$_3$) δ) 9.15-9.14 (m, 2H), 8.34-8.27 (m, 3H), 8.19-8.13 (m, 2H), 8.07-7.99 (m, 2H), 7.87-7.85 (m, 1H), 7.76-7.75 (m, 1H), 7.63-758 (m, 2H), 7.51-7.39 (m, 2H), 7.21 (s, 1H), 7.13-7.11 (m, 1H), 7.04-7.03 (m, 1H), 5.48-5.42 (m, 2H), 4.81-4.71 (m, 2H), 4.09-4.00 (m, 4H), 1.16 (s, 3H), 1.14 (s, 3H). $^{13}$C NMR (100 MHz) (CDCl$_3$) δ 169.97, 151.26, 144.28, 137.97, 136.92, 133.75, 133.51, 133.31, 129.12, 126.84, 126.66, 125.78, 124.02, 123.91, 122.22, 61.20, 54.88, 54.71, 14.34, 14.19.

Example LH830: 2,2'-(Naphthalene-1,4-diylbis ((quinolin-8-ylsulfonyl)azanediyl))diacetic Acid

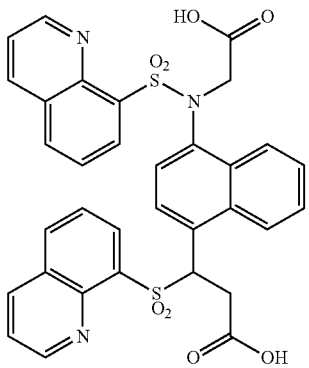 [SMILES: O=C(O)CC(c1ccc(N(CC(=O)O)S(=O)(=O)c2cccc3cccnc23)c2ccccc12)S(=O)(=O)c1cccc2cccnc12]

Prepared as described in the general procedure for hydrolysis of ethyl ester to get di-acidic compounds (Method C1) (basic hydrolysis) to get the title compound as a beige solid; the yield (18 mg, 74% yield). $^1$H NMR (400 MHz) (DMSO) δ) 9.18-9.13 (m, 2H), 8.58 (d, 2H, J=8.0 Hz), 8.29-8.22 (m, 2H), 7.98 (d, 2H, J=7.2 Hz), 7.78-7.51 (m, 6H), 7.22-7.06 (m, 4H), 5.27-5.05 (m, 2H), 4.80-4.71 (m, 2H). $^{13}$C NMR (100 MHz) (DMSO) δ 170.80, 151.50, 143.13, 137.17, 136.92, 136.66, 136.49, 134.28, 132.41, 128.72, 128.39, 126.08, 125.57, 123.60, 122.62, 54.23. HRMS (ESI) Calcd for C$_{32}$H$_{24}$N$_4$O$_8$S$_2$ (M+H)$^+$ 657.1108, found 657.1092.

Intermediate: N,N'-(Naphthalene-1,4-diyl)bis(quinoline-8-sulfonamide)

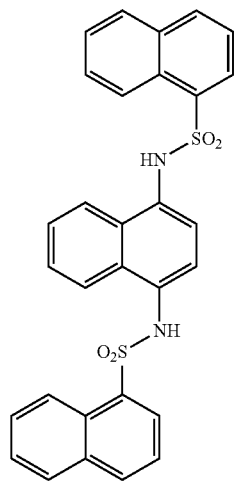 [SMILES: O=S(=O)(Nc1ccc(NS(=O)(=O)c2cccc3ccccc23)c2ccccc12)c1cccc2ccccc12]

Prepared as described in the general procedure for synthesis of sulfonamides (method A1) to get the title compound as an off-white solid; the yield (414 mg, 77% yield). $^1$H NMR (400 MHz) (DMSO) δ 10.49 (br, 2H), 8.72-8.70 (m, 2H), 8.14 (d, 3H, J=8.0 Hz), 8.03-8.01 (m, 2H), 7.92 (d, 2H, J=7.2 Hz), 7.78-7.75 (m, 3H), 7.62-7.60 (m, 4H), 7.48 (t, 2H, J=8.0 Hz), 7.11-7.09 (m, 2H), 6.93 (s, 2H). $^{13}$C NMR (100 MHz) (DMSO) δ 134.94, 134.13, 133.63, 130.67, 129.73, 129.21, 128.90, 127.77, 127.48, 126.78, 125.83, 124.46, 124.30, 122.93, 122.39.

Intermediate: Diethyl 2,2'-(naphthalene-1,4-diylbis ((naphthalen-1-ylsulfonyl)azanediyl))diacetate

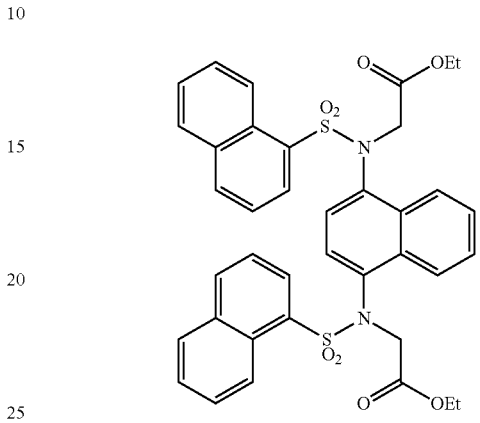

Prepared as described in the general procedure for synthesis of alkylated sulfonamides (method B) to get the title compound as oily product; the yield (90 mg, 63% yield). $^1$H NMR (400 MHz) (CDCl$_3$) δ) 8.43 (d, 1H, J=8.8 Hz), 8.35 (d, 1H, J=8.8 Hz), 8.18-8.13 (m, 2H), 8.06 (d, 1H, J=8.0 Hz), 8.00 (d, 1H, J=8.0 Hz), 7.90 (d, 1H, J=8.0 Hz), 7.84-7.78 (m, 2H), 7.72-7.69 (m, 1H), 7.55-7.40 (m, 5H), 7.33-7.28 (m, 2H), 7.23 (s, 2H), 7.15-7.12 (m, 1H), 4.79-4.69 (m, 2H), 4.29-4.21 (m, 2H), 4.14-3.89 (m, 4H), 1.11-1.04 (m, 6H). $^{13}$C NMR (100 MHz) (CDCl$_3$) δ 168.69, 168.58, 137.01, 136.94, 134.86, 134.82, 134.44, 134.35, 132.86, 132.74, 130.82, 129.08, 128.90, 128.84, 128.67, 128.24, 127.81, 127.30, 127.09, 127.06, 126.86, 125.66, 125.58, 124.21, 124.15, 124.03, 123.92, 61.62, 61.56, 53.34, 53.19, 14.05, 14.02.

Example LH831: 2,2'-(Naphthalene-1,4-diylbis ((naphthalen-1-ylsulfonyl)azanediyl))diacetic Acid

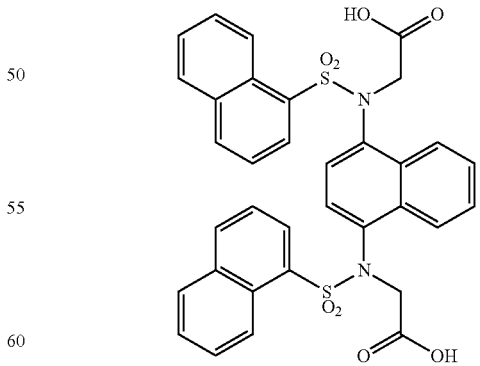

Prepared as described in the general procedure for hydrolysis of ethyl ester to get di-acidic compounds (Method C1) (basic hydrolysis) to get the title compound as a white solid; the yield (27 mg, 78% yield). $^1$H NMR (400 MHz) (MeOH-d4) δ) 8.38-8.36 (m, 1H), 8.14-7.94 (m, 5H), 8.00-7.95 (m, 1 H), 7.94-7.82 (m, 1H), 7.60-7.37 (m, 8H), 7.29-7.27 (m, 2H), 7.00-6.96 (m, 2H), 4.79-4.67 (m, 2H), 4.34-4.20 (m, 2H). $^{13}$C NMR (100 MHz) (MeOH-d4) δ 171.96, 170.94, 138.12, 138.02, 136.01, 135.89, 135.68, 133.76, 131.95, 131.85, 131.60, 131.49, 130.16, 130.00, 129.96, 129.75, 129.07, 128.59, 128.00, 127.77, 127.66, 127.53, 126.53, 126.48, 126.19, 125.27, 124.90, 124.80, 54.28, 53.94. HRMS (ESI) Calcd for C34H26N2O8S2 (M+H)$^+$654.1203, found 655.1194.

Intermediate: N,N'-(Naphthalene-1,4-diyl)bis(4-bromonaphthalene-1-sulfonamide)

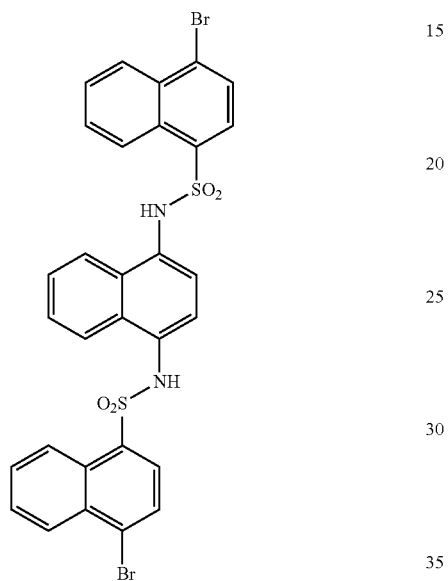

Prepared as described in the general procedure for synthesis of sulfonamides (method A1) to get the title compound as a yellow solid; the yield (468 mg, 67% yield). $^1$H NMR (400 MHz) (DMSO) δ 10.65 (s, 2H), 8.77 (d, 2H, J=8.4 Hz), 8.25 (d, 2H, J=8.4 Hz), 7.92-7.69 (m, 10H), 7.13 (dd, 2H, J=2.8 Hz, 6.0 Hz), 6.99 (s, 2H). $^{13}$C NMR (100 MHz) (DMSO) δ 135.39, 131.60, 130.66, 129.87, 129.52, 128.79, 128.77, 128.69, 128.61, 128.43, 127.50, 126.02, 125.29, 122.92, 122.85.

Intermediate: Diethyl 2,2'-(naphthalene-1,4-diylbis(((4-bromonaphthalen-1-yl)sulfonyl)azanediyl))diacetate

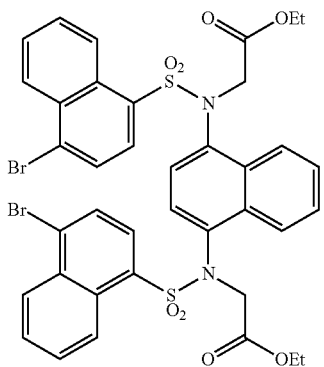 [SMILES: CCOC(=O)CN(c1ccc(N(CC(=O)OCC)S(=O)(=O)c2ccc(Br)c3ccccc23)c2ccccc12)S(=O)(=O)c1ccc(Br)c2ccccc12]

Prepared as described in the general procedure for synthesis of alkylated sulfonamides (method B) to get the title compound as oily product; the yield (111 mg, 64% yield). $^1$H NMR (400 MHz) (CDCl$_3$) δ) 8.42-8.28 (m, 2H), 8.30 (d, 1H, J=8.4 Hz), 8.04-7.98 (m, 2H), 7.84-7.81 (m, 2H), 7.76 (d, 1H, J=8.0 Hz), 7.72-7.69 (m, 1H), 7.63 (t, 1H, J=8.4 Hz), 7.57 (t, 1H, J=8.4 Hz), 7.45 (t, 1H, J=7.6 Hz), 7.37 (s, 1 H), 7.34-7.28 (m, 2H), 7.20-7.17 (m, 1H), 4.80-4.70 (m, 2H), 4.28-4.18 (m, 2H), 4.10-3.86 (m, 4H), 1.13-1.05 (m, 6H). $^{13}$C NMR (100 MHz) (CDCl$_3$) δ 168.50, 168.41, 136.86, 136.81, 134.88, 134.70, 132.73, 132.68, 132.63, 130.63, 130.59, 130.45, 130.40, 129.92, 128.96, 128.88, 128.69, 128.56, 128.52, 128.47, 128.23, 128.16, 128.12, 127.50, 127.29, 126.09, 126.02, 123.91, 123.81, 61.71, 61.63, 53.27, 53.12, 14.03, 13.99.

Example LH833: 2,2'-(Naphthalene-1,4-diylbis(((4-bromonaphthalen-1-yl)sulfonyl)azanediyl))diacetic Acid

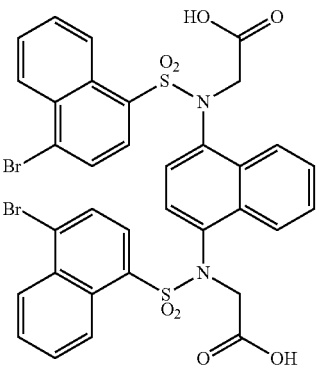 [SMILES: O=C(O)CN(c1ccc(N(CC(=O)O)S(=O)(=O)c2ccc(Br)c3ccccc23)c2ccccc12)S(=O)(=O)c1ccc(Br)c2ccccc12]

Prepared as described in the general procedure for hydrolysis of ethyl ester to get di-acidic compounds (Method C1) (basic hydrolysis) to get the title compound as yellow solid; the yield (14 mg, 71% yield). $^1$H NMR (400 MHz) (DMSO) δ) 8.32 (t, 2H, J=8.0 Hz), 8.20 (d, 1H, J=8.4 Hz), 8.11-8.00 (m, 4H), 7.94 (d, 1H, J=8.0 Hz), 7.90-7.87 (m, 1H), 7.77 (t, 1H, J=7.6 Hz), 7.72-7.70 (m, 1H), 7.62 (t, 1H, J=8.0 Hz), 7.50 (t, 1H, J=8.0 Hz), 7.38 (s, 1H), 7.31-7.27 (m, 2H), 7.19-7.16 (m, 1H), 7.10 (s, 1H), 4.69-4.61 (m, 2H), 4.40-4.27 (m, 2H). $^{13}$C NMR (100 MHz) (DMSO) δ 171.88, 169.61, 136.29, 134.35, 134.01, 132.28, 132.05, 131.76, 131.54, 130.77, 130.52, 129.22, 129.17, 129.07, 129.01, 128.90, 128.67, 128.48, 128.33, 128.20, 127.88, 127.42, 127.13, 126.49, 125.60, 125.46, 123.90, 123.63, 55.08, 52.75. HRMS (ESI) Calcd for C$_{34}$H$_{24}$Br$_2$N$_2$O$_8$S$_2$ (M+H)$^+$ 810.9414, found 810.9452

Intermediate: N,N'-(Naphthalene-1,4-diyl)bis(2,3-dihydrobenzo[b][1,4]dioxine-6-sulfonamide)

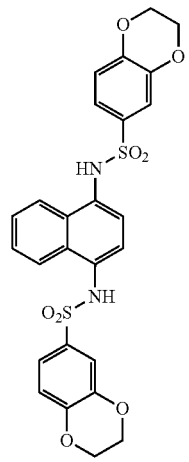 [SMILES: O=S(=O)(Nc1ccc(NS(=O)(=O)c2ccc3c(c2)OCCO3)c2ccccc12)c1ccc2c(c1)OCCO2]

Prepared as described in the general procedure for synthesis or sulfonamides (method A1) to get the title compound as an off-white solid; the yield (439 mg, 79% yield). $^1$H NMR (400 MHz) (DMSO) δ 10.26 (s, 2H), 8.19-8.16 (m, 2H), 7.65-7.62 (m, 2H), 7.32 (d, 2H, J=2.0 Hz), 7.28 (d, 1H, J=2.0 Hz), 7.26-7.25 (m, 3H), 7.12 (s, 1H), 7.10 (s, 1 ah), 4.48-4.44 (m, 8H). $^{13}$C NMR (100 MHz) (DMSO) δ 147.03, 143.15, 132.16, 131.02, 130.02, 126.09, 123.30, 122.62, 120.30, 117.35, 115.68, 64.33, 63.98.

Intermediate: Diethyl 2,2'-(naphthalene-1,4-diylbis(((2,3-dihydrobenzo[b][1,4]dioxin-6-yl)sulfonyl)azanediyl))diacetate

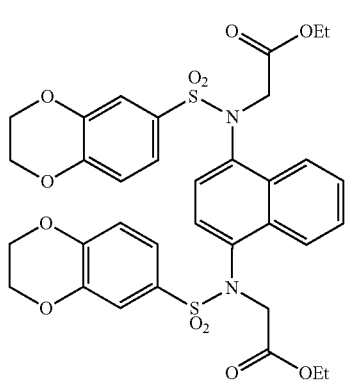 [SMILES: O=C(O)CN(c1ccc(N(CC(=O)O)S(=O)(=O)c2ccc3c(c2)OCCO3)c2ccccc12)S(=O)(=O)c1ccc2c(c1)OCCO2]

Prepared as described in the general procedure for synthesis of alkylated sulfonamides (method B) to get the title compound as oily product; the yield (94 mg, 65% yield). $^1$H NMR (400 MHz) (CDCl$_3$) δ 8.13-8.10 (m, 2H), 7.57-7.52 (m, 2H) 7.29-7.14 (m, 6H), 6.90 (t, 2H, J=8.4 Hz), 74.70-4.56 (m, 2H), 4.33-4.26 (m, 10H), 4.15-4.09 (m, 4H), 41.27-1.17 (m, 6H). $^{13}$C NMR (100 MHz) (CDCl$_3$) δ 168.73, 168.66, 147.79, 147.75, 143.41, 143.39, 137.26, 137.11, 133.11, 133.04, 131.36, 130.65, 127.57, 127.43, 127.24, 124.25, 121.97, 121.76, 117.69, 117.62, 117.50, 117.45, 64.56, 64.12, 61.44, 53.22, 53.10, 13.99.

Example LH837: 2,2'-(Naphthalene-1,4-diylbis(((2,3-dihydrobenzo[b][1,4] dioxin-6-yl) sulfonyl) azanediyl)) diacetic Acid

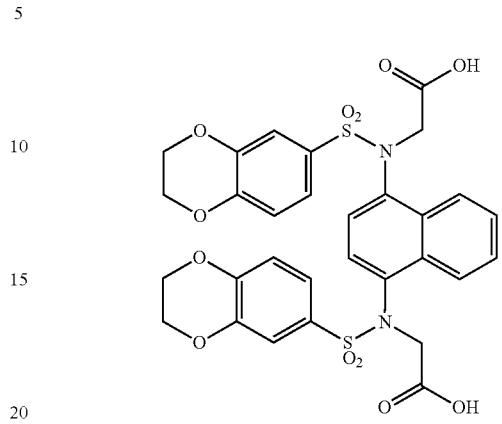

Prepared as described in the general procedure for hydrolysis of ethyl ester to get di-acidic compounds (Method C1) (basic hydrolysis) to get the title compound as a beige solid; the yield (21 mg, 76% yield). $^1$H NMR (400 MHz) (DMSO) δ) 8.26-8.13 (m, 2H), 7.58-7.56 (m, 2H), 7.20-7.15 (m, 3H), 7.06-6.96 (m, 5H), 4.50-4.30 (m, 12 H). $^{13}$C NMR (100 MHz) (DMSO) δ 169.82, 147.66, 143.33, 137.01, 132.86, 132.74, 130.20, 129.66, 126.79, 126.53, 126.36, 124.54, 124.41, 121.60, 121.36, 117.44, 117.31, 116.75, 116.62, 64.49, 64.05, 53.10. HRMS (ESI) Calcd for $C_{30}H_{26}N_2O_{12}S_2$ (M+H)$^+$ 671.1000, found 671.0994.

Intermediate: N,N'-(Naphthalene-1,4-diyl)bis(7-chloro-2,3-dihydrobenzo[b][1,4]dioxine-6-sulfonamide)

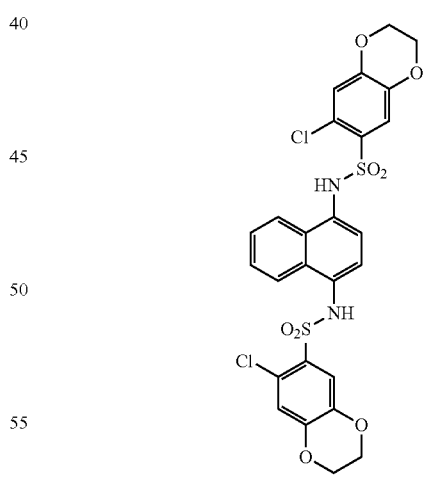

Prepared as described in the general procedure for synthesis or sulfonamides (method A1) to get the title compound as a pink solid; the yield (368 mg, 59% yield). 41 NMR (400 MHz) (DMSO) δ 10.35 (s, 2H), 8.15 (dd, 2H, J=3.2 Hz, 6.4 Hz), 7.50 (dd, 2H, J=3.2 Hz, 6.4 Hz), 7.25 (s, 2H), 7.12 (d, 2H, J=3.2 Hz), 4.29 (t, 4H, J=2.8 Hz), 4.24 (t, 4H, J=3.2 Hz). $^{13}$C NMR (100 MHz) (DMSO) δ 147.36, 141.76, 130.23, 129.57, 126.31, 1213.34, 122.70, 122.66, 119.73, 119.36, 64.52, 63.99, 59.70, 20.71, 14.05.

Intermediate: Diethyl 2,2'-(naphthalene-1,4-diylbis (((7-chloro-2,3-dihydrobenzo[b][1,4]dioxin-6-yl)sulfonyl) azanediyl))diacetate

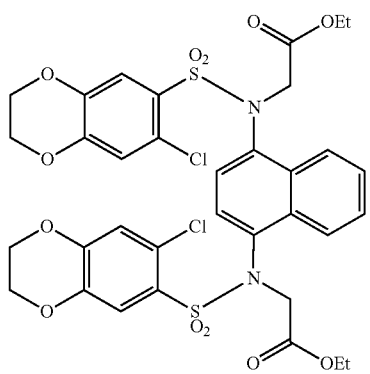

Prepared as described in the general procedure for synthesis of alkylated sulfonamides (method B) to get the title compound as oily product; the yield (97 mg, 61% yield). $^1$H NMR (400 MHz) (DMSO) δ) 8.08-8.06 (m, 2H), 7.53-7.47 (m, 4H), 7.18-7.14 (m, 4H), 4.82-4.73 (m, 2H), 4.55-4.49 (m, 2H), 4.33-4.24 (m, 8H), 4.06-4.02 (m, 4H), 1.12-1.06 (m, 6H). $^{13}$C NMR (100 MHz) (DMSO) δ 168.58, 168.37, 147.79, 141.87, 136.09, 132.15, 128.26, 127.89, 126.76, 123.73, 123.18, 120.34, 120.03, 119.90, 64.65, 64.00, 60.94, 53.63, 13.79.

Example LH835: 2,2'-(Naphthalene-1,4-diylbis(((7-chloro-2,3-dihydrobenzo[b][1,4]dioxin-6-yl)sulfonyl) azanediyl))diacetic Acid

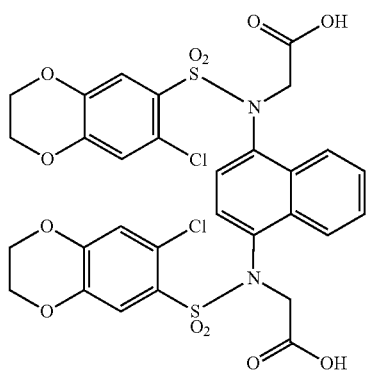 [SMILES: CCOC(=O)CN(c1ccc(N(CC(=O)OCC)S(=O)(=O)c2cc3c(cc2Cl)OCCO3)c2ccccc12)S(=O)(=O)c1cc2c(cc1Cl)OCCO2]

Prepared as described in the general procedure for hydrolysis of ethyl ester to get di-acidic compounds (Method C1) (basic hydrolysis) to get the title compound as a pink solid; the yield (26 mg, 75% yield). $^1$H NMR (400 MHz) (DMSO) δ) 12.92 (s, 2H), 8.05-8.03 (m, 2H), 7.56 (s, 1 H), 7.50-7.13 (m, 3H), 7.17 (s, 2H), 7.15 (s, 1H), 7.13 (s, 1H), 4.77-4.67 (m, 2H), 4.44-4.39 (m, 2H), 4.34-4.28 (m, 4H), 4.28-4.23 (m, 4H). $^{13}$C NMR (100 MHz) (DMSO) δ 170.08, 169.92, 147.74, 141.90, 136.16, 132.18, 128.53, 128.26, 126.88, 126.71, 123.75, 123.22, 120.35, 120.16, 120.02, 119.92, 64.70, 64.06, 53.68. HRMS (ESI) Calcd for $C_{30}H_{24}Cl_2N_2O_{12}S_2$ (M+H)$^+$ 739.0220, found 739.0238.

Intermediate: N,N'-(Naphthalene-1,4-diyl)bis(chromane-6-sulfonamide)

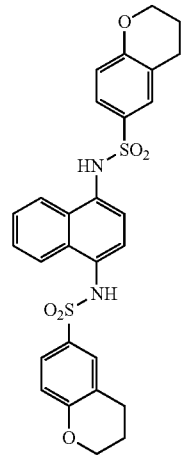 [SMILES: O=S(=O)(Nc1ccc(NS(=O)(=O)c2ccc3c(c2)CCCO3)c2ccccc12)c1ccc2c(c1)CCCO2]

Prepared as described in the general procedure for synthesis of sulfonamides (method A1) to get the title compound as a beige solid; the yield (452 mg, 81% yield). $^1$H NMR (400 MHz) (DMSO) δ 9.97 (s, 2H), 7.97 (dd, 2H, J=3.2 Hz, 6.4 Hz), 7.42 (dd, 2H, J=3.2 Hz, 6.4 Hz), 7.36-7.32 (m, 4H), 7.04 (s, 2H), 6.77 (d, 2H, J=8.4 Hz), 4.17 (t, 4H, J=4.8 Hz), 2.64 (t, 4H, J=6.0 Hz), 1.88-1.86 (m, 4H). $^{13}$C NMR (100 MHz) (DMSO) δ 157.86, 131.12, 130.79, 130.04, 128.86, 126.12, 125.94, 123.36, 122.82, 122.56, 116.67, 66.49, 23.96, 21.05.

Intermediate: Diethyl 2,2'-(naphthalene-1,4-diylbis ((chroman-6-ylsulfonyl)azanediyl))diacetate

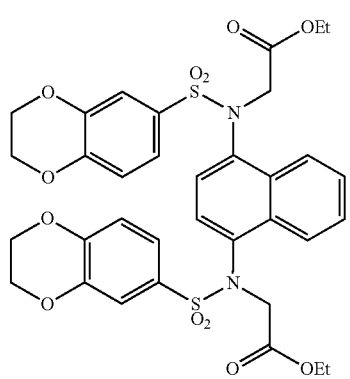

Prepared as described in the general procedure for synthesis of alkylated sulfonamides (method B) to get the title compound as oily product; the yield (88 mg, 61% yield). $^1$H NMR (400 MHz) (CDCl$_3$) δ) 8.09 (dd, 1H, J=3.2 Hz, 6.4 Hz), 8.00 (dd, 1H, J=3.2 Hz, 6.4 Hz), 7.52 (dd, 2H, J=3.2 Hz, 6.4 Hz), 7.47-7.22 (m, 6H), 6.82-6.78 (m, 3H), 4.65-4.54 (m, 2H), 4.29-4.28 (m, 2H), 4.25-4.21 (m, 4H), 4.13-4.07 (m, 4H), 2.72-2.68 (m, 4H), 2.00-1.98 (m, 4 H), 1.17 (t, 6H, J=7.2 Hz). $^{13}$C NMR (100 MHz) (CDCl$_3$) δ 168.84, 168.75, 158.99, 158.95, 137.31, 137.19, 133.15, 132.99, 130.38, 130.27, 129.63, 129.26, 127.87, 127.57, 127.47, 127.08, 124.35, 124.19, 122.63, 122.56, 117.14, 66.98, 61.41, 53.07, 24.70, 21.66, 14.02.

Example LH838: N-(4-(N-(Carboxymethyl)chromane-6-sulfonamido)naphthalen-1-yl)-N-(chroman-7-ylsulfonyl) glycine

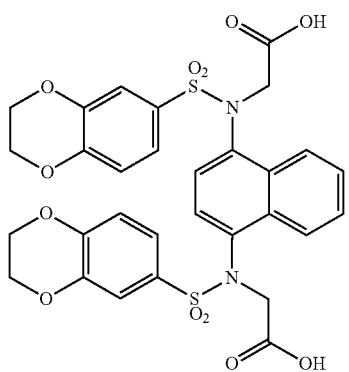 [SMILES: O=C(O)CN(c1ccc(N(CC(=O)O)S(=O)(=O)c2ccc3c(c2)OCCO3)c2ccccc12)S(=O)(=O)c1ccc2c(c1)OCCO2]

Prepared as described in the general procedure for hydrolysis of ethyl ester to get di-acidic compounds (Method C1) (basic hydrolysis) to get the title compound as an off-white solid; the yield (19 mg, 77% yield). $^1$H NMR (400 MHz) (DMSO) δ) 8.21-8.20 (m, 2H), 7.57-7.55 (m, 2H), 7.42 (s, 1H), 7.32-7.27 (m, 3H), 7.12 (s, 1H), 7.09 (s, 1H), 6.88-6.83 (m, 2H), 4.41 (s, 2H), 4.39 (s, 2H), 4.23 (t, 4H, J=6.8 Hz), 2.76-2.69 (m, 4H), 1.95-1.94 (m, 4H). $^{13}$C NMR (100 MHz) (DMSO) δ 169.93, 158.49, 137.13, 137.07, 132.84, 129.99, 128.44, 127.26, 127.05, 126.71, 126.44, 124.55, 123.16, 116.78, 116.63, 66.70, 53.09, 24.09, 23.96, 21.11. HRMS (ESI) Calcd for $C_{32}H_{30}N_2O_{10}S_2$ $(M+H)^+$ 667.1415, found 667.1410.

Intermediate: N,N'-(Naphthalene-1,4-diyl)bis(benzo[d][1,3]dioxole-5-sulfonamide)

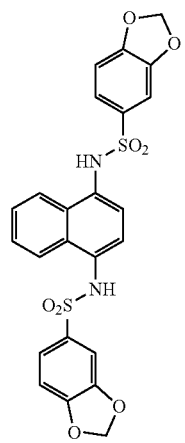 [SMILES: O=S(=O)(Nc1ccc(NS(=O)(=O)c2ccc3c(c2)OCO3)c2ccccc12)c1ccc2c(c1)OCO2]

Prepared as described in the general procedure for synthesis of sulfonamides (method A1) to get the title compound as a light pink solid; the yield (401 mg, 74% yield). $^1$H NMR (400 MHz) (DMSO) δ 10.15 (s, 2H), 8.05-8.03 (m, 2H), 7.50-7.48 (m, 2H), 7.18 (d, 1H, J=2.0 Hz), 7.16 (s, 3H), 7.09 (s, 2H), 6.99 (d, 2H, J=8.8 Hz), 6.16 (s, 4H). $^{13}$C NMR (100 MHz) (DMSO) δ 150.93, 147.73, 133.04, 131.10, 130.19, 126.24, 123.41, 122.88, 122.50, 108.15, 106.57, 102.49.

Intermediate: Diethyl 2,2'-(naphthalene-1,4-diylbis ((benzo[d][1,3]dioxol-5-ylsulfonyl) azanediyl)) diacetate

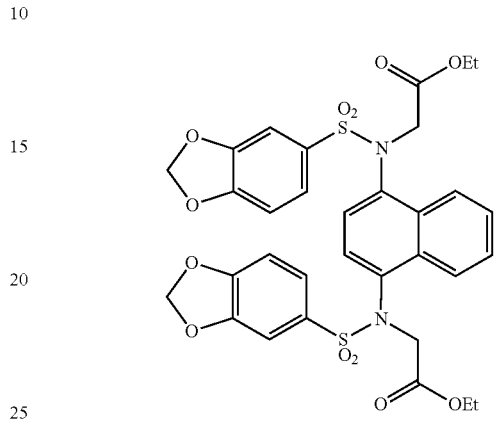

Prepared as described in the general procedure for synthesis of alkylated sulfonamides (method B) to get the title compound as oily product; the yield (106 mg, 76% yield). $^1$H NMR (400 MHz) (DMSO) δ) 8.36 (dd, 1H, J=2.8 Hz, 6.0 Hz), 8.23 (dd, 1H, J=3.2 Hz, 6.0 Hz), 7.64-7.62 (m, 2H), 7.24-7.16 (m, 5H), 7.17 (d, 1H, J=8.4 Hz), 7.02-6.99 (m, 2H), 6.21 (d, 2H, J=2.0 Hz), 6.16 (d, 2H, J=6.0 Hz), 4.64-4.47 (m, 4H), 4.07-3.97 (m, 4H), 1.10-1.04 (m, 6H). $^{13}$C NMR (100 MHz) (DMSO) δ 168.15, 151.29, 151.22, 147.63, 136.70, 132.67, 132.49, 130.52, 129.89, 126.50, 126.40, 125.96, 124.33, 124.11, 123.66, 123.35, 107.85, 107.28, 107.18, 102.37, 60.60, 53.02, 52.92, 13.42.

Example LH843: 2,2'-(Naphthalene-1,4-diylbis ((benzo[d][1,3]dioxol-5-ylsulfonyl) azanediyl)) diacetic Acid

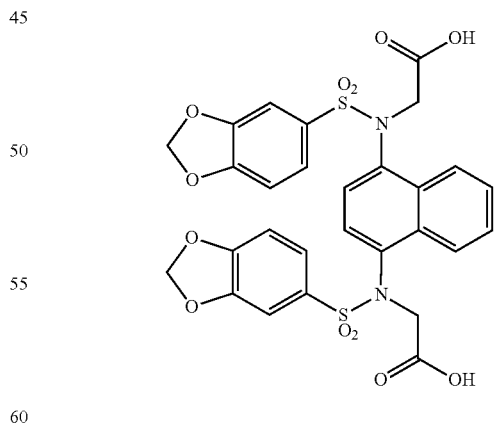

Prepared as described in the general procedure for hydrolysis of ethyl ester to get di-acidic compounds (Method C1) (basic hydrolysis) to get the title compound as a pink solid; the yield (17 mg, 62% yield). $^1$H NMR (400 MHz) (DMSO) δ) 8.29 (s, 1H), 8.17 (s, 1H), 7.58 (s, 2H), 7.19-7.00 (m, 8H), 6.21-6.17 (m, 4H), 4.48-4.35 (m, 4H). $^{13}$C NMR (100 MHz) (DMSO) δ 169.88, 151.48, 151.42, 147.90, 147.86, 137.00, 132.92, 132.75, 131.07, 130.41, 126.88, 126.67, 126.57, 126.34, 124.63, 124.43, 123.89, 123.62, 108.12, 107.58, 107.48, 102.63, 53.23, 53.12. HRMS (ESI) Calcd for $C_{28}H_{22}N_2O_8S_2$ (M+H)$^+$ 643.0687, found 643.0683.

Example LH839: 2,2'-(Naphthalene-1,4-diylbis(((2, 3-dihydrobenzofuran-5-yl)sulfonyl) azanediyl)) diacetic Acid

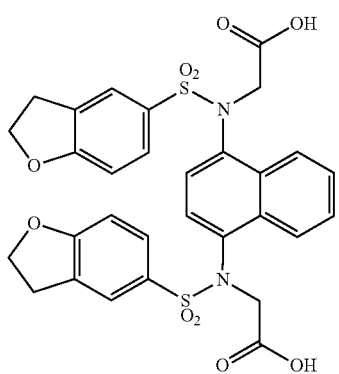 [SMILES: O=C(O)CN(c1ccc(N(CC(=O)O)S(=O)(=O)c2ccc3c(c2)CCO3)c2ccccc12)S(=O)(=O)c1ccc2c(c1)CCO2]

Prepared as described in the general procedure for hydrolysis of ethyl ester to get di-acidic compounds (Method C1) (basic hydrolysis) to get the title compound as light-pink solid; the yield (21 mg, 72% yield). $^1$H NMR (400 MHz) (DMSO) δ) 12.75 (s, 1H), 8.27-8.22 (m, 2H), 7.59-7.56 (m, 3H), 7.48 (s, 1H), 7.37 (d, 1H, J=8.4 Hz), 7.33 (d, 1H, J=8.4 Hz), 7.11 (s, 1H), 7.05 (s, 1H), 6.90 (d, 1H, J=8.8 Hz), 6.86 (d, 1H, J=8.8 Hz), 4.71-4.63 (m, 4H), 4.42 (s, 2H), 4.40 (s, 2H), 3.28-3.19 (m, 4H). $^{13}$C NMR (100 MHz) (DMSO) δ 169.43, 163.21, 136.68, 132.41, 128.89, 132.41, 128.89, 128.65, 128.44, 126.21, 126.02, 124.65, 124.11, 108.48, 108.33, 71.87, 52.65, 27.95. HRMS (ESI) Calcd for $C_{30}H_{26}N_2O_{10}S_2$(M+H)$^+$ 639.1102, found 639.1115.

Intermediate: N,N'-(Naphthalene-1,4-diyl)bis(N-(cyanomethyl)-4-methoxybenzenesulfonamide)

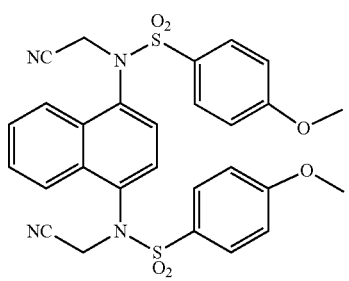 [SMILES: COc1ccc(S(=O)(=O)N(CC#N)c2ccc(N(CC#N)S(=O)(=O)c3ccc(OC)cc3)c3ccccc23)cc1]

Prepared as described in the general procedure for synthesis of alkylated sulfonamides (method B) to get the title compound as oily product; the yield (128 mg, 74% yield). $^1$H NMR (400 MHz) (CDCl$_3$) 8.09-8.08 (m, 2H), 8.19-8.09 (m, 2H), 7.75-6.36 (m, 6H), 7.05-7.00 (m, 6H), 5.11-4.93 (m, 2H), 4.32-4.25 (m, 2H), 3.93 (s, 3H), 3.89 (s, 3H). $^{13}$C NMR (100 MHz) (CDCl$_3$) δ 164.14, 136.77, 133.47, 130.61, 130.46, 129.16, 129.00, 126.81, 126.48, 123.86, 114.84, 114.81, 114.63, 55.90, 40.07, 39.98.

Example LH715: N-((1H-Tetrazol-5-yl)methyl)-N-(4-0N-((2H-tetrazol-5-yl)methyl)-4-methoxyphenyl) sulfonamido)naphthalen-1-yl)-4-methoxybenzene-sulfonamide

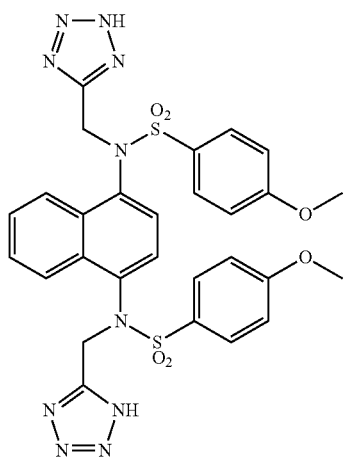 [SMILES: COc1ccc(S(=O)(=O)N(Cc2nn[nH]n2)c2ccc(N(Cc3nnn[nH]3)S(=O)(=O)c3ccc(OC)cc3)c3ccccc23)cc1]

Prepared as described in the general procedure for synthesis of tetrazole (Method D) to get the title compound as a white solid; the yield (23 mg, 77% yield). $^1$H NMR (400 MHz) (DMSO) δ) 8.15-8.13 (m, 1H), 8.05-8.02 (m, 1H), 7.60-7.49 (m, 6H), 7.17 (d, 2H, J=8.8 Hz), 7.07 (d, 2H, J=8.8 Hz), 6.79 (s, 1H), 6.75 (s, 1H), 5.35-5.23 (m, 2H), 5.12-4.97 (m, 2H), 3.91 (s, 3H), 3.86 (s, 3H). $^{13}$C NMR (100 MHz) (DMSO) δ 163.19, 163.12, 162.36, 136.55, 136.00, 133.08, 132.88, 130.28, 130.10, 123.10, 128.01, 126.96, 126.33, 125.95, 124.09, 123.97, 114.52, 114.47, 55.85, 55.78, 45.38, 44.82. HRMS (ESI) Calcd for $C_{28}H_{26}N_{10}O_6S_2$ (M+H)$^+$ 663.1551, found 663.1538.

Intermediate: N,N'-(Naphthalene-1,4-diyl)bis(N-(cyanomethyl)-2,6-difluorobenzenesulfonamide)

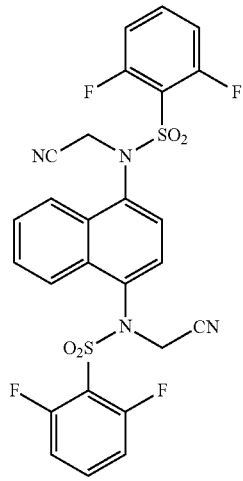 [SMILES: N#CCN(c1ccc(N(CC#N)S(=O)(=O)c2c(F)cccc2F)c2ccccc12)S(=O)(=O)c1c(F)cccc1F]

Prepared as described in the general procedure for synthesis of alkylated sulfonamides (method B) to get the title compound as oily product; the yield (128 mg, 73% yield). $^1$H NMR (400 MHz) (DMSO) δ 8.17-8.15 (m, 1H), 8.09-

8.08 (m, 1H), 7.95-7.83 (m, 2H), 7.79-7.76 (m, 2H), 7.41-7.35 (m, 5H), 7.27 (s, 1H) 5.22-5.08 (m, 4H). $^{13}$C NMR (100 MHz) (DMSO) δ 162.31, 160.18, 157.71, 157.60, 137.39, 135.43, 135.37, 132.65, 132.45, 128.28, 128.23, 126.93, 126.38, 123.55, 123.49, 115.80, 115.69, 115.13, 114.56, 114.42, 114.11, 113.99, 113.87, 113.75, 38.87. $^{19}$F NMR (377 MHz, DMSO): δ 105.27 (s, 1F) 104.29 (s, 1F).

Example LH814: N-((1H-Tetrazol-5-yl)methyl)-N-(4-((N-((2H-tetrazol-5-yl)methyl)-2,6-difluorophenyl) sulfonamido)naphthalen-1-yl)-2,6-difluorobenzenesulfonamide

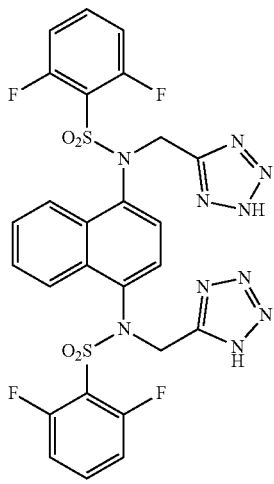 [SMILES: O=S(=O)(c1c(F)cccc1F)N(Cc1nn[nH]n1)c1ccc(N(Cc2nnn[nH]2)S(=O)(=O)c2c(F)cccc2F)c2ccccc12]

Prepared as described in the general procedure for synthesis of tetrazole (Method D) to get the title compound as a beige solid; the yield (19 mg, 72% yield). $^1$H NMR (400 MHz) (MeOH-d4) δ) 7.94-7.91 (m, 1H), 7.85-7.83 (m, 1H), 7.71-7.66 (m, 3H), 7.48-7.41 (m, 2H), 7.21 (s, 1H), 7.17-7.08 (m, 4H), 5.50-5.33 (m, 4H). $^{13}$C NMR (100 MHz) (MeOH-d$_4$) δ 162.50, 155.48, 137.56, 137.22, 136.97, 134.51, 134.30, 129.15, 128.78, 128.56, 124.90, 124.81, 114.78, 114.56, 61.54, $^{19}$F NMR (377 MHz, MeOH-d4): δ-106.04 (s, 2F), 106.21 (s, 2F). HRMS (ESI) Calcd for C$_{26}$H$_{18}$F$_4$N$_{10}$O$_4$S$_2$ (M+H)$^+$ 675.0963, found 675.0954.

Intermediate: N,N'-(Naphthalene-1,4-diyl)bis(N-(cyanomethyl)-4-(trifluoromethyl) benzenesulfonamide)

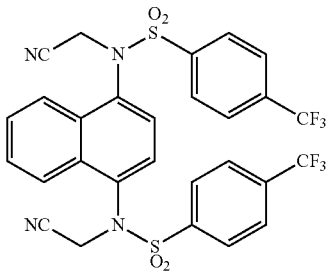 [SMILES: N#CCN(c1ccc(N(CC#N)S(=O)(=O)c2ccc(C(F)(F)F)cc2)c2ccccc12)S(=O)(=O)c1ccc(C(F)(F)F)cc1]

Prepared as described in the general procedure for synthesis of alkylated sulfonamides (method B) to get the title compound as oily product; the yield (17 mg, 69% yield). $^1$H NMR (400 MHz) (DMSO) 8.14-7.99 (m, 10H), 7.78-7.72 (m, 2H), 7.23 s, 1H), 6.95 (s, 1H), 5.14-5.00 (m, 4H). $^{13}$C NMR (100 MHz) (DMSO) δ 141.05, 140.30, 136.17, 135.94, 133.85, 133.72, 133.53, 133.39, 132.82, 132.71, 129.04, 128.75, 128.20, 126.87, 126.75, 126.47, 124.65, 123.61, 121.94, 116.04, 115.92, 114.53. $^{19}$F NMR (377 MHz, DMSO): δ-61.72 (s, 3F), -61.89 (s, 3F).

Example LH819: N-((1H-Tetrazol-5-yl)methyl)-N-(4-((N-((2H-tetrazol-5-yl)methyl)-4-(trifluoromethyl) phenyl)sulfonamido)naphthalen-1-yl)-4-(trifluoromethyl)benzenesulfonamide

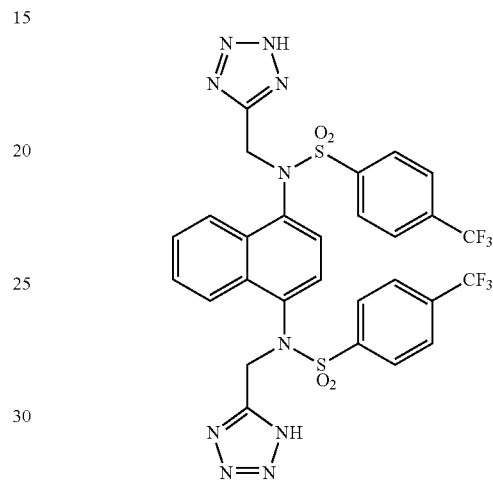

Prepared as described in the general procedure for synthesis of tetrazole (Method D) to get the title compound as a light yellow solid; the yield (23 mg, 77% yield). $^1$H NMR (400 MHz) (MeOH-d4) δ) 7.95-7.79 (m, 10H), 7.44-7.38 (m, 2H), 6.83 (s, 1H), 6.80 (s, 1H), 5.33-5.19 (m, 2H), 5.12-4.97 (m, 2H), 3.91 (s, 3H), 3.86 (s, 3H). $^{13}$C NMR (100 MHz) (MeOH-d4) δ 156.16, 143.35, 142.79, 137.71, 137.26, 135.94, 135.61, 134.74, 134.57, 130.10, 130.02, 128.52, 128.45, 128.42, 128.34, 127.51, 127.47, 126.19, 125.00, 124.97, 123.48.46.64. $^{19}$F NMR (377 MHz, MeOH-d4): δ-64.56 (s, 3F), -64.60 (s, 3F). HRMS (ESI) Calcd for C$_{28}$H$_{20}$F$_6$N$_{10}$O$_4$S$_2$ (M+H)$^+$ 739.1087, found 739.1070.

Intermediate: N,N'-(Naphthalene-1,4-diyl)bis(N-(cyanomethyl)-2,3-dihydrobenzo[b][1,4]dioxine-6-sulfonamide)

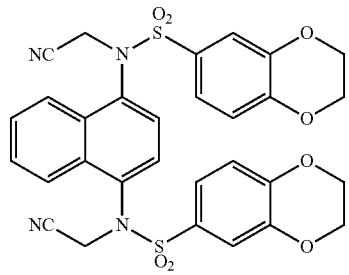 [SMILES: N#CCN(c1ccc(N(CC#N)S(=O)(=O)c2ccc3c(c2)OCCO3)c2ccccc12)S(=O)(=O)c1ccc2c(c1)OCCO2]

Prepared as described in the general procedure for synthesis of alkylated sulfonamides (method B) to get the title compound as oily product; the yield (148 mg, 78% yield).

$^1$H NMR (400 MHz) (DMSO) 8.15-8.12 (m, 1H), 8.08-8.6 (m, 1H), 7.77-7.74 (m, 2H), 7.35-7.33 (m, 2H), 7.23-7.18 (m, 3H), 7.14-7.08 (m, 3H), 5.06-5.00 (m, 4H), 4.41-4.33 (m, 8H). $^{13}$C NMR (100 MHz) (DMSO) δ 162.28, 148.32, 148.24, 143.68, 136.47, 136.32, 132.93, 132.87, 129.32, 128.66, 127.94, 126.47, 126.15, 123.69, 121.78, 121.50, 117.91, 117.80, 116.89, 116.76, 116.34, 116.24, 64.58, 64.09, 64.05, 38.90.

Example LH841: N-((1H-Tetrazol-5-yl)methyl)-N-(4-((N-((2H-tetrazol-5-yl)methyl)-2,3-dihydrobenzo[b] b[1,4]dioxine)-6-sulfonamido)naphthalen-1-yl)-2,3-dihydrobenzo[b] [1,4]dioxine-6-sulfonamide

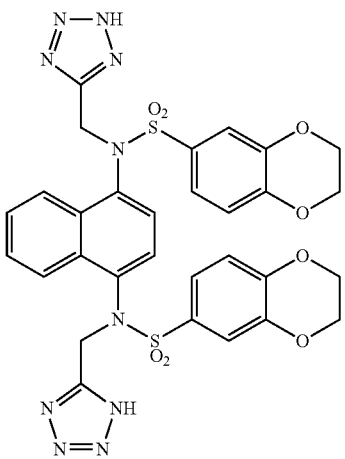 [SMILES: O=S(=O)(c1ccc2c(c1)OCCO2)N(Cc1nn[nH]n1)c1ccc(N(Cc2nnn[nH]2)S(=O)(=O)c2ccc3c(c2)OCCO3)c2ccccc12]

Prepared as described in the general procedure for synthesis of tetrazole (Method D) to get the title compound as a light yellow solid; the yield (35 mg, 75% yield). $^1$H NMR (400 MHz) (DMSO) δ) 8.13-8.10 (m, 1H), 8.04-8.02 (m, 1H), 7.56-7.54 (m, 2H), 7.26 (s, 1H), 7.22 (s, 1 H), 7.09-6.88 (m, 6H), 5.35-5.25 (m, 2H), 5.14-5.01 (m, 2H), 4.41-4.34 (m, 8H). $^{13}$C NMR (100 MHz) (DMSO) δ 147.96, 147.87, 143.52, 136.55, 136.14, 132.98, 132.82, 128.80, 128.53, 126.90, 126.33, 125.92, 124.00, 123.91, 121.79, 121.67, 117.47, 116.85, 116.69, 64.52, 64.07, 48.57. HRMS (ESI) Calcd for $C_{30}H_{26}N_{10}O_8S_2$ (M+H)$^+$ 719.1449, found 719.1440.

Intermediate: 2-Iodo-4-nitronaphthalen-1-amine (68)

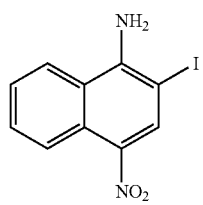 [SMILES: Nc1c(I)cc([N+](=O)[O-])c2ccccc12]

To a stirred solution of 4-nitronaphthalene-1-amine (2.0 g, 10.6 mmol) in methanol/water (10 mL/60 mL), potassium iodide (1.17 g, 7.1 mmol) and potassium iodate (0.76 g, 3.05 mmol) were added and the mixture was stirred for 10 min. Then, dilute HCl (1.2 mL diluted to 10 mL) was added during a period of 1 hour, and the reaction stirred overnight at room temperature. Upon completion, the reaction mixture filtered, and the yellow solid washed with water, dilute sodium thiosulfate solution and dried to get the desired product as a yellow solid 3.06 g yield: (91%). $^1$H NMR (400 MHz) (CDCl$_3$) δ) 8.90 (d, 1H, J=8.8 Hz), 8.75 (s, 1H), 7.83 (d, 1H, J=8.8 Hz), 7.76-7.72 (m, 1H), 7.60-7.56 (m, 1H), 5.44 (br, 2H). $^{13}$C NMR (100 MHz) (CDCl$_3$) δ 149.25, 136.78, 130.10, 127.06, 125.10, 121.60, 120.94.

General Procedure for Suzuki Coupling: (Method F)

To a Schlenk tube under argon atmosphere was added 2-iodo-4-nitronaphthalen-1-amine (1 equiv.), phenylboronic acid (1.2 equiv.), PdCl$_2$(PPh$_3$)$_2$ (0.02 equiv.), DME:H$_2$O (1:1), and K$_2$CO$_3$ (2 equiv.). and then the flask was degassed with argon three times. The reaction mixture was stirred at 80° C. for overnight. After completion of the reaction, the mixture was diluted with water, and extracted with EtOAc. The organic layer washed with brine, dried over anhydrous Na$_2$SO$_4$ and concentrated under reduced pressure followed by purification on an ISCO using silica gel and hexane/ethyl acetate.

Intermediate: 4-Nitro-2-phenylnaphthalen-1-amine

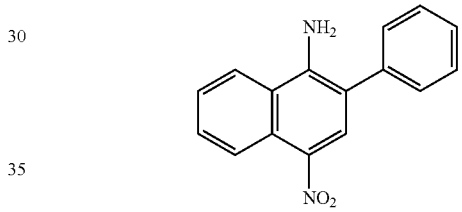

Prepared as described in the general procedure for Suzuki coupling (Method F) to get the title compound as a yellow solid; 449 mg, yield 85. $^1$H NMR (400 MHz) (CDCl$_3$) δ) 9.00 (d, 1H, J=8.8 Hz), 8.99 (s, 1 H), 7.90 (d, 1H, J=8.8 Hz), 7.76-7.72 (m, 1H), 7.61-7.43 (m, 6H), 5.11 (br, 2H). $^{13}$C NMR (100 MHz) (CDCl$_3$) δ 146.33, 137.54, 136.35, 130.01, 129.88, 129.61, 129.60, 128.42, 127.09, 126.41, 124.88, 122.25, 121.55, 119.52.

Intermediate: 2-(4-Methoxyphenyl)-4-nitronaphthalen-1-amine

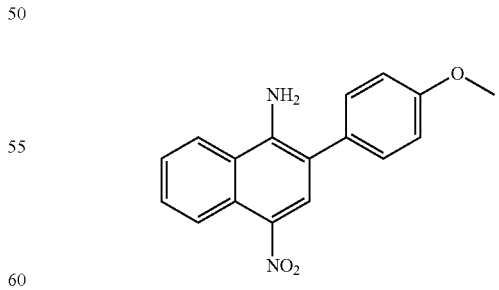

Prepared as described in the general procedure for Suzuki coupling (Method F) to get the title compound as a yellow solid; 232 mg, yield 79%. $^1$H NMR (400 MHz) (DMSO) δ) 8.90 (d, 1H, J=8.8 Hz), 8.47 (d, 1H, J=8.4 Hz), 8.23 (s, 1H), 7.76-7.72 (m, 1H), 7.56 (t, 1H, J=8.0 Hz), 7.42 (d, 2H, J=8.0 Hz), 7.07 (d, 2H, J=8.8 Hz), 7.00 (br, 2H), 3.81 (s, 3H). $^{13}$C NMR (100 MHz) (DMSO) δ 158.78, 149.71, 132.26, 130.82, 130.50, 130.02, 129.57, 126.79, 125.39, 123.90, 123.31, 121.28, 117.38, 114.63, 55.12.

Intermediate: 4-(1-Amino-4-nitronaphthalen-2-yl) benzonitrile

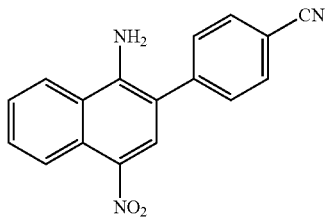 [SMILES: N#Cc1ccc(-c2cc([N+](=O)[O-])c3ccccc3c2N)cc1]

Prepared as described in the general procedure for Suzuki coupling (Method F) to get the title compound as dark brown solid; 453 mg, yield 77%. $^1$H NMR (400 MHz) (DMSO) δ) 8.86 (d, 1H, J=8.8 Hz), 8.49 (d, 1H, J=8.8 Hz), 8.23 (s, 1H), 7.97 (d, 2H, J=8.4 Hz), 7.81-7.77 (m, 1H), 7.72 (d, 2H, J=8.4 Hz), 7.61-7.57 (m, 1 H), 7.22 (br, 2H). $^{13}$C NMR (100 MHz) (DMSO) δ 149.32, 142.47, 132.73, 130.26, 130.22, 126.76, 125.41, 123.70, 123.03, 121.22, 118.56, 115.27, 109.93.

Intermediate: tert-Butyl (4-(1-amino-4-nitronaphthalen-2-yl) phenyl) carbamate

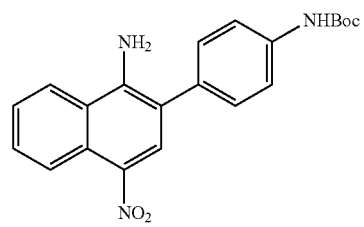 [SMILES: CC(C)(C)OC(=O)Nc1ccc(-c2cc([N+](=O)[O-])c3ccccc3c2N)cc1]

Prepared as described in the general procedure for Suzuki coupling (Method F) to get the title compound as a yellow solid; 585 mg, yield 77%. $^1$H NMR (400 MHz) (CDCl$_3$) δ) 8.97 (d, 1H, J=8.8 Hz), 8.36 (s, 1H), 7.88 (d, 1H, J=8.8 Hz), 7.71-7.67 (m, 1 H), 7.56-7.50 (m, 3H), 7.39 (d, 1H, J=8.4 Hz), 6.71 (s, 1H), 5.15 (br, 2H), 1.54 (s, 9H). $^{13}$C NMR (100 MHz) (CDCl$_3$) δ 152.93, 146.72, 138.52, 136.02, 131.91, 130.16, 130.04, 129.79, 127.00, 126.29, 124.72, 122.14, 121.65, 119.58, 118.96, 81.07, 28.46.

Intermediate: 2-Phenylnaphthalene-1,4-diamine

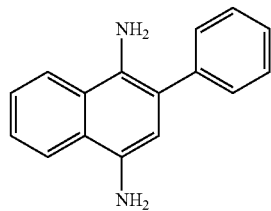 [SMILES: Nc1cc(-c2ccccc2)c(N)c2ccccc12]

Prepared as described in the general procedure for nitro group reduction (Method E2) to get the title compound as dark yellow solid; 344 mg, quantitative. $^1$H NMR (400 MHz) (CDCl$_3$) δ) 7.94-7.89 (m, 2H), 7.52-7.47 (m, 6H), 7.40-7.36 (m, 1H), 6.72 (s, 1H), 3.82 (br, 4H). $^{13}$C NMR (100 MHz) (CDCl$_3$) δ. 129.72, 129.01, 127.25, 125.67, 125.22, 122.28, 121.90.

Intermediate: 2-(4-Methoxyphenyl)naphthalene-1,4-diamine

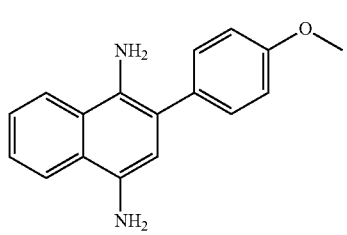 [SMILES: COc1ccc(-c2cc(N)c3ccccc3c2N)cc1]

Prepared as described in the general procedure for nitro group reduction (Method E2) to get the title compound as a yellow solid; 261 mg, quantitative. $^1$H NMR (400 MHz) (DMSO) δ) 7.90-7.85 (m, 2H), 7.53-7.46 (m, 3H), 7.41 (d, 2H, J=8.8 Hz), 7.00 (d, 2H, J=8.8 Hz), 3.85 (s, 3H). $^{13}$C NMR (100 MHz) (DMSO) δ 158.78, 149.71, 132.26, 130.82, 130.50, 130.02, 129.57, 126.79, 125.39, 123.90, 123.31, 121.28, 117.38, 114.63, 55.12.

Intermediate: 4-(1,4-Diaminonaphthalen-2-yl) benzonitrile

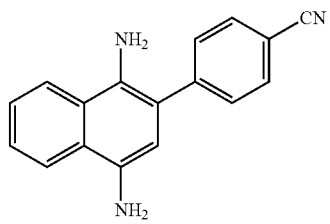

Prepared as described in the general procedure for nitro group reduction (Method E2) to get the title compound as dark solid; 378 mg, quantitative. $^1$H NMR (400 MHz) (CDCl$_3$) δ) 7.92-7.87 (m, 2H), 7.74 (d, 2H, J=8.4 Hz), 7.64 (d, 2H, J=8.4 Hz), 7.55-7.52 (m, 2H), 6.23 (s, 1H), 3.87 (br, 4H). $^{13}$C NMR (100 MHz) (CDCl$_3$) δ. 159.09, 143.72, 131.08, 130.99, 130.76, 125.80, 125.30, 125.24, 123.37, 122.43, 122.08, 121.59, 114.77, 114.65, 55.73.

Intermediate: tert-Butyl (4-(1,4-diaminonaphthalen-2-yl) phenyl) carbamate

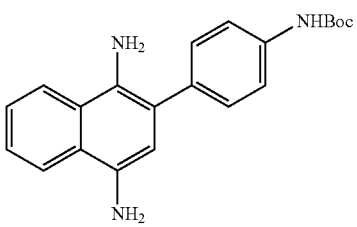

Prepared as described in the general procedure for nitro group reduction (Method E2) to get the title compound as an off-white solid; 519 mg, yield quantitative. $^1$H NMR (400 MHz) (CDCl$_3$) δ) 7.92-7.86 (m, 2H), 7.53-7.40 (m, 6H), 3.86 (br, 4H), 1.55 (s, 9H). $^{13}$C NMR (100 MHz) (CDCl$_3$) δ. 153.75, 137.23, 134.73, 134.12, 131.36, 129.99, 125.34, 125.04, 124.83, 124.48, 122.68, 121.96, 121.60, 118.90, 113.26, 80.54, 28.25.

Intermediate: N,N'-(2-Phenylnaphthalene-1,4-diyl)bis(4-methoxybenzenesulfonamide)

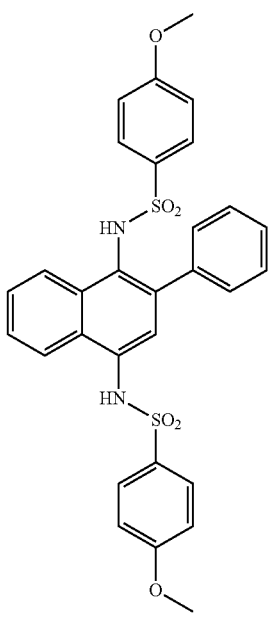 [SMILES: COc1ccc(S(=O)(=O)Nc2cc(-c3ccccc3)c(NS(=O)(=O)c3ccc(OC)cc3)c3ccccc23)cc1]

Using general procedure (method A2), 489 mg, yield 85%. $^1$H NMR (400 MHz) (DMSO) δ) 10.16 (s, 1H), 9.76 (s, 1H), 8.14-8.11 (m, 2H), 7.64 (d, 2H, J=8.8 Hz), 7.52-7.50 (m, 2H), 7.24-7.18 (m, 2H), 7.09-7.03 (m, 2H), 6.89 (s, 1H), 6.70 (d, 2H, J=8.8 Hz), 3.82 (s, 3H), 3.80 (s, 3H). $^{13}$C NMR (100 MHz) (DMSO) δ. 162.53, 161.76, 138.80, 138.68, 133.86, 132.51, 132.41, 131.06, 129.38, 129.15, 129.02, 128.04, 127.75, 126.92, 126.64, 126.58, 126.10, 125.27, 125.17, 123.21, 114.30, 113.82, 55.67, 55.47.

Intermediate: N,N'-(2-(4-Methoxyphenyl)naphthalene-1,4-diyl)bis(4-methoxybenzenesulfonamide)

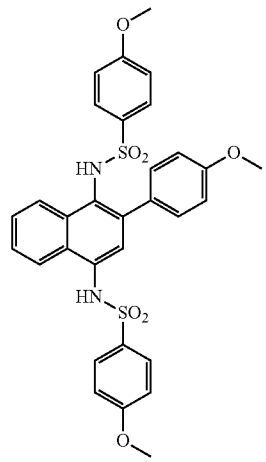 [SMILES: COc1ccc(-c2cc(NS(=O)(=O)c3ccc(OC)cc3)c3ccccc3c2NS(=O)(=O)c2ccc(OC)cc2)cc1]

Using general procedure (method A2), Prepared as described in the general procedure for synthesis of sulfonamides (method A1) to get the title compound as a beige solid; 472 mg, yield 78%. $^1$H NMR (400 MHz) (CDCl$_3$) δ) 8.50 (d, 1H, J=8.4 Hz), 7.68-7.66 (m, 2H), 7.55 (t, 1H, J=7.2 Hz), 7.48-7.44 (m, 1H), 7.24 (s, 1H), 7.07-7.05 (m, 3H), 6.98 (s, 1H), 6.84-6.82 (m, 2H), 6.77-6.70 (m, 4H), 6.61 (d, 2H, J=8.8 Hz), 3.85 (s, 3H), 3.83 (s, 3H), 3.79 (s, 3H). $^{13}$C NMR (100 MHz) (CDCl$_3$) δ) 163.25, 162.80, 158.92, 136.82, 133.01, 131.36, 130.80, 130.59, 130.39, 129.80, 129.56.29.04, 128.38, 127.06, 126.94, 126.81, 126.49, 124.06, 120.93, 114.15, 114.07, 113.82, 55.61, 55.58, 55.32.

Intermediate: N,N'-(2-(4-Cyanophenyl)naphthalene-1,4-diyl)bis(4-methoxybenzenesulfonamide)

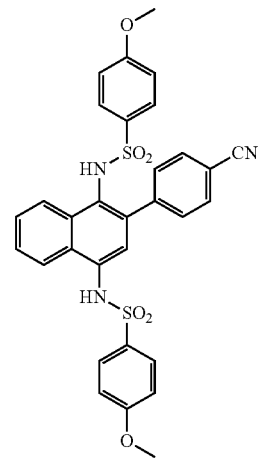 [SMILES: COc1ccc(S(=O)(=O)Nc2cc(-c3ccc(C#N)cc3)c(NS(=O)(=O)c3ccc(OC)cc3)c3ccccc23)cc1]

Using general procedure (method A2), Prepared as described in the general procedure for synthesis of sulfonamides (method A1) to get the title compound as a yellow solid; 408 mg, yield 68%. $^1$H NMR (400 MHz) (CDCl$_3$) δ) 8.30-8.28 (m, 1H), 7.84-7.81 (m, 1H), 7.69 (d, 2H, J=8.8 Hz), 7.52-7.45 (m, 5H), 7.29 (s, 1H), 7.16-7.14 (m, 4H), 6.95 (br, 1H), 6.83 (d, 2H, J=9.2 Hz), 6.64 (d, 2H, J=8.8 Hz), 3.87 (s, 3H), 3.79 (s, 3H). $^{13}$C NMR (100 MHz) (CDCl$_3$) δ. 163.55, 163.38, 163.25, 162.83, 143.52, 136.64, 133.40, 132.91, 132.56, 1310.16, 130.64, 130.32, 130.09, 129.86, 129.69, 129.64, 129.10, 128.80, 127.81, 127.75, 126.79, 125.76, 122.81, 121.43, 118.69, 114.41, 114.30, 114.19, 114.12, 111.29, 55.85, 55.79, Intermediate: tert-Butyl (4-(1,4-bis((4-methoxyphenyl) sulfonamido) naphthalen-2-yl) phenyl) carbamate

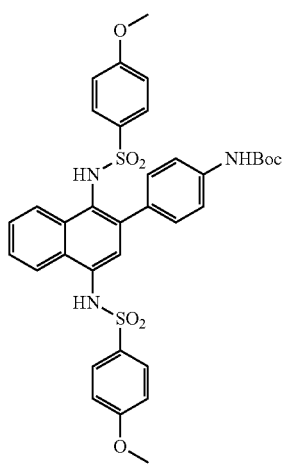 [SMILES: COc1ccc(S(=O)(=O)Nc2cc(-c3ccc(NC(=O)OC(C)(C)C)cc3)c(NS(=O)(=O)c3ccc(OC)cc3)c3ccccc23)cc1]

Using general procedure (method A2), Prepared as described in the general procedure for synthesis of sulfonamides (method A1) to get the title compound as an off-white solid; 421 mg, yield 62%. $^1$H NMR (400 MHz) (MeOH-d$_4$) δ) 8.31 (d, 1H, J=8.4 Hz), 8.04 (d, 1H, J=8.4 Hz), 7.75 (d, 1H, J=8.8 Hz), 7.64 (s, 1H), 7.62 (d, 1H, J=8.8 Hz), 7.51-7.41 (m, 2H), 7.18 (d, 1H, J=8.8 Hz), 7.11-7.09 (m, 2H), 7.00 (s, 1H), 6.89 (d, 4H, J=9.2 Hz), 6.61 (d, 2H, J=9.2 Hz), 3.82 (s, 3H), 3.81 (s, 3H), 1.55 (s, 9H). $^{13}$C NMR (100 MHz) (MeOH-d$_4$) δ. 162.93, 162.37, 137.88, 132.82, 132.19, 131.56, 130.83, 129.30, 129.20, 128.42, 126.58, 126.47, 126.13, 125.26, 124.94, 122.19, 117.95, 113.81, 113.48, 80.10, 55.22, 55.11, 27.94.

Intermediate: tert-Butyl (4-(1,4-bis((4-methoxyphenyl) sulfonamido) naphthalen-2-yl) phenyl) carbamate

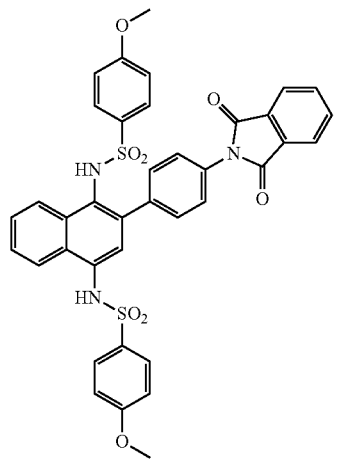 [SMILES: COc1ccc(S(=O)(=O)Nc2cc(-c3ccc(N4C(=O)c5ccccc5C4=O)cc3)c(NS(=O)(=O)c3ccc(OC)cc3)c3ccccc23)cc1]

Prepared as described in the general procedure for removal of acid sensitive protecting group (Method C2) to get the title compound as an off-white solid; 270 mg, yield 79%. $^1$H NMR (400 MHz) (MeOH-d$_4$) δ) 8.01-8.00 (m, 1H), 7.93-7.91 (m, 1H), 7.63 (d, 2H, J=9.2 Hz), 7.45 (s, 1H), 7.41-7.34 (m, 2H), 7.16-7.12 (m, 4H), 7.08 (d, 2H, J=8.4 Hz), 6.85 (d, 2H, J=8.8 Hz), 6.66 (d, 2H, J=8.8 Hz), 3.81 (s, 3H), 3.79 (s, 3H).

Intermediate: N,N'-(2-(4-(1,3-Dioxoisoindolin-2-yl) phenyl)naphthalene-1,4-diyl)bis(4-methoxybenzenesulfonamide)

Intermediate compound (74) (197 mg, 0.33 mmol) and phthalic anhydride (50 mg, 0.33 mmol) were taken in acetic acid 3 ml and the mixture refluxed for overnight. After completion, acetic acid removed, and the product purified by ISCO chromatography using ethyl acetate/hexane to get 154 mg, yield 65%. $^1$H NMR (400 MHz) (DMSO) δ) 10.21 (s, 1H), 9.84 (s, 1H), 8.21-8.16 (m, 2H), 8.02-8.01 (m, 2H), 7.94-7.93 (m, 2H), 7.66 (d, 2H, J=8.8 Hz), 7.55-7.52 (m, 2H), 7.37 (d, 2H, J=8.0 Hz), 7.19 37 (d, 2H, J=8.0 Hz), 7.08 37 (d, 4H, J=8.8 Hz), 6.95 (s, 1H), 6.80 37 (d, 2H, J=8.8 Hz), 3.81 (s, 3H), 3.74 (s, 3 H). $^{13}$C NMR (100 MHz) (DMSO) δ. 167.05, 162.60, 162.01, 138.48, 138.04, 134.80, 133.83, 132.70, 131.89, 131.54, 131.05, 130.97, 130.87, 129.60, 129.46, 129.27, 128.27, 126.79, 126.72, 126.57, 126.33, 125.35, 125.10, 123.51, 123.33, 114.34, 114.05, 55.72, 55.41.

Intermediate: Diethyl 2,2'((2-phenylnaphthalene-1,4-diyl) bis(((4-methoxyphenyl) sulfonyl) azanediyl)) diacetate

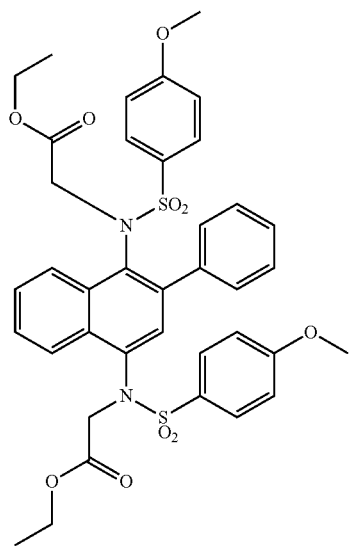 [SMILES: CCOC(=O)CCN(c1c(-c2ccccc2)cc(N(CC(=O)OCC)S(=O)(=O)c2ccc(OC)cc2)c2ccccc12)S(=O)(=O)c1ccc(OC)cc1]

Prepared as described in the general procedure for synthesis of alkylated sulfonamides (method B) to get the title compound as oily product; 127 mg, yield 82%. $^1$H NMR (400 MHz) (CDCl$_3$) δ) 8.24 (t, 1H, J=8.0 Hz), 8.15 (t, 1H, J=8.4 Hz), 7.72 (d, 1H, J=8.8 Hz), 7.63 (t, 2H, J=8.8 Hz), 7.55-7.50 (m, 2H), 7.40-7.29 (m, 6H), 7.08-7.02 (m, 1H), 6.95-6.85 (m, 4 H), 4.39-4.32 (m, 3H), 4.16-3.94 (m, 5H), 3.93-3.86 (m, 6H), 1.18-1.14 (m, 3H), 1.09-1.02 (m, 3H). $^{13}$C NMR (100 MHz) (CDCl$_3$) δ. 168.87, 168.81, 163.44, 163.37, 139.64, 138.57, 136.73, 136.31, 134.02, 132.61, 132.20, 131.57, 131.35, 130.77, 130.72, 130.57, 129.49, 128.30, 128.14, 128.10, 127.92, 127.37, 126.94, 126.84, 126.43, 124.22, 124.13, 114.08, 113.82, 61.61, 61.40, 55.76, 54.39, 53.67, 53.33, 14.32, 14.10, 13.97.

Intermediate: Di-tert-butyl 2,2'-(2-(4-methoxyphenyl) naphthalene-1,4-diyl) bis (((4-methoxyphenyl) sulfonyl) azanediyl)) diacetate

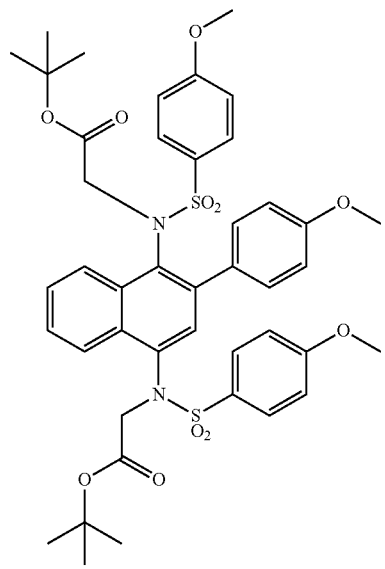 [SMILES: COc1ccc(-c2cc(N(CC(=O)OC(C)(C)C)S(=O)(=O)c3ccc(OC)cc3)c3ccccc3c2N(CCC(=O)OC(C)(C)C)S(=O)(=O)c2ccc(OC)cc2)cc1]

Prepared as described in the general procedure for synthesis of alkylated sulfonamides (method B) to get the title compound as oily product; 123 mg, yield 74%. $^1$H NMR (400 MHz) (CDCl$_3$) δ) 8.22-8.17 (m, 2H), 7.74-7.69 (m, 1H), 7.65-7.63 (m, 2H), 7.61-7.47 (m, 2H), 7.36 (t, 1H, J=8.0 Hz), 7.30 (d, 1H, J=8.4 Hz), 7.23 (d, 1H, J=8.4 Hz), 7.08-7.05 (m, 1H), 6.94-6.85 (m, 6H), 4.49-4.20 (m, 3H), 3.89-3.81 (m, 9H), 3.77-3.60 (m, 1H), 1.33 (s, 9H), 1.23-1.22 (m, 9H). $^{13}$C NMR (100 MHz) (CDCl$_3$) δ) 167.76, 167.63, 167.58, 163.36, 163.31, 163.22, 163.14, 162.61, 159.41, 159.28, 139.90, 139.17, 136.83, 136.78, 136.09, 135.93, 134.22, 134.12, 132.47, 132.42, 132.33, 132.23, 131.51, 131.43, 131.26, 130.96, 130.64, 130.47, 130.32, 129.95, 127.05, 126.95, 126.81, 126.70, 124.17, 114.06, 113.81, 113.68, 82.44, 82.17, 77.47, 77.16, 76.84, 55.73, 55.36, 55.21, 54.48, 54.24, 54.19, 27.99, 27.86.

Intermediate: Di-tert-butyl 2,2'-((2-(4-cyanophenyl) naphthalene-1,4-diyl) bis(((4-methoxyphenyl) sulfonyl) azanediyl)) diacetate

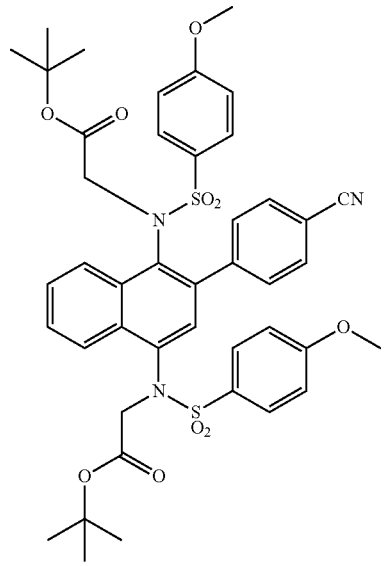 [SMILES: COc1ccc(S(=O)(=O)N(CC(=O)OC(C)(C)C)c2cc(-c3ccc(C#N)cc3)c(N(CCC(=O)OC(C)(C)C)S(=O)(=O)c3ccc(OC)cc3)c3ccccc23)cc1]

Prepared as described in the general procedure for synthesis of alkylated sulfonamides (method B) to get the title compound as oily product; 118 mg, yield 71%. $^1$H NMR (400 MHz) (CDCl$_3$) δ 8.16-8.05 (m, 2H), 7.69-7.63 (m, 4H), 7.57-7.38 (m, 6H), 7.14-7.08 (m, 1H), 6.91-6.83 (m, 4H), 4.57-4.48 (m, 1H), 4.29-4.12 (m, 2H), 3.92-3.84 (m, 6H), 3.80-3.76 (m, 1H), 1.34-1.33 (m, 9H), 1.24 (s, 9H). $^{13}$C NMR (100 MHz) (CDCl$_3$) δ 167.65, 167.07, 167.00, 163.47, 163.44, 143.93, 143.67, 138.82, 138.23, 137.32, 136.04, 135.81, 133.91, 133.77, 133.02, 132.90, 131.94, 131.83, 131.62, 131.41, 130.65, 130.56, 130.48, 130.42, 130.08, 127.85, 127.69, 127.45, 126.82, 126.38, 124.31, 118.84, 114.09, 113.90, 111.89, 111.73, 82.58, 82.50, 55.82, 55.79, 55.29, 54.77, 54.04, 53.90, 28.02, 27.87.

Intermediate: Di-tert-butyl 2,2'-((2-(4-(1,3-dioxoisoindolin-2-yl) phenyl) naphthalene-1,4-diyl) bis(((4-methoxyphenyl) sulfonyl) azanediyl)) diacetate

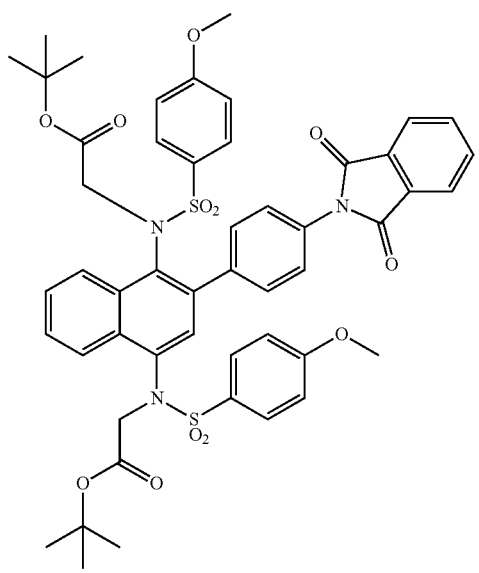 [SMILES: COc1ccc(S(=O)(=O)N(CC(=O)OC(C)(C)C)c2cc(-c3ccc(N4C(=O)c5ccccc5C4=O)cc3)c(N(CCC(=O)OC(C)(C)C)S(=O)(=O)c3ccc(OC)cc3)c3ccccc23)cc1]

Prepared as described in the general procedure for synthesis of alkylated sulfonamides (method B) to get the title compound as oily product; 58 mg, yield 61%. $^1$H NMR (400 MHz) (CDCl$_3$) δ 8.32-8.29 (m, 2H), 8.01-7.99 (m, 2H), 7.85-7.82 (m, 2H), 7.70 (d, 1H, J=8.8 Hz), 7.65 (d, 1H, J=8.8 Hz), 7.56 (d, 2H, J=8.8 Hz), 7.51-7.39 (m, 6H), 7.06-6.89 (m, 5H), 4.48-4.26 (m, 3H), 3.90-3.85 (m, 6H), 3.78-3.75 (m, 1H), 1.34-1.33 (m, 9H), 1.24 (s, 9H). $^{13}$C NMR (100 MHz) (CDCl$_3$) δ 167.54, 167.29, 167.25, 163.45, 163.34, 138.90, 138.45, 137.16, 134.65, 134.17, 132.99, 131.87, 131.77, 131.57, 130.83, 130.72, 130.53, 130.25, 130.17, 127.41, 127.22, 127.00, 125.98, 125.89, 124.49, 123.94, 114.14, 114.01, 82.51, 82.27, 55.81, 55.74, 28.01, 27.88.

Example LH890: 2,2'-(2-Phenylnaphthalene-1,4-diyl)bis(((4-methoxyphenyl)sulfonyl)azanediyl)) diacetic Acid

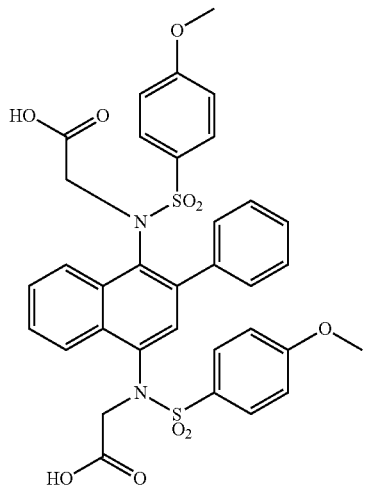 [SMILES: COc1ccc(S(=O)(=O)N(CC(=O)O)c2cc(-c3ccccc3)c(N(CCC(=O)O)S(=O)(=O)c3ccc(OC)cc3)c3ccccc23)cc1]

Prepared as described in the general procedure for hydrolysis of ethyl ester to get di-acidic compounds (Method C1) (basic hydrolysis) to get the title compound as a white solid; 32 mg, yield 92%. $^1$H NMR (500 MHz, 100° C.) (DMSO) δ) 8.27 (d, 2H, J=7.6 Hz), 7.62 (d, 2H, J=7.2 Hz), 7.55-749 (m, 3H), 7.42-7.27 (m, 6H), 7.05 (d, 2H, J=7.2 Hz), 6.95 (s, 1H), 6.87-6.86 (m, 1H), 6.70-6.69 (m, 1H), 4.43-4.4.24 (m, 2H), 3.90 (s, 3H), 3.87 (s, 2H), 3.85 (s, 3H). $^{13}$C NMR (100 MHz) (DMSO) δ 169.99, 169.95, 169.68, 169.55, 162.91, 162.81, 162.66, 139.64, 138.79, 138.58, 138.36, 136.55, 136.47, 135.41, 134.91, 133.68, 133.45, 132.34, 131.34, 130.99, 130.73, 130.22, 130.09, 129.87, 129.15, 128.99, 128.94, 127.83, 127.60, 127.44, 126.60, 126.47, 126.21, 124.37, 124.13, 114.26, 114.00, 55.74, 53.27, 53.04. HRMS (ESI) Calcd for C$_{34}$H$_{30}$N$_2$O$_{10}$S$_2$(M+H)$^+$ 691.1415, found 691.1414.

Example LH924: 2,2'-((2-(4-Methoxyphenyl) naphthalene-1,4-diyl) bis(((4-methoxyphenyl) sulfonyl) azanediyl)) diacetic Acid

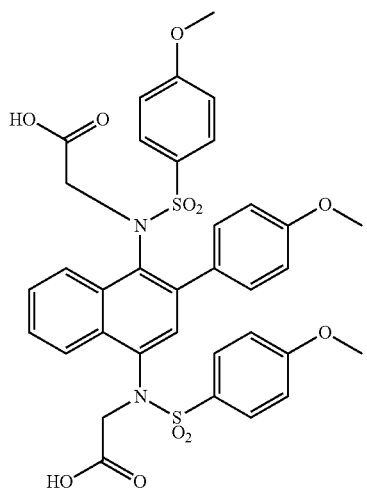 [SMILES: COc1ccc(-c2cc(N(CC(=O)O)S(=O)(=O)c3ccc(OC)cc3)c3ccccc3c2N(CCC(=O)O)S(=O)(=O)c2ccc(OC)cc2)cc1]

Prepared as described in the general procedure for removal of acid sensitive protecting group (Method C2) to get the title compound as a yellow solid; 17 mg, yield 71%. $^1$H NMR (500 MHz, 100° C.) (DMSO) δ) 8.30 (br, 1H), 8.24 (d, 1H, J=6.8 Hz), 7.62 (d, 2H, J=7.2 Hz), 7.54-7.51 (m, 3H), 7.40 (t, 1H, J=6.0 Hz), 7.17 (s, 2H), 7.05 (d, 2H, J=7.6 Hz), 6.99 (d, 2H, J=6.4 Hz), 6.96 (s, 1H), 6.87 (d, 2H, J=6.8 Hz), 4.44-3.89 (m, 4H), 3.85 (s, 3H), 3.83 (s, 3H). $^{13}$C NMR (125 MHz, 100° C.) (DMSO) δ 168.98, 168.53, 162.57, 162.38, 158.44, 135.93, 134.74, 133.22, 131.47, 131.18, 130.60, 130.42, 129.73, 129.48, 129.43, 129.37, 125.94, 125.66, 125.56, 123.47, 113.79, 113.49, 112.91, 55.22, 55.20, 54.67, 52.72. HRMS (ESI) Calcd for $C_{35}H_{32}N_2O_{11}S_2(M+H)^+$ 721.1520, found 721.1532.

Example LH935: 2,2'-(2-(4-Cyanophenyl)naphthalene-1,4-diyl)bis(((4-methoxyphenyl)sulfonyl) azanediyl)) diacetic Acid

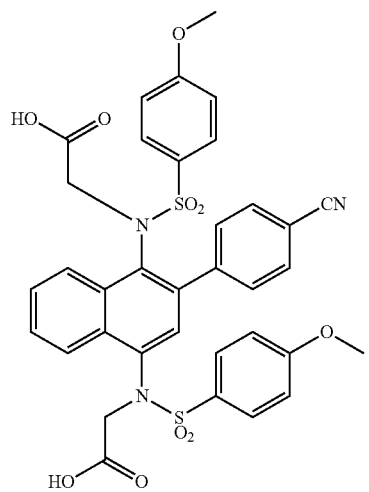 [SMILES: COc1ccc(S(=O)(=O)N(CC(=O)O)c2cc(-c3ccc(C#N)cc3)c(N(CCC(=O)O)S(=O)(=O)c3ccc(OC)cc3)c3ccccc23)cc1]

Prepared as described in the general procedure for removal of acid sensitive protecting group (Method C2) to get the title compound as brown solid; 13 mg, yield 61%. $^1$H NMR (500 MHz, 100° C.) (DMSO) δ) 8.30 (d, 1H, J=8.5 Hz), 8.22 (d, 1H, J=8.5 Hz), 7.74 (d, 2H, J=8.0 Hz), 7.62-7.56 (m, 3H), 7.47-7.44 (m, 5H), 7.05 (d, 2H, J=7.0 Hz), 6.96 (d, 3H, J=9.0 Hz), 4.45-4.30 (m, 4H), 3.90 (s, 3H), 3.85 (s, 3H). $^{13}$C NMR (125 MHz, 100° C.) (DMSO) δ 168.79, 168.19, 162.46, 162.37, 142.93, 137.72, 136.33, 134.49, 132.66, 131.96, 130.69, 130.48, 129.65, 129.36, 129.26, 128.96, 126.06, 125.97, 125.32, 123.70, 117.74, 113.63, 113.37, 109.97, 55.10, 55.08, 52.51. HRMS (ESI) Calcd for $C_{35}H_{29}N_3O_{10}S_2$ $(M+H)^+$ 716.1367, found 716.1373.

Example LH936: 2,2'-((2-(4-(1,3-Dioxoisoindolin-2-yl) phenyl) naphthalene-1,4-diyl) bis (((4-methoxyphenyl) sulfonyl) azanediyl)) diacetic Acid

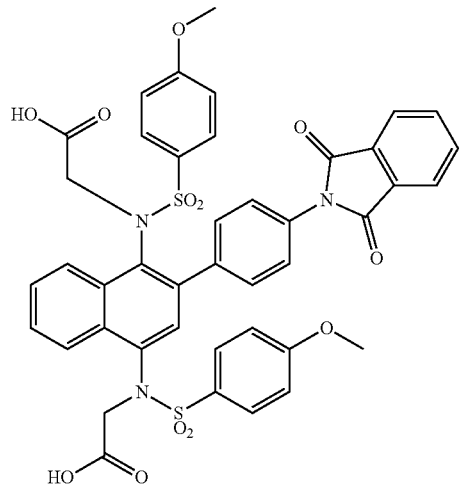 [SMILES: COc1ccc(S(=O)(=O)N(CC(=O)O)c2cc(-c3ccc(N4C(=O)c5ccccc5C4=O)cc3)c(N(CCC(=O)O)S(=O)(=O)c3ccc(OC)cc3)c3ccccc23)cc1]

Prepared as described in the general procedure for removal of acid sensitive protecting group (Method C2) to get the title compound as a yellow solid; 15 mg, yield 60%. $^1$H NMR (500 MHz, 100° C.) (DMSO) δ) 8.34 (d, 2H, J=8.0 Hz), 8.03-8.01 (m, 2H), 7.96-7.94 (m, 2H), 7.63 (d, 2H, J=8.5 Hz), 7.58 (t, 1H, J=7.0 Hz), 7.48-7.43 (m, 7H), 7.08 (d, 2H, J=8.5 Hz), 7.08 (d, 2H, J=8.5 Hz), 7.00 (s, 1 H), 4.47-4.33 (m, 4H), 3.87 (s, 3H), 3.86 (s, 3H). $^{13}$C NMR (125 MHz, 100° C.) (DMSO) δ 169.08, 168.48, 166.33, 162.71, 162.59, 137.88, 136.34, 134.67, 134.23, 133.12, 132.02, 131.17, 130.73, 130.16, 129.62, 129.60, 129.17, 125.97, 125.85, 125.66, 123.92, 122.92, 113.92, 113.75, 55.36, 55.23, 52.90. HRMS (ESI) Calcd for $C_{42}H_{33}N_3O_{12}S_2(M+H)^+$ 836.1578, found 836.1587.

General Procedure for Synthesis of (Method G)

To a Schlenk tube equipped with a magnetic stir bar under argon atmosphere was added 2-iodo-4-nitronaphthalen-1-amine (1 equiv.), acrylate (1.4 equiv.), Pd(OAc)$_2$ (0.06 equiv.), P(o-tolyl) (0.12 equiv.), TEA (1.4 equiv.), in CH$_3$CN, and then the tube was degassed with argon three times and refluxed for 24 hours. Upon completion, the mixture diluted with EtOAc and extracted with water, brine, dried over Na$_2$SO$_4$, and organic layer removed under reduced pressure. The crude product purified by ISCO using ethyl acetate/hexane to get the desired product.

Intermediate: tert-Butyl (Z)-3-(1-amino-4-nitronaphthalen-2-yl) acrylate

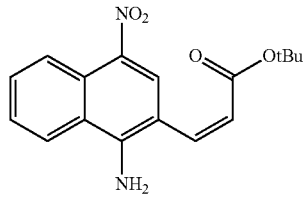 [SMILES: CC(C)(C)OC(=O)/C=C\c1cc([N+](=O)[O-])c2ccccc2c1N]

Prepared as described in the general procedure for Heck coupling (Method G) to get the title compound as brown solid; 521 mg, yield 83%. $^1$H NMR (400 MHz) (CDCl$_3$) δ) 8.88 (d, 1H, J=8.8 Hz), 8.54 (s, 1H), 7.88 (d, 1H, J=8.4 Hz), 7.80 (d, 1H, J=15.6 Hz), 7.74-7.70 (m, 1H), 7.60-7.56 (m, 1H), 6.45 (d, 1H, J=15.6 Hz), 5.35 (br, 2H), 1.56 (s, 9H). $^{13}$C NMR (100 MHz) (CDCl$_3$) δ) 166.22, 147.37, 137.07, 136.47, 130.56, 127.55, 126.89, 126.51, 124.99, 122.63, 122.35, 121.61, 111.47, 81.24, 28.35.

Intermediate: (Z)-3-(1-Amino-4-nitronaphthalen-2-yl)-N-isopropylacrylamide

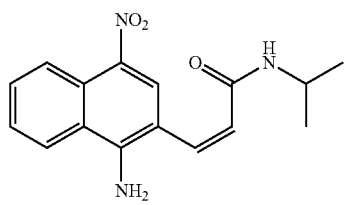 [SMILES: CC(C)NC(=O)/C=C\c1cc([N+](=O)[O-])c2ccccc2c1N]

Prepared as described in the general procedure for Heck coupling (Method G) to get the title compound as a beige solid; 468 mg, yield 78%. $^1$H NMR (400 MHz) (DMSO) δ) 8.80 (d, 1H, J=8.0 Hz), 8.59 (s, 1H), 8.46 (d, 1H, J=8.8 Hz), 7.99 (d, 1H, J=7.6 Hz), 7.86 (d, 1H, J=15.6 Hz), 7.76-7.73 (m, 3H), 7.58-7.54 (m, 1H), 6.64 (d, 1H, J=15.6 Hz), 3.99-3.97 (m, 1H), 1.13 (d, 6H, J=6.8 Hz). $^{13}$C NMR (100 MHz) (DMSO) δ) 164.05, 150.70, 132.87, 132.47, 130.45, 127.11, 126.69, 125.88, 123.97, 123.50, 122.74, 122.00, 110.27, 22.48.

Intermediate: (Z)-3-(1-Amino-4-nitro naphthalen-2-yl)-1-morpholinoprop-2-en-1-one

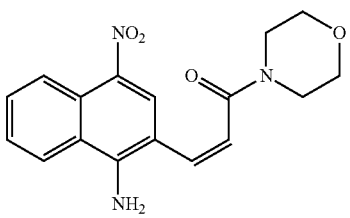 [SMILES: Nc1c(/C=C\C(=O)N2CCOCC2)cc([N+](=O)[O-])c2ccccc12]

Prepared as described in the general procedure for Heck coupling (Method G) to get the title compound as an off-white solid; 504 mg, yield 77%. $^1$H NMR (400 MHz) (DMSO) δ) 8.72-7.70 (m, 2H), 8.46 (d, 1H, J=8.8 Hz), 7.96 (d, 1H, J=15.2 Hz), 7.74 (t, 1H, J=8.0 Hz), 7.69 (br, 2H), 7.56 (t, 1H, J=8.0 Hz), 3.74 (br, 2H), 3.61 (br, 6H). $^{13}$C NMR (100 MHz) (DMSO) δ) 164.74, 150.38, 135.83, 133.37, 130.25, 127.00, 126.91, 125.76, 123.84, 123.22, 121.88, 117.90, 110.30, 66.34, 45.59, 41.96.

Intermediate: tert-Butyl 3-(1,4-diaminonaphthalen-2-yl) propanoate

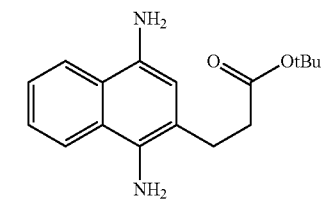

Prepared as described in the general procedure for nitro group reduction (Method E1) to get the title compound as an off-white solid; 409 mg, quantitative. $^1$H NMR (400 MHz) (CDCl$_3$) δ) 7.86-7.81 (m, 2H), 7.48-7.41 (m, 2H), 6.60 (s, 1H), 3.94 (br, 2H), 3.76 (br, 2H), 2.93 (t, 2H, J=8.0 Hz), 2.59 (t, 2H, J=7.6 Hz), 1.44 (s, 9H). $^{13}$C NMR (100 MHz) (CDCl$_3$) δ) 172.83, 134.27, 131.85, 125.21, 125.16, 124.34, 124.07, 121.67, 121.47, 120.65, 113.14, 80.56, 35.44, 28.12, 26.98.

Intermediate: 3-(1,4-Diaminonaphthalen-2-yl)-N-isopropyl propanamide

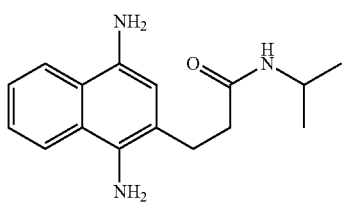 [SMILES: CC(C)NC(=O)CCc1cc(N)c2ccccc2c1N]

Prepared as described in the general procedure for nitro group reduction (Method E1) to get the title compound as a beige solid; 4.07 mg, quantitative. $^1$H NMR (400 MHz) (CDCl$_3$) δ) 7.81-7.78 (m, 2H), 7.45-7.40 (m, 2H), 6.52 (s, 1H), 5.37 (br, 1H), 4.03-3.96 (br, 2H), 3.75 (br, 2H), 2.95 (t, 2H, J=7.6 Hz), 2.43 (t, 2H, J=7.6 Hz), 0.98 (d, 6H, J=6.4 Hz). $^{13}$C NMR (100 MHz) (CDCl$_3$) δ) 171.77, 134.27, 132.12, 125.28, 124.45, 124.17, 121.74, 121.57, 120.91, 113.44, 41.46, 36.95, 27.53, 22.69.

Intermediate: tert-Butyl 3-(1,4-bis((4-methoxyphenyl) sulfonamido) naphthalen-2-yl) propanoate

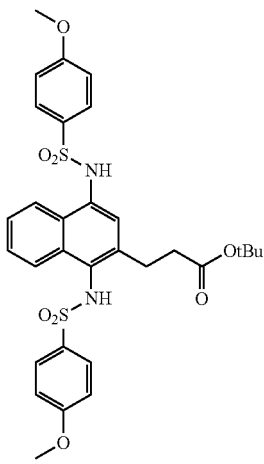 [SMILES: COc1ccc(S(=O)(=O)Nc2cc(CCC(=O)OC(C)(C)C)c(NS(=O)(=O)c3ccc(OC)cc3)c3ccccc23)cc1]

Prepared as described in the general procedure for synthesis of sulfonamides (method A1) to get the title compound as an off-white solid; 464 mg, yield 74%. $^1$H NMR (400 MHz) (DMSO) δ) 10.03 (s, 1H), 9.69 (s, 1H), 7.96 (d, 1H, J=8.4 Hz), 7.66 (d, 1H, J=7.6 Hz), 7.60 (d, 2H, J=8.8 Hz), 7.47 (d, 2H, J=8.4 Hz), 7.33 (t, 1H, J=8.0 Hz), 7.23 (t, 1H, J=7.6 Hz), 7.02 (d, 2H, J=8.0 Hz), 6.98 (d, 2H, J=8.8 Hz), 6.94 (s, 1H). 3.80 (s, 3H), 3.78 (s, 3H), 2.69 (br, 2H), 2.14 (br, 2H), 1.39 (s, 9H). $^{13}$C NMR (100 MHz) (DMSO) δ) 171.17, 162.42, 162.39, 137.50, 132.55, 132.49, 132.17, 131.29, 129.04, 128.86, 128.63, 127.89, 125.89, 125.30, 124.29, 124.20, 123.05, 114.26, 114.18, 79.70, 55.61, 35.19, 27.69, 26.47.

Intermediate: 3-(1,4-Bis((4-methoxyphenyl) sulfonamido) naphthalen-2-yl) propanoic Acid

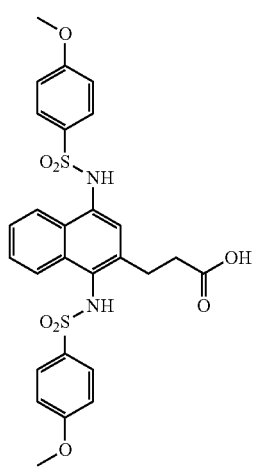 [SMILES: COc1ccc(S(=O)(=O)Nc2cc(CCC(=O)O)c(NS(=O)(=O)c3ccc(OC)cc3)c3ccccc23)cc1]

Prepared as described in the general procedure for removal of acid sensitive protecting group (Method C2) to get the title compound as an off-white solid; 102 mg, yield 89%. $^1$H NMR (400 MHz) (MeOH-d$_4$) δ) 7.96 (d, 1H, J=8.4 Hz), 7.75 (d, 1H, J=8.4 Hz), 7.60 (d, 2H, J=8.8 Hz), 7.49 (d, 2H, J=9.2 Hz), 7.33-7.29 (m, 1H), 7.24-7.20 (m, 1H), 7.03 (s, 1H), 6.95-6.90 (m, 4H), 3.83 (s, 3H), 3.81 (s, 3H), 2.80 (br, 2H), 2.36 (t, 2H, J=8.0 Hz). $^{13}$C NMR (100 MHz) (MeOH-d$_4$) δ) 176.57, 164.67, 164.63, 139.05, 134.25, 133.88, 133.38, 132.28, 130.74, 130.61, 130.29, 129.58, 127.18, 126.59, 125.86, 125.64, 124.04, 115.24, 115.10, 56.16, 56.14, 35.36, 27.63.

Intermediate: 3-(1,4-Bis((4-methoxyphenyl) sulfonamido) naphthalen-2-yl) propanamide

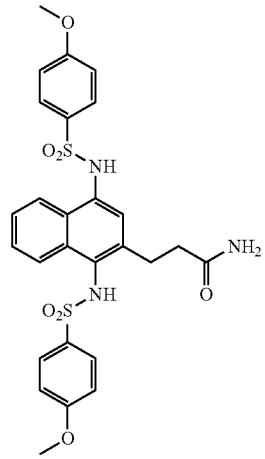 [SMILES: COc1ccc(S(=O)(=O)Nc2cc(CCC(N)=O)c(NS(=O)(=O)c3ccc(OC)cc3)c3ccccc23)cc1]

To a stirred solution of (83) (96 mg, 0.128 mmol) in DCM (2 ml): DMF (0.2 ml), PyAOP (93 mg, 0.18 mmol), TEA (95 uL, 0.7 mmol) were added at 0° C. under nitrogen. Then, NH$_3$/DCM (1.5 N, 100 uL) was added and reaction stirred at 0° C. for 10 min and then room temperature for 3 hours Upon completion, the reaction diluted with ethyl acetate and washed with 1 N HCl, brine, dried over Na$_2$SO$_4$, and the organic layer removed under reduced pressure. The crude product purified by ISCO using ethyl acetate hexane to get the desired product as a beige solid 63 mg, yield 84%. $^1$H NMR (400 MHz) (DMSO) δ) 10.38 (s, 1H), 10.01 (s, 1H), 8.28 (d, 1H, J=8.0 Hz), 8.07 (d, 1H, J=8.4 Hz), 7.95 (d, 2H, J=8.8 Hz), 7.79 (d, 2H, J=8.8 Hz), 7.67-7.56 (m, 3H), 7.36-7.30 (m, 5H), 7.17 (s, 1H), 4.14 (s, 3H), 4.10 (s, 3H), 3.67 (br, 3H), 2.83 (br, 1H). $^{13}$C NMR (100 MHz) (DMSO) δ) 173.61, 162.42, 162.39, 138.06, 132.40, 132.17, 132.05, 131.39, 128.99, 128.68, 128.60, 127.78, 125.79, 125.22, 124.52, 124.10, 122.85, 114.25, 114.19, 55.62, 55.58, 35.64, 26.35.

Intermediate: 3-(1,4-Bis((4-methoxyphenyl) sulfonamido) naphthalen-2-yl)-N-isopropylpropanamide

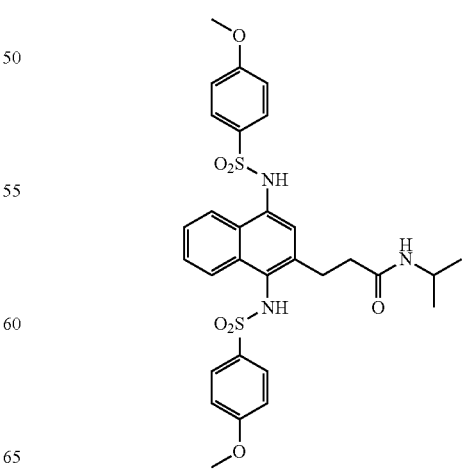

Prepared as described in the general procedure for synthesis of sulfonamides (method A1) to get the title compound as a beige solid; 416 mg, yield 68%. $^1$H NMR (400 MHz) (DMSO) δ) 7.93 (d, 1H, J=8.4 Hz), 7.74 (d, 1H, J=8.4 Hz), 7.64-7.59 (m, 3H), 7.47-7.44 (m, 2H), 7.33-7.23 (m, 2H), 7.04-6.97 (m, 5H), 3.80 (s, 4H), 3.77 (s, 3H), 2.60 (br, 2H), 2.13 (t, 2H, J=7.6 Hz), 1.01 (d, 6H, J=6.8 Hz). $^{13}$C NMR (100 MHz) (DMSO) δ) 170.34, 162.42, 162.39, 138.06, 132.46, 132.22, 132.05, 131.45, 128.98, 128.69, 128.62, 127.78, 125.80, 125.22, 124.54, 124.27, 122.86, 114.25, 114.19, 55.62, 55.60, 36.11, 26.68, 22.32.

Intermediate: N,N'-(2-3-Morpholino-3-oxopropyl) naphthalene-1,4-diyl)bis(4-methoxybenzene-sulfonamide)

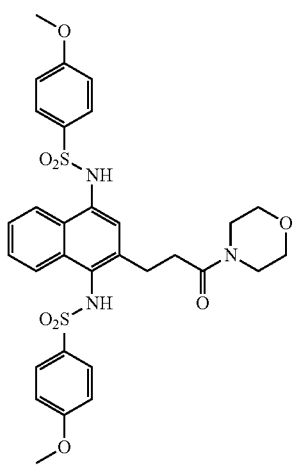 [SMILES: COc1ccc(S(=O)(=O)Nc2cc(CCC(=O)N3CCOCC3)c(NS(=O)(=O)c3ccc(OC)cc3)c3ccccc23)cc1]

Using general procedure (method E1) intermediate (78d) to get the diamine (440 mg, quantitative) which was dissolved in pyridine using general procedure (method A2) to get the title compound, 317 mg, yield 65%. $^1$H NMR (400 MHz) (DMSO) δ) 10.06 (s, 1H), 9.75 (s, 1H), 7.99 (d, 1H, J=8.4 Hz), 7.75 (d, 1H, J=8.4 Hz), 7.65 (d, 2H, J=8.8 Hz), 7.48 (d, 2H, J=8.8 Hz), 7.37-7.33 (m, 1H), 7.29-7.27 (m, 1H), 7.04-6.98 (m, 5H), 3.81 (s, 3H), 3.78 (s, 3H), 3.53-3.52 (m, 4H), 3.43-3.32 (m, 4H), 2.65 (br, 2H), 2.31 (t, 2H, J=7.6 Hz). $^{13}$C NMR (100 MHz) (DMSO) δ) 170.07, 162.46, 162.43, 137.97, 132.55, 132.32, 132.21, 131.45, 129.12, 128.79, 128.74, 127.96, 125.93, 125.35, 124.53, 124.23, 123.05, 114.33, 114.23, 66.02, 55.68, 55.65, 45.28, 41.55, 33.24, 26.56.

Intermediate: tert-Butyl 3-(1,4-bis((N-(2-amino-2-oxoethyl)-4-methoxyphenyl) sulfonamido) naphthalen-2-yl) propanoate

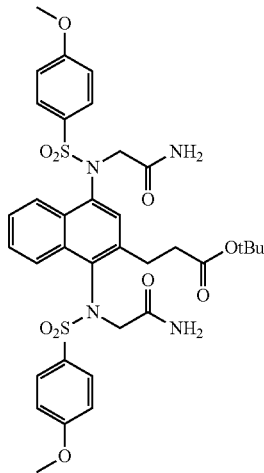 [SMILES: COc1ccc(S(=O)(=O)N(CC(N)=O)c2cc(CCC(=O)OC(C)(C)C)c(N(CC(N)=O)S(=O)(=O)c3ccc(OC)cc3)c3ccccc23)cc1]

Prepared as described in the general procedure for synthesis of alkylated sulfonamides (method B) to get the title compound as oily product; 61 mg, yield 82%.%. $^1$H NMR (400 MHz) (CDCl$_3$) δ) 8.08-7.95 (m, 1H), 7.66-7.59 (m, 4H), 7.37-7.30 (m, 1H), 7.16-7.15 (m, 2H), 6.99-6.55 (m, 7H), 5.97-5.88 (m, 2H), 4.48-4.20 (m, 4H), 3.88-3.84 (m, 6H), 3.21-2.82 (2H), 2.55-2.26 (m, 2H), 1.46 (s, 9H). $^{13}$C NMR (100 MHz) (CDCl$_3$) δ) 171.92, 171.76, 170.46, 170.31, 170.16, 163.72, 162.55, 140.61, 137.77, 137.64, 134.76, 134.69, 132.08, 132.02, 131.95, 131.78, 130.62, 130.50, 130.37, 130.30, 130.13, 129.94, 128.55, 128.35, 128.31, 127.15, 126.63, 124.25, 114.44, 114.37, 114.25, 80.72, 80.63, 55.72, 36.44, 36.30, 35.90, 31.55, 31.41, 28.11.

Intermediate: Di-tert-butyl 2,2'-(2-(3-amino-3-oxopropyl) naphthalene-1,4-diyl) bis (((4-methoxyphenyl) sulfonyl) azanediyl)) diacetate

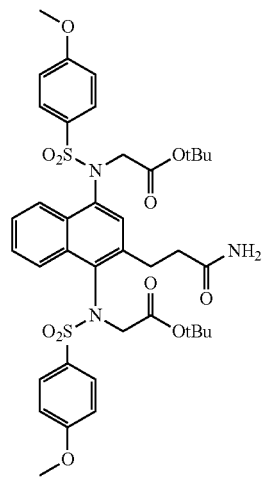 [SMILES: COc1ccc(S(=O)(=O)N(CC(=O)OC(C)(C)C)c2cc(CCC(N)=O)c(N(CC(=O)OC(C)(C)C)S(=O)(=O)c3ccc(OC)cc3)c3ccccc23)cc1]

Prepared as described in the general procedure for synthesis of alkylated sulfonamides (method B) to get the title compound as oily product; 29 mg, yield 72%. $^1$H NMR (400 MHz) (CDCl$_3$) δ 8.49-8.45 (m, 1H), 7.84 (d, 2H, J=8.8 Hz), 7.80-7.77 (m, 2H), 7.67-7.59 (m, 1H), 7.45-7.44 (m, 2H), 7.39-7.32 (m, 1H), 7.17-7.14 (m, 2H), 7.07-7.04 (m, 2H), 4.81-4.55 (m, 2H), 4.41-4.29 (m, 2H), 4.09 (s, 3H), 4.03 (s, 3H), 3.81-3.73 (m, 1H), 3.13-3.04 (m, 1H), 2.47-2.42 (m, 2H), 1.64-1.59 (m, 9H), 1.53-1.51 (m, 9 H). $^{13}$C NMR (100 MHz) (CDCl$_3$) δ) 174.91, 174.83, 168.77, 168.40, 167.56, 167.42, 163.65, 140.91, 140.72, 138.03, 137.96, 134.93, 132.69, 132.42, 130.81, 130.50, 130.44, 130.35, 129.95, 129.79, 128.85, 128.77, 127.38, 127.20, 126.66, 126.42, 125.40, 124.8, 123.88, 114.36, 114.29, 55.86, 55.83, 54.44, 54.08, 38.17, 37.71, 28.20, 28.13, 28.04.

Intermediate: Di-tert-butyl 2,2'-(2-(3-(isopropylamino)-3-oxopropyl) naphthalene-1,4-diyl) bis(((4-methoxyphenyl) sulfonyl) azanediyl)) diacetate

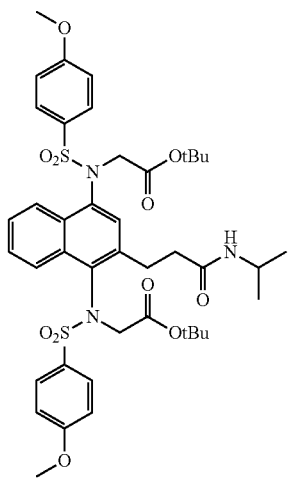 [SMILES: COc1ccc(S(=O)(=O)N(CC(=O)OC(C)(C)C)c2cc(CCC(=O)NC(C)C)c(N(CC(=O)OC(C)(C)C)S(=O)(=O)c3ccc(OC)cc3)c3ccccc23)cc1]

Prepared as described in the general procedure for synthesis of alkylated sulfonamides (method B) to get the title compound as oily product; 60 mg, yield 71%. $^1$H NMR (400 MHz) (CDCl$_3$) δ 8.32 (d, 1H, J=8.4 Hz), 7.67-7.60 (m, 3H), 7.52-7.18 (m, 4H), 7.04-6.86 (m, 5H), 6.38-6.30 (m, 1H), 4.72-4.02 (m, 5H), 3.91 (s, 1H), 3.84 (s, 3H), 3.47-3.40 (m, 1H), 2.77-2.70 (m, 1H), 2.20-2.07 (m, 2H), 1.47-1.33 (m, 18H), 1.17-1.11 (m, 6H). $^{13}$C NMR (100 MHz) (CDCl$_3$) δ 171.39, 168.79, 167.37, 163.64, 163.52, 140.70, 138.01, 134.97, 132.69, 131.01, 130.40, 130.34, 129.95, 128.77, 127.45, 126.64, 125.37, 124.20, 114.35, 114.27, 114.21, 82.71, 82.59, 82.40, 55.87, 55.72, 54.49, 54.05, 41.24, 39.16, 29.49, 28.13, 28.08, 28.01, 22.89, 22.82, 22.73.

Intermediate: di-tert-butyl 2,2'-((2-(3-morpholino-3-oxopropyl) naphthalene-1,4-diyl) bis(((4-methoxyphenyl) sulfonyl) azanediyl))diacetate

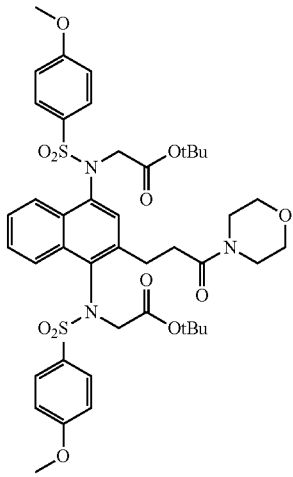 [SMILES: COc1ccc(S(=O)(=O)N(CC(=O)OC(C)(C)C)c2cc(CCC(=O)N3CCOCC3)c(N(CC(=O)OC(C)(C)C)S(=O)(=O)c3ccc(OC)cc3)c3ccccc23)cc1]

Prepared as described in the general procedure for synthesis of alkylated sulfonamides (method B) to get the title compound as oily product; 60 mg, yield 71%. $^1$H NMR (400 MHz) (CDCl$_3$) δ 8.18-8.13 (m, 1H), 7.67-7.60 (m, 4H), 7.42-7.36 (m, 2H), 7.26-7.11 (m, 2H), 6.95-6.86 (m, 4H), 4.46-4.14 (m, 4H), 3.86 (s, 3H), 3.85 (s, 3H), 3.75-3.01 (m, 10H), 2.72-2.25 (m, 2H), 1.40-1.32 (m, 18H). $^{13}$C NMR (100 MHz) (CDCl$_3$) δ) 170.94, 170.77, 167.45, 167.35, 167.30, 163.27, 163.17, 163.14, 162.35, 140.65, 140.49, 137.42, 137.39, 135.28, 135.18, 132.43, 132.16, 132.00, 131.91, 130.63, 130.52, 130.21, 130.06, 130.00, 129.82, 129.06, 128.97, 126.82, 126.72, 126.26, 126.15, 124.62, 124.46, 124.10, 113.97, 113.93, 82.07, 82.04, 66.89, 66.75, 55.54, 54.41, 54.29, 53.80, 53.76, 46.05, 45.95, 41.90, 34.01, 33.91, 27.81, 27.74, 20.88.

Example LH914: 3-(1,4-Bis((N-(2-amino-2-oxoethyl)-4-methoxyphenyl) sulfonamido) naphthalen-2-yl) propanoic Acid

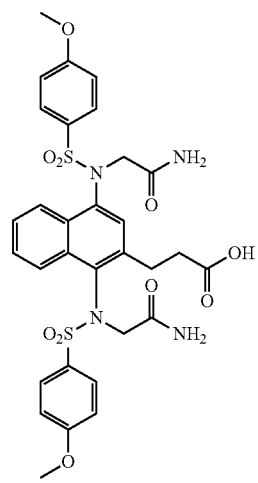 [SMILES: COc1ccc(S(=O)(=O)N(CC(N)=O)c2cc(CCC(=O)O)c(N(CC(N)=O)S(=O)(=O)c3ccc(OC)cc3)c3ccccc23)cc1]

Prepared as described in the general procedure for removal of acid sensitive protecting group (Method C2) to get the title compound as a yellow solid; 18 mg, yield 78%. $^1$H NMR (500 MHz, 100° C.) (DMSO) δ) 8.18 (d, 1H, J=6.4 Hz), 7.86-7.83 (m, 1H), 7.64-7.59 (m, 4H), 7.44-7.41 (m, 1H), 7.32-7.29 (m, 1H), 7.08-7.06 (m, 3H), 7.01 (d, 1H, J=6.8 Hz), 6.84 (br, 4H), 4.35-4.23 (m, 4H), 3.87 (s, 3H), 3.86 (s, 3H), 2.96-2.90 (br, 1H), 2.75 (br, 1H), 2.26 (br, 2H). $^{13}$C NMR (125 MHz, 100° C.) (DMSO) δ 172.73, 168.48, 168.35, 162.64, 162.62, 139.27, 136.77, 134.39, 132.28, 131.28, 130.89, 129.64, 129.51, 129.43, 129.37, 129.34, 128.07, 125.68, 125.61, 125.10, 125.03, 124.53, 124.04, 113.99, 113.93, 113.85, 113.83, 55.31, 55.26, 53.90, 53.77, 33.69, 26.12. HRMS (ESI) Calcd for $C_{31}H_{32}N_4O_{10}S_2$ (M+H)$^+$ 685.1633, found 685.1628.

Example LH927: 2,2'-((2-(3-Amino-3-oxopropyl) naphthalene-1,4-diyl) bis(((4-methoxyphenyl) sulfonyl) azanediyl)) diacetic Acid Prepared as described in the general procedure for removal of acid sensitive protecting group (Method C2) to get the title compound as an off-white solid; 21 mg, yield 75%. $^1$H NMR (500 MHz, 100° C.) (DMSO) δ) 8.18 (d, 1H, J=6.8 Hz), 7.90 (d, 1H, J=6.8 Hz), 7.62-7.59 (m, 4H), 7.44 (t, 1H, J=6.0 Hz), 7.34 (t, 1H, J=6.0 Hz), 7.15 (s, 1H), 7.10 (d, 2H, J=6.8 Hz), 7.03 (d, 2H, J=6.8 Hz), 6.63 (br, 2H), 4.40 (s, 4H), 3.89 (s, 3H), 3.87 (s, 3H), 2.99-2.95 (m, 2H), 2.74-2.68 (m, 2H), 2.23 (br, 2H). $^{13}$C NMR (125 MHz, 100° C.) (DMSO) δ 172.59, 169.02, 168.90, 162.66, 162.62, 139.86, 136.80, 134.18, 132.30, 131.05, 130.35, 129.41, 129.39, 129.34, 128.22, 125.68, 125.00, 124.35, 123.87, 113.92, 113.88, 55.28, 55.26, 52.98, 52.69, 35.17, 26.51. HRMS (ESI) Calcd for $C_{31}H_{31}N_3O_{11}S_2$ (M+H)$^+$ 686.1473, found 686.1471.

Example LH915: 2,2'-(2-(3-(Isopropylamino)-3-oxopropyl) naphthalene-1,4-diyl) bis (((4-methoxyphenyl) sulfonyl) azanediyl)) diacetic Acid

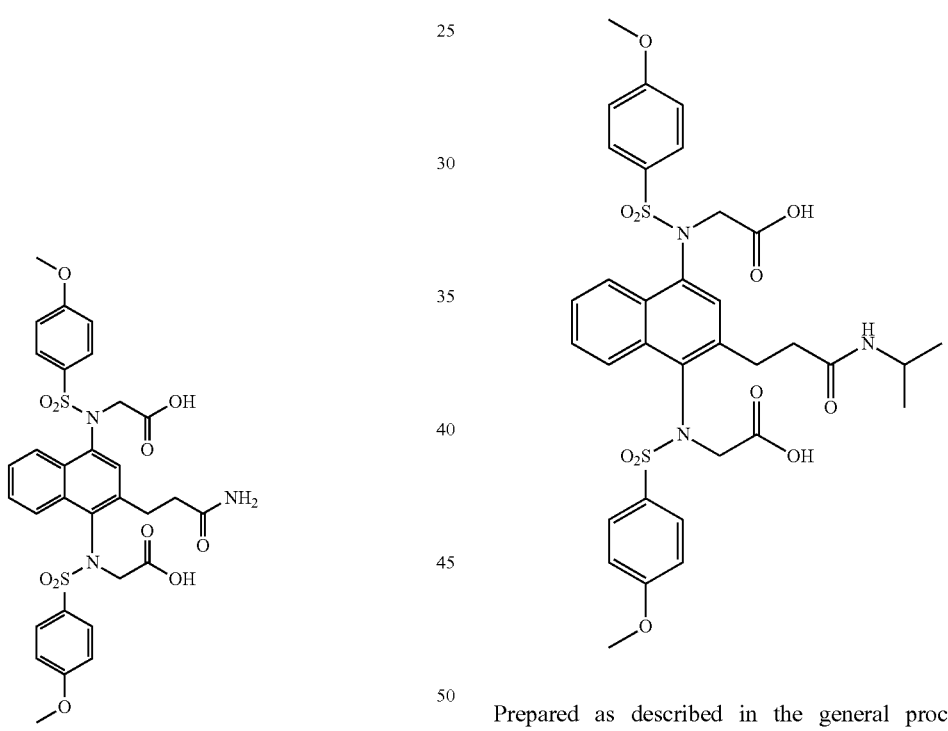

Prepared as described in the general procedure for removal of acid sensitive protecting group (Method C2) to get the title compound as an off-white solid; 19 mg, yield 71%. $^1$H NMR (500 MHz, 100° C.) (DMSO) δ) 8.18 (d, 1H, J=8.5 Hz), 7.94 (d, 1H, J=9.0 Hz), 7.61-7.59 (m, 4H), 7.43 (t, 1H, J=7.0 Hz), 7.36-7.33 (m, 1H), 7.13 (s, 1H), 7.09-7.08 (m, 3H), 7.03 (d, 2H, J=9.0 Hz), 4.39-4.38 (m, 4H), 3.87-3.86 (m, 6H), 2.93-2.87 (m, 1H), 2.71-2.65 (m, 1H), 2.19 (br, 2H), 1.09-1.06 (m, 6H). $^{13}$C NMR (125 MHz, 100° C.) (DMSO) δ 169.68, 169.10, 162.74, 162.72, 139.88, 136.90, 134.32, 132.47, 131.14, 130.46, 129.51, 129.43, 128.33, 125.79, 125.10, 124.51, 123.97, 114.01, 113.96, 55.34, 53.08, 52.78, 35.70, 26.74, 21.84. HRMS (ESI) Calcd for $C_{34}H_{37}N_3O_{11}S_2$ (M+H)$^+$ 728.1942, found 728.1928.

Example LH916: 2,2'-(2-(3-Morpholino-3-oxopropyl)naphthalene-1,4-diyl)bis(((4-methoxyphenyl)sulfonyl) azanediyl)) diacetic Acid

Intermediate: Di-tert-butyl 2,2'-((2-(3-hydroxypropyl) naphthalene-1,4-diyl) bis(((4-methoxyphenyl)sulfonyl) azanediyl)) diacetate

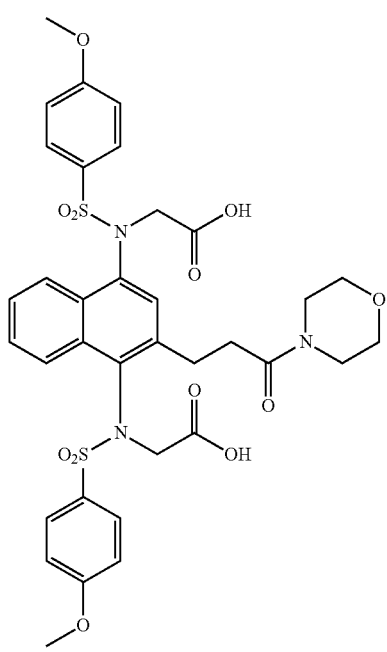 [SMILES: COc1ccc(S(=O)(=O)N(CC(=O)O)c2cc(CCC(=O)N3CCOCC3)c(N(CC(=O)O)S(=O)(=O)c3ccc(OC)cc3)c3ccccc23)cc1]

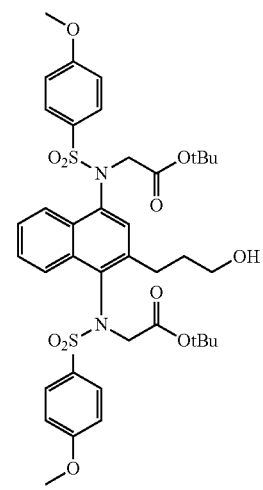 [SMILES: COc1ccc(S(=O)(=O)N(CC(=O)OC(C)(C)C)c2cc(CCCO)c(N(CC(=O)OC(C)(C)C)S(=O)(=O)c3ccc(OC)cc3)c3ccccc23)cc1]

Prepared as described in the general procedure for removal of acid sensitive protecting group (Method C2) to get the title compound as a pink solid; 17 mg, yield 68%. $^1$H NMR (500 MHz, 100° C.) (DMSO) δ) 12.37 (br, 2H), 8.18 (d, 1H, J=6.8 Hz), 7.83 (d, 1H, J=6.8 Hz), 7.62-7.58 (m, 4 H), 7.43 (t, 1H, J=5.6 Hz), 7.32 (t, 1H, J=5.6 Hz), 7.14 (s, 1H), 7.07 (d, 2H, J=5.6 Hz), 7.02 (d, 2H, J=7.2 Hz), 4.43-4.34 (m, 4H), 3.87 (s, 3H), 3.86 (s, 3H), 3.58 (t, 4H, J=4.0 Hz), 3.43 (t, 4H, J=3.6 Hz), 2.94-2.92 (m, 1H), 2.83-2.77 (m, 1H), 2.40 (br, 2H). $^{13}$C NMR (125 MHz, 100° C.) (DMSO) δ 169.41, 168.83, 162.57, 162.45, 139.62, 136.68, 134.12, 132.09, 130.99, 130.24, 129.38, 129.35, 129.25, 128.10, 125.59, 124.93, 124.18, 123.84, 113.80, 113.73, 65.48, 55.18, 55.17, 52.84, 52.60, 31.96, 26.24. HRMS (ESI) Calcd for $C_{35}H_{37}N_3O_{12}S_2$ (M+H)$^+$ 756.1891, found 756.1877.

To a stirred solution of (83) (100 mg, 0.18 mmol) in anhydrous THF (2 ml) under nitrogen at 0° C., LAH (20 mg, 0.53 mmol) was added at room temperature and the mixture refluxed for 8 hours. Upon completion, the reaction quenched with methanol and diluted with ethyl acetate, washed with bine, dried over anhydrous $Na_2SO_4$, and the organic layer removed and the crude product then diluted with DMF and using general procedure (method B) to give the desired product as oily product 71 mg, yield 51%. $^1$H NMR (400 MHz) (CDCl$_3$) δ 8.18-8.10 (m, 1H), 7.70-7.66 (m, 2H), 7.64-7.61 (m, 2H), 7.54-7.37 (m, 2H), 7.32-7.21 (m, 1H), 7.19-7.14 (m, 1H), 6.96-6.93 (m, 2H), 6.90-6.86 (m, 2H), 4.56-4.43 (m, 2H), 4.31-4.17 (m, 2H), 3.87-3.85 (m, 6H), 3.62-3.56 (m, 2H), 3.29-3.21 (m, 1H), 2.59-2.52 (m, 1H), 1.87-1.58 (m, 2H), 1.43-1.34 (m, 18H). $^{13}$C NMR (100 MHz) (CDCl$_3$) δ) 168.21, 168.03, 167.81, 167.69, 163.47, 163.35, 141.54, 141.43, 137.35, 137.30, 135.41, 135.36, 132.98, 132.84, 132.03, 131.81, 131.13, 131.02, 130.54, 130.52, 130.46, 130.42, 130.31, 129.64, 129.31, 127.12, 126.90, 126.46, 126.28, 124.74, 124.71, 124.59, 124.52, 114.13, 82.59, 82.42, 82.40, 62.21, 55.76, 54.61, 54.05, 33.31, 33.07, 31.67, 28.09, 28.04, 28.02, 22.73.

Intermediate: Di-tert-butyl 2,2'-((2-(3-(tosyloxy) propyl) naphthalene-1,4-diyl) bis(((4-methoxyphenyl) sulfonyl)azanediyl)) diacetate

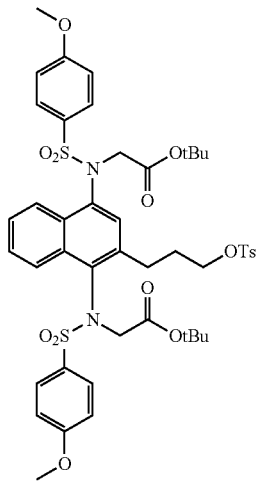 [SMILES: COc1ccc(S(=O)(=O)N(CC(=O)OC(C)(C)C)c2cc(CCCOS(=O)(=O)c3ccc(C)cc3)c(N(CC(=O)OC(C)(C)C)S(=O)(=O)c3ccc(OC)cc3)c3ccccc23)cc1]

Prepared as described in the general procedure for synthesis of sulfonamides (method A2) to get the title compound as brown solid; 67 mg, yield 91%. $^1$H NMR (400 MHz) (CDCl$_3$) δ 8.22-8.14 (m, 1H), 7.78 (d, 2H, J=8.4 Hz), 7.68-7.52 (m, 4H), 7.46-719 (m, 5H), 7.07-6.84 (m, 5H), 4.50-4.38 (m, 2H), 4.28-4.01 (m, 4H), 3.89-3.85 (m, 6H), 3.56-2.47 (m, 4H), 2.44 (s, 3H), 1.40-1.34 (m, 18H). $^{13}$C NMR (100 MHz) (CDCl$_3$) δ) 167.72, 167.54, 163.46, 144.77, 140.67, 137.61, 135.15, 135.06, 133.16, 132.71, 132.24, 130.98, 130.38, 130.30, 130.25, 129.97, 129.65, 129.24, 128.83, 127.96, 127.75, 127.16, 126.99, 126.52, 126.36, 124.91, 124.71, 124.50, 114.16, 82.19, 70.39, 55.85, 55.74, 54.34, 54.04, 30.14, 28.04, 27.98, 27.62, 21.70.

Intermediate: Di-tert-butyl 2,2'-(2-(3-(1,3-dioxoisoindolin-2-yl) propyl) naphthalene-1,4-diyl) bis (((4-methoxyphenyl) sulfonyl) azanediyl)) diacetate

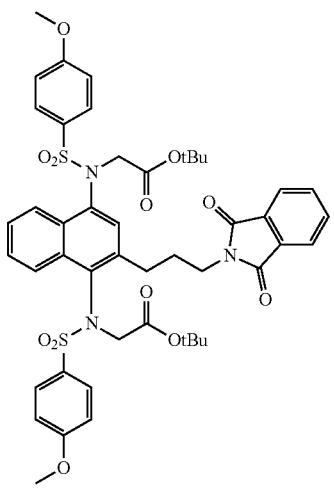 [SMILES: COc1ccc(S(=O)(=O)N(CC(=O)OC(C)(C)C)c2cc(CCCN3C(=O)c4ccccc4C3=O)c(N(CC(=O)OC(C)(C)C)S(=O)(=O)c3ccc(OC)cc3)c3ccccc23)cc1]

To a stirred solution of (86) (30 mg, 0.03 mmol) in 1 ml DMF, Phthalimide potassium salt (9 mg, 0.045 mmol) and K$_2$CO$_3$ (12 mg, 0.06 mmol) were added and the reaction mixture stirred at room temperature for 3 hours. Then, the mixture diluted with ethyl acetate and washed with brine, dried over anhydrous Na$_2$SO$_4$. The organic layer removed under reduced pressure and the crude mixture purified by ISCO using ethyl acetate hexane to get the desired product 24 mg, yield 84%. $^1$H NMR (400 MHz) (CDCl$_3$) δ 8.22-8.16 (m, 1H), 7.87-7.32 (m, 11H), 7.08-7.05 (m, 1H), 6.93-6.87 (m, 4H), 4.51-4.16 (m, 4H), 3.87-3.73 (m, 6H), 3.72-3.62 (m, 2H), 3.08-3.00 (m, 1H), 2.85-2.81 (m, 1H), 2.49-2.41 (m, 1H), 1.74-1.66 (m, 1H), 1.39-1.32 (m, 18H). $^{13}$C NMR (100 MHz) (CDCl$_3$) δ) 171.20, 168.33, 168.27, 167.78, 167.70, 167.64, 167.57, 163.36, 140.59, 137.57, 135.43, 135.28, 134.48, 133.88, 133.70, 133.28, 132.41, 132.17, 132.01, 131.16, 130.43, 130.34, 130.01, 129.07, 128.88, 127.24, 127.02, 126.55, 126.33, 125.08, 124.76, 123.24, 123.06, 114.17, 113.96, 82.09, 55.72, 55.63, 54.71, 54.50, 54.26, 54.15, 38.07, 32.02, 22.79, 21.13.

Intermediate: Di-tert-butyl 2,2'-((2-(3-(benzyl (methyl) amino) propyl) naphthalene-1,4-diyl) bis (((4-methoxyphenyl) sulfonyl) azanediyl)) diacetate

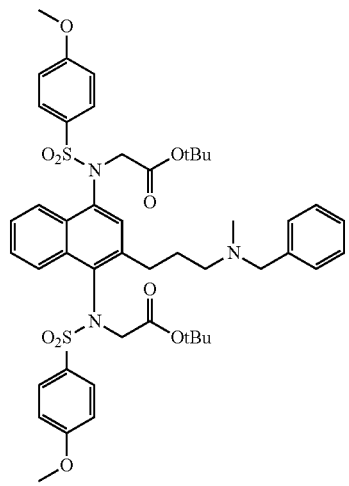 [SMILES: COc1ccc(S(=O)(=O)N(CC(=O)OC(C)(C)C)c2cc(CCCN(C)Cc3ccccc3)c(N(CC(=O)OC(C)(C)C)S(=O)(=O)c3ccc(OC)cc3)c3ccccc23)cc1]

To a stirred solution of (86) (30 mg, 0.03 mmol) in 1 ml DMF, N-Benzylmethylamine (5 uL, 0.045 mmol) and K$_2$CO$_3$ (12 mg, 0.06 mmol) were added and the reaction mixture stirred at room temperature for 1 hour. Then, the mixture diluted with ethyl acetate and washed with brine, dried over anhydrous Na$_2$SO$_4$. The organic layer removed under reduced pressure and the crude mixture purified by ISCO using ethyl acetate hexane to get the desired product 18 mg, yield 69%. $^1$H NMR (400 MHz) (CDCl$_3$) δ 8.15 (d, 1H, J=8.8 Hz), 7.66 (d, 2H, J=8.8 Hz), 7.61 (d, 2H, J=8.8 Hz), 7.46-7.28 (m, 7H), 724-7.17 (m, 2H), 7.00-6.92 (m, 2H), 6.88-6.85 (m, 2H), 4.47-4.12 (m, 4H), 3.85-3.81 (m, 6H), 3.56-3.51 (m, 2H), 2.85-2.79 (m, 2H), 2.59-2.39 (m, 2H), 2.27-2.07 (m, 2H), 1.60 (s, 3H), 1.42-1.35 (m, 18H). $^{13}$C NMR (100 MHz) (CDCl$_3$) δ) 167.31, 167.20, 167.09, 162.83, 162.77, 129.79, 128.98, 128.68, 128.01, 126.47, 125.89, 125.69, 124.07, 113.56, 81.75, 55.14, 54.06, 53.50, 27.51, 27.44.

Example LH918: 2,2'-(2-(3-(1,3-Dioxoisoindolin-2-yl) propyl) naphthalene-1,4-diyl) bis(((4-methoxyphenyl) sulfonyl) azanediyl)) diacetic Acid

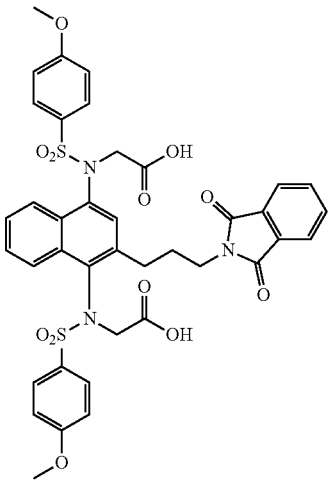 [SMILES: COc1ccc(S(=O)(=O)N(CC(=O)O)c2cc(CCCN3C(=O)c4ccccc4C3=O)c(N(CC(=O)O)S(=O)(=O)c3ccc(OC)cc3)c3ccccc23)cc1]

Prepared as described in the general procedure for hydrolysis of ethyl ester to get di-acidic compounds (Method C2) to get the title compound as a pink solid; 17 mg, yield 68%. $^1$H NMR (500 MHz, 100° C.) (DMSO) δ) 8.22 (d, 1H, J=6.8 Hz), 7.93 (d, 1H, J=6.8 Hz), 7.90-7.84 (m, 4H), 7.58 (d, 2H, J=7.2 Hz), 7.56 (d, 2H, J=7.2 Hz), 7.46-7.43 (m, 1H), 7.37-7.34 (m, 1H), 7.08 (s, 1H), 7.01 (d, 4H, J=6.8 Hz), 4.41 (s, 2H), 4.33 (s, 2H), 3.86 (s, 3H), 3.76 (s, 3H), 3.57 (t, 2H, J=6.0 Hz), 2.76 (t, 2H, J=6.0 Hz), 1.72 (t, 2H, J=6.0 Hz). $^{13}$C NMR (125 MHz, 100° C.) (DMSO) δ 168.82, 168.76, 167.08, 162.54, 162.47, 139.37, 136.74, 134.08, 133.55, 132.29, 131.20, 130.21, 129.31, 129.23, 129.19, 127.91, 125.63, 124.94, 124.32, 123.85, 122.25, 113.77, 113.68, 55.15, 55.13, 55.02, 55.00, 52.80, 52.66, 36.99, 27.90. HRMS (ESI) Calcd for $C_{39}H_{35}N_3O_{12}S_2$ (M+H)$^+$ 802.1735, found 802.1733.

Example LH919: 2,2'-((2-(3-(Benzyl (methyl) amino) propyl) naphthalene-1,4-diyl) bis (((4-methoxyphenyl) sulfonyl) azanediyl)) diacetic Acid

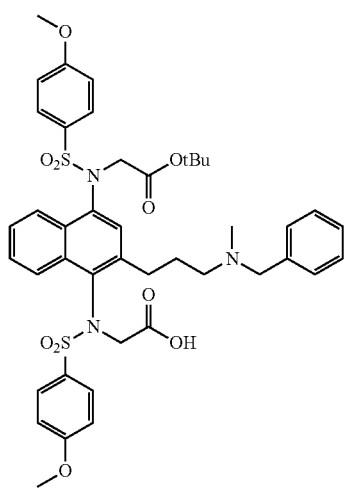 [SMILES: COc1ccc(S(=O)(=O)N(CC(=O)OC(C)(C)C)c2cc(CCCN(C)Cc3ccccc3)c(N(CC(=O)O)S(=O)(=O)c3ccc(OC)cc3)c3ccccc23)cc1]

Prepared as described in the general procedure for hydrolysis of ethyl ester to get di-acidic compounds (Method C2) to get the title compound as a yellow solid; 17 mg, yield 68%. $^1$H NMR (500 MHz, 100° C.) (DMSO) δ) 8.03 (d, 1H, J=6.8 Hz), 7.61 (d, 2H, J=7.2 Hz), 7.56-7.52 (m, 5H), 7.47-7.45 (m, 3H), 7.38 (t, 1H, J=6.0 Hz), 7.32 (s, 1H), 7.26 (t, 1H, J=6.4 Hz), 7.06 (d, 2H, J=7.2 Hz), 6.99 (d, 2H, J=7.2 Hz), 4.49-4.46 (m, 1H), 4.28-4.26 (m, 3H), 3.84 (s, 3H), 3.82 (s, 3H), 3.09-3.07 (m, 2H), 3.01-2.94 (m, 1H), 2.69-2.68 (m, 1H), 2.67 (s, 3H), 1.94-1.90 (m, 2H). $^{13}$C NMR (125 MHz 100° C.) (DMSO) δ 168.83, 168.69, 162.48, 162.30, 139.06, 136.58, 133.97, 131.55, 130.73, 130.19, 129.97, 129.48, 129.28, 129.13, 128.74, 128.19, 128.04, 125.64, 124.93, 123.57, 113.70, 113.63, 58.20, 55.06, 55.01, 54.38, 52.77, 52.27, 27.63, 23.27. HRMS (ESI) Calcd for $C_{39}H_{41}N_3O_{10}S_2$ (M+H)$^+$ 776.2306, found 776.2308.

Intermediate: 2,2'-((2-(3-(Benzyl(methyl) amino) propyl) naphthalene-1,4-diyl) bis(((4-methoxyphenyl) sulfonyl) azanediyl)) diacetic Acid

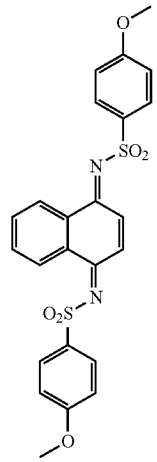 [SMILES: COc1ccc(S(=O)(=O)/N=C2C=C/C(=N\S(=O)(=O)c3ccc(OC)cc3)c3ccccc3/2)cc1]

Ceric ammonium nitrate (219 mg, 0.4 mmol) was added to a solution of (2c) (99 mg, 0.2 mmol) in acetonitrile (20 mL). Then, the reaction mixture was stirred at room temperature and checked by TLC and LCMS; upon completion, the reaction mixture was filtered and the yellow solid product was collected and washed with diethyl ether to get the pure product yellow solid (99 mg, quantitative). $^1$H NMR (400 MHz) (CDCl$_3$) δ 8.34 (s, 2H), 8.20-8.18 (m, 2H), 8.00 (d, 4H, J=8.8 Hz), 7.61-7.58 (m, 2H), 7.05 (d, 2H, J=8.8 Hz), 3.90 (s, 6H). $^{13}$C NMR (100 MHz) (CDCl$_3$) δ 163.77, 161.44, 133.30, 132.93, 132.40, 130.60, 129.93, 126.97, 114.51, 55.87.

Intermediate: N,N'-(2-(Phenylthio)naphthalene-1,4-diyl)bis(4-methoxybenzenesulfonamide)

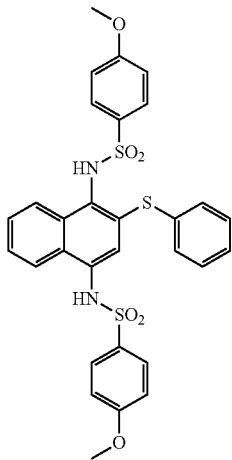 [SMILES: COc1ccc(S(=O)(=O)Nc2cc(Sc3ccccc3)c(NS(=O)(=O)c3ccc(OC)cc3)c3ccccc23)cc1]

To a suspension of the above intermediate (40 mg, 0.08 mmol) in toluene (1 mL), thiophenol (11 uL, 0.1 mmol) and DiPEA (29 uL, 0.1 mmol) were added; The reaction mixture was stirred at room temperature and checked by TLC and LCMS. Then, the reaction mixture was filtered and the crude product purified by ISCO using ethyl acetate:hexane to get the title compound as a pink solid 33 mg, yield 68%. $^1$H NMR (400 MHz) (DMSO) δ 9.01 (s, 1H), 9.95 (s, 1H), 8.00 (d, 1H, J=8.0 Hz), 7.70 (d, 1H, J=8.4 Hz), 7.57 (d, 2H, J=8.8 Hz), 7.41-7.3 (m, 7H), 7.12-7.10 (m, 2H), 6.98 (d, 2H, J=8.8 Hz), 6.91 (d, 2H, J=8.8 Hz), 6.77 (s, 1H), 3.79 (s, 3H), 3.77 (s, 3H). $^{13}$C NMR (100 MHz) (DMSO) δ 162.46, 162.32, 135.56, 133.45, 132.99, 132.79, 132.29, 131.41, 129.52, 128.99, 128.89, 128.62, 128.14, 127.99, 127.83, 126.80, 125.89, 124.23, 123.22, 122.11, 114.30, 114.15, 55.63.

Intermediate: Diethyl 2,2'-((2-(phenylthio) naphthalene-1,4-diyl) bis(((4-methoxyphenyl) sulfonyl) azanediyl)) diacetate

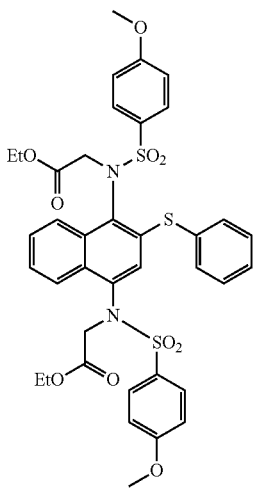 [SMILES: CCOC(=O)CN(c1cc(Sc2ccccc2)c(N(CC(=O)OCC)S(=O)(=O)c2ccc(OC)cc2)c2ccccc12)S(=O)(=O)c1ccc(OC)cc1]

Prepared as described in the general procedure for synthesis of alkylated sulfonamides (method B) to get the title compound as oily product; 27 mg, yield 69%. $^1$H NMR (400 MHz) (CDCl$_3$) δ 8.47-8.38 (m, 1H), 8.08-7.95 (m, 1H), 7.72-7.68 (m, 2H), 7.55-7.45 (m, 4H), 7.31-7.27 (m, 3H), 7.14-7.13 (m, 2H), 7.12 (s, 1H), 6.92-6.89 (m, 2H), 6.83 (d, 1H, J=8.8 Hz), 6.67 (d, 1H, J=8.8 Hz), 4.89-4.83 (m, 1H), 4.58-4.35 (m, 1H), 4.22-3.99 (m, 6H), 3.88-3.81 (m, 6H), 1.25-1.09 (m, 6H). $^{13}$C NMR (100 MHz) (CDCl$_3$) δ 169.14, 168.50, 163.64, 163.32, 163.16, 138.25, 137.91, 137.55, 135.22, 134.94, 134.03, 132.15, 131.34, 131.09, 130.93, 130.81, 130.74, 130.52, 130.29, 130.05, 129.61, 129.53, 128.01, 127.82, 127.70, 127.66, 127.58, 127.45, 126.78, 126.44, 123.87, 114.20, 114.16, 114.11, 61.68, 61.61, 61.56, 61.49, 55.81, 55.71, 53.30, 53.15, 52.90, 14.20, 14.10.

Example LH913: 2,2'-((2-(Phenylthio) naphthalene-1,4-diyl) bis (((4-methoxyphenyl) sulfonyl) azanediyl)) diacetic Acid

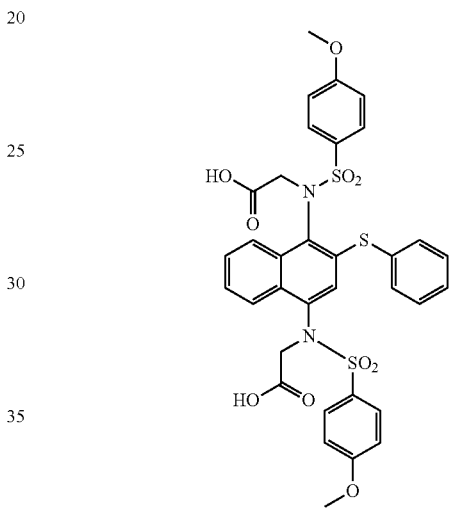

Prepared as described in the general procedure for removal of acid sensitive protecting group (Method C2) to get the title compound as a yellow solid; 19 mg, yield 68%. $^1$H NMR (500 MHz, 100° C.) (DMSO) δ 8.49 (d, 1H, J=6.4 Hz), 8.09 (d, 1H, J=6.4 Hz), 7.66 (d, 2H, J=6.8 Hz), 7.58-7.46 (m, 5H), 7.35-7.34 (m, 3H), 7.16-7.15 (m, 2H), 7.06 (d, 2H, J=7.2 Hz), 6.93-6.92 (m, 2H), 4.71-4.17 (m, 4H), 3.87 (s, 6H). $^{13}$C NMR (125 MHz, 100° C.) (DMSO) δ 169.01, 168.67, 162.96, 162.58, 137.45, 133.95, 131.23, 130.83, 129.81, 129.24, 129.08, 127.48, 126.23, 126.17, 126.00, 123.54, 113.98, 55.44, 55.40, 52.57, 52.28. HRMS (ESI) Calcd for C$_{34}$H$_{30}$N$_2$O$_{10}$S$_3$ (M+H)$^+$ 723.1135, found 723.1133.

Intermediate: 2-Methyl-5-nitro-1H-indole

To a vigorously stirred solution of commercially available 2-methyl-indole (262 mg, 2 mmol) in H$_2$SO$_4$ (2 mL) at 0° C., A solution of NaNO$_3$ (187 mg, 2.2 mmol) in H$_2$SO$_4$ (2 mL) was added dropwise. Then, the reaction was stirred for another 10 minutes, and then poured into 8 mL of ice-water, precipitating a yellow product. The product was isolated via filtration and washed with cold water. 335 mg of yellow solid (96%). $^1$H NMR (400 MHz) (DMSO) δ) 11.68 (s, 1H), 8.38 (s, 1H), 7.90 (d, 1H, J=8.8 Hz), 7.40 (d, 1H, J=8.8 Hz), 6.37 (s, 1H), 2.41 (s, 3H). $^{13}$C NMR (100 MHz) (DMSO) δ 140.48, 139.90, 139.42, 127.96, 115.81, 115.61, 110.63, 101.58, 13.32.

Intermediate: tert-Butyl 2-methyl-5-nitro-1H-indole-1-carboxylate

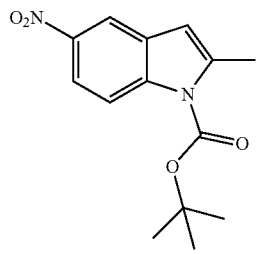 [SMILES: Cc1cc2cc([N+](=O)[O-])ccc2n1C(=O)OC(C)(C)C]

Prepared as described in the general procedure (method B) to get the title compound as brown oily product; the yield 449 mg, quantitative). $^1$H NMR (400 MHz) (CDCl$_3$) δ) 8.32 (d, 1H, J=2.4 Hz), 8.20 (d, 1H, J=9.2 Hz), 8.11 (dd, 1H, J=2.4 Hz, 9.2 Hz), 6.45 (s, 1H) 2.62 (s, 3H), 1.70 (s, 9H). $^{13}$C NMR (100 MHz) (CDCl$_3$) δ 149.91, 143.59, 141.15, 139.82, 129.18, 118.41, 115.59, 115.49, 108.34, 85.22, 28.23, 17.26.

Intermediate: tert-Butyl 2-(bromomethyl)-5-nitro-1H-indole-1-carboxylate

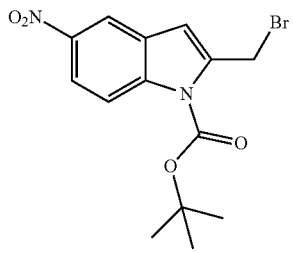 [SMILES: CC(C)(C)OC(=O)n1c(CBr)cc2cc([N+](=O)[O-])ccc21]

The above intermediate (415 mg, 1.5 mmol), NBS (320 mg, 1.8 mmol), and AIBN (50 mg, 0.3 mmol) were taken in DCM (7 ml) in sealed tube and the reaction mixture stirred at 80° C. for 8 hours and checked for reaction completion using TLC. Then, filter and the organic layer removed under reduced pressure to get the crude product which was purified using ISCO (Ethyl acetate:Hexane), the yield (329 mg, 62% yield). $^1$H NMR (400 MHz) (CDCl$_3$) δ) 8.42 (d, 1H, J=2.4 Hz), 8.28 (d, 1H, J=9.2 Hz), 8.20 (dd, 1H, J=2.4 Hz, 9.2 Hz), 6.84 (s, 1H), 4.90 (s, 2H), 1.75 (s, 9H). $^{13}$C NMR (100 MHz) (CDCl$_3$) δ 149.14, 144.05, 140.63, 139.31, 128.07, 120.35, 117.13, 116.24, 111.78, 86.54, 28.11, 26.26.

Intermediate: Methyl ((4-methoxyphenyl) sulfonyl) glycinate

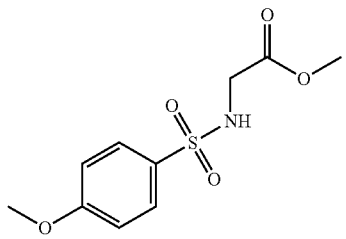

Prepared as described in the general procedure for synthesis of sulfonamides (method A1) to get the title compound as a white solid; the yield 129 mg, 88% yield). $^1$H NMR (400 MHz) (DMSO) δ) 8.05 (s, 1H), 7.71 (d, 2H, J=8.8 Hz), 7.08 (d, 2H, J=8.8 Hz), 3.82 (s, 3H), 3.65 (s, 2H), 3.52 (s, 3H), 3.37 (s, 3H). $^{13}$C NMR (100 MHz) (DMSO) δ 169.22, 161.99, 131.93, 128.46, 114.01, 55.41, 51.58, 43.51.

Intermediate: tert-Butyl 2-(((4-methoxy-N-(2-methoxy-2-oxoethyl)phenyl)sulfonamido)methyl)-5-nitro-1H-indole-1-carboxylate

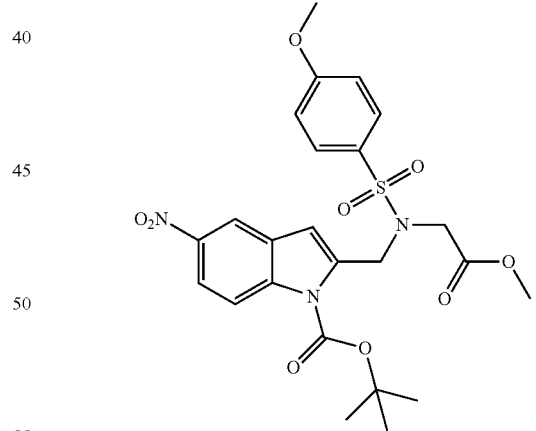

Prepared as described in the general procedure for synthesis of alkylated sulfonamides (method B) to get the title compound as oily product; the yield (129 mg, 88% yield). $^1$H NMR (400 MHz) (DMSO) δ) 8.51 (s, 1H), 8.14 (s, 2H), 7.77 (d, 2H, J=8.8 Hz), 7.08 (d, 2H, J=8.8 Hz), 6.88 (s, 1H), 4.79 (s, 2H), 4.21 (s, 2H), 3.83 (s, 3H), 3.52 (s, 3H), 1.61 (s, 9H). $^{13}$C NMR (100 MHz) (DMSO) δ 169.20, 168.94, 162.50, 148.66, 142.91, 140.18, 139.19, 132.00, 130.26, 129.14, 128.44, 128.21, 118.69, 116.25, 115.18, 114.15, 114.00, 108.33, 85.67, 55.49, 55.42, 51.63, 51.57, 48.83, 47.60, 43.51, 27.31.

Intermediate: tert-Butyl 5-amino-2-(((4-methoxy-N-(2-methoxy-2-oxoethyl) phenyl) sulfonamido) methyl)-1H-indole-1-carboxylate

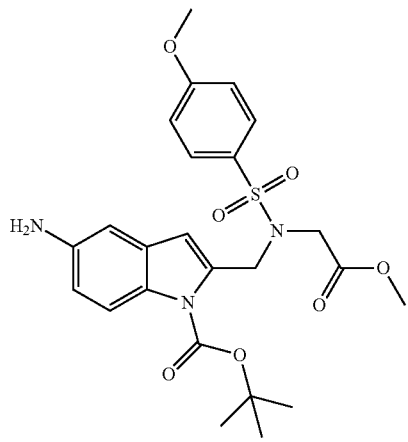 [SMILES: COC(=O)CN(Cc1cc2cc([N+](=O)[O-])ccc2n1C(=O)OC(C)(C)C)S(=O)(=O)c1ccc(OC)cc1]

Prepared as described in the general procedure for nitro group reduction (Method E2) to get the title compound as a beige solid; the yield (129 mg, 88% yield). $^1$H NMR (400 MHz) (CDCl$_3$) δ 7.76 (m, 3H), 6.86 (d, 2H, J=9.2 Hz), 6.70 (d, 1H, J=2.0 Hz), 6.60 (dd, 2H, J=2.4 Hz, 8.8 Hz), 6.41 (s, 1H), 4.85 (s, 2H), 4.16 (s, 2H), 3.79 (s, 3H), 3.57 (s, 3H), 1.60 (s, 9H). $^{13}$C NMR (100 MHz) (CDCl$_3$) δ 169.50, 162.55, 150.22, 142.25, 136.17, 131.55, 130.64, 129.87, 129.47, 116.03, 113.92, 113.39, 109.00, 105.47, 83.98, 55.55, 52.08, 48.63, 47.77, 28.19.

Intermediate: tert-Butyl 2-(((4-methoxy-N-(2-methoxy-2-oxoethyl) phenyl) sulfonamido) methyl)-5-((4-methoxyphenyl) sulfonamido)-1H-indole-1-carboxylate

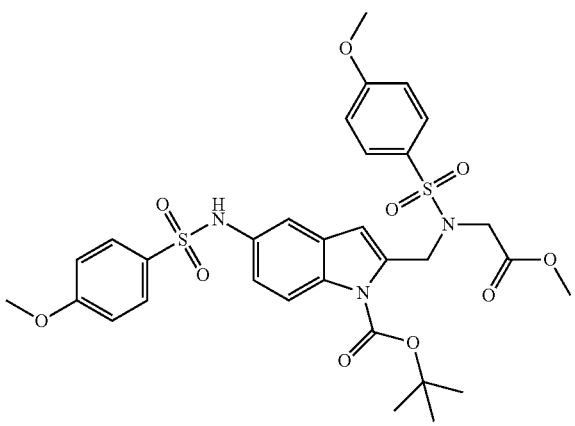

Prepared as described in the general procedure for synthesis of sulfonamides (method A2) to get the title compound as a beige solid; the yield (129 mg, 88% yield). $^1$H NMR (400 MHz) (CDCl$_3$) δ 7.80 (d, 1H, J=8.8 Hz), 7.76 (d, 2H, J=9.2 Hz), 7.12 (d, 1H, J=1.6 Hz), 7.08 (s, 1H), 6.95 (dd, 1H, J=2.4 Hz, 8.8 Hz), 6.89 (d, 2H, J=8.8 Hz), 6.82 (d, 2H, J=8.8 Hz), 6.51 (s, 1H), 4.87 (s, 2H), 4.18 (s, 2H), 3.82 (s, 3 H), 3.78 (s, 3H), 3.58 (s, 3H), 1.62 (s, 9H). $^{13}$C NMR (100 MHz) (CDCl$_3$) δ 169.46, 163.09, 163.04, 150.04, 137.33, 134.69, 131.79, 131.40, 130.69, 129.62, 129.48, 129.37, 119.54, 116.04, 114.38, 114.21, 114.10, 108.94, 84.89, 55.69, 55.62, 52.25, 48.78, 47.98, 28.25.

Intermediate: tert-Butyl 5-((N-(2-ethoxy-2-oxo-ethyl)-4-methoxyphenyl) sulfonamido)-2-(((4-methoxy-N-(2-methoxy-2-oxoethyl) phenyl) sulfonamido) methyl)-1H-indole-1-carboxylate

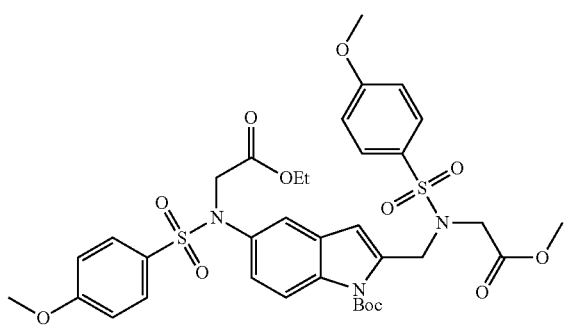

Prepared as described in the general procedure for synthesis of alkylated sulfonamides (method B) to get the title compound as oily product; the yield (129 mg, 88% yield). $^1$H NMR (400 MHz) (CDCl$_3$) δ 7.88 (d, 1H, J=8.8 Hz), 7.75 (d, 2H, J=8.8 Hz), 7.60 (d, 2H, J=8.8 Hz), 7.27 (d, 1H, J=2.0 Hz), 7.13 (dd, 1H, J=2.0 Hz, 8.8 Hz), 6.92-6.89 (m, 4H), 6.57 (s, 1H), 4.88 (s, 2H), 4.42 (s, 2H), 4.17-4.11 (m, 4H), 3.86 (s, 3H), 3.85 (s, 3H), 3.60 (s, 3H), 1.63 (s, 9H), 1.22 (t, 3H, J=7.2 Hz). $^{13}$C NMR (100 MHz) (CDCl$_3$) δ 169.40, 168.99, 163.07, 150.00, 137.48, 136.06, 134.95, 131.37, 130.68, 130.03, 129.57, 129.26, 125.12, 120.89, 116.00, 114.08, 113.98, 109.16, 85.05, 61.46, 55.68, 55.66, 53.25, 52.21, 48.68, 47.86, 28.22, 14.17.

Example LH938: N-((5-((N-(Carboxymethyl)-4-methoxyphenyl) sulfonamido)-1H-indol-2-yl) methyl)-N-((4-methoxyphenyl) sulfonyl) glycine

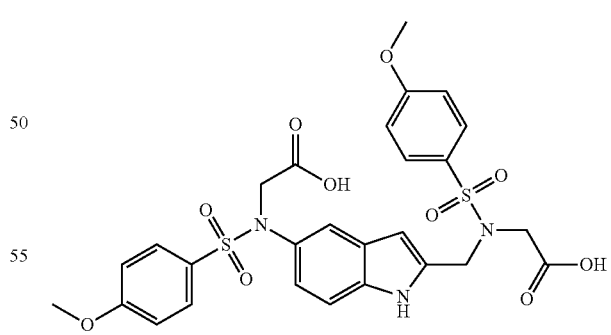

Prepared as described in the general procedure for hydrolysis of ethyl ester to get di-acidic compounds (Method C1) (base hydrolysis) to get the title compound as an off-white solid; the yield (129 mg, 88% yield). $^1$H NMR (400 MHz) (DMSO) δ 12.73 (br, 2H), 11.13 (s, 1H), 7.77 (d, 2H, J=8.8 Hz), 7.56 (d, 2H, J=8.8 Hz), 7.26-7.22 (m, 2H), 7.08-7.05 (m, 4H), 6.78 (dd, 1H, J=2.0 Hz, 8.8 Hz), 6.20 (s, 1 H), 4.53 (s, 2H), 4.34 (s, 2H), 3.89 (s, 2H), 3.84 (s, 6H). $^{13}$C NMR (100 MHz) (DMSO) δ 170.18, 169.85, 162.51, 162.46, 135.54, 134.85, 131.37, 130.93, 130.65, 129.49, 129.30, 127.49, 121.86, 120.53, 114.26, 114.14, 111.40, 101.88, 55.66, 53.16, 47.58, 44.87. HRMS (ESI) Calcd for $C_{27}H_{27}N_3O_{10}S_2$ (M+H)$^+$ 618.1211, found 618.1217.

Intermediate: 5-Nitro-1H-indole-3-carbaldehyde

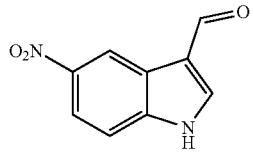 [SMILES: O=Cc1c[nH]c2ccc([N+](=O)[O-])cc12]

To a stirred solution of commercially available 5-nitroindole (486 mg, 3 mmol) in anhydrous DMF under nitrogen, phosphorus chloride oxide (0.834 ml, 9 mmol) was added at 0° C. The reaction mixture stirred at room temperature for 1 h and then poured into cold saturated aqueous NaHCO$_3$ solution and stirred for 0.5 h and extracted by EtOAc (3×). The organic layer washed with brine, dried over anhydrous Na$_2$SO$_4$, and the organic layer removed using rotovap. The crude product purified by ISCO to get the desired product, 519 mg, yield 91%. $^1$H NMR (400 MHz) (DMSO) δ) 12.68 (s, 1H) 10.02 (s, 1H) 8.43 (s, 1H) 8.92 (d, J=2.0 Hz, 1H) 8.56 (s, 1H), 7.96 (dd, J=2.4 Hz, 8.8 Hz, 1H) 7.71 (d, J=8.8 Hz, 1H). $^{13}$C NMR (100 MHz) (DMSO) δ 185.48, 123.50, 119.04, 118.75, 117.03, 113.19.

Intermediate: 4-Nitro-1H-indole-3-carbaldehyde

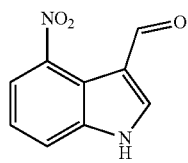 [SMILES: O=Cc1c[nH]c2cccc([N+](=O)[O-])c12]

To a stirred solution of commercially available 4-nitroindole (486 mg, 3 mmol) in anhydrous DMF under nitrogen, phosphorus chloride oxide (0.834 ml, 9 mmol) was added at 0° C. The reaction mixture stirred at room temperature for 1 h and then poured into cold saturated aqueous NaHCO$_3$ solution and stirred for 0.5 h and extracted by EtOAc (3×). The organic layer washed with brine, dried over anhydrous Na$_2$SO$_4$, and the organic layer removed using rotovap. The crude product purified by ISCO to get the desired product, 461 mg, yield 81% $^1$H NMR (400 MHz) (DMSO) δ) 12.86 (s, 1H) 10.12 (s, 1H) 8.50 (s, 1H), 7.92-7.86 (m, 2H), 7.42 (t, J=8.0 Hz, 1H); $^{13}$C NMR (100 MHz) (DMSO) δ 185.02, 142.29, 138.92, 138.11, 122.23, 118.33, 117.90, 116.30, 115.49.

Intermediate: 1-Methyl-5-nitro-1H-indole-3-carbaldehyde

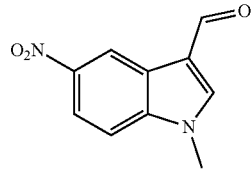

Prepared as described in the general procedure for synthesis of alkylated sulfonamides (method B) to get the title compound as oily product; the yield (351 mg, 86% yield). $^1$H NMR (400 MHz) (DMSO) δ) 9.94 (s, 1 H), 8.81 (d, J=2.4 Hz, 1H) 8.48 (s, 1H), 8.12 (dd, J=2.4 Hz, 8.8 Hz, 1H), 7.73 (d, J=9.2 Hz, 1H), 3.94 (s, 1H). $^{13}$C NMR (100 MHz) (DMSO) δ 184.84, 144.29, 142.95, 140.39, 123.69, 118.51, 117.84, 116.92, 111.69, 33.75.

Intermediate: 1-Methyl-4-nitro-1H-indole-3-carbaldehyde

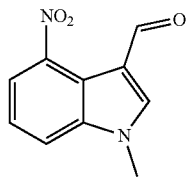

Prepared as described in the general procedure for synthesis of alkylated sulfonamides (method B) to get the title compound as oily product; the yield 343 mg, 86% yield). 41 NMR (400 MHz) (DMSO) δ) 10.07 (s, 1H) 8.51 (s, 1H), 8.03-7.92 (m, 2H), 7.49 (s, 1H), 3.97 (s, 3H); $^{13}$C NMR (100 MHz) (DMSO) δ 184.95, 142.54, 141.72, 139.64, 122.52, 118.58, 117.32, 116.23, 115.27, 33.83.

Intermediate: 4-Nitro-1-((2-(trimethylsilyl) ethoxy) methyl)-1H-indole-3-carbaldehyde

Prepared as described in the general procedure (method A2) to get the title compound as a yellow solid; the yield 129 mg, 88% yield). $^1$H NMR (400 MHz) (acetone-d$_6$) δ) 10.25 (s, 1H) 8.50 (s, 1H), 8.12 (d, J=8.8 Hz, 1H), 8.01 (d, J=8.4 Hz, 1H), 7.55 (t, J=8.0 Hz, 1H), 5.86 (s, 2H), 3.64 (t, J=8.0 Hz, 2H), 2.82 (s, 6H), 0.93 (t, J=8.0 Hz, 2H), −0.06 (s, 9H); $^{13}$C NMR (100 MHz) (acetone-d$_6$) δ 186.18, 140.27, 140.19, 123.73, 120.03, 118.59, 118.55, 117.81, 77.65, 67.19, 18.24, −1.35

Intermediate: (1-Methyl-5-nitro-1H-indol-3-yl) methanol

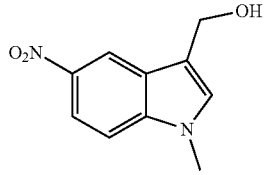

To a stirred solution of (306 mg, 1.5 mmol) in EtOH:THF (1:1) (10 ml) at 0° C., NaBH4 (121 mg, 3 mmol) was added and the reaction stirred at 0° C. for 2 h and monitor the reaction by TLC. Then, reaction mixture diluted with ethyl acetate and washed with 1N HCl, brine, dried over anhydrous $Na_2SO_4$, and the organic layer concentrated under reduced pressure to get the desired product, the yield 251 mg, 81% yield). $^1$H NMR (400 MHz) (Acetone-$d_6$) δ 8.65 (d, J=2.0 Hz, 1H), 8.07 (dd, J=2.4 Hz, 5.2 Hz, 1H), 7.54 (d, J=5.2 Hz, 1H), 7.42 (s, 1H), 4.85 (d, J=5.2 Hz, 2H), 4.11 (t, J=5.2 Hz, 1H), 3.90 (s, 1H). $^{13}$C NMR (100 MHz) (Acetone-$d_6$) δ 142.00, 141.00, 131.77, 127.48, 119.60, 117.49, 117.30, 110.59, 56.49, 33.24.

Intermediate: (1-Methyl-4-nitro-1H-indol-3-yl) methanol

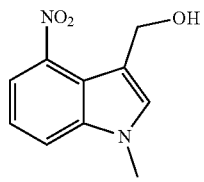

To a stirred solution of (306 mg, 1.5 mmol) in EtOH:THF (1:1) (10 ml) at 0° C., NaBH4 (121 mg, 3 mmol) was added and the reaction stirred at 0° C. for 2 h and monitor the reaction by TLC. Then, reaction mixture diluted with ethyl acetate and washed with 1N HCl, brine, dried over anhydrous $Na_2SO_4$, and the organic layer concentrated under reduced pressure to get the desired product, the yield 244 mg, 79% yield). $^1$H NMR (400 MHz) (CDCl$_3$) δ 7.93 (d, 1H, J=8.0 Hz), 7.53 (d, 1H, J=8.4 Hz), 7.22-7.18 (m, 2H), 4.82 (s, 2H), 3.76 (s, 3H), 2.39 (s, 1H); $^{13}$C NMR (100 MHz) (CDCl$_3$) δ 142.46, 140.10, 133.73, 120.69, 119.18, 118.19, 116.09, 114.94, 58.46, 33.25.

Intermediate: (4-Nitro-1-((2-(trimethylsilyl) ethoxy) methyl)-1H-indol-3-yl) methanol

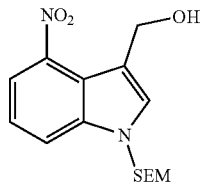 [SMILES: C[Si](C)(C)CCOCn1cc(CO)c2c([N+](=O)[O-])cccc21]

To a stirred solution of (485 mg, 1.5 mmol) in EtOH:THF (1:1) (10 ml) at 0° C., NaBH4 (121 mg, 3 mmol) was added and the reaction stirred at 0° C. for 2 h and monitor the reaction by TLC. Then, reaction mixture diluted with ethyl acetate and washed with 1N HCl, brine, dried over anhydrous $Na_2SO_4$, and the organic layer concentrated under reduced pressure to get the desired product, the yield 387 mg, 80% yield). $^1$H NMR (400 MHz) (acetone-$d_6$) δ 8.01 (d, J=8.0 Hz, 1H), 7.91 (d, J=7.6 Hz, 1H), 7.77 (s, 1H), 7.41 (t, J=8.0 Hz, 1H), 5.74 (s, 2H), 4.95 (s, 2H), 3.97 (br, 1H), 3.63 (t, J=8.0 Hz, 2H), 0.00 (s, 9H); $^{13}$C NMR (100 MHz) (acetone-$d_6$) δ 143.56, 140.27, 132.58, 121.48, 120.02, 118.04, 117.36, 116.83, 76.40, 66.47, 58.67, 18.13, −1.33.

Intermediate: Methyl N-((4-methoxyphenyl) sulfonyl)-N-((1-methyl-5-nitro-1H-indol-3-yl) methyl) glycinate

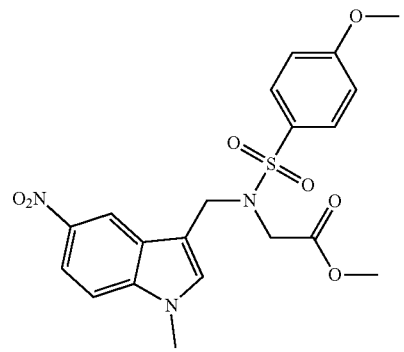 [SMILES: COC(=O)CN(Cc1cn(C)c2ccc([N+](=O)[O-])cc12)S(=O)(=O)c1ccc(OC)cc1]

A mixture of the above intermediate (206 mg, 1 mmol), PPh$_3$ (314 mg, 1.2 mmol), DIAD (242 mg, 1.2 mmol), in anhydrous THF (5 ml) under nitrogen atmosphere was stirred at room temperature overnight till reaction completion. Then the organic layer concentrated under reduced pressure and the crude mixture purified by ISCO using ethyl acetate:hexane to get the desired product, the yield (308 mg, 69% yield). $^1$H NMR (400 MHz) (Acetone-$d_6$) δ 8.57 (d, J=6.4 Hz, 1H), 8.06 (dd, J=2.0 Hz, 8.8 Hz, 1H), 7.85 (d, J=8.8 Hz, 2H), 7.55 (d, J=9.2 Hz, 1H), 7.43 (s, 1H), 7.10 (d, J=8.8 Hz, 1H), 4.69 (s, 2H), 3.96 (s, 2H), 3.91 (s, 3 H), 3.89 (s, 3H), 3.46 (s, 3H). $^{13}$C NMR (100 MHz) (Acetone-$d_6$) δ 170.02, 164.01, 142.42, 141.04, 134.46, 132.63, 130.36, 127.55, 117.32, 117.19, 115.03, 111.77, 110.87, 56.13, 52.06, 47.64, 43.43, 33.44.

Intermediate: Methyl N-((4-methoxyphenyl)sulfonyl)-N-((1-methyl-4-nitro-1H-indol-3-yl)methyl) glycinate

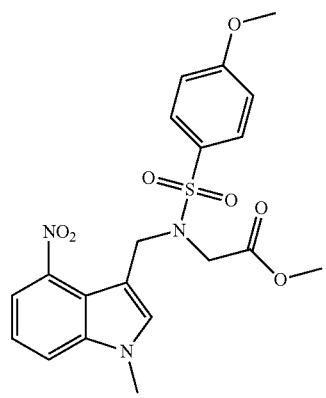 [SMILES: COC(=O)CN(Cc1cn(C)c2cccc([N+](=O)[O-])c12)S(=O)(=O)c1ccc(OC)cc1]

A mixture of the above intermediate (206 mg, 1 mmol), PPh3 (314 mg, 1.2 mmol), DIAD (242 mg, 1.2 mmol), in anhydrous THF (5 ml) under nitrogen atmosphere was stirred at room temperature overnight till reaction completion. Then the organic layer concentrated under reduced pressure and the crude mixture purified by ISCO using ethyl acetate:hexane to get the desired product, the yield 273 mg, 61% yield). $^1$H NMR (400 MHz) (Acetone-$d_6$) δ) 7.65 (d, J=8.0 Hz, 1H), 7.54 (d, J=8.8 Hz, 2H), 7.47 (s, 1H), 7.22 (t, J=8.0 Hz, 1H), 6.99 (d, J=7.2 Hz, 1H), 6.81 (d, J=8.8 Hz, 2H), 5.46 (s, 2H), 4.71 (s, 2H), 4.03 (s, 3H), 3.87 (s, 3 H), 3.55 (s, 3H).

Intermediate: Methyl N-((4-methoxyphenyl) sulfonyl)-N-((4-nitro-1-((2-(trimethylsilyl) ethoxy) methyl)-1H-indol-3-yl) methyl)glycinate A mixture of the above intermediate (323 mg, 1 mmol), PPh3 (314 mg, 1.2 mmol), DIAD (242 mg, 1.2 mmol), in anhydrous THF (5 ml) under nitrogen atmosphere was stirred at room temperature overnight till reaction completion. Then the organic layer concentrated under reduced pressure and the crude mixture purified by ISCO using ethyl acetate:hexane to get the desired product, the yield (361 mg, 64% yield). $^1$H NMR (400 MHz) (CDCl$_3$) δ) 7.89 (d, 1H, J=8.0 Hz), 7.78 (d, 1H, J=8.4 Hz), 7.71-7.69 (m, 3H), 7.31-7.26 (m, 1H), 6.87 (d, 2H, J=8.8 Hz), 5.54 (s, 2H), 4.80 (s, 2H), 4.12 (s, 2H), 3.86 (s, 3H), 3.66 (s, 3H), 3.55 (t, 2H, J=8.0 Hz), 0.94 (t, 2H, J=8.8 Hz), 0.00 (s, 9H). $^{13}$C NMR (100 MHz) (CDCl$_3$) δ 169.70, 162.63, 142.44, 139.12, 133.56, 131.38, 129.25, 120.99, 119.85, 118.36, 113.78, 109.95, 76.17, 66.39, 55.52, 52.07, 49.23, 46.62, 17.69, −1.44.

Intermediate: Methyl N-((5-amino-1-methyl-1H-indol-3-yl) methyl)-N-((4-methoxyphenyl) sulfonyl) glycinate

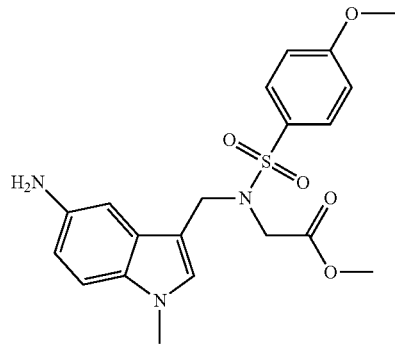

Prepared as described in the general procedure for nitro group reduction (Method E2) to get the title compound as a light pink solid; the yield 245 mg, quantitative). $^1$H NMR (400 MHz) (Acetone-$d_6$) δ) 7.60 (d, J=8.8 Hz, 2H), 6.89 (d, J=8.8 Hz, 1H), 6.83 (d, J=8.8 Hz, 2H), 6.61 (s, 1 H), 6.56 (d, J=2.0 Hz, 1H), 8.06 (dd, J=2.0 Hz, 8.4 Hz, 1H), 4.34 (s, 2H), 3.68 (s, 3H), 3.66 (s, 2H), 3.45 (s, 3H), 3.27 (s, 3H). $^{13}$C NMR (100 MHz) (Acetone-$d_6$) δ 170.02, 162.50, 142.30, 138.50, 134.10, 132.00, 130.90, 128.92, 127.00, 117.00, 113.54, 109.50, 108.06, 55.03, 54.91, 47.10, 43.05, 33.07.

Intermediate: Methyl N-((4-amino-1-methyl-1H-indol-3-yl) methyl)-N-((4-methoxyphenyl) sulfonyl) glycinate

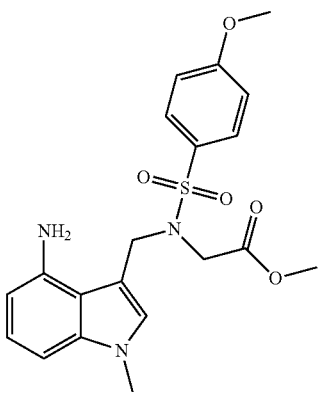

Prepared as described in the general procedure for nitro group reduction (Method E2) to get the title compound as a yellow solid; the yield 201 mg, quantitative). $^1$H NMR (400 MHz) (CDCl$_3$) δ) 7.70 (d, 2H, J=8.8 Hz), 6.92-6.89 (m, 3H), 6.56-6.54 (m, 2H), 6.24 (d, 1H, J=7.6 Hz), 4.54 (s, 2H), 3.81 (s, 2H), 3.78 (s, 3H), 3.52 (s, 3H), 3.26 (s, 3H). $^{13}$C NMR (100 MHz) (CDCl$_3$) δ 169.53, 163.28, 145.13, 141.81, 139.60, 130.00, 128.73, 123.89, 115.95, 114.25, 106.68, 105.00, 99.69, 55.74, 51.82, 46.55, 44.77, 31.53.

Intermediate: Methyl N-((4-amino-1-((2-(trimethylsilyl)ethoxy)methyl)-1H-indol-3-yl)methyl)-N-((4-methoxyphenyl)sulfonyl)glycinate

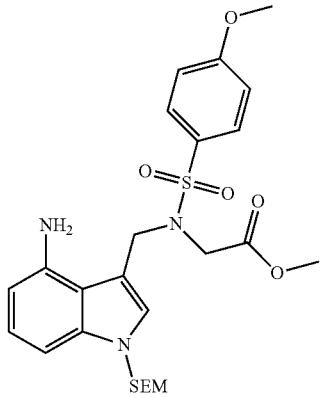 [SMILES: COC(=O)CN(Cc1cn(COCC[Si](C)(C)C)c2cccc([N+](=O)[O-])c12)S(=O)(=O)c1ccc(OC)cc1]

Prepared as described in the general procedure for nitro group reduction (Method E2) to get the title compound as a yellow solid; the yield 245 mg, quantitative). $^1$H NMR (400 MHz) (DMSO) δ) 7.81 (d, 2H, J=8.8 Hz), 7.01-6.99 (m, 3H), 6.82-6.78 (m, 2H), 6.36 (d, 2H, J=7.6 Hz), 5.30 (s, 2H), 4.63 (s, 2H), 3.90-3.87 (m, 5), 3.40 (t, 2H, J=8.0 Hz), 3.34 (s, 3 H), 0.84 (t, 2H, J=8.0 Hz), −0.09 (s, 9H). $^{13}$C NMR (100 MHz) (DMSO) δ 169.37, 166.34, 141.82, 139.29, 130.03, 127.85, 124.45, 122.22, 116.30, 114.28, 111.89, 108.25, 105.82, 100.38, 75.64, 65.92, 55.74, 51.82, 46.69, 44.78, 17.84, −1.35.

Intermediate: Methyl N-((5-((4-methoxyphenyl)sulfonamido)-1-methyl-1H-indol-3-yl) methyl)-N-((4-methoxyphenyl) sulfonyl) glycinate

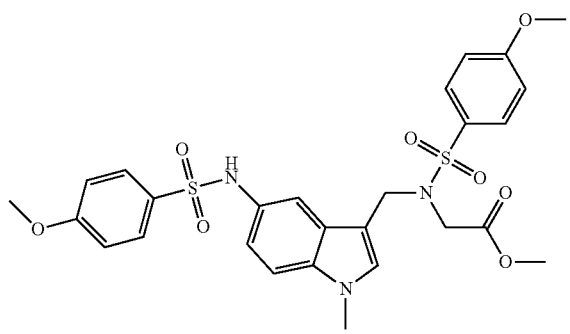

Prepared as described in the general procedure for synthesis of sulfonamides (method A2) to get the title compound as a yellow solid; the yield (215 mg, 73% yield). $^1$H NMR (400 MHz) (acetone-d$_6$) δ) 8.63 (s, 1H), 7.81 (d, 2H, J=8.8 Hz), 7.70 (d, 2H, J=8.8 Hz), 7.36 (d, 1H, J=2.0 Hz), 7.25 (d, 1H, J=8.8 Hz), 7.11-7.08 (m, 4H), 6.98 (d, 2H, J=8.8 Hz), 4.55 (s, 2H), 3.92 (s, 3H), 3.83 (s, 3H), 3.79 (s, 2 H), 3.72 (s, 3H), 3.41 (s, 3H). $^{13}$C NMR (100 MHz) (acetone-d$_6$) δ 169.96, 163.89, 163.65, 136.16, 132.76, 132.72, 131.83, 131.05, 130.37, 130.27, 128.52, 119.12, 114.98, 114.79, 114.00, 110.73, 108.32, 56.14, 55.98, 51.97, 47.07, 43.41, 32.95.

Intermediate: Methyl N-((4-((4-methoxyphenyl) sulfonamido)-1-methyl-1H-indol-3-yl) methyl)-N-((4-methoxyphenyl) sulfonyl) glycinate

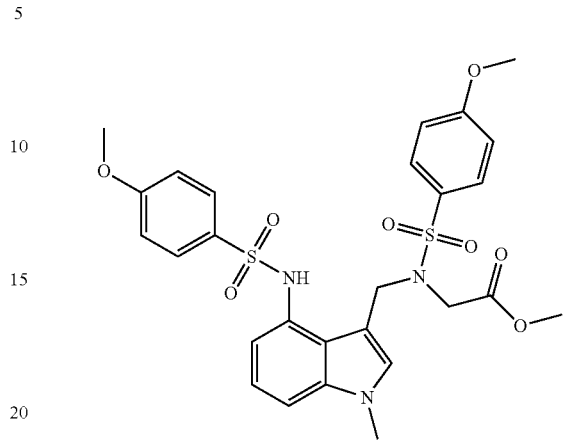

Prepared as described in the general procedure for synthesis of sulfonamides (method A2) to get the title compound as a yellow solid; the yield (203 mg, 69% yield). $^1$H NMR (400 MHz) (Acetone-d$_6$) δ) 8.19 (s, 1H), 7.82 (d, 2H, J=8.8 Hz), 7.72 (d, 2H, J=8.8 Hz), 7.21 (d, 1H, J=8.0 Hz), 7.12-7.06 (m, 4H), 7.00 (t, 3H, J=8.4 Hz), 4.42 (s, 2H), 3.92 (s, 3H), 3.88 (s, 2H), 3.85 (s, 3H), 3.72 (s, 3H), 3.31 (s, 3H). $^{13}$C NMR (100 MHz) (Acetone-d$_6$) δ 169.89, 164.21, 163.89, 139.87, 133.44, 132.14, 131.12, 130.79, 130.49, 130.31, 122.87, 122.66, 117.25, 115.07, 114.75, 108.68, 107.56, 56.20, 56.09, 51.97, 48.66, 45.72, 33.08.

Intermediate: Methyl N-((4-((4-methoxyphenyl) sulfonamido)-1-((2-(trimethylsilyl) ethoxy) methyl)-1H-indol-3-yl) methyl)-N-((4-methoxyphenyl) sulfonyl) glycinate

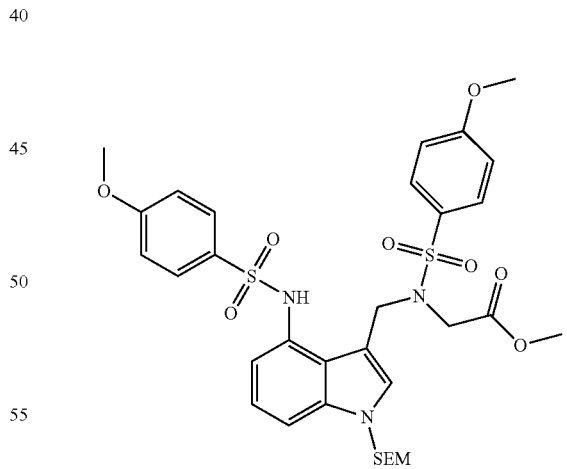

Prepared as described in the general procedure for synthesis of sulfonamides (method A2) to get the title compound as a yellow solid; the yield (249 mg, 71% yield). $^1$H NMR (400 MHz) (CDCl$_3$) δ) 7.94 (s, 1H), 7.82-7.79 (m, 4H), 7.25-7.13 (m, 3H), 6.95 (d, 2H, J=8.8 Hz), 6.91 (s, 1H), 6.86 (d, 2H, J=8.8 Hz), 5.33 (s, 2 H), 4.35 (s, 2H), 3.86 (s, 3H), 3.81 (s, 5H), 3.40 (t, 2H, J=8.0 Hz), 3.29 (s, 3H), 0.85 (t, 2H, J=8.0 Hz), −0.08 (s, 9H). $^{13}$C NMR (100 MHz) (CDCl$_3$) δ 169.31, 163.36, 162.86, 138.46, 132.50, 130.19, 129.91, 129.60, 129.40, 123.39, 121.56, 116.51, 114.24, 113.93, 108.04, 107.49, 75.80, 66.15, 55.75, 55.64, 51.96, 47.73, 44.61, 17.79, −1.36.

Intermediate: Ethyl N-(3-(((4-methoxy-N-(2-methoxy-2-oxoethyl) phenyl) sulfonamido) methyl)-1-methyl-1H-indol-5-yl)-N-((4-methoxyphenyl) sulfonyl) glycinate

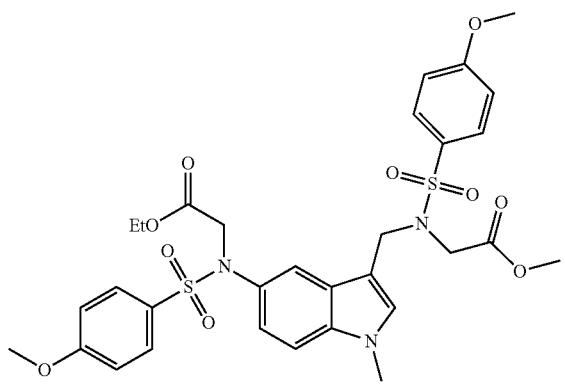

Prepared as described in the general procedure for synthesis of alkylated sulfonamides (method B) to get the title compound as oily product; the yield (114 mg, 85% yield). $^1$H NMR (400 MHz) (CDCl$_3$) δ 7.80 (d, 2H, J=8.8 Hz), 7.63 (d, 2H, J=8.8 Hz), 7.26 (d, 1H, J=2.0 Hz), 7.17 (d, 2H, J=1.2 Hz), 7.00 (d, 2H, J=8.8 Hz), 6.96 (s, 1H), 6.93 (d, 1H, J=8.8 Hz), 4.50 (s, 2H), 4.39 (s, 2H), 4.13 (q, 2H, J=7.2 Hz), 3.89 (s, 3H), 3.87 (s, 3H), 3.84 (s, 2H), 3.70 (s, 3H), 3.51 (s, 3H), 1.22 t, 3H, J=7.2 Hz). $^{13}$C NMR (100 MHz) (CDCl$_3$) δ 169.61, 169.07, 163.02, 163.00, 136.57, 132.35, 131.32, 130.91, 130.56, 129.94, 129.64, 127.44, 124.17, 119.69, 114.17, 114.03, 109.80, 108.34, 61.30, 55.67, 55.62, 53.55, 51.91, 46.36, 42.68, 33.00, 14.13.

Intermediate: Ethyl N-(3-(((4-methoxy-N-(2-methoxy-2-oxoethyl) phenyl) sulfonamido) methyl)-1-methyl-1H-indol-4-yl)-N-((4-methoxyphenyl) sulfonyl) glycinate

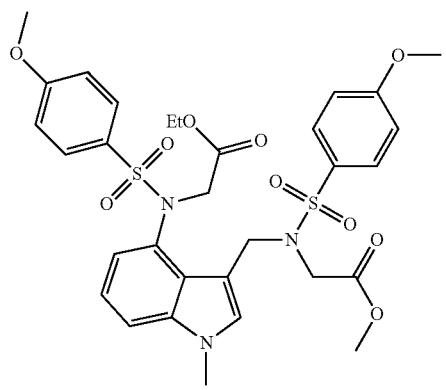 [SMILES: CCOC(=O)CN(c1cccc2c1c(CN(CC(=O)OC)S(=O)(=O)c1ccc(OC)cc1)cn2C)S(=O)(=O)c1ccc(OC)cc1]

Prepared as described in the general procedure for synthesis of alkylated sulfonamides (method B) to get the title compound as oily product; the yield (109 mg, 81% yield). $^1$H NMR (400 MHz) (CDCl$_3$) δ 7.92 (d, 2H, J=9.2 Hz), 7.53 (d, 2H, J=9.2 Hz), 7.39 (s, 1H), 7.24 (d, 1H, J=7.6 Hz), 7.01 (d, 2H, J=9.2 Hz), 6.95 (d, 1H, J=7.4 Hz), 6.91 (d, 2H, J=8.8 Hz), 6.32 (d, 1H, J=7.2 Hz), 5.02 (q, 2H, J=8.0 Hz), 4.43-4.26 (m, 2H), 4.13 (d, 2H, J=5.2 Hz), 4.02 (q, 2H, J=7.2 Hz), 3.89 (s, 3H), 3.87 (s, 3H), 3.77 (s, 3H), 3.55 (s, 3H), 1.09 (t, 1H, J=7.2 Hz). $^{13}$C NMR (100 MHz) (CDCl$_3$) δ 169.93, 168.39, 163.27, 162.96, 138.95, 132.36, 131.54, 130.73, 130.58, 129.98, 129.73, 126.63, 120.95, 119.27, 114.17, 113.83, 110.57, 110.41, 61.29, 55.71, 55.69, 53.74, 51.95, 48.48, 45.41, 33.19, 14.10.

Intermediate: Ethyl N-(3-(((4-methoxy-N-(2-methoxy-2-oxoethyl) phenyl) sulfonamido) methyl)-1-((2-(trimethylsilyl) ethoxy) methyl)-1H-indol-4-yl)-N-((4-methoxyphenyl) sulfonyl) glycinate

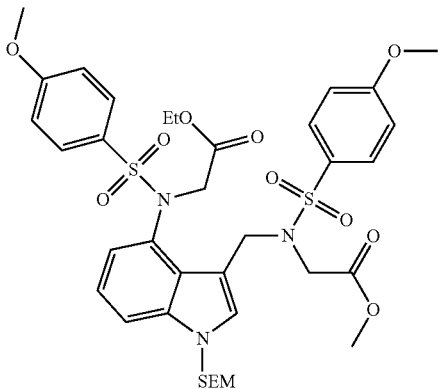 [SMILES: CCOC(=O)CN(c1cccc2c1c(CN(CC(=O)OC)S(=O)(=O)c1ccc(OC)cc1)cn2COCC[Si](C)(C)C)S(=O)(=O)c1ccc(OC)cc1]

Prepared as described in the general procedure for synthesis of alkylated sulfonamides (method B) to get the title compound as oily product; the yield (117 mg, 74% yield). $^1$H NMR (400 MHz) (CDCl$_3$) δ 7.92 (d, 2H, J=8.8 Hz), 7.51-7.48 (m, 3H), 7.42 (d, 1H, J=8.4 Hz), 7.01 (d, 2H, J=6.8 Hz), 6.97-6.89 (m, 3H), 6.32 (d, 1H, J=7.6 Hz), 5.43 (q, 2H, J=8.8 Hz), 5.02 (q, 2H, J=8.4 Hz), 4.44-4.22 (m, 2H), 4.10 (d, 2H, J=2.4 Hz), 4.05-3.98 (m, 2H), 3.87 (s, 3H), 3.86 (s, 3H), 3.54 (s, 3H), 3.50 (t, 2H, J=8.0 Hz). $^{13}$C NMR (100 MHz) (CDCl$_3$) δ 169.78, 168.22, 163.24, 162.90, 138.45, 132.39, 131.21, 130.63, 129.89, 129.60, 129.33, 127.44, 121.53, 119.93, 114.11, 113.78, 111.81, 111.26, 76.09, 66.10, 61.21, 55.65, 55.62, 53.69, 51.90, 48.48, 45.38, 17.77, 14.00, −1.37.

Example LH941: N-((5-((N-(Carboxymethyl)-4-methoxyphenyl) sulfonamido)-1-methyl-1H-indol-3-yl) methyl)-N-((4-methoxyphenyl) sulfonyl) glycine

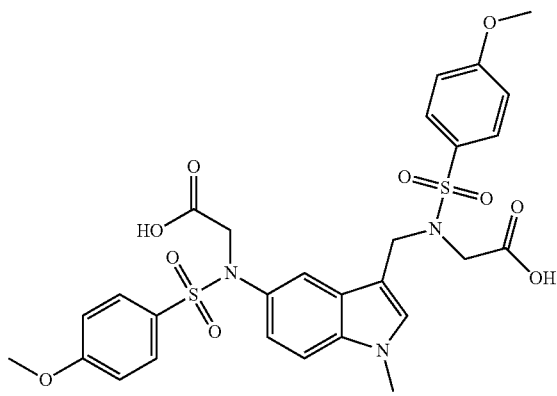 [SMILES: COc1ccc(S(=O)(=O)N(CC(=O)O)Cc2cn(C)c3ccc(N(CC(=O)O)S(=O)(=O)c4ccc(OC)cc4)cc23)cc1]

Prepared as described in the general procedure for hydrolysis of ethyl ester to get di-acidic compounds (Method C1) (base hydrolysis) to get the title compound as a yellow solid; the yield (14 mg, 80% yield). $^1$H NMR (400 MHz) (acetone-d$_6$) δ) 7.65 (d, 2H, J=8.8 Hz), 7.51 (d, 2H, J=8.8 Hz), 7.17 (d, 1H, J=8.8 Hz), 7.13 (d, 2H, J=1.6 Hz), 7.06 (d, 2H, J=2.0 Hz), 7.04 (s, 1H), 6.96-6.92 (m, 4H), 4.42 (s, 2H), 4.29 (s, 2H), 3.79 (s, 6H), 3.73 (s, 2H), 3.65 (s, 3H). $^{13}$C NMR (100 MHz) (acetone-d$_6$) δ 170.60, 170.45, 164.04, 163.82, 137.49, 133.44, 133.11, 132.12, 131.95, 130.75, 130.39, 128.25, 124.92, 120.06, 114.95, 114.91, 110.52, 109.20, 56.12, 53.94, 46.99, 43.27, 33.03. HRMS (ESI) Calcd for C$_{28}$H$_{29}$N$_3$O$_{10}$S$_2$ (M+H)$^+$ 632.1367, found 632.1364.

Example LH940: N-((4-((N-(Carboxymethyl)-4-methoxyphenyl) sulfonamido)-1-methyl-1H-indol-3-yl) methyl)-N-((4-methoxyphenyl) sulfonyl) glycine

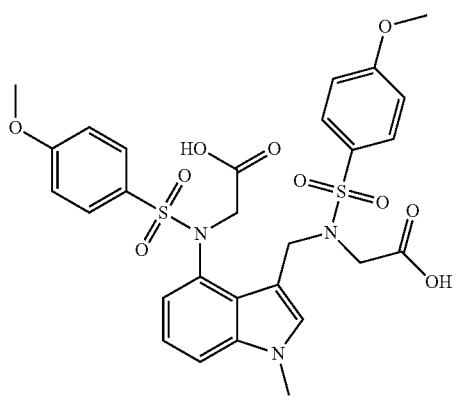 [SMILES: COc1ccc(S(=O)(=O)N(CC(=O)O)Cc2cn(C)c3cccc(N(CC(=O)O)S(=O)(=O)c4ccc(OC)cc4)c23)cc1]

Prepared as described in the general procedure for hydrolysis of ethyl ester to get di-acidic compounds (Method C1) (base hydrolysis) to get the title compound as a yellow solid; the yield (15 mg, 84% yield). $^1$H NMR (400 MHz) (Acetone-d$_6$) δ) 7.92 (d, 2H, J=8.8 Hz), 7.55 (d, 2H, J=8.8 Hz), 7.34 (d, 1H, J=8.8 Hz), 7.28 (s, 1 H), 7.13 (d, 2H, J=8.8 Hz), 7.06 (d, 2H, J=8.8 Hz), 6.96 (t, 1H, J=8.0 Hz), 6.49 (d, 1H, J=7.6 Hz), 5.14-4.90 (m, 2H), 4.59-4.34 (m, 2H), 4.00 (d, 2H, J=6.8 Hz), 3.92 (s, 3H), 3.91 (s, 3H), 3.78 (s, 3H). $^{13}$C NMR (100 MHz) (Acetone-d$_6$) δ 170.77, 170.08, 164.19, 163.91, 139.84, 133.42, 132.25, 131.30, 131.05, 130.85, 130.75, 127.52, 121.61, 120.18, 114.99, 114.71, 111.15, 111.10, 56.16, 56.11, 54.01, 49.23, 46.99, 33.12. HRMS (ESI) Calcd for C$_{28}$H$_{29}$N$_3$O$_{10}$S$_2$ (M+H)$^+$ 632.1367, found 632.1360.

Example LH939: N-((4-((N-(Carboxymethyl)-4-methoxyphenyl) sulfonamido)-1-((2-(trimethylsilyl) ethoxy) methyl)-1H-indol-3-yl) methyl)-N-((4-methoxyphenyl) sulfonyl) glycine

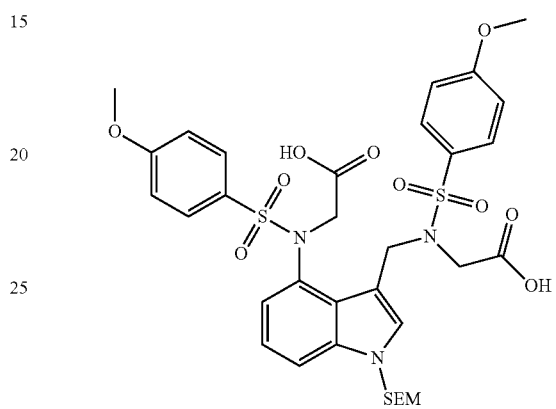

Prepared as described in the general procedure for hydrolysis of ethyl ester to get di-acidic compounds (Method C1) (base hydrolysis) to get the title compound as light brown solid; the yield (25 mg, 88% yield). $^1$H NMR (400 MHz) (Acetone-d$_6$) δ) 7.94 (d, 2H, J=8.4 Hz), 7.55 (d, 2H, J=8.8 Hz), 7.50 (d, 1H, J=8.0 Hz), 7.45 (s, 1H), 7.13 (d, 2H, J=8.8 Hz), 7.06 (d, 2H, J=8.8 Hz), 7.00 (t, 1H, J=8.0 Hz), 6.52 (d, 1H, J=7.2 Hz), 5.53 (s, 2H), 5.18-4.95 (m, 2H), 4.62-4.33 (m, 2H), 4.00 (d, 2H, J=8.4 Hz), 3.92 (s, 3H), 3.91 (s, 3H), 3.55 (t, 2H, J=7.6 Hz), 0.87 (d, 2H, J=8.0 Hz), −0.06 (s, 9H). $^{13}$C NMR (100 MHz) (Acetone-d$_6$) δ 164.22, 163.90, 139.43, 133.67, 132.20, 131.32, 310.75, 130.14, 128.36, 122.17, 120.88, 115.01, 114.73, 112.56, 111.93, 76.44, 66.42, 56.17, 56.11, 54.06, 49.28, 46.94, 18.24, −1.24. HRMS (ESI) Calcd for C$_{33}$H$_{41}$N$_3$O$_{11}$S$_2$ (M+H)$^+$ 748.2025, found 748.2022.

Intermediate: 2-Methyl-4-nitro-1H-indole

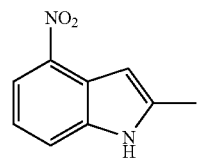

In open flask under air, to a stirred solution of 3-nitroaniline (690 mg, 5 mmol) and acetone (0.882 ml, 7 mmol) in DMSO (15 mL) at 15° C., t-BuOK (1.34 g, 12 mmol) was added in one portion results in red-violet colored reaction mixture which indicate the reaction progress. The reaction kept at room temperature overnight and then diluted with ethyl acetate (150 mL) and washed with aqueous NH4Cl (60 mL), brine, dried over Na$_2$SO$_4$, and the organic layer concentrated under vacuum to get the crude product. The crude product purified by ISCO using hexane-toluene as a mobile phase to get the desired product as a yellow solid (the yield (461 mg, 52% yield). $^1$H NMR (400 MHz) (DMSO) δ) 11.86 (s, 1 H), 8.00 (d, 1H, J=8.4 Hz), 7.75 (d, 1H, J=8.0 Hz), 7.20 (t, 1H, J=8.0 Hz), 6.81 (s, 1H). $^{13}$C NMR (100 MHz) (DMSO) δ 142.30, 138.46, 138.04, 122.61, 119.13, 117.97, 116.51, 99.80, 13.42.

Intermediate: 7-Chloro-2-methyl-4-nitro-1H-indole

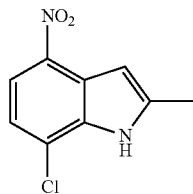

In open flask under air, to a stirred solution of 2-chloro-5-nitroaniline (860 mg, 5 mmol) and acetone (0.882 ml, 7 mmol) in DMSO (15 mL) at 15° C., t-BuOK (1.34 g, 12 mmol) was added in one portion results in red-violet colored reaction mixture which indicate the reaction progress. The reaction kept at room temperature overnight and then diluted with ethyl acetate (150 mL) and washed with aqueous NH4Cl (60 mL), brine, dried over Na$_2$SO$_4$, and the organic layer concentrated under vacuum to get the crude product. The crude product purified by ISCO using hexane-toluene as a mobile phase to get the desired product as a yellow solid (the yield (441 mg, 42% yield). $^1$H NMR (400 MHz) (DMSO) δ) 12.11 (br, 1H), 7.94 (d, 1H, J=8.4 Hz), 7.23 (d, 1H, J=8.4 Hz), 6.82 (s, 1H), 2.49 (s, 3H). $^{13}$C NMR (100 MHz) (DMSO) δ 143.88, 136.93, 134.80, 123.86, 122.41, 118.91, 117.62, 101.12, 13.34.

Intermediate: tert-Butyl 2-methyl-4-nitro-1H-indole-1-carboxylate

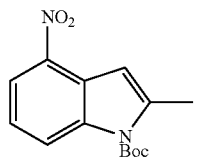 [SMILES: Cc1cc2c([N+](=O)[O-])cccc2n1C(=O)OC(C)(C)C]

Toa stirred solution of the above intermediate (345 mg, 2 mmole) in DCM (10 ml), (Boc)$_2$O (872 mg, 4 mmol), TEA (0.415 ml, 3 mmol), DMAP (25 mg, 0.2 mmol) were added and the reaction mixture stirred under nitrogen for 3 hours then diluted with DCM (100 mL) and washed with aqueous NH$_4$Cl (20 mL), brine, dried over Na$_2$SO$_4$, and the organic layer concentrated under vacuum to get the crude product. The crude product purified by ISCO using hexane—DCM as a mobile phase to get the desired product as oily product. The yield (547 mg, quantitative). $^1$H NMR (400 MHz) (DMSO) δ) 8.43 (d, 1H, J=8.4 Hz), 8.09-8.07 (m, 1H), 7.27-7.25 (m, 1H), 7.07 (s, 1H), 2.64 (d, 3H, J=0.8 Hz), 1.69 (s, 9H). $^{13}$C NMR (100 MHz) (CDCl$_3$) δ 149.91, 142.74, 139.27, 138.50, 12419, 122.27, 121.57, 119.43, 107.39, 85.21, 28.23, 17.40.

Intermediate: tert-Butyl 7-chloro-2-methyl-4-nitro-1H-indole-1-carboxylate

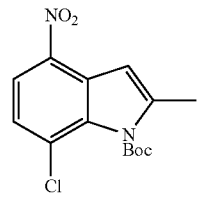 [SMILES: Cc1cc2c([N+](=O)[O-])ccc(Cl)c2n1C(=O)OC(C)(C)C]

To a stirred solution of the above intermediate (420 mg, 2 mmole) in DCM (10 ml), (Boc)$_2$O (872 mg, 4 mmol), TEA (0.415 ml, 3 mmol), DMAP (25 mg, 0.2 mmol) were added and the reaction mixture stirred under nitrogen for 3 hours then diluted with DCM (100 mL) and washed with aqueous NH$_4$Cl (20 mL), brine, dried over Na$_2$SO$_4$, and the organic layer concentrated under vacuum to get the crude product. The crude product purified by ISCO using hexane—DCM as a mobile phase to get the desired product as oily product. The yield (615 mg, quantitative). $^1$H NMR (400 MHz) (CDCl3) δ) 8.22 (d, 1H, J=8.4 Hz), 7.41 (d, 1H, J=8.4 Hz), 7.26 (s, 1H), 2.71 (s, 3H), 1.82 (s, 9H). $^{13}$C NMR (100 MHz) (DMSO) δ 149.00, 143.39, 138.24, 134.43, 126.50, 125.65, 123.39, 119.94, 105.29, 86.26, 27.82, 14.87.

Intermediate: tert-Butyl 2-(bromomethyl)-4-nitro-1H-indole-1-carboxylate

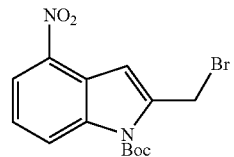 [SMILES: CC(C)(C)OC(=O)n1c(CBr)cc2c([N+](=O)[O-])cccc21]

The above intermediate (415 mg, 1.5 mmol), NBS (320 mg, 1.8 mmol), and AIBN (50 mg, 0.3 mmol) were taken in DCM (7 ml) in sealed tube and the reaction mixture stirred at 80° C. for 8 hours and checked for reaction completion using TLC. Then, filter and the organic layer removed under reduced pressure to get the crude product which was purified using ISCO (Ethyl acetate:hexane), the yield (239 mg, 45% yield). $^1$H NMR (400 MHz) (CDCl$_3$) δ) 8.59 (d, 1H, J=8.4 Hz), 8.20 (d, 1H, J=8.0 Hz), 7.50 (s, 1H), 7.44 (t, 1H, J=8.4 Hz), 4.95 (s, 2H), 1.78 (s, 9H). $^{13}$C NMR (100 MHz) (CDCl$_3$) δ 148.90, 140.09, 139.96, 138.99, 124.23, 122.03, 119.81, 110.27, 86.25, 27.82, 25.85.

Intermediate: tert-Butyl 2-(bromomethyl)-7-chloro-4-nitro-1H-indole-1-carboxylate

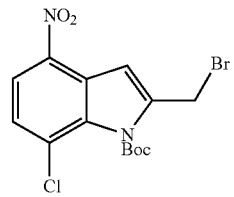 [SMILES: CC(C)(C)OC(=O)n1c(CBr)cc2c([N+](=O)[O-])ccc(Cl)c21]

The above intermediate (465 mg, 1.5 mmol), NBS (320 mg, 1.8 mmol), and AIBN (50 mg, 0.3 mmol) were taken in DCM (7 ml) in sealed tube and the reaction mixture stirred at 80° C. for 8 hours and checked for reaction completion using TLC. Then, filter and the organic layer removed under reduced pressure to get the crude product which was purified using ISCO (Ethyl acetate:hexane), the yield (233 mg, 40% yield). $^1$H NMR (400 MHz) (CDCl$_3$) δ) 8.12 (d, 1H, J=8.8 Hz), 7.46 (s, 1H), 7.39 (d, 1H, J=8.8 Hz), 4.82 (s, 2H), 1.71 (s, 9H). $^{13}$C NMR (100 MHz) (CDCl$_3$) δ 148.08, 141.27, 139.21, 134.90, 126.55, 125.50, 125.32, 120.44, 108.20, 87.48, 27.83, 22.97.

Intermediate: tert-Butyl 2-(((4-methoxy-N-(2-methoxy-2-oxoethyl) phenyl) sulfonamido) methyl)-4-nitro-1H-indole-1-carboxylate

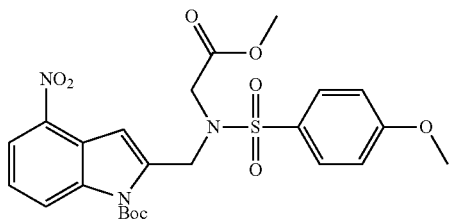 [SMILES: COC(=O)CN(Cc1cc2c([N+](=O)[O-])cccc2n1C(=O)OC(C)(C)C)S(=O)(=O)c1ccc(OC)cc1]

Prepared as described in the general procedure for synthesis of alkylated sulfonamides (method B) to get the title compound as oily product; the yield (234 mg, 88% yield). $^1$H NMR (400 MHz) (CDCl$_3$) δ) 8.39 (d, 1H, J=8.4 Hz), 8.14 (d, 1H, J=8.0 Hz), 7.78 (d, 1H, J=8.8 Hz), 7.34 (t, 1H, J=8.0 Hz), 7.18 (s, 1H), 6.92 (d, 1H, J=8.8 Hz), 5.00 (s, 2H), 4.20 (s, 2H), 3.84 (s, 3H), 3.65 (s, 3H), 1.69 (s, 9H). $^{13}$C NMR (100 MHz) (CDCl$_3$) δ 169.45, 163.31, 149.53, 140.92, 140.07, 138.74, 131.34, 129.66, 123.51, 123.42, 121.66, 119.80, 114.28, 107.89, 86.32, 55.73, 52.36, 48.92, 47.94, 28.26.

Intermediate: tert-Butyl 7-chloro-2-(((4-methoxy-N-(2-methoxy-2-oxoethyl) phenyl) sulfonamido) methyl)-4-nitro-1H-indole-1-carboxylate

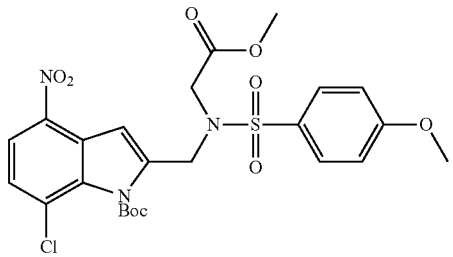 [SMILES: COC(=O)CN(Cc1cc2c([N+](=O)[O-])ccc(Cl)c2n1C(=O)OC(C)(C)C)S(=O)(=O)c1ccc(OC)cc1]

Prepared as described in the general procedure for synthesis of alkylated sulfonamides (method B) to get the title compound as oily product; the yield (234 mg, 88% yield). $^1$H NMR (400 MHz) (CDCl$_3$) δ) 8.07 (d, 1H, J=8.8 Hz), 7.77 (d, 2H, J=9.2 Hz), 7.33 (d, 1H, J=8.8 Hz), 7.12 (s, 1H), 6.95 (d, 2H, J=9.2 Hz), 4.86 (s, 2H), 4.13 (s, 2H), 3.85 (s, 3H), 3.61 (s, 3H), 1.65 (s, 9H). $^{13}$C NMR (100 MHz) (CDCl$_3$) δ 169.20, 163.44, 148.44, 140.81, 138.85, 134.82, 130.80, 129.98, 129.75, 126.26, 125.65, 124.68, 120.27, 114.34, 114.10, 107.03, 87.51, 55.75, 52.33, 48.47, 45.57, 27.75.

Intermediate: tert-Butyl 4-amino-2-(((4-methoxy-N-(2-methoxy-2-oxoethyl) phenyl) sulfonamido) methyl)-1H-indole-1-carboxylate

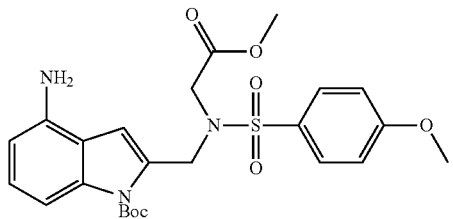

Prepared as described in the general procedure for nitro group reduction (Method E1) to get the title compound as a yellow solid; the yield (61 mg, 61% yield). $^1$H NMR (400 MHz) (CDCl$_3$) δ) 7.75 (d, 1H, J=8.8 Hz), 7.39 (d, 1H, J=8.4 Hz), 7.03 (t, 1H, J=8.0 Hz), 6.89 (d, 1H, J=8.8 Hz), 6.54 (s, 1H), 6.49 (d, 1H, J=8.0 Hz), 4.90 (s, 2H), 4.19 (s, 2H), 3.82 (s, 3H), 3.61 (s, 3H), 1.63 (s, 9H). $^{13}$C NMR (100 MHz) (CDCl$_3$) δ 169.66, 163.04, 150.57, 139.08, 137.97, 134.09, 131.82, 129.67, 125.39, 117.39, 114.45, 114.07, 108.04, 106.53, 105.85, 84.47, 55.70, 52.25, 48.90, 48.00, 28.34.

Intermediate: tert-Butyl 4-amino-7-chloro-2-(((4-methoxy-N-(2-methoxy-2-oxoethyl) phenyl) sulfonamido) methyl)-1H-indole-1-carboxylate

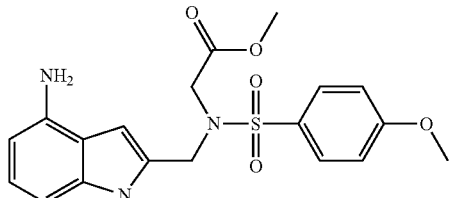

Prepared as described in the general procedure for nitro group reduction (Method E1) to get the title compound as a yellow solid; the yield (58 mg, 54% yield). $^1$H NMR (400 MHz) (CDCl$_3$) δ) 7.72 (d, 2H, J=8.4 Hz), 7.00 (d, 1H, J=8.4 Hz), 6.89 (d, 2H, J=8.8 Hz), 6.46 (s, 1H), 6.39 (d, 1H, J=8.4 Hz), 4.75 (s, 2H), 4.13 (s, 2H), 3.82 (s, 3H), 3.57 (s, 3H), 1.58 (s, 9H). $^{13}$C NMR (100 MHz) (CDCl$_3$) δ 169.47, 163.04, 149.58, 138.15, 134.14, 133.99, 131.27, 129.62, 126.49, 119.95, 114.06, 109.10, 108.27, 104.76, 85.58, 55.66, 52.15, 48.41, 45.93, 27.71.

Intermediate: tert-Butyl 2-(((4-methoxy-N-(2-methoxy-2-oxoethyl) phenyl) sulfonamido) methyl)-4-((4-methoxyphenyl) sulfonamido)-1H-indole-1-carboxylate

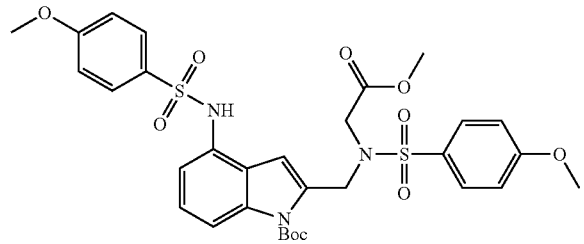

Prepared as described in the general procedure for synthesis of sulfonamides (method A2) to get the title compound as a yellow solid; the yield (44 mg, 81% yield). $^1$H NMR (400 MHz) (DMSO) δ) 10.14 (s, 1H), 7.74-7.70 (m, 5H), 7.15-7.09 (m, 2H), 7.05-7.01 (m, 4H), 6.93 (s, 1H), 4.73 (s, 2H), 4.17 (s, 2H), 3.84 (s, 2H), 3.83 (s, 3H), 3.77 (s, 3H), 3.54 (s, 2H), 3.52 (s, 3H). $^{13}$C NMR (100 MHz) (DMSO) δ 169.00, 162.55, 162.31, 149.35, 136.97, 135.68, 131.61, 130.92, 129.25, 129.16, 128.85, 128.66, 124.18, 122.72, 115.94, 114.24, 114.22, 114.18, 111.78, 106.06, 84.65, 55.64, 55.51, 51.79, 48.37, 47.25, 43.73, 27.58.

Intermediate: tert-Butyl 7-chloro-2-(((4-methoxy-N-(2-methoxy-2-oxoethyl) phenyl) sulfonamido) methyl)-4-((4-methoxyphenyl) sulfonamido)-1H-indole-1-carboxylate

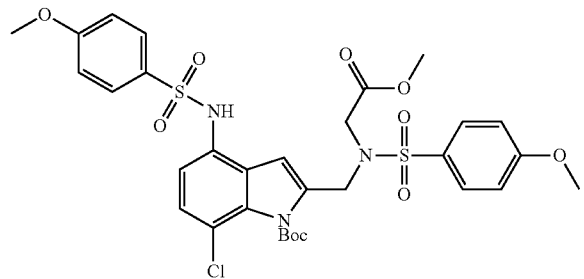

Prepared as described in the general procedure for synthesis of sulfonamides (method A2) to get the title compound as brown solid; the yield (44 mg, 78% yield). $^1$H NMR (400 MHz) (CDCl$_3$) δ) 7.80 (d, 2H, J=8.8 Hz), 7.55 (d, 2H, J=8.8 Hz), 7.38 (s, 1H), 7.10 (d, 2H, J=8.4 Hz), 6.93 (d, 2H, J=8.8 Hz), 6.64 (s, 1H), 6.58 (d, 2H, J=8.8 Hz), 4.74 (s, 2H), 4.18 (s, 2H), 3.85 (s, 3 H), 3.58 (s, 3H), 1.53 (s, 9H). $^{13}$C NMR (100 MHz) (CDCl$_3$) δ 169.45, 163.25, 163.14, 148.96, 136.94, 133.91, 131.03, 130.64, 129.91, 129.53, 127.63, 125.89, 125.79, 116.87, 116.70, 114.25, 114.19, 104.09, 86.22, 55.72, 55.56, 52.22, 48.34, 45.86, 27.72.

Intermediate: tert-Butyl 4-((N-(2-ethoxy-2-oxoethyl)-4-methoxyphenyl) sulfonamido)-2-(((4-methoxy-N-(2-methoxy-2-oxoethyl) phenyl) sulfonamido) methyl)-1H-indole-1-carboxylate

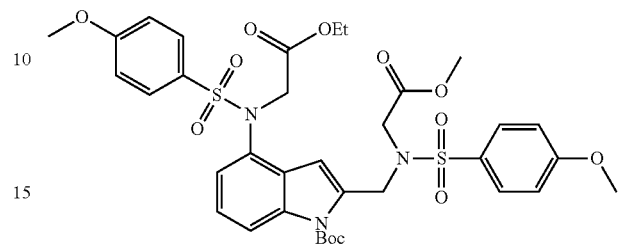

Prepared as described in the general procedure for synthesis of alkylated sulfonamides (method B) to get the title compound as oily product; the yield (30 mg, 79% yield). $^1$H NMR (400 MHz) (CDCl$_3$) δ) 7.99 (d, 1H, J=8.4 Hz), 7.80 (d, 2H, J=9.2 Hz), 7.66 (d, 2H, J=8.8 Hz), 7.16 (t, 1H, J=8.0 Hz), 7.05 (d, 1H, J=8.0 Hz), 6.97-6.93 (m, 4H), 6.48 (s, 1H), 4.93 (s, 2H), 4.40 (s, 2H), 4.15 (q, 2H, J=7.2 Hz), 4.11 (s, 2H), 3.88 (s, 3H), 3.87 (s, 3H), 3.66 (s, 3H), 1.67 (s, 9H), 1.24 (d, 3H, J=7.2 Hz). $^{13}$C NMR (100 MHz) (CDCl$_3$) δ 169.57, 168.97, 163.19, 163.10, 149.98, 138.10, 137.04, 131.61, 131.52, 131.17, 130.08, 129.69, 128.51, 124.56, 124.26, 116.09, 114.24, 114.13, 107.08, 85.12, 61.53, 55.69, 52.84, 52.28, 48.60, 47.67, 28.30, 14.25.

Intermediate: tert-Butyl 7-chloro-4-((N-(2-ethoxy-2-oxoethyl)-4-methoxyphenyl) sulfonamido)-2-(((4-methoxy-N-(2-methoxy-2-oxoethyl) phenyl) sulfonamido) methyl)-1H-indole-1-carboxylate

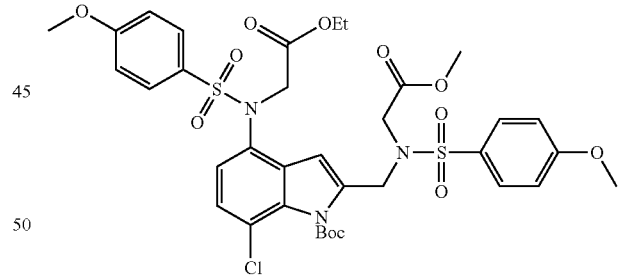

Prepared as described in the general procedure for synthesis of alkylated sulfonamides (method B) to get the title compound as oily product; the yield (43 mg, 87% yield). $^1$H NMR (400 MHz) (CDCl$_3$) δ) 7.75 (d, 2H, J=8.8 Hz), 7.62 (d, 2H, J=8.8 Hz), 7.10 (d, 2H, J=8.0 Hz), 6.96 (d, 2H, J=8.8 Hz), 6.90 (d, 2H, J=8.8 Hz), 6.88 (d, 1H, J=8.0 Hz), 6.42 (s, 1H), 4.77 (s, 2H), 4.33 (s, 2H), 4.11 (q, 2H, J=7.2 Hz), 4.03 (s, 2 H), 3.85 (s, 3H), 3.54 (s, 3H), 3.60 (s, 3H), 1.62 (s, 9H), 1.19 (t, 3H, J=7.2 Hz). $^{13}$C NMR (100 MHz) (CDCl$_3$) δ 169.29, 168.77, 163.22, 163.19, 148.90, 137.10, 134.21, 131.18, 131.01, 130.74, 130.50, 130.04, 129.70, 125.57, 124.67, 120.04, 114.25, 114.12, 106.08, 86.29, 61.53, 55.68, 55.67, 52.68, 52.24, 48.08, 45.62, 27.74, 14.16.

Intermediate: Ethyl N-(7-chloro-2-(((4-methoxy-N-(2-methoxy-2-oxoethyl) phenyl) sulfonamido)methyl)-1H-indol-4-yl)-N-((4-methoxyphenyl) sulfonyl) glycinate

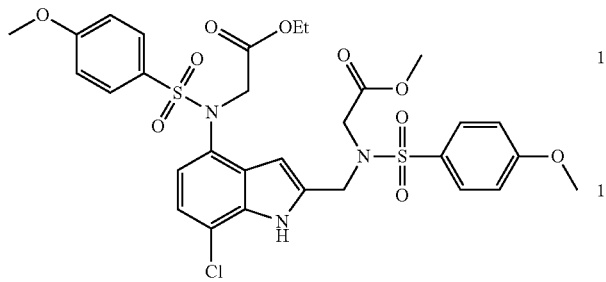

Prepared as described in the general procedure for removal of acid sensitive protecting group (Method C2) to get the title compound as dark brown solid; the yield (17 mg, quantitative). $^1$H NMR (400 MHz) (CDCl$_3$) δ 7.75 (d, 2H, J=8.8 Hz), 7.64 (d, 2H, J=8.8 Hz), 7.02 (d, 1H, J=8.0 Hz), 6.92-6.88 (m, 4H), 6.74 (d, 1H, J=2.0 Hz), 4.44 (s, 2H), 4.41 (s, 2H), 4.11 (q, 2H, J=7.2 Hz), 4.08 (s, 2H), 3.84 (s, 3H), 3.83 (s, 3H), 3.70 (s, 3H), 1.19 (t, 3H, J=7.2 Hz). $^{13}$C NMR (100 MHz) (CDCl$_3$) δ 170.12, 169.27, 163.42, 163.25, 135.14, 134.12, 130.74, 130.58, 130.43, 130.19, 129.72, 128.45, 121.93, 121.74, 117.28, 114.38, 114.03, 102.94, 66.15, 61.63, 55.74, 55.71, 52.65, 52.65, 48.14, 45.70, 14.15.

Intermediate: N-(7-Chloro-2-(((4-methoxy-N-(2-methoxy-2-oxoethyl) phenyl)sulfonamido)methyl)-1-methyl-1H-indol-4-yl)-N-((4-methoxyphenyl)sulfonyl)glycine

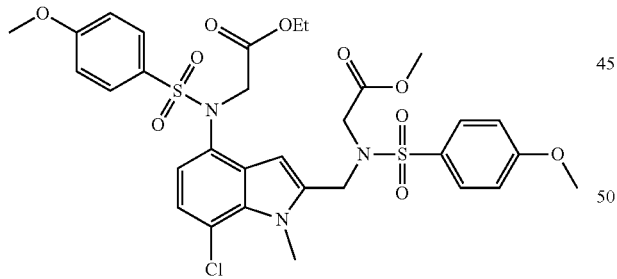

Prepared using general procedure (method B), oily product, the yield (11 mg, 62% yield). $^1$H NMR (400 MHz) (CDCl$_3$) δ 7.79 (d, 2H, J=9.2 Hz), 7.63 (d, 2H, J=9.2 Hz), 7.02 (d, 2H, J=9.2 Hz), 6.98 (d, 1H, J=8.0 Hz), 6.89 (d, 2H, J=8.8 Hz), 6.64 (d, 1H, J=8.0 Hz), 6.42 (s, 1H), 4.61 (s, 2H), 4.35 (s, 2H), 4.13 (s, 3H), 4.08 (q, 2H, J=7.2 Hz), 3.90 (s, 3H), 3.85 (s, 3H), 3.82 (s, 3H), 3.48 (s, 3H), 1.17 (t, 3H, J=7.2 Hz). $^{13}$C NMR (100 MHz) (CDCl$_3$) δ 168.96, 168.83, 163.46, 163.19, 134.87, 134.68, 130.99, 130.81, 130.22, 130.18, 129.79, 129.50, 124.06, 121.42, 117.72, 114.46, 113.98, 104.15, 61.43, 55.81, 55.71, 52.62, 52.23, 46.90, 44.48, 32.97, 14.19.

N-((4-((N-(Carboxymethyl)-4-methoxyphenyl) sulfonamido)-1H-indol-2-yl)methyl)-N-((4-methoxyphenyl)sulfonyl)glycine

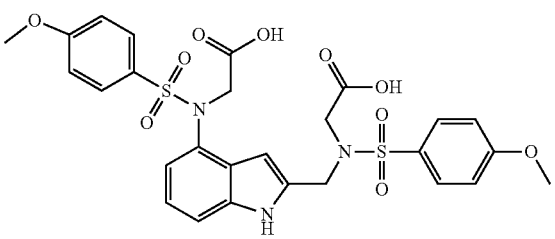

Prepared using general procedure (method C1), yellow product, the yield (14 mg, 75% yield). $^1$H NMR (400 MHz) (DMSO) δ 11.21 (s, 1H), 7.70 (d, 2H, J=8.8 Hz), 7.55 (d, 2H, J=8.8 Hz), 7.26 (d, 2H, J=8.0 Hz), 7.03-6.96 (m, 5H), 6.89 (d, 1H, J=7.6 Hz), 5.58 (s, 1H), 4.50 (s, 2H), 4.25 (s, 2H), 3.81 (s, 8H). $^{13}$C NMR (100 MHz) (DMSO) δ 170.09, 169.98, 162.48, 162.40, 137.49, 134.30, 131.26, 131.19, 130.53, 129.38, 129.13, 125.65, 121.21, 120.77, 114.17, 114.09, 111.60, 98.66, 55.58, 51.76, 47.53, 44.56. HRMS (ESI) Calcd for C$_{27}$H$_{27}$N$_3$O$_{10}$S$_2$ (M+H)$^+$ 618.1211, found 618.1221.

Example LH917: N-((4-((N-(Carboxymethyl)-4-methoxyphenyl)sulfonamido)-7-chloro-1H-indol-2-yl)methyl)-N-((4-methoxyphenyl)sulfonyl)glycine Prepared using general procedure (method C1), light brown product, the yield (11 mg, 71% yield). $^1$H NMR (400 MHz) (MeOH-d$_4$) δ 7.59-7.56 (m, 4H), 7.01 (s, 1H), 6.94 (d, 2, J=9.2 Hz), 6.83 (d, 2H, J=8.8 Hz), 5.81 (s, 1H), 4.56 (s, 2H), 4.37 (s, 2H), 4.04 (s, 2H), 3.84 (s, 3H), 3.77 (s, 3H). $^{13}$C NMR (100 MHz) (MeOH-d$_4$) δ 172.62, 172.08, 164.47, 164.15, 136.57, 135.64, 132.39, 132.03, 130.96, 130.64, 130.12, 129.97, 128.65, 123.65, 121.54, 117.52, 114.90, 114.75, 101.66, 61.24, 55.94, 55.87, 46.32. HRMS (ESI) Calcd for C$_{27}$H$_{26}$ClN$_3$O$_{10}$S$_2$ (M+H)$^+$ 652.0821, found 652.0830.

Example LH937: N-((4-((N-(Carboxymethyl)-4-methoxyphenyl) sulfonamido)-7-chloro-1-methyl-1H-indol-2-yl) methyl)-N-((4-methoxyphenyl) sulfonyl) glycine

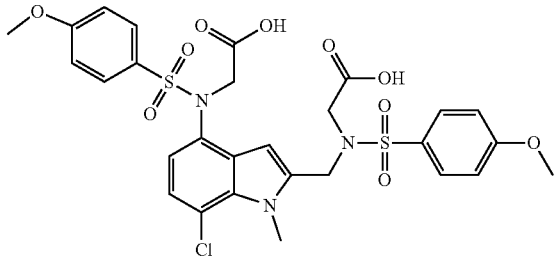

Prepared using general procedure (method B), brown solid, the yield (129 mg, 88% yield). $^1$H NMR (400 MHz) (CDCl$_3$) δ) 7.78 (d, 2H, J=9.2 Hz), 7.54 (d, 2H, J=8.8 Hz), 7.01 (d, 2H, J=8.8 Hz), 6.94 (d, 1H, J=8.0 Hz), 6.89 (d, 2H, J=8.8 Hz), 6.63 (s, 1H), 6.31 (d, 1H, J=8.4 Hz), 4.53 (s, 2H), 4.27 (s, 2H), 4.11 (s, 3H), 3.87 (s, 3H), 3.85 (s, 3H), 3.76 (s, 2H). $^{13}$C NMR (100 MHz) (CDCl$_3$) δ 174.45, 173.68, 163.57, 163.39, 134.68, 134.41, 131.04, 130.38, 130.03, 129.85, 129.74, 129.71, 124.08, 119.54, 117.86, 114.65, 114.26, 105.74, 55.84, 55.78, 52.80, 46.88, 44.71, 32.88. HRMS (ESI) Calcd for C$_{28}$H$_{28}$ClN$_3$O$_{10}$S$_2$ (M+H)$^+$ 666.0977, found 666.0990.

Intermediate: tert-Butyl (3-methylbenzo[b]thiophen-5-yl)carbamate

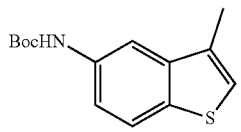 [SMILES: Cc1csc2ccc(NC(=O)OC(C)(C)C)cc12]

To a Schlenk tube equipped with a magnetic stir bar under argon atmosphere was added commercially available 5-chloro-3-methyl-1-benzothiophene (183 mg, 11 mmol), t-butyl carbamate (165 mg, 1.4 mmol), Pd(OAc)2 (15 mg, 0.06 mmol), XPhos (57 mg, 0.12 mmol), sodium tert-butoxide (134 mg, 1.4 mmol), dioxane (5 ml), and then the tube was degassed with argon three times and refluxed for 24 hours. Upon completion, the mixture diluted with EtOAc and extracted with water, brine, dried over Na$_2$SO$_4$, and organic layer removed under reduced pressure. The crude product purified by ISCO using ethyl acetate/hexane to get the desired product, the yield (170 mg, 65% yield). $^1$H NMR (400 MHz) (CDCl$_3$) δ) 7.89 (s, 1H), 7.71 (d, 1H, J=8.8 Hz), 7.26-7.21 (m, 1H), 7.06 (s, 1H), 6.80 (s, 1H), 2.39 (s, 3H), 1.57 (s, 9H). $^{13}$C NMR (100 MHz) (CDCl$_3$) δ 153.13, 140.40, 135.18, 134.94, 132.12, 122.93, 122.57, 116.73, 111.42, 80.48, 28.45, 13.95.

Intermediate: 3-Methylbenzo[b]thiophen-5-amine

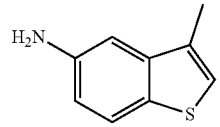

Prepared as described in the general procedure for removal of acid sensitive protecting group (Method C2) to get the title compound as a white solid; the yield (76 mg, 82% yield). $^1$H NMR (400 MHz) (DMSO) δ) 9.42 (s, 2H), 8.01 (d, 1H, J=8.4 Hz), 7.64 (s, 1H), 7.49 (s, 1 H), 7.28 (d, 1H, J=8.0 Hz), 2.37 (s, 3H). $^{13}$C NMR (100 MHz) (DMSO) δ 139.90, 136.93, 131.30, 131.17, 124.38, 123.82, 118.28, 114.06, 13.22.

Intermediate: 4-Methoxy-N-(3-methylbenzo[b]thiophen-5-yl) benzenesulfonamide

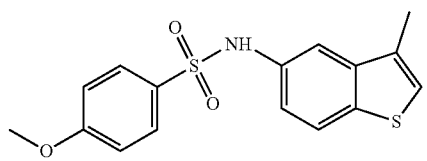 [SMILES: COc1ccc(S(=O)(=O)Nc2ccc3scc(C)c3c2)cc1]

Prepared as described in the general procedure for synthesis of sulfonamides (method A2) to get the title compound as a beige solid; the yield (112 mg, 78% yield). $^1$H NMR (400 MHz) (CDCl$_3$) δ) 7.75 (d, 2H, J=8.8 Hz), 7.65 (d, 1H, J=8.4 Hz), 7.47 (d, 1H, J=2.0 Hz), 7.37 (s, 1H), 7.08 (d, 1H, J=2.4 Hz), 7.06 (d, 1H, J=1.2 Hz), 6.85 (d, 2H, J=9.2 Hz), 3.78 (s, 3H), 2.34 (d, 3H, J=2.0 Hz). $^{13}$C NMR (100 MHz) (CDCl$_3$) δ 163.20, 140.52, 137.54, 133.32, 132.22, 130.62, 129.64, 123.47, 123.16, 119.56, 115.53, 114.28, 55.64, 13.93.

Intermediate: Ethyl N-((4-methoxyphenyl)sulfonyl)-N-(3-methylbenzo[b]thiophen-5-yl)glycinate

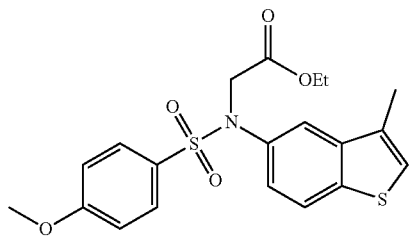 [SMILES: CCOC(=O)CN(c1ccc2scc(C)c2c1)S(=O)(=O)c1ccc(OC)cc1]

Prepared as described in the general procedure for synthesis of alkylated sulfonamides (method B) to get the title compound as oily product; the yield (108 mg, 86% yield). $^1$H NMR (400 MHz) (CDCl$_3$) δ) 7.71 (d, 1H, J=8.4 Hz), 7.62 (d, 2H, J=8.8 Hz), 7.56 (d, 1H, J=2.0 Hz), 7.12-7.08 (m, 2H), 6.89 (d, 2H, J=8.8 Hz), 4.45 (s, 2H), 4.14 (q, 2H, J=7.2 Hz), 3.84 (s, 3H), 2.33 (d, 3H, J=0.8 Hz), 1.21 (t, 3H, J=7.2 Hz). $^{13}$C NMR (100 MHz) (CDCl$_3$) δ 168.98, 163.16, 140.40, 140.16, 136.39, 132.39, 130.76, 130.20, 124.74, 123.36, 123.15, 122.93, 113.93, 61.48, 55.66, 53.32, 14.16, 13.87.

Intermediate: Ethyl N-(3-(bromomethyl) benzo[b]thiophen-5-yl)-N-((4-methoxyphenyl) sulfonyl) glycinate

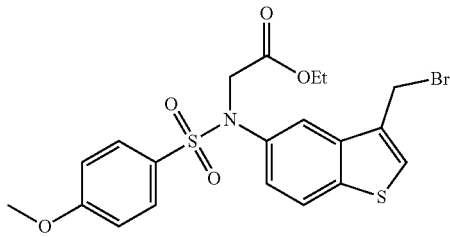 [SMILES: CCOC(=O)CN(c1ccc2scc(CBr)c2c1)S(=O)(=O)c1ccc(OC)cc1]

The above intermediate (63 mg, 0.15 mmol), NBS (32 mg, 0.18 mmol), and AIBN (5 mg, 0.03 mmol) were taken in DCM (5 ml) in sealed tube and the reaction mixture stirred at 80° C. for 8 hours and checked for reaction completion using TLC. Then, filter and the organic layer removed under reduced pressure to get the crude product which was purified using ISCO (Ethyl acetate:hexane), the yield (39 mg, 52% yield). $^1$H NMR (400 MHz) (CDCl$_3$) δ 7.78 (d, 1H, J=8.8 Hz), 7.64 (d, 2H, J=8.4 Hz), 7.52 (s, 1H), 7.31 (dd, 1H, J=2.0 Hz, 8.4 Hz), 6.91 (d, 2H, J=9.2 Hz), 4.61 (s, 2H), 4.47 (s, 2H), 4.15 (q, 2H, J=7.2 Hz), 3.84 (s, 3H), 1.23 (t, 3H, J=7.2 Hz). $^{13}$C NMR (100 MHz) (CDCl$_3$) δ 168.84, 163.10, 140.25, 137.80, 136.87, 132.08, 130.42, 130.04, 129.56, 127.81, 126.14, 123.64, 123.56, 122.38, 114.23, 114.18, 114.07, 61.51, 55.57, 53.14, 25.38, 14.08.

Intermediate: Ethyl N-(3-(((4-methoxy-N-(2-methoxy-2-oxoethyl) phenyl) sulfonamido) methyl) benzo[b]thiophen-5-yl)-N-((4-methoxyphenyl)sulfonyl)glycinate

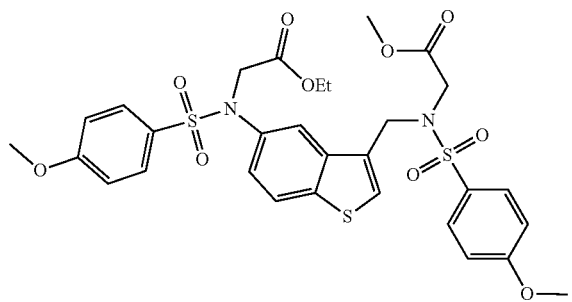

Prepared as described in the general procedure for synthesis of alkylated sulfonamides (method B) to get the title compound as oily product; the yield (36 mg, 68% yield). $^1$H NMR (400 MHz) (CDCl$_3$) δ 7.78 (d, 2H, J=9.2 Hz), 7.75 (d, 1H, J=8.8 Hz), 7.63-7.61 (m, 2H), 6.99 (d, 2H, J=8.8 Hz), 6.93 (d, 2H, J=8.8 Hz), 4.56 (s, 2H), 4.44 (s, 2H), 4.14 (q, 2H, J=7.2 Hz), 3.88 (s, 3H), 3.86 (s, 3H), 3.84 (s, 2H), 3.49 (s, 3H), 1.21 (t, 1H, J=7.2 Hz). $^{13}$C NMR (100 MHz) (CDCl$_3$) δ 168.79, 168.38, 162.79, 162.78, 139.80, 138.00, 136.77, 130.37, 130.27, 129.97, 129.71, 129.58, 129.43, 129.31, 127.57, 125.89, 122.87, 121.45, 113.86, 113.76, 113.67, 61.05, 55.26, 55.21, 52.61, 51.62, 46.64, 45.07, 13.71.

Example LH920: N-((5-((N-(Carboxymethyl)-4-methoxyphenyl)sulfonamido)benzo[b]thiophen-3-yl)methyl)-N-((4-methoxyphenyl)sulfonyl)glycine

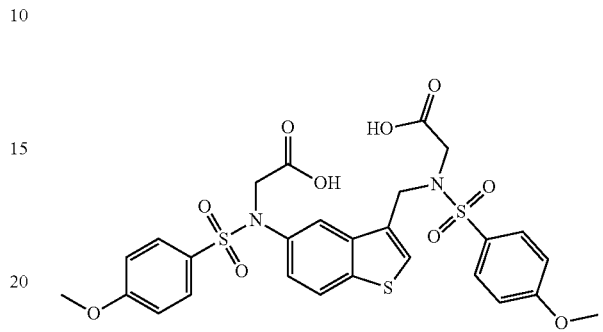

Prepared as described in the general procedure for hydrolysis of ethyl ester to get di-acidic compounds (Method C1) (base hydrolysis) to get the title compound as a beige solid; the yield (14 mg, 86% yield). $^1$H NMR (400 MHz) (DMSO) δ) 7.93 (d, 1H, J=8.8 Hz), 7.71 (d, 2H, J=8.8 Hz), 7.64 (s, 1H), 7.60 (d, 2H, J=8.8 Hz), 7.54 (d, 1H, J=1.6 Hz), 7.26 (dd, 1H, J=1.6 Hz, 8.4 Hz), 7.09 (d, 2H, J=8.8 Hz), 7.05 (d, 2H, J=8.8 Hz), 4.51 (s, 2H), 4.38 (s, 2H), 3.84 (s, 8H). $^{13}$C NMR (100 MHz) (DMSO) δ 169.55, 169.47, 162.42, 162.12, 138.74, 137.64, 136.49, 130.39, 129.92, 129.53, 129.24, 128.91, 127.67, 125.34, 122.74, 120.67, 114.05, 113.98, 113.85, 55.30, 52.13, 47.59, 45.25. HRMS (ESI) Calcd for C$_{27}$H$_{26}$N$_2$O$_{10}$S$_3$ (M+H)$^+$ 635.0822, found 635.0827.

Intermediate: Ethyl ((4-methoxyphenyl) sulfonyl) glycinate

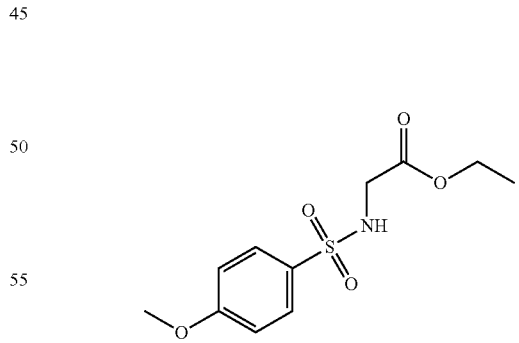

Prepared as described in the general procedure for synthesis of sulfonamides (method A2) to get the title compound as a white solid; the yield (712 mg, 87% yield). $^1$H NMR (400 MHz) (DMSO) δ) 8.01 (s, 1 H), 7.70 (d, 2H, J=8.8 Hz), 7.06 (d, 2H, J=8.8 Hz), 3.94 (d, 2H, J=7.2 Hz), 3.79 (s, 3H), 3.62 (s, 2 H), 1.06 (t, 3H, J=7.2 Hz). $^{13}$C NMR (100 MHz) (DMSO) δ 168.69, 162.00, 132.05, 128.48, 113.96, 60.40, 55.37, 43.65, 13.63.

Intermediate: Ethyl N-((4-methoxyphenyl)sulfonyl)-N-((5-nitrobenzofuran-2-yl)methyl)glycinate

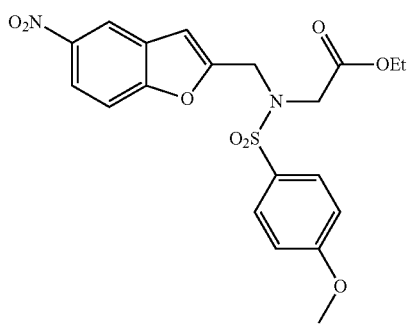 [SMILES: CCOC(=O)CN(Cc1cc2cc([N+](=O)[O-])ccc2o1)S(=O)(=O)c1ccc(OC)cc1]

Prepared using general procedure (method B) using commercially available 2-(bromomethyl)-5-nitrobenzofuran, the yield (461 mg, 84% yield). $^1$H NMR (400 MHz) (CDCl$_3$) δ 8.44 (d, 1H, J=2.0 Hz), 8.20 (dd, 1H, J=2.0 Hz, 8.8 Hz), 7.79 (d, 2H, J=8.8 Hz), 7.44 (d, 1H, J=9.2 Hz), 6.93 (d, 2H, J=8.8 Hz), 6.77 (s, 1H), 4.71 (s, 2H), 4.11-4.06 (m, 4H), 3.85 (s, 3H), 1.19 (d, 3H, J=7.2 Hz). $^{13}$C NMR (100 MHz) (CDCl$_3$) δ 168.67, 163.34, 157.95, 156.02, 144.47, 131.22, 129.77, 128.48, 120.58, 117.74, 114.27, 111.70, 107.02, 61.66, 55.77, 48.08, 44.89, 14.19.

Intermediate: Ethyl N-((5-aminobenzofuran-2-yl)methyl)-N-((4-methoxyphenyl)sulfonyl)glycinate

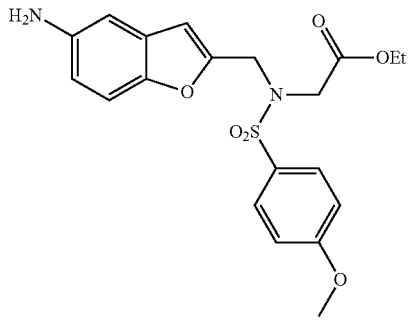

Prepared as described in the general procedure for nitro group reduction (Method E1) to get the title compound as a yellow solid; the yield (173 mg, 50%). $^1$H NMR (400 MHz) (CDCl$_3$) δ 7.78 (d, 2H, J=8.8 Hz), 7.09 (d, 2H, J=8.4 Hz), 6.97-6.90 (m, 2H), 6.74 (d, 1H, J=2.0 Hz), 6.61 (dd, 1H, J=2.4 Hz, 8.8 Hz), 6.41 (s, 1H), 4.62 (s, 2H), 4.12-4.03 (m, 4H), 3.83 (s, 3H), 1.17 (t, 3H, J=7.2 Hz). $^{13}$C NMR (100 MHz) (CDCl$_3$) δ 168.88, 163.23, 163.08, 152.23, 149.76, 142.34, 131.51, 129.69, 129.52, 128.80, 114.38, 114.10, 113.85, 111.47, 106.27, 105.88, 61.95, 61.42, 55.72, 55.68, 47.69, 44.85, 44.27, 14.12, 14.09.

Intermediate: Ethyl N-((5-((4-methoxyphenyl)sulfonamido) benzofuran-2-yl) methyl)-N-((4-methoxyphenyl) sulfonyl) glycinate

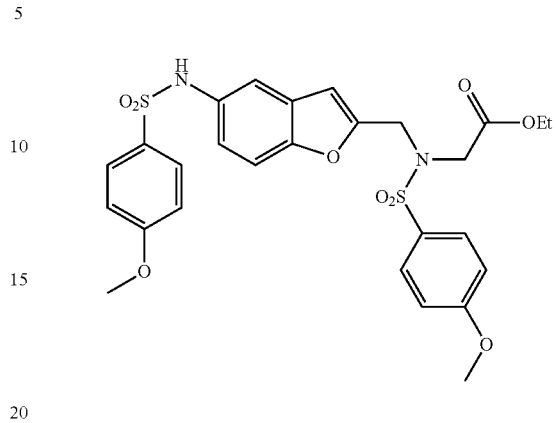

Prepared as described in the general procedure for synthesis of sulfonamides (method A2) to get the title compound as a beige solid; the yield (92 mg, 79% yield). $^1$H NMR (400 MHz) (CDCl$_3$) δ) 7.78 (d, 2H, J=8.8 Hz), 7.62 (d, 2H, J=8.8 Hz), 7.19 (d, 1H, J=8.8 Hz), 6.93-6.86 (m, 5 H), 6.53 (s, 1H), 6.45 (s, 1H), 4.64 (s, 2H), 4.09-4.04 (m, 4H), 3.85 (s, 3H), 3.82 (s, 3H), 1.17 (t, 2H, J=7.2 Hz). $^{13}$C NMR (100 MHz) (CDCl$_3$) 168.81, 163.24, 153.61, 153.38, 131.77, 131.41, 131.03, 130.70, 129.76, 129.58, 128.75, 120.94, 116.34, 114.30, 114.21, 111.77, 106.55, 61.56, 55.76, 55.72, 47.85, 44.86, 14.18.

Intermediate: Ethyl N-(2-(((4-methoxy-N-(2-methoxy-2-oxoethyl)phenyl) sulfonamido) methyl) benzofuran-5-yl)-N-((4-methoxyphenyl) sulfonyl) glycinate

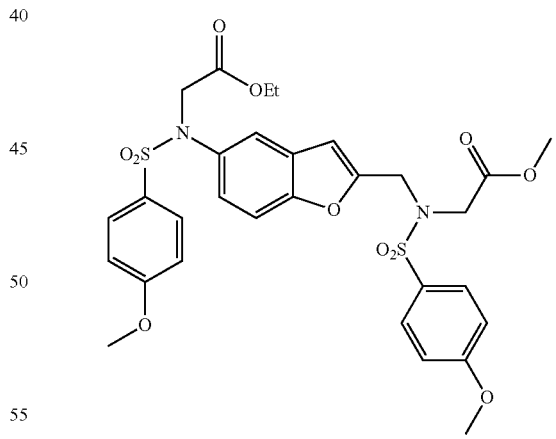

Prepared as described in the general procedure for synthesis of alkylated sulfonamides (method B) to get the title compound as oily product; the yield (77 mg, 86% yield). $^1$H NMR (400 MHz) (CDCl$_3$) δ) 7.78 (d, 2H, J=8.8 Hz), 7.60 (d, 2H, J=8.8 Hz), 7.41 (d, 1H, J=2.4 Hz), 7.23 (d, 1H, J=8.8 Hz), 7.03 (dd, 1H, J=2.0 Hz, 8.8 Hz), 6.93 (d, 2H, J=8.8 Hz), 6.90 (d, 2H, J=8.8 Hz), 6.54 (s, 1H), 4.65 (s, 2H), 4.40 (s, 2H), 4.16-4.03 (m, 6H), 1.25-1.16 (m, 6H). $^{13}$C NMR (100 MHz) (CDCl$_3$) 169.04, 168.75, 163.21, 163.17, 154.42, 153.52, 135.18, 131.36, 130.74, 130.11, 129.72, 128.57, 125.76, 122.62, 114.19, 114.02, 111.71, 106.77, 61.53.55.70, 53.39, 47.69, 44.76, 14.20, 14.15.

Example LH882: N-((5-((N-(Carboxymethyl)-4-methoxyphenyl)sulfonamido)benzofuran-2-yl)methyl)-N-((4-methoxyphenyl)sulfonyl)glycine

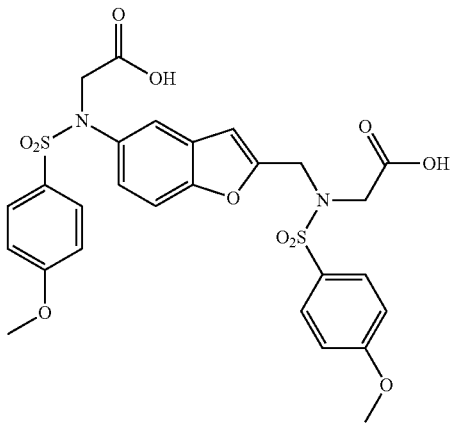 [SMILES: COc1ccc(S(=O)(=O)N(CC(=O)O)Cc2cc3cc(N(CC(=O)O)S(=O)(=O)c4ccc(OC)cc4)ccc3o2)cc1]

Prepared as described in the general procedure for hydrolysis of ethyl ester to get di-acidic compounds (Method C1) (base hydrolysis) to get the title compound as a beige solid; the yield (19 mg, 77% yield). $^1$H NMR (400 MHz) (CD$_3$CN) δ) 7.71 (d, 2H, J=9.2 Hz), 7.60 (d, 2H, J=9.2 Hz), 7.31 (d, 1H, J=2.0 Hz), 7.21 (d, 1H, J=8.8 Hz), 7.00 (dd, 1H, J=2.0 Hz, 8.8 Hz), 6.97-6.92 (m, 4H), 6.57 (s, 1H), 4.56 (s, 2H), 4.35 (s, 2H), 3.97 (s, 2H), 3.82 (s, 3H), 3.78 (s, 3H). $^{13}$C NMR (100 MHz) (CD$_3$CN)) 170.50, 170.35, 164.28, 164.13, 154.99, 154.83, 136.23, 132.27, 131.34, 130.75, 130.42, 129.34, 126.48, 123.02, 118.26, 115.09, 112.13, 107.48, 60.96, 56.51, 53.64, 48.72, 45.72. HRMS (ESI) Calcd for C$_{27}$H$_{26}$N$_2$O$_{11}$S$_2$ (M+H)$^+$ 619.1051, found 619.1047.

Intermediate: tert-Butyl 7-chloro-2-((1,3-dioxoisoindolin-2-yl)methyl)-4-nitro-1H-indole-1-carboxylate

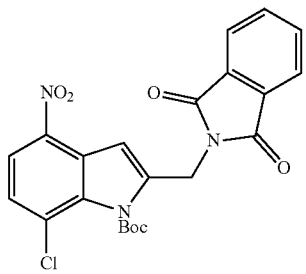 [SMILES: CC(C)(C)OC(=O)n1c(CN2C(=O)c3ccccc3C2=O)cc2c([N+](=O)[O-])ccc(Cl)c21]

Prepared as described in the general procedure for alkylation (method B) to get the title compound as oily product; the yield (117 mg, 78% yield). $^1$H NMR (400 MHz) (CDCl$_3$) δ) 8.07 (d, 1H, J=8.4 Hz), 7.94-7.92 (m, 2H), 7.80-7.78 (m, 2H), 7.33 (d, 1H, J=8.8 Hz), 7.03 (t, 1H, J=1.2 Hz), 5.16 (d, 2H, J=1.2 Hz), 1.70 (s, 9H). $^{13}$C NMR (100 MHz) (CDCl$_3$) δ 167.85, 167.59, 167.33, 148.50, 141.46, 138.70, 134.83, 134.60, 132.02, 126.71, 126.20, 124.71, 123.96, 120.45, 104.82, 87.32, 35.85, 27.89.

Intermediate: tert-Butyl 4-amino-7-chloro-2-((1,3-dioxoisoindolin-2-yl)methyl)-1H-indole-1-carboxylate

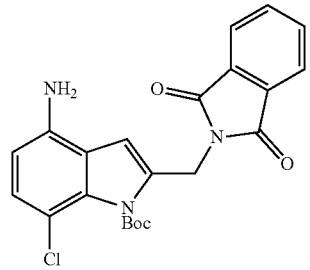

Prepared as described in the general procedure for nitro group reduction (Method E1) to get the title compound as a yellow solid; the yield (94 mg, 79% yield). $^1$H NMR (400 MHz) (CDCl$_3$) δ) 7.93-7.91 (m, 2H), 7.79-7.76 (m, 2H), 7.03 (d, 1H, J=8.0 Hz), 6.38 (d, 1H, J=8.4 Hz), 6.15 (s, 1H), 5.14 (s, 2H), 1.70 (s, 9H). $^{13}$C NMR (100 MHz) (CDCl$_3$) δ 167.73, 149.65, 137.84, 134.68, 134.37, 133.85, 132.20, 126.45, 123.73, 123.49, 120.37, 109.68, 108.63, 101.90, 85.68, 36.04, 27.95.

Intermediate: tert-Butyl 7-chloro-2-((1,3-dioxoisoindolin-2-yl)methyl)-4-((4-methoxyphenyl) sulfonamido)-1H-indole-1-carboxylate

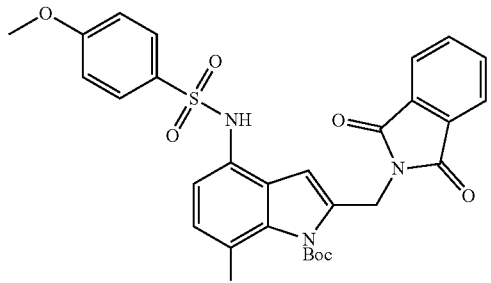

Prepared as described in the general procedure for synthesis of sulfonamides (method A2) to get the title compound as an off-white solid; the yield (75 mg, 86% yield). $^1$H NMR (400 MHz) (CDCl$_3$) δ) 7.89-7.88 (m, 2H), 7.77-7.75 (m, 2H), 7.51 (d, 2H, J=9.2 Hz), 7.11 (d, 1H, J=8.4 Hz), 7.03 (d, 1H, J=8.4 Hz), 6.85 (s, 1H), 6.69 (d, 2H, J=8.8 Hz), 5.03 (d, 1H, J=1.2 Hz), 3.81 (s, 3H), 1.66 (s, 9H). $^{13}$C NMR (100 MHz) (CDCl$_3$) δ 167.83, 167.64, 163.26, 163.13, 149.03, 136.99, 134.51, 133.71, 132.01, 130.62, 129.37, 127.15, 126.13, 126.02, 123.84, 117.51, 117.25, 114.24, 101.57, 86.30, 55.67, 36.03, 27.95.

Intermediate: tert-Butyl 4-((N-(2-(tert-butoxy)-2-oxoethyl)-4-methoxyphenyl)sulfonamido)-7-chloro-2-((1,3-dioxoisoindolin-2-yl)methyl)-1H-indole-1-carboxylate

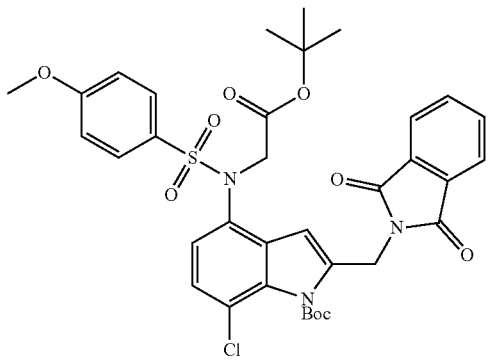 [SMILES: COc1ccc(S(=O)(=O)N(CC(=O)OC(C)(C)C)c2ccc(Cl)c3c2cc(CN2C(=O)c4ccccc4C2=O)n3C(=O)OC(C)(C)C)cc1]

Prepared as described in the general procedure for synthesis of alkylated sulfonamides (method B) to get the title compound as oily product; the yield (75 mg, 81% yield). $^1$H NMR (400 MHz) (CDCl$_3$) δ) 7.95-7.93 (m, 2H), 7.82-7.80 (m, 2H), 7.50 (d, 2H, J=8.8 Hz), 7.15 (d, 2H, J=8.4 Hz), 7.03 (d, 1H, J=8.0 Hz), 6.85 (s, 1H), 6.75 (d, 2H, J=8.8 Hz), 5.05 (s, 2H), 4.14 (s, 2 H), 3.89 (s, 3H), 1.66 (s, 9H), 1.32 (s, 9H). $^{13}$C NMR (100 MHz) (CDCl$_3$) δ 167.59, 167.23, 162.83, 148.85, 137.29, 134.14, 133.90, 131.83, 130.90, 130.60, 130.26, 129.66, 125.35, 123.61, 123.35, 120.07, 113.68, 102.96, 85.97, 81.98, 55.41, 53.24, 35.77, 27.78, 27.70.

Example LH934: N-(7-Chloro-2-((1,3-dioxoisoindolin-2-yl)methyl)-1H-indol-4-yl)-N-((4-methoxyphenyl) sulfonyl) glycine

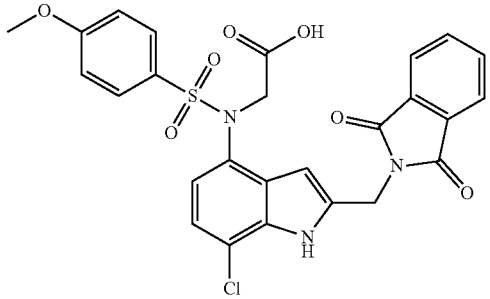 [SMILES: COc1ccc(S(=O)(=O)N(CC(=O)O)c2ccc(Cl)c3[nH]c(CN4C(=O)c5ccccc5C4=O)cc23)cc1]

Prepared as described in the general procedure for removal of acid sensitive protecting group (Method C2) to get the title compound as a beige solid; the yield (21 mg, 71% yield). $^1$H NMR (400 MHz) (CDCl$_3$) δ) 9.03 (s, 1H), 8.63 (br, 2H), 7.88-7.86 (m, 2H), 7.75-7.73 (m, 2H), 7.58 (d, 2H, J=8.8 Hz), 7.05 (d, 2H, J=8.4 Hz), 6.87-6.84 (m, 3H), 6.35 (s, 1H), 4.92 (s, 2H), 4.45 (s, 2 H), 3.85 (s, 3H). $^{13}$C NMR (100 MHz) (CDCl$_3$) δ 168.40, 163.38, 134.82, 134.71, 134.56, 131.89, 130.48, 130.38, 130.10, 127.85, 123.86, 122.86, 122.01, 117.40, 114.14, 102.11, 55.71, 52.44, 34.69. HRMS (ESI) Calcd for C$_{26}$H$_{20}$ClN$_3$O$_7$S (M+H)$^+$ 554.0783, found 554.0795.

Fluorescence Polarization (FP) Assay for Determination of the Inhibitory Potency of Designed Analogs Fluorescence polarization assay was performed on a Wallac Victor 3V multi-label counter/plate reader (PerkinElmer, Shelton, CT) using 484 nm excitation and 535 nm emission filters for the fluorophore used in the binding experiment. The plate used for the FP measurement was Corning 3575 384-well plate, loaded with 40 μL of assay solution per well. The buffer used in FP assays is 10 mM HEPES buffer, pH 7.4, containing 150 mM NaCl, 50 mM EDTA, and 0.005% Tween-20. Deionized water from a Millipore water purification used to prepare all aqueous solutions in FP assay. The fluorescent probe used in this assay is 9-mer Nrf2 ETGE motif derived peptide, FITC-LDEETGEFL-NH$_2$. In each well, the final volume is 40 μL that consisted of 10 μL of 400 nM Keap1 Kelch domain protein, and 20 μL of 20 nM FITC-9mer Nrf2 peptide amide, and 10 μL of an inhibitor compound of different concentrations. The experiments were done in triplicates, with initial concentration of the inhibitor typically 5 μM and 50 μM. Then, the plate was centrifuged for 2 mM to ensure thorough mixing and get rid of any air bubbles in the solution. The plate was covered and shacked for 30 mM at room temperature and then centrifuged for 2 mM prior to FP measurements.

The determination of FP is by measuring the parallel and perpendicular fluorescence intensity (F∥ and F⊥) with respect to the linearly polarized excitation light. The measurement of IC$_{50}$ of the inhibitors was determined from the plot of % inhibition against concentration of the inhibitor analyzed by Sigma Plot 12.3 software.

Time-Resolved Fluorescence Resonance Energy Transfer (TR-FRET) Assay

TR-FRET assay was performed on a Wallac Victor 3V multi-label counter/plate reader (PerkinElmer, Shelton, CT). The plate used for the FP measurement was 384-well plates (Corning® 384 Well Low Flange White Flat Bottom Polystyrene NBS™ Microplate), loaded with 20 μL of assay solution per well. The buffer used in FP assays is TR-FRET dilution buffer from ThermoFisher (PV3574). The fluorescent probe used in this assay is 9-mer Nrf2 ETGE motif derived peptide, FITC-LDEETGEFL-NH$_2$. In each well, the final volume is 20 μL containing 5 nM of Keap1, 25 nM of FITC-Nrf2-9mer-NH$_2$ and 0.5 nM of Terbium labeled anti-HIS antibody+inhibitor compound of different concentrations in DMSO or DMSO alone (1% final concentration) in assay buffer in triplicate. Then, the plate was centrifuged for 2 mM to ensure thorough mixing and get rid of any air bubbles in the solution. The plate was covered and shaked for 60 mM at room temperature and then centrifuged for 2 mM and TR-FRET was measured on a Victor 3V microplate reader. After excitation at 340 nm, well fluorescence was monitored at 495 nm and 520 nm. The measurement of IC$_{50}$ of the inhibitors was determined from the plot of % inhibition against concentration of the inhibitor analyzed by Sigma Plot 12.3 software.

All references cited herein are incorporated herein by reference in their entireties. It will be appreciated by persons skilled in the art that the present invention is not limited to what has been particularly shown and described. Rather, the scope of the present invention is defined by the claims which follow. It should further be understood that the above description is only representative of illustrative examples of embodiments. The description has not attempted to exhaustively enumerate all possible variations. The alternate embodiments may not have been presented for a specific portion of the invention, and may result from a different combination of described portions, or that other un-described alternate embodiments may be available for a portion, is not to be considered a disclaimer of those alternate embodiments. It will be appreciated that many of those un-described embodiments are within the literal scope of the following claims, and others are equivalent.

We claim:
1. A compound or

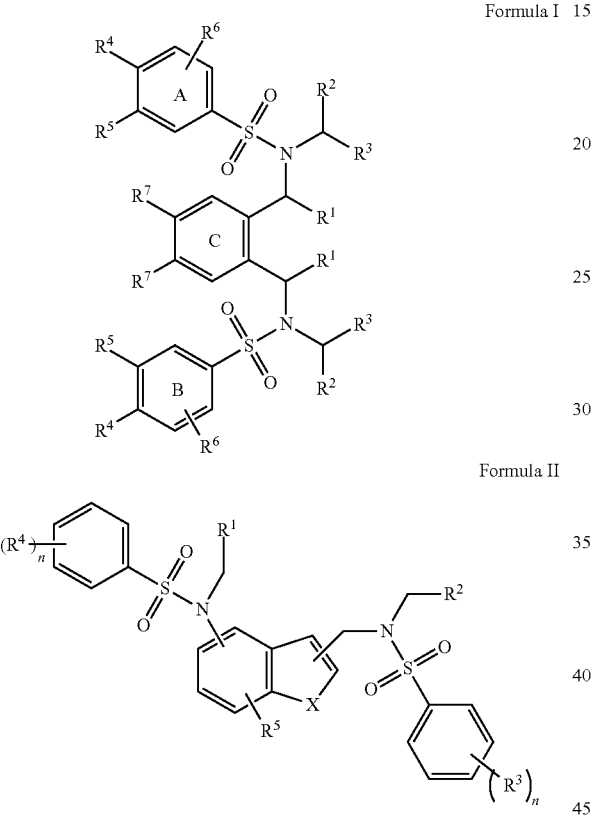

Formula I

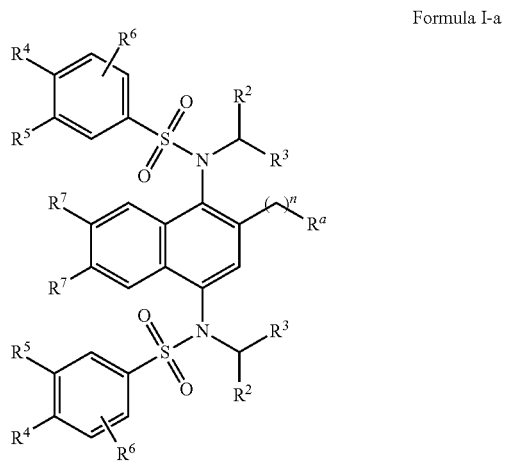

Formula II a pharmaceutically acceptable salt, an isomer, or a prodrug thereof, wherein the compound is Formula I or Formula II,
wherein Formula I is defined as follows:
$R^1$ is
(a) hydrogen; or
(b) two $R^1$ groups link up to each other together with the carbons they are attached to and ring C to form a ring;
$R^2$ is C1-C4 alkyl;
$R^3$ is carboxylic acid or carboxamide or tetrazole;
$R^4$ is selected from the group consisting of hydrogen, C1-C4 alkoxy, C1-C6 alkyl, halogen, CF3, sulfonamido, amido, carboxamide, amino, nitro, trifluoroacetamido, aryl, heteoaryl, and aryl-C1-C2 alkoxy;
$R^5$ is selected from the group consisting of hydrogen, C1-C6 alkyl, C1-C4 alkoxy, halogen, $CF_3$, sulfonamido, amido, trifluoroacetamido, aryl, heteroaryl, or aryl-C1-C2 alkoxy;
alternatively $R^4$ and $R^5$ link up together with the ring to which they are attached to form a bicylic or tricyclic ring;
$R^6$ is hydrogen, C1-C6 alkyl, halogen, or $CF_3$;
$R^7$ is hydrogen, halogen, C1-C3 alkyl, or C1-C3 alkoxy;
provided that when the two $R^1$ groups link up to each other together with the carbons they are attached to and ring C to form a ring, the compound is one of (a), (b), (c), and (d):
(a) the compound is represented as Formula I-a

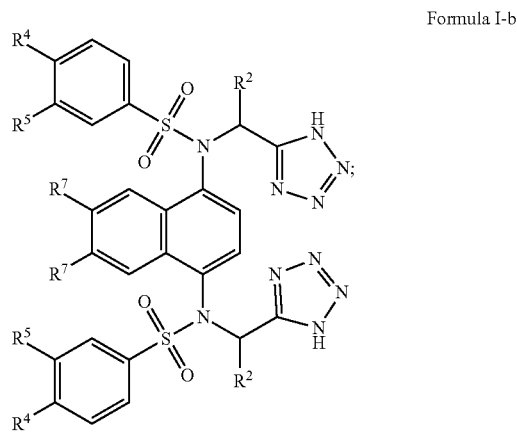

Formula I-a

Wherein
n is an integer of 0 to 5 inclusive;
$R^a$ is selected from the group consisting of —CONR$^c$R$^d$, aryl, heteroaryl, O-aryl, S-aryl, O-heteroaryl, S-heteroaryl, and phthalimide, wherein the aryl, heteroaryl, O-aryl, S-aryl, O-heteroaryl, S-heteroaryl, or phthalimide is optionally substituted with halogen or C1-C4 alkyl, and wherein $R^c$ and $R^d$ are independently H or alkyl, or $R^c$ and $R^d$ link up to form a ring 3 to 8 membered carbocycle or heterocycle;
(b) the compound is represented as Formula I-b Formula I-b (c) the compound is represented as Formula I-c

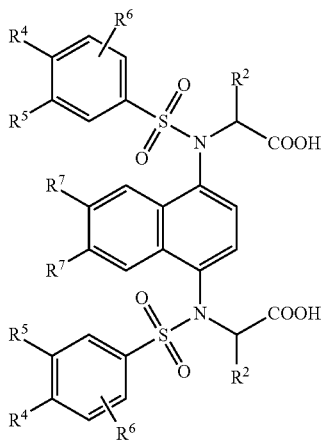

Formula I-c wherein R⁴ is selected from the group consisting of sulfonamido, trifluoroacetamido, aryl, heteoaryl, and aryl-C1-C2 alkoxy; and (d) R⁴ and R⁵ link up together with the ring to which they are attached to form a bicylic ring, wherein at least one of the ring atom in the bicyclic ring is a sp3 hybridized carbon, further wherein the bicyclic ring is optionally substituted with halogen or C1-C4 alkyl;

and

Formula II is defined as follows:

wherein X is S or NR$^a$;

R$^a$ is hydrogen or C1-C4 alkyl;

R¹ and R² are independently carboxylic acid (COOH) or tetrazole;

R³ and R⁴ are independently selected from the group consisting of C1-C4 alkoxy, C1-C6 alkyl, halogen, CF₃, sulfonamido, amido, trifluoroacetamido, aryl, heteoaryl, and aryl-C1-C2 alkoxy;

R⁵ is hydrogen, C1-C4 alkyl, or halogen; and n in each instance is independently an integer of 1 to 3, inclusive.

2. The compound or the pharmaceutically acceptable salt, isomer, or prodrug thereof of claim 1, wherein R⁶ is hydrogen and R⁷ is hydrogen.

3. The compound or the pharmaceutically acceptable salt, isomer, or prodrug thereof of claim 1, wherein R¹ is hydrogen.

4. The compound or the pharmaceutically acceptable salt, isomer, or prodrug thereof of claim 1, wherein R¹ is hydrogen;

R⁴ is selected from the group consisting of C1-C4 alkoxy, C1-C6 alkyl, halogen, CF₃, sulfonamido, amido, trifluoroacetamido, aryl, heteoaryl, and aryl-C1-C2 alkoxy; and R⁵ is hydrogen, C1-C4 alkyl, or halogen.

5. The compound or the pharmaceutically acceptable salt, isomer, or prodrug thereof of claim 1, wherein R¹ is hydrogen;

R² is C1-C4 alkyl;

R⁴ is selected from the group consisting of C1-C4 alkoxy, C1-C6 alkyl, halogen, CF₃, sulfonamido, amido, trifluoroacetamido, aryl, heteoaryl, and aryl-C1-C2 alkoxy; and R⁵ is hydrogen, C1-C4 alkyl, or halogen.

6. The compound or the pharmaceutically acceptable salt, isomer, or prodrug thereof of claim 1, wherein R¹ is hydrogen;

R² is C1-C4 alkyl;

R⁴ is C1-C4 alkoxy; and

R⁵ is hydrogen.

7. The compound or the pharmaceutically acceptable salt, isomer, or prodrug thereof of claim 1, wherein the compound is represented as Formula I-a;

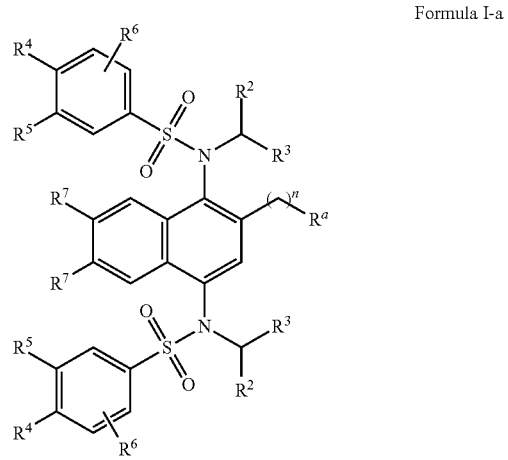

Formula I-a

Wherein n is an integer of 1 to 5 inclusive;

R$^a$ is phthalimide optionally substituted with halogen or C1-C4 alkyl, or —CONR$^c$R$^d$, wherein R$^c$ and R$^d$ are independently H or alkyl, or R$^c$ and R$^d$ link up to form a ring 3 to 8 membered carbocycle or heterocycle.

8. The compound or the pharmaceutically acceptable salt, isomer, or prodrug thereof of claim 1, wherein the compound is represented as Formula I-a, R⁴ is C1-C4 alkoxy, C1-C6 alkyl, halogen, CF₃, sulfonamido, amido, trifluoroacetamido, aryl, heteoaryl, or aryl-C1-C2 alkoxy;

R⁵ is hydrogen, C1-C4 alkyl, or halogen; and

R$^a$ is phthalimide optionally substituted with halogen or C1-C4 alkyl, or —CONR$^c$R$^d$, wherein R$^c$ and R$^d$ link up to form 3 to 8 membered heterocycle.

9. The compound or the pharmaceutically acceptable salt, isomer, or prodrug thereof of claim 1, wherein the compound is represented as Formula I-b,

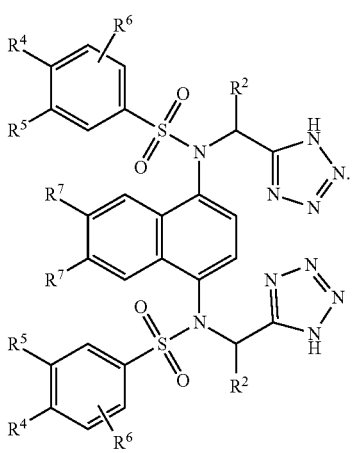

Formula I-b

10. The compound or the pharmaceutically acceptable salt, isomer, or prodrug thereof of claim 1, wherein the compound is represented as Formula I-b; and
$R^4$ and $R^5$ link up together with the ring to which they are attached to form a bicylic or tricyclic ring.

11. The compound or the pharmaceutically acceptable salt, isomer, or prodrug thereof of claim 1, wherein the compound is represented as Formula I-c,

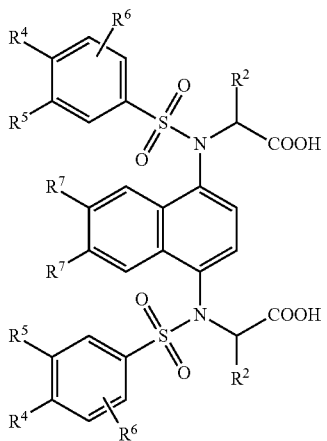

Formula I-c wherein $R^4$ is sulfonamido, trifluoroacetamido, aryl, heteoaryl, or aryl-C1-C2 alkoxy.

12. The compound or the pharmaceutically acceptable salt, isomer, or prodrug thereof of claim 1, wherein $R^4$ and $R^5$ link up together with the ring to which they are attached to form the bicyclic ring, wherein at least one of the ring atom in the bicyclic ring is a sp3 hybridized carbon, further wherein the bicyclic ring is optionally substituted with halogen or C1-C4 alkyl.

13. The compound or the pharmaceutically acceptable salt, isomer, or prodrug thereof of claim 1, wherein the compound is represented as Formula II-a,

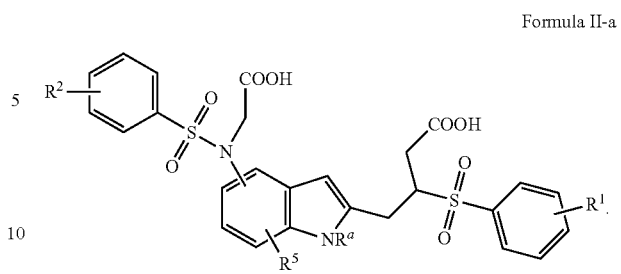

Formula II-a

14. The compound or the pharmaceutically acceptable salt, isomer, or prodrug thereof of claim 13, wherein $R^a$ is hydrogen.

15. The compound or the pharmaceutically acceptable salt, isomer, or prodrug thereof of claim 14, wherein $R^a$ is hydrogen, and $R^5$ is a halogen at 7-position of indole ring.

16. The compound or the pharmaceutically acceptable salt, isomer, or prodrug thereof of claim 1, wherein the compound is represented as Formula II-b,

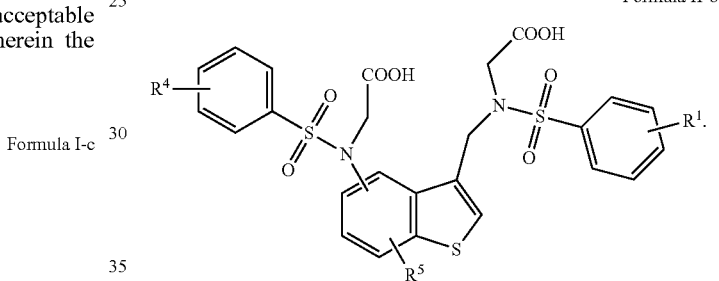

Formula II-b

17. The compound or the pharmaceutically acceptable salt, isomer, or prodrug thereof of claim 16, wherein $R^5$ is a halogen at 7-position of thiophene ring.

18. A pharmaceutical composition comprising the compound or the pharmaceutically acceptable salt, isomer, or prodrug thereof of claim 1.

19. A method of ameliorating a disease selected from the group consisting of cancer, chronic obstructive pulmonary diseases (COPD), Alzheimer's disease, Parkinson's disease, chronic kidney diseases (CKD), diabetes, and inflammatory bowel disease, comprising administering to a subject in need the compound or the pharmaceutically acceptable salt, isomer, or prodrug thereof of claim 1 in an amount effective to inhibit Keap1-Nrf2 protein-protein interaction and thereby activate therapeutic levels of Nrf2.

20. The method of claim 19, wherein the disease is selected from the group consisting of chronic obstructive pulmonary diseases (COPD), Alzheimer's disease, Parkinson's disease, chronic kidney diseases (CKD), diabetes, and inflammatory bowel disease.

21. The method of claim 19, wherein the inflammatory bowel disease is ulcerative colitis.

* * * * *

UNITED STATES PATENT AND TRADEMARK OFFICE
CERTIFICATE OF CORRECTION

PATENT NO. : 12,122,742 B2
APPLICATION NO. : 17/423688
DATED : October 22, 2024
INVENTOR(S) : Longqin Hu et al.

Page 1 of 1

It is certified that error appears in the above-identified patent and that said Letters Patent is hereby corrected as shown below:

In the Claims

At Column 182, Claim number 16, Line number 30 should read:

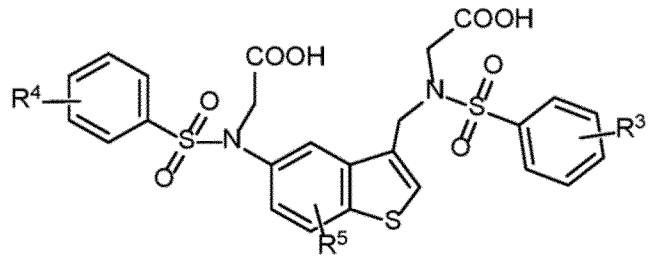

Formula II-b.

Signed and Sealed this
Seventeenth Day of December, 2024

Derrick Brent
*Acting Director of the United States Patent and Trademark Office*